US008697852B2

(12) United States Patent
Burns et al.

(10) Patent No.: US 8,697,852 B2
(45) Date of Patent: Apr. 15, 2014

(54) GENETIC FINGERPRINTING AND IDENTIFICATION METHOD

(71) Applicant: E. I. du Pont de Nemours and Company, Wilmington, DE (US)

(72) Inventors: Frank R. Burns, Media, PA (US); Xuan Peng, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/914,987

(22) Filed: Jun. 11, 2013

(65) Prior Publication Data

US 2013/0274458 A1    Oct. 17, 2013

Related U.S. Application Data

(62) Division of application No. 12/858,508, filed on Aug. 18, 2010, now Pat. No. 8,481,267.

(60) Provisional application No. 61/235,999, filed on Aug. 21, 2009.

(51) Int. Cl.
 *C12Q 1/68* (2006.01)
(52) U.S. Cl.
 USPC ........................................................ 536/23.1
(58) Field of Classification Search
 None
 See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,879,214 | A | 11/1989 | Kornher et al. |
| 5,126,239 | A | 6/1992 | Livak et al. |
| 5,874,215 | A | 2/1999 | Kuiper et al. |
| 6,263,286 | B1 | 7/2001 | Gilmanshin et al. |

OTHER PUBLICATIONS

Benecke, M., "Random amplified polymorphic DNA (RAPD) typing of necrophageous insects . . . ", Forensic Science International, vol. 98, No. 3, pp. 157-168 (1998).
Healy Mimi, et al., "Microbial DNA typing by automated repetitive-sequence based PCR", Journal of Clinical Microbiology, vol. 43, No. 1, pp. 119-207, Jan. 2005.
Healy M, et al., "Use of the Diversi Lab system for Species . . . ", Journal of Clinical Microbiology, vol. 43, No. 10, pp. 5278-5280, Oct. 2005.
Hilton A.C., et al., "Random amplification of polymorphic DNA (RAPD) of *Salmonella* . . . ", The Journal of Applied Bacteriology, vol. 81, No. 6, pp. 575-584, Dec. 1996.
Kuske CR, et al., "Small-scale DNA sample prepration method for field PCR . . . " Applied and Envioronmental Microbiology, vol. 64, No. 7, pp. 2463-2472, Jul. 1998.
Pounder, June I., et al., "Repetitive-sequence-PCR-based DNA fingerprinting . . . ", Journal of Clinical Microbiology, Bol. 43, No. 5, pp. 2141-2147, May 2005.
Pounder, June I., et al., "Clinical evaluation of repetitive sequence-based . . . ", Diagnostic Microbiology and Infectious Disease, vol. 54, No. 3, pp. 183-187, Mar. 2006.
Shutt, Cheryl, et al., "Clinical evaluation of the DiversiLab microbial . . . ", Journal of Clinical Microbiology, vol. 43, No. 3, pp. 1187-1192, Mar. 2005.
PCT Search Report and Written Opinion ofr Internaitonal Application No. PCT/US2010/046004 dated Apr. 11, 2011.
Versalovic, James, et al., "Genomic Fingerprinting of Bacteria Using . . . " Methods Mol. Cell., Biol. 5:25-40 (1994).
Chan, Eugene, et al., "DNA Mapping Using Microfluidic Stretching . . . ", Genome Research, 14:1137-1146 (2004).
Jeffreys, A.J., et al., "Individual-specific 'fingerprints' of human DNA", Nature, vol. 316, pp. 76-79 (1985).
Louws, F.J., et al., "Specific genomic fingerpritns of phytopathogenic Xanthomonas . . . ", Appl. and Environ. Microbiol. 60(7):2286-2295 (1994).
Wiliams, John G.K., et al., "CNA polymorphisms amplified by arbitrary primers are useful as genetic markers", Nucleic Acids res. 18:6531-35 (1990).

*Primary Examiner* — Christopher M Babic
*Assistant Examiner* — Aaron Priest

(57) ABSTRACT

The present disclosure provides methods for molecular fingerprinting for the characterization and identification of organisms. More specifically, in one aspect the present invention provides a method of identifying an organism in a sample comprising: (a) providing a sample comprising said organism, said organism comprising at least one nucleic acid; (b) combining said sample or the at least one nucleic acid therefrom with an amplification mix comprising at least one labeled oligonucleotide primer; (c) generating at least one labeled amplification product from the at least one nucleic acid of said organism using a nucleotide amplification technique employing said at least one labeled oligonucleotide primer; (d) combining said at least one labeled amplification product with products of a DNA sequencing reaction to create a separation mix; and (e) separating said separation mix on the basis of oligonucleotide length in a fluorescent DNA sequencing instrument to generate a sequence embedded fingerprint pattern for said organism.

2 Claims, 2 Drawing Sheets

```
                       SEQUENCE LISTING

<160> NUMBER OF SEQ ID NOS: 51

<210> SEQ ID NO 1
<211> LENGTH: 36
<212> TYPE: DNA
<213> ORGANISM: Artificial Sequence
<220> FEATURE:
<223> OTHER INFORMATION: Primer

<400> SEQUENCE: 1
cgcttcgcgt tttaaaaacc gacatgagta caatac                            36

<210> SEQ ID NO 2
<211> LENGTH: 36
<212> TYPE: DNA
<213> ORGANISM: Artificial Sequence
<220> FEATURE:
<223> OTHER INFORMATION: Primer

<400> SEQUENCE: 2
cgcttcgcgt tttaaaaacc gacatgagta caatcc                            36

<210> SEQ ID NO 3
<211> LENGTH: 36
<212> TYPE: DNA
<213> ORGANISM: Artificial Sequence
<220> FEATURE:
<223> OTHER INFORMATION: Primer
```

-continued

```
<400> SEQUENCE: 3
cgcttcgcgt tttaaaaacc gacatgagta caatgc                           36

<210> SEQ ID NO 4
<211> LENGTH: 36
<212> TYPE: DNA
<213> ORGANISM: Artificial Sequence
<220> FEATURE:
<223> OTHER INFORMATION: Primer

<400> SEQUENCE: 4
cgcttcgcgt tttaaaaacc gacatgagta caattc                           36

<210> SEQ ID NO 5
<211> LENGTH: 821
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (5)..(5)
<223> OTHER INFORMATION: n is unknown
<220> FEATURE:
<221> NAME/KEY: misc_feature
<222> LOCATION: (8)..(9)
<223> OTHER INFORMATION: n is unknown
<220> FEATURE:
<221> NAME/KEY: misc_feature
<222> LOCATION: (35)..(35)
<223> OTHER INFORMATION: n is unknown
<220> FEATURE:
<221> NAME/KEY: misc_feature
<222> LOCATION: (40)..(40)
<223> OTHER INFORMATION: n is unknown
<220> FEATURE:
<221> NAME/KEY: misc_feature
<222> LOCATION: (270)..(273)
<223> OTHER INFORMATION: n is unknown
<220> FEATURE:
<221> NAME/KEY: misc_feature
<222> LOCATION: (275)..(282)
<223> OTHER INFORMATION: n is unknown
<220> FEATURE:
<221> NAME/KEY: misc_feature
<222> LOCATION: (345)..(345)
<223> OTHER INFORMATION: n is unknown
<220> FEATURE:
<221> NAME/KEY: misc_feature
<222> LOCATION: (347)..(347)
<223> OTHER INFORMATION: n is unknown
<220> FEATURE:
<221> NAME/KEY: misc_feature
<222> LOCATION: (353)..(359)
<223> OTHER INFORMATION: n is unknown
<220> FEATURE:
<221> NAME/KEY: misc_feature
<222> LOCATION: (529)..(530)
<223> OTHER INFORMATION: n is unknown
<220> FEATURE:
<221> NAME/KEY: misc_feature
<222> LOCATION: (532)..(533)
<223> OTHER INFORMATION: n is unknown
<220> FEATURE:
<221> NAME/KEY: misc_feature
<222> LOCATION: (535)..(537)
<223> OTHER INFORMATION: n is unknown
<220> FEATURE:
<221> NAME/KEY: misc_feature
<222> LOCATION: (539)..(548)
<223> OTHER INFORMATION: n is unknown
<220> FEATURE:
<221> NAME/KEY: misc_feature
<222> LOCATION: (782)..(782)
<223> OTHER INFORMATION: n is unknown
```

```
<220> FEATURE:
<221> NAME/KEY: misc_feature
<222> LOCATION: (812)..(813)
<223> OTHER INFORMATION: n is unknown

<400> SEQUENCE: 5
gttgntcnnc tgctgacaat gctgctgctg cttcncctcn ctgtctccac ttccttgaac      60
aatgcgccgt catgcttctt ttgcctcccg ctgctccaga aagctaggcc gcagatcaga     120
accaccacag tcaatatcac caccttcctc ttatagattc ggaatctcat gatagggct      180 cagcctctgt gcgagtggag agaagtttgc aggcgagctg aggagcaatt gcaggtgata     240
tgatgtgctc ggctcaagaa gcgggcccgn nnngnnnnnn nncgtgccgg ggctaattat     300
tggcaaaacg agctcttgtt gtaaacattg atccaactgg aatgncncta atnnnnnnnt     360
caatattcca taaggcatga tggttgctca gaggcaggag aagagcaacg aatacgatcc     420
tataaaagat aaaacataaa taaacagtct tgattatatt ctgggtatta aagccacaat     480
cagaacaaat atatgctttg tatctttct tgccttcttc attaccaann gnntnnncnn      540
nnnnnnnnag agaacttgtg gtaagataag aagatatttt attcgttctg ctgacttgct     600
ggatgtcggg aaatattctg catttgataa gaggcggtta attgcagata taattggtag     660 tgaaagggt cgttgctatg gtcaccgtga agcgagtaca gcagcacaag aatgtgtgcc      720
gttctcagtt aatattgttt gaatatggta acctgtttta gtcggtttaa aggtaagaag     780
anctaaccaa aaacaacact gcagtgactg anngtagtat t                         821

<210> SEQ ID NO 6
<211> LENGTH: 807
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (3)..(3)
<223> OTHER INFORMATION: n is unknown
<220> FEATURE:
<221> NAME/KEY: misc_feature
<222> LOCATION: (5)..(5)
<223> OTHER INFORMATION: n is unknown
<220> FEATURE:
<221> NAME/KEY: misc_feature
<222> LOCATION: (29)..(29)
<223> OTHER INFORMATION: n is unknown
<220> FEATURE:
<221> NAME/KEY: misc_feature
<222> LOCATION: (34)..(36)
<223> OTHER INFORMATION: n is unknown
<220> FEATURE:
<221> NAME/KEY: misc_feature
<222> LOCATION: (265)..(276)
<223> OTHER INFORMATION: n is unknown
<220> FEATURE:
<221> NAME/KEY: misc_feature
<222> LOCATION: (337)..(337)
<223> OTHER INFORMATION: n is unknown
<220> FEATURE:
<221> NAME/KEY: misc_feature
<222> LOCATION: (339)..(339)
<223> OTHER INFORMATION: n is unknown
<220> FEATURE:
<221> NAME/KEY: misc_feature
<222> LOCATION: (341)..(341)
<223> OTHER INFORMATION: n is unknown
<220> FEATURE:
<221> NAME/KEY: misc_feature
<222> LOCATION: (346)..(351)
<223> OTHER INFORMATION: n is unknown
<220> FEATURE:
<221> NAME/KEY: misc_feature
```

-continued

```
<222> LOCATION: (520)..(520)
<223> OTHER INFORMATION: n is unknown
<220> FEATURE:
<221> NAME/KEY: misc_feature
<222> LOCATION: (522)..(539)
<223> OTHER INFORMATION: n is unknown
<220> FEATURE:
<221> NAME/KEY: misc_feature
<222> LOCATION: (767)..(767)
<223> OTHER INFORMATION: n is unknown

<400> SEQUENCE: 6
tcncngctga caatgctgct gctgcttcnc ctcnnngtct ccacttcctt gaacaatgcg      60
ccgtcatgct tcttttgcct cccgctgctc cagaaagcta ggccgcagat cagaaccacc    120
acagtcaata tcaccacctt cctcttatag attcggaatc tcatgatagg ggctcagcct    180
ctgtgcgagt ggagagaagt ttgcaggcga gctgaggagc aattgcaggt gatatgatgt    240
gctcggctca agaagcgggc ccggnnnnnn nnnnnncgtg ccggggctaa ttattggcaa    300
aacgagctct tgttgtaaac attgatccaa ctggaangnc nctaannnnn natcaatatt    360
ccataaggca tgatggttgc tcagaggcag gagaagagca acgaatacga tcctataaaa    420
gataaaacat aaataaacag tcttgattat attctgggta ttaaagccac aatcagaaca    480
aatatatgct ttgtatcttt tcttgccttc ttcattaccn annnnnnnnn nnnnnnnnnt    540
aagagaactt gtggtaagat aagaagatat tttattcgtt ctgctgactt gctggatgtc    600
gggaaatatt ctgcatttga taagaggcgg ttaattgcag atataattgg tagtgaaaag    660
ggtcgttgct atggtcaccg tgaagcgagt acagcagcac aagaatgtgt gccgttctca    720
gttaatattg tttgaatatg gtaacctgtt ttagtcggtt taaaggnaag aagatctaac    780
caaaaacaac actgcagtga ctgattg                                        807

<210> SEQ ID NO 7
<211> LENGTH: 818
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (3)..(5)
<223> OTHER INFORMATION: n is unknown
<220> FEATURE:
<221> NAME/KEY: misc_feature
<222> LOCATION: (46)..(47)
<223> OTHER INFORMATION: n is unknown
<220> FEATURE:
<221> NAME/KEY: misc_feature
<222> LOCATION: (284)..(284)
<223> OTHER INFORMATION: n is unknown
<220> FEATURE:
<221> NAME/KEY: misc_feature
<222> LOCATION: (286)..(287)
<223> OTHER INFORMATION: n is unknown
<220> FEATURE:
<221> NAME/KEY: misc_feature
<222> LOCATION: (351)..(351)
<223> OTHER INFORMATION: n is unknown
<220> FEATURE:
<221> NAME/KEY: misc_feature
<222> LOCATION: (353)..(353)
<223> OTHER INFORMATION: n is unknown
<220> FEATURE:
<221> NAME/KEY: misc_feature
<222> LOCATION: (358)..(366)
<223> OTHER INFORMATION: n is unknown
<220> FEATURE:
<221> NAME/KEY: misc_feature
<222> LOCATION: (540)..(542)
<223> OTHER INFORMATION: n is unknown
```

<220> FEATURE:
<221> NAME/KEY: misc_feature
<222> LOCATION: (548)..(548)
<223> OTHER INFORMATION: n is unknown
<220> FEATURE:
<221> NAME/KEY: misc_feature
<222> LOCATION: (550)..(550)
<223> OTHER INFORMATION: n is unknown
<220> FEATURE:
<221> NAME/KEY: misc_feature
<222> LOCATION: (553)..(553)
<223> OTHER INFORMATION: n is unknown
<220> FEATURE:
<221> NAME/KEY: misc_feature
<222> LOCATION: (761)..(761)
<223> OTHER INFORMATION: n is unknown
<220> FEATURE:
<221> NAME/KEY: misc_feature
<222> LOCATION: (794)..(794)
<223> OTHER INFORMATION: n is unknown

<400> SEQUENCE: 7

```
gtnnngttgc tactactgct gacaatgctg ctgctgcttc tcctcnntgt ctccacttcc      60
ttgaacaatg cgccgtcatg cttcttttgc ctcccgctgc tccagaaagc taggccgcag     120
atcagaacca ccacagtcaa tatcaccacc ttcctcttat agattcggaa tctcatgata     180
ggggctcagc ctctgtgcga gtggagagaa gtttgcaggc gagctgagga gcaattgcag     240
gtgatatgat gtgctcggct caagaagcgg gcccggagag gaananntcg tgccggggct     300
aattattggc aaaacgagct cttgttgtaa acattgatcc aactggaatg ncnctaannn     360
nnnnnnaata ttccataagg catgatggtt gctcagaggc aggagaagag caacgaatac     420
gatcctataa aagataaaac ataaataaac agtcttgatt atattctggg tattaaagcc     480
acaatcagaa caaatatatg ctttgtatct tttcttgcct tcttcattac caactgcttn     540
nncggccncn ttnagagaac ttgtggtaag ataagaagat attttattcg ttctgctgac     600
ttgctggatg tcgggaaata ttctgcattt gataagaggc ggttaattgc agatataatt     660
ggtagtgaaa agggtcgttg ctatggtcac cgtgaagcga gtacagcagc acaagaatgt     720
gtgccgttct cagttaatat tgtttgaata tggtaacctg ntttagtcgg tttaaaggta     780
agaagatcta accnaaaaca acactgcagt gactgatt                            818
```

<210> SEQ ID NO 8
<211> LENGTH: 874
<212> TYPE: DNA
<213> ORGANISM: Artificial Sequence
<220> FEATURE:
<223> OTHER INFORMATION: S. cerevisiae PCR reaction /DNA sequence
      standard
<220> FEATURE:
<221> NAME/KEY: misc_feature
<222> LOCATION: (72)..(72)
<223> OTHER INFORMATION: n is unknown
<220> FEATURE:
<221> NAME/KEY: misc_feature
<222> LOCATION: (74)..(74)
<223> OTHER INFORMATION: n is unknown
<220> FEATURE:
<221> NAME/KEY: misc_feature
<222> LOCATION: (100)..(100)
<223> OTHER INFORMATION: n is unknown
<220> FEATURE:
<221> NAME/KEY: misc_feature
<222> LOCATION: (104)..(104)
<223> OTHER INFORMATION: n is unknown
<220> FEATURE:
<221> NAME/KEY: misc_feature
<222> LOCATION: (106)..(106)
<223> OTHER INFORMATION: n is unknown
<220> FEATURE:

```
<221> NAME/KEY: misc_feature
<222> LOCATION: (121)..(121)
<223> OTHER INFORMATION: n is unknown
<220> FEATURE:
<221> NAME/KEY: misc_feature
<222> LOCATION: (150)..(150)
<223> OTHER INFORMATION: n is unknown
<220> FEATURE:
<221> NAME/KEY: misc_feature
<222> LOCATION: (258)..(260)
<223> OTHER INFORMATION: n is unknown
<220> FEATURE:
<221> NAME/KEY: misc_feature
<222> LOCATION: (266)..(266)
<223> OTHER INFORMATION: n is unknown
<220> FEATURE:
<221> NAME/KEY: misc_feature
<222> LOCATION: (269)..(279)
<223> OTHER INFORMATION: n is unknown
<220> FEATURE:
<221> NAME/KEY: misc_feature
<222> LOCATION: (281)..(281)
<223> OTHER INFORMATION: n is unknown
<220> FEATURE:
<221> NAME/KEY: misc_feature
<222> LOCATION: (283)..(283)
<223> OTHER INFORMATION: n is unknown
<220> FEATURE:
<221> NAME/KEY: misc_feature
<222> LOCATION: (285)..(286)
<223> OTHER INFORMATION: n is unknown
<220> FEATURE:
<221> NAME/KEY: misc_feature
<222> LOCATION: (339)..(339)
<223> OTHER INFORMATION: n is unknown
<220> FEATURE:
<221> NAME/KEY: misc_feature
<222> LOCATION: (342)..(342)
<223> OTHER INFORMATION: n is unknown
<220> FEATURE:
<221> NAME/KEY: misc_feature
<222> LOCATION: (346)..(351)
<223> OTHER INFORMATION: n is unknown
<220> FEATURE:
<221> NAME/KEY: misc_feature
<222> LOCATION: (353)..(353)
<223> OTHER INFORMATION: n is unknown
<220> FEATURE:
<221> NAME/KEY: misc_feature
<222> LOCATION: (355)..(366)
<223> OTHER INFORMATION: n is unknown
<220> FEATURE:
<221> NAME/KEY: misc_feature
<222> LOCATION: (368)..(373)
<223> OTHER INFORMATION: n is unknown
<220> FEATURE:
<221> NAME/KEY: misc_feature
<222> LOCATION: (376)..(376)
<223> OTHER INFORMATION: n is unknown
<220> FEATURE:
<221> NAME/KEY: misc_feature
<222> LOCATION: (424)..(424)
<223> OTHER INFORMATION: n is unknown
<220> FEATURE:
<221> NAME/KEY: misc_feature
<222> LOCATION: (473)..(474)
<223> OTHER INFORMATION: n is unknown
<220> FEATURE:
<221> NAME/KEY: misc_feature
<222> LOCATION: (476)..(476)
<223> OTHER INFORMATION: n is unknown
<220> FEATURE:
<221> NAME/KEY: misc_feature
<222> LOCATION: (478)..(478)
<223> OTHER INFORMATION: n is unknown
<220> FEATURE:
<221> NAME/KEY: misc_feature
<222> LOCATION: (480)..(480)
<223> OTHER INFORMATION: n is unknown
<220> FEATURE:
```

-continued

```
<221> NAME/KEY: misc_feature
<222> LOCATION: (482)..(482)
<223> OTHER INFORMATION: n is unknown
<220> FEATURE:
<221> NAME/KEY: misc_feature
<222> LOCATION: (502)..(507)
<223> OTHER INFORMATION: n is unknown
<220> FEATURE:
<221> NAME/KEY: misc_feature
<222> LOCATION: (509)..(511)
<223> OTHER INFORMATION: n is unknown
<220> FEATURE:
<221> NAME/KEY: misc_feature
<222> LOCATION: (517)..(522)
<223> OTHER INFORMATION: n is unknown
<220> FEATURE:
<221> NAME/KEY: misc_feature
<222> LOCATION: (524)..(537)
<223> OTHER INFORMATION: n is unknown
<220> FEATURE:
<221> NAME/KEY: misc_feature
<222> LOCATION: (544)..(550)
<223> OTHER INFORMATION: n is unknown
<220> FEATURE:
<221> NAME/KEY: misc_feature
<222> LOCATION: (561)..(565)
<223> OTHER INFORMATION: n is unknown
<220> FEATURE:
<221> NAME/KEY: misc_feature
<222> LOCATION: (586)..(586)
<223> OTHER INFORMATION: n is unknown
<220> FEATURE:
<221> NAME/KEY: misc_feature
<222> LOCATION: (722)..(722)
<223> OTHER INFORMATION: n is unknown
<220> FEATURE:
<221> NAME/KEY: misc_feature
<222> LOCATION: (749)..(749)
<223> OTHER INFORMATION: n is unknown
<220> FEATURE:
<221> NAME/KEY: misc_feature
<222> LOCATION: (789)..(789)
<223> OTHER INFORMATION: n is unknown
<220> FEATURE:
<221> NAME/KEY: misc_feature
<222> LOCATION: (797)..(804)
<223> OTHER INFORMATION: n is unknown
<220> FEATURE:
<221> NAME/KEY: misc_feature
<222> LOCATION: (806)..(806)
<223> OTHER INFORMATION: n is unknown
<220> FEATURE:
<221> NAME/KEY: misc_feature
<222> LOCATION: (808)..(812)
<223> OTHER INFORMATION: n is unknown
<220> FEATURE:
<221> NAME/KEY: misc_feature
<222> LOCATION: (814)..(815)
<223> OTHER INFORMATION: n is unknown
<220> FEATURE:
<221> NAME/KEY: misc_feature
<222> LOCATION: (817)..(827)
<223> OTHER INFORMATION: n is unknown
<220> FEATURE:
<221> NAME/KEY: misc_feature
<222> LOCATION: (834)..(840)
<223> OTHER INFORMATION: n is unknown
<220> FEATURE:
<221> NAME/KEY: misc_feature
<222> LOCATION: (848)..(849)
<223> OTHER INFORMATION: n is unknown
<220> FEATURE:
<221> NAME/KEY: misc_feature
<222> LOCATION: (851)..(851)
<223> OTHER INFORMATION: n is unknown
<220> FEATURE:
<221> NAME/KEY: misc_feature
<222> LOCATION: (864)..(869)
<223> OTHER INFORMATION: n is unknown
```

<400> SEQUENCE: 8

```
tgttgctact actgctgaca atgctgctgc tgcttctcct cactgtctcc acttccttga    60
acaatgcgcc gncntgcttc ttttgcctcc cgctgctccn gagngntagg ccgcagatca   120
naaccaccac agtcaatatc accaccttcn tcttatagat tcggaatctc atgataggg    180
ctcagcctct gtgcgagtgg agagaagttt gcaggcgagc tgaggagcaa ttgcaggtga   240
tatgatgtgc tcggctcnnn gggcgnggnn nnnnnnnnna ngncnngccg gggctaatta   300
ttggcaaaac gagctcttgt tgtaaacatt gatccgggng gnatgnnnnn nangnnnnnn   360
nnnnnngnnn nnnggnatga tggttgctca gaggcaggag aagagcaacg aatacgatcc   420
tatnaaagat aaaacataaa taaacagtct tgattatatt ctgggtatta aanncncngn   480
cngaacaaat atatgctttg tnnnnnntnn ngccttnnnn nngnnnnnnn nnnnnnnncgg   540
ccannnnnnn agaacttgtg nnnnnataag aagatatttt attcgntctg ctgacttgct   600
ggatgtcggg aaatattctg catttgataa gaggcggtta attgcagata taattggtag   660
tgaaagggt cgttgctatg gtcaccgtga agcgagtaca gcagcacaag aatgtgtgcc   720
gntctcagtt aatattgttt gaatatggna acctgtttta gtcggtttaa aggtaagaag   780
atctaaccna aaacaannnn nnnngncnnn nngnngnnnn nnnnnnntta cttnnnnnnn   840
attttggnng naaacatcaa cggnnnnnnt caac                               874
```

<210> SEQ ID NO 9
<211> LENGTH: 881
<212> TYPE: DNA
<213> ORGANISM: Artificial Sequence
<220> FEATURE:
<223> OTHER INFORMATION: S. cerevisiae PCR reaction /DNA sequence
    standard
<220> FEATURE:
<221> NAME/KEY: misc_feature
<222> LOCATION: (4)..(4)
<223> OTHER INFORMATION: n is unknown
<220> FEATURE:
<221> NAME/KEY: misc_feature
<222> LOCATION: (79)..(79)
<223> OTHER INFORMATION: n is unknown
<220> FEATURE:
<221> NAME/KEY: misc_feature
<222> LOCATION: (81)..(81)
<223> OTHER INFORMATION: n is unknown
<220> FEATURE:
<221> NAME/KEY: misc_feature
<222> LOCATION: (107)..(107)
<223> OTHER INFORMATION: n is unknown
<220> FEATURE:
<221> NAME/KEY: misc_feature
<222> LOCATION: (111)..(111)
<223> OTHER INFORMATION: n is unknown
<220> FEATURE:
<221> NAME/KEY: misc_feature
<222> LOCATION: (140)..(140)
<223> OTHER INFORMATION: n is unknown
<220> FEATURE:
<221> NAME/KEY: misc_feature
<222> LOCATION: (154)..(155)
<223> OTHER INFORMATION: n is unknown
<220> FEATURE:
<221> NAME/KEY: misc_feature
<222> LOCATION: (157)..(158)
<223> OTHER INFORMATION: n is unknown
<220> FEATURE:
<221> NAME/KEY: misc_feature
<222> LOCATION: (242)..(242)
<223> OTHER INFORMATION: n is unknown
<220> FEATURE:
<221> NAME/KEY: misc_feature
<222> LOCATION: (265)..(267)
<223> OTHER INFORMATION: n is unknown

```
<220> FEATURE:
<221> NAME/KEY: misc_feature
<222> LOCATION: (271)..(273)
<223> OTHER INFORMATION: n is unknown
<220> FEATURE:
<221> NAME/KEY: misc_feature
<222> LOCATION: (276)..(276)
<223> OTHER INFORMATION: n is unknown
<220> FEATURE:
<221> NAME/KEY: misc_feature
<222> LOCATION: (278)..(285)
<223> OTHER INFORMATION: n is unknown
<220> FEATURE:
<221> NAME/KEY: misc_feature
<222> LOCATION: (287)..(287)
<223> OTHER INFORMATION: n is unknown
<220> FEATURE:
<221> NAME/KEY: misc_feature
<222> LOCATION: (289)..(289)
<223> OTHER INFORMATION: n is unknown
<220> FEATURE:
<221> NAME/KEY: misc_feature
<222> LOCATION: (291)..(292)
<223> OTHER INFORMATION: n is unknown
<220> FEATURE:
<221> NAME/KEY: misc_feature
<222> LOCATION: (342)..(345)
<223> OTHER INFORMATION: n is unknown
<220> FEATURE:
<221> NAME/KEY: misc_feature
<222> LOCATION: (348)..(350)
<223> OTHER INFORMATION: n is unknown
<220> FEATURE:
<221> NAME/KEY: misc_feature
<222> LOCATION: (353)..(359)
<223> OTHER INFORMATION: n is unknown
<220> FEATURE:
<221> NAME/KEY: misc_feature
<222> LOCATION: (362)..(362)
<223> OTHER INFORMATION: n is unknown
<220> FEATURE:
<221> NAME/KEY: misc_feature
<222> LOCATION: (364)..(366)
<223> OTHER INFORMATION: n is unknown
<220> FEATURE:
<221> NAME/KEY: misc_feature
<222> LOCATION: (369)..(371)
<223> OTHER INFORMATION: n is unknown
<220> FEATURE:
<221> NAME/KEY: misc_feature
<222> LOCATION: (374)..(379)
<223> OTHER INFORMATION: n is unknown
<220> FEATURE:
<221> NAME/KEY: misc_feature
<222> LOCATION: (382)..(382)
<223> OTHER INFORMATION: n is unknown
<220> FEATURE:
<221> NAME/KEY: misc_feature
<222> LOCATION: (430)..(430)
<223> OTHER INFORMATION: n is unknown
<220> FEATURE:
<221> NAME/KEY: misc_feature
<222> LOCATION: (452)..(452)
<223> OTHER INFORMATION: n is unknown
<220> FEATURE:
<221> NAME/KEY: misc_feature
<222> LOCATION: (479)..(480)
<223> OTHER INFORMATION: n is unknown
<220> FEATURE:
<221> NAME/KEY: misc_feature
<222> LOCATION: (482)..(484)
<223> OTHER INFORMATION: n is unknown
<220> FEATURE:
<221> NAME/KEY: misc_feature
<222> LOCATION: (486)..(487)
<223> OTHER INFORMATION: n is unknown
<220> FEATURE:
<221> NAME/KEY: misc_feature
<222> LOCATION: (506)..(513)
<223> OTHER INFORMATION: n is unknown
```

```
<220> FEATURE:
<221> NAME/KEY: misc_feature
<222> LOCATION: (516)..(517)
<223> OTHER INFORMATION: n is unknown
<220> FEATURE:
<221> NAME/KEY: misc_feature
<222> LOCATION: (519)..(519)
<223> OTHER INFORMATION: n is unknown
<220> FEATURE:
<221> NAME/KEY: misc_feature
<222> LOCATION: (521)..(544)
<223> OTHER INFORMATION: n is unknown
<220> FEATURE:
<221> NAME/KEY: misc_feature
<222> LOCATION: (566)..(572)
<223> OTHER INFORMATION: n is unknown
<220> FEATURE:
<221> NAME/KEY: misc_feature
<222> LOCATION: (592)..(592)
<223> OTHER INFORMATION: n is unknown
<220> FEATURE:
<221> NAME/KEY: misc_feature
<222> LOCATION: (745)..(745)
<223> OTHER INFORMATION: n is unknown
<220> FEATURE:
<221> NAME/KEY: misc_feature
<222> LOCATION: (762)..(762)
<223> OTHER INFORMATION: n is unknown
<220> FEATURE:
<221> NAME/KEY: misc_feature
<222> LOCATION: (809)..(810)
<223> OTHER INFORMATION: n is unknown
<220> FEATURE:
<221> NAME/KEY: misc_feature
<222> LOCATION: (812)..(812)
<223> OTHER INFORMATION: n is unknown
<220> FEATURE:
<221> NAME/KEY: misc_feature
<222> LOCATION: (814)..(814)
<223> OTHER INFORMATION: n is unknown
<220> FEATURE:
<221> NAME/KEY: misc_feature
<222> LOCATION: (816)..(822)
<223> OTHER INFORMATION: n is unknown
<220> FEATURE:
<221> NAME/KEY: misc_feature
<222> LOCATION: (825)..(835)
<223> OTHER INFORMATION: n is unknown
<220> FEATURE:
<221> NAME/KEY: misc_feature
<222> LOCATION: (841)..(848)
<223> OTHER INFORMATION: n is unknown
<220> FEATURE:
<221> NAME/KEY: misc_feature
<222> LOCATION: (856)..(857)
<223> OTHER INFORMATION: n is unknown
<220> FEATURE:
<221> NAME/KEY: misc_feature
<222> LOCATION: (871)..(877)
<223> OTHER INFORMATION: n is unknown
<220> FEATURE:
<221> NAME/KEY: misc_feature
<222> LOCATION: (880)..(880)
<223> OTHER INFORMATION: n is unknown

<400> SEQUENCE: 9
ctgntaatgt tgctactact gctgacaatg ctgctgctgc ttctcctcac tgtctccact      60
tccttgaaca atgcgccgnc ntgcttcttt tgcctcccgc tgctccngag ngctaggccg     120
cagatcagaa ccaccacagn caatatcacc accnncnnct tatagattcg gaatctcatg     180 atagggctc agcctctgtg cgagtggaga gaagtttgca ggcgagctga ggagcaattg      240
cnggtgatat gatgtgctcg gctcnnnggg nnggngngnnn nnnnnangnc nngccggggc    300
taattattgg caaaacgagc tcttgttgta acattgatc cnnnnggnnn gtnnnnnnng     360
gngnnngann ntgnnnnnng gnatgatggt tgctcagagg caggagaaga gcaacgaata    420
```

-continued

```
cgatcctatn aaagataaaa cataaataaa cngtcttgat tatattctgg gtattaaann    480
cnnngnnaga acaaatatat gctttnnnnn nnntcnngnc nnnnnnnnnn nnnnnnnnn     540 nnnnggccac attaagagaa cttgtnnnnn nntaagaaga tattttattc gntctgctga    600
cttgctggat gtcgggaaat attctgcatt tgataagagg cggttaattg cagatataat    660
tggtagtgaa aagggtcgtt gctatggtca ccgtgaagcg agtacagcag cacaagaatg    720
tgtgccgttc tcagttaata ttgtntgaat atggtaacct gntttagtcg gtttaaaggt    780
aagaagatct aaccaaaaac aacactgcnn gncngnnnnn nnggnnnnnn nnnnnttact    840
nnnnnnnnat tttggnntaa acatcaacgg nnnnnnncan c                       881
```

```
<210> SEQ ID NO 10
<211> LENGTH: 883
<212> TYPE: DNA
<213> ORGANISM: Artificial Sequence
<220> FEATURE:
<223> OTHER INFORMATION: S. cerevisiae PCR reaction /DNA sequence
      standard
<220> FEATURE:
<221> NAME/KEY: misc_feature
<222> LOCATION: (1)..(1)
<223> OTHER INFORMATION: n is unknown
<220> FEATURE:
<221> NAME/KEY: misc_feature
<222> LOCATION: (3)..(3)
<223> OTHER INFORMATION: n is unknown
<220> FEATURE:
<221> NAME/KEY: misc_feature
<222> LOCATION: (5)..(9)
<223> OTHER INFORMATION: n is unknown
<220> FEATURE:
<221> NAME/KEY: misc_feature
<222> LOCATION: (11)..(11)
<223> OTHER INFORMATION: n is unknown
<220> FEATURE:
<221> NAME/KEY: misc_feature
<222> LOCATION: (50)..(50)
<223> OTHER INFORMATION: n is unknown
<220> FEATURE:
<221> NAME/KEY: misc_feature
<222> LOCATION: (82)..(82)
<223> OTHER INFORMATION: n is unknown
<220> FEATURE:
<221> NAME/KEY: misc_feature
<222> LOCATION: (108)..(109)
<223> OTHER INFORMATION: n is unknown
<220> FEATURE:
<221> NAME/KEY: misc_feature
<222> LOCATION: (111)..(112)
<223> OTHER INFORMATION: n is unknown
<220> FEATURE:
<221> NAME/KEY: misc_feature
<222> LOCATION: (114)..(114)
<223> OTHER INFORMATION: n is unknown
<220> FEATURE:
<221> NAME/KEY: misc_feature
<222> LOCATION: (267)..(267)
<223> OTHER INFORMATION: n is unknown
<220> FEATURE:
<221> NAME/KEY: misc_feature
<222> LOCATION: (272)..(294)
<223> OTHER INFORMATION: n is unknown
<220> FEATURE:
<221> NAME/KEY: misc_feature
<222> LOCATION: (350)..(351)
<223> OTHER INFORMATION: n is unknown
<220> FEATURE:
<221> NAME/KEY: misc_feature
<222> LOCATION: (354)..(359)
<223> OTHER INFORMATION: n is unknown
<220> FEATURE:
<221> NAME/KEY: misc_feature
<222> LOCATION: (364)..(364)
```

```
<223> OTHER INFORMATION: n is unknown
<220> FEATURE:
<221> NAME/KEY: misc_feature
<222> LOCATION: (366)..(373)
<223> OTHER INFORMATION: n is unknown
<220> FEATURE:
<221> NAME/KEY: misc_feature
<222> LOCATION: (378)..(382)
<223> OTHER INFORMATION: n is unknown
<220> FEATURE:
<221> NAME/KEY: misc_feature
<222> LOCATION: (482)..(482)
<223> OTHER INFORMATION: n is unknown
<220> FEATURE:
<221> NAME/KEY: misc_feature
<222> LOCATION: (484)..(484)
<223> OTHER INFORMATION: n is unknown
<220> FEATURE:
<221> NAME/KEY: misc_feature
<222> LOCATION: (488)..(488)
<223> OTHER INFORMATION: n is unknown
<220> FEATURE:
<221> NAME/KEY: misc_feature
<222> LOCATION: (510)..(511)
<223> OTHER INFORMATION: n is unknown
<220> FEATURE:
<221> NAME/KEY: misc_feature
<222> LOCATION: (514)..(516)
<223> OTHER INFORMATION: n is unknown
<220> FEATURE:
<221> NAME/KEY: misc_feature
<222> LOCATION: (518)..(518)
<223> OTHER INFORMATION: n is unknown
<220> FEATURE:
<221> NAME/KEY: misc_feature
<222> LOCATION: (528)..(546)
<223> OTHER INFORMATION: n is unknown
<220> FEATURE:
<221> NAME/KEY: misc_feature
<222> LOCATION: (553)..(558)
<223> OTHER INFORMATION: n is unknown
<220> FEATURE:
<221> NAME/KEY: misc_feature
<222> LOCATION: (567)..(567)
<223> OTHER INFORMATION: n is unknown
<220> FEATURE:
<221> NAME/KEY: misc_feature
<222> LOCATION: (570)..(570)
<223> OTHER INFORMATION: n is unknown
<220> FEATURE:
<221> NAME/KEY: misc_feature
<222> LOCATION: (572)..(573)
<223> OTHER INFORMATION: n is unknown
<220> FEATURE:
<221> NAME/KEY: misc_feature
<222> LOCATION: (594)..(594)
<223> OTHER INFORMATION: n is unknown
<220> FEATURE:
<221> NAME/KEY: misc_feature
<222> LOCATION: (720)..(721)
<223> OTHER INFORMATION: n is unknown
<220> FEATURE:
<221> NAME/KEY: misc_feature
<222> LOCATION: (744)..(744)
<223> OTHER INFORMATION: n is unknown
<220> FEATURE:
<221> NAME/KEY: misc_feature
<222> LOCATION: (746)..(748)
<223> OTHER INFORMATION: n is unknown
<220> FEATURE:
<221> NAME/KEY: misc_feature
<222> LOCATION: (764)..(764)
<223> OTHER INFORMATION: n is unknown
<220> FEATURE:
<221> NAME/KEY: misc_feature
<222> LOCATION: (790)..(790)
<223> OTHER INFORMATION: n is unknown
<220> FEATURE:
<221> NAME/KEY: misc_feature
<222> LOCATION: (811)..(820)
```

<220> FEATURE:
<221> NAME/KEY: misc_feature
<222> LOCATION: (826)..(836)
<223> OTHER INFORMATION: n is unknown
<220> FEATURE:
<221> NAME/KEY: misc_feature
<222> LOCATION: (842)..(845)
<223> OTHER INFORMATION: n is unknown
<220> FEATURE:
<221> NAME/KEY: misc_feature
<222> LOCATION: (847)..(850)
<223> OTHER INFORMATION: n is unknown
<220> FEATURE:
<221> NAME/KEY: misc_feature
<222> LOCATION: (853)..(855)
<223> OTHER INFORMATION: n is unknown
<220> FEATURE:
<221> NAME/KEY: misc_feature
<222> LOCATION: (858)..(858)
<223> OTHER INFORMATION: n is unknown
<220> FEATURE:
<221> NAME/KEY: misc_feature
<222> LOCATION: (860)..(860)
<223> OTHER INFORMATION: n is unknown
<220> FEATURE:
<221> NAME/KEY: misc_feature
<222> LOCATION: (868)..(868)
<223> OTHER INFORMATION: n is unknown
<220> FEATURE:
<221> NAME/KEY: misc_feature
<222> LOCATION: (872)..(879)
<223> OTHER INFORMATION: n is unknown

<400> SEQUENCE: 10

```
ncngnnnnng ntgctactac tgctgacaat gctgctgctg cttctcctcn ctgtctccac      60
ttccttgaac aatgcgccgt cntgcttctt ttgcctcccg ctgctccnna nngntaggcc     120
gcagatcaga accaccacag tcaatatcac caccttcctc ttatagattc ggaatctcat     180
gataggggct cagcctctgt gcgagtggag agaagtttgc aggcgagctg aggagcaatt     240
gcaggtgata tgatgtgctc ggctcanggg gnnnnnnnnn nnnnnnnnnn nnnngccggg     300
gctaattatt ggcaaaacga gctcttgttg taaacattga tccaactggn nggnnnnnna     360
tggngnnnnn nnntgccnnn nngcatgatg gttgctcaga ggcaggagaa gagcaacgaa     420
tacgatccta taaagataaa acataaata aacagtcttg attatattct gggtattaaa      480
gncncagnca gaacaaatat atgctttgtn nctnnncntg ccttcttnnn nnnnnnnnnn     540
nnnnnnggcc acnnnnnnag aacttgnggn gnnataagaa gatatttat tcgntctgct      600
gacttgctgg atgtcgggaa atattctgca tttgataaga ggcggttaat tgcagatata     660
attggtagtg aaaagggtcg ttgctatggt caccgtgaag cgagtacagc agcacaagan     720
ngtgtgccgt tctcagttaa tatngnnnga atatggtaac ctgntttagt cggtttaaag     780
gtaagaagan ctaaccaaaa acaacactgc nnnnnnnnnn ggggnnnnn nnnnnnttac      840
tnnnngnnnn ttnnggngn aaacatcnac gnnnnnnnnc aac                        883
```

<210> SEQ ID NO 11
<211> LENGTH: 880
<212> TYPE: DNA
<213> ORGANISM: Artificial Sequence
<220> FEATURE:
<223> OTHER INFORMATION: S. cerevisiae PCR reaction /DNA sequence
    standard
<220> FEATURE:
<221> NAME/KEY: misc_feature
<222> LOCATION: (44)..(44)
<223> OTHER INFORMATION: n is unknown
<220> FEATURE:
<221> NAME/KEY: misc_feature -continued

```
<222> LOCATION: (49)..(49)
<223> OTHER INFORMATION: n is unknown
<220> FEATURE:
<221> NAME/KEY: misc_feature
<222> LOCATION: (79)..(79)
<223> OTHER INFORMATION: n is unknown
<220> FEATURE:
<221> NAME/KEY: misc_feature
<222> LOCATION: (81)..(81)
<223> OTHER INFORMATION: n is unknown
<220> FEATURE:
<221> NAME/KEY: misc_feature
<222> LOCATION: (107)..(107)
<223> OTHER INFORMATION: n is unknown
<220> FEATURE:
<221> NAME/KEY: misc_feature
<222> LOCATION: (111)..(111)
<223> OTHER INFORMATION: n is unknown
<220> FEATURE:
<221> NAME/KEY: misc_feature
<222> LOCATION: (113)..(113)
<223> OTHER INFORMATION: n is unknown
<220> FEATURE:
<221> NAME/KEY: misc_feature
<222> LOCATION: (140)..(140)
<223> OTHER INFORMATION: n is unknown
<220> FEATURE:
<221> NAME/KEY: misc_feature
<222> LOCATION: (154)..(154)
<223> OTHER INFORMATION: n is unknown
<220> FEATURE:
<221> NAME/KEY: misc_feature
<222> LOCATION: (157)..(158)
<223> OTHER INFORMATION: n is unknown
<220> FEATURE:
<221> NAME/KEY: misc_feature
<222> LOCATION: (165)..(165)
<223> OTHER INFORMATION: n is unknown
<220> FEATURE:
<221> NAME/KEY: misc_feature
<222> LOCATION: (266)..(267)
<223> OTHER INFORMATION: n is unknown
<220> FEATURE:
<221> NAME/KEY: misc_feature
<222> LOCATION: (272)..(292)
<223> OTHER INFORMATION: n is unknown
<220> FEATURE:
<221> NAME/KEY: misc_feature
<222> LOCATION: (349)..(350)
<223> OTHER INFORMATION: n is unknown
<220> FEATURE:
<221> NAME/KEY: misc_feature
<222> LOCATION: (353)..(358)
<223> OTHER INFORMATION: n is unknown
<220> FEATURE:
<221> NAME/KEY: misc_feature
<222> LOCATION: (363)..(363)
<223> OTHER INFORMATION: n is unknown
<220> FEATURE:
<221> NAME/KEY: misc_feature
<222> LOCATION: (365)..(367)
<223> OTHER INFORMATION: n is unknown
<220> FEATURE:
<221> NAME/KEY: misc_feature
<222> LOCATION: (369)..(372)
<223> OTHER INFORMATION: n is unknown
<220> FEATURE:
<221> NAME/KEY: misc_feature
<222> LOCATION: (375)..(380)
<223> OTHER INFORMATION: n is unknown
<220> FEATURE:
<221> NAME/KEY: misc_feature
<222> LOCATION: (423)..(423)
<223> OTHER INFORMATION: n is unknown
<220> FEATURE:
<221> NAME/KEY: misc_feature
<222> LOCATION: (480)..(485)
<223> OTHER INFORMATION: n is unknown
<220> FEATURE:
<221> NAME/KEY: misc_feature
```

-continued

```
<222> LOCATION: (487)..(487)
<223> OTHER INFORMATION: n is unknown
<220> FEATURE:
<221> NAME/KEY: misc_feature
<222> LOCATION: (508)..(512)
<223> OTHER INFORMATION: n is unknown
<220> FEATURE:
<221> NAME/KEY: misc_feature
<222> LOCATION: (514)..(515)
<223> OTHER INFORMATION: n is unknown
<220> FEATURE:
<221> NAME/KEY: misc_feature
<222> LOCATION: (517)..(517)
<223> OTHER INFORMATION: n is unknown
<220> FEATURE:
<221> NAME/KEY: misc_feature
<222> LOCATION: (520)..(523)
<223> OTHER INFORMATION: n is unknown
<220> FEATURE:
<221> NAME/KEY: misc_feature
<222> LOCATION: (525)..(528)
<223> OTHER INFORMATION: n is unknown
<220> FEATURE:
<221> NAME/KEY: misc_feature
<222> LOCATION: (531)..(545)
<223> OTHER INFORMATION: n is unknown
<220> FEATURE:
<221> NAME/KEY: misc_feature
<222> LOCATION: (550)..(550)
<223> OTHER INFORMATION: n is unknown
<220> FEATURE:
<221> NAME/KEY: misc_feature
<222> LOCATION: (552)..(556)
<223> OTHER INFORMATION: n is unknown
<220> FEATURE:
<221> NAME/KEY: misc_feature
<222> LOCATION: (567)..(573)
<223> OTHER INFORMATION: n is unknown
<220> FEATURE:
<221> NAME/KEY: misc_feature
<222> LOCATION: (593)..(594)
<223> OTHER INFORMATION: n is unknown
<220> FEATURE:
<221> NAME/KEY: misc_feature
<222> LOCATION: (716)..(716)
<223> OTHER INFORMATION: n is unknown
<220> FEATURE:
<221> NAME/KEY: misc_feature
<222> LOCATION: (719)..(720)
<223> OTHER INFORMATION: n is unknown
<220> FEATURE:
<221> NAME/KEY: misc_feature
<222> LOCATION: (745)..(745)
<223> OTHER INFORMATION: n is unknown
<220> FEATURE:
<221> NAME/KEY: misc_feature
<222> LOCATION: (789)..(789)
<223> OTHER INFORMATION: n is unknown
<220> FEATURE:
<221> NAME/KEY: misc_feature
<222> LOCATION: (796)..(796)
<223> OTHER INFORMATION: n is unknown
<220> FEATURE:
<221> NAME/KEY: misc_feature
<222> LOCATION: (810)..(815)
<223> OTHER INFORMATION: n is unknown
<220> FEATURE:
<221> NAME/KEY: misc_feature
<222> LOCATION: (817)..(817)
<223> OTHER INFORMATION: n is unknown
<220> FEATURE:
<221> NAME/KEY: misc_feature
<222> LOCATION: (824)..(836)
<223> OTHER INFORMATION: n is unknown
<220> FEATURE:
<221> NAME/KEY: misc_feature
<222> LOCATION: (842)..(859)
<223> OTHER INFORMATION: n is unknown
<220> FEATURE:
<221> NAME/KEY: misc_feature
```

```
<222> LOCATION: (865)..(866)
<223> OTHER INFORMATION: n is unknown
<220> FEATURE:
<221> NAME/KEY: misc_feature
<222> LOCATION: (869)..(876)
<223> OTHER INFORMATION: n is unknown

<400> SEQUENCE: 11
ctgttaatgt tgctactact gctgacaatg ctgctgctgc ttcnccctcnc tgtctccact    60
tccttgaaca atgcgccgnc ntgcttcttt tgcctcccgc tgctccngag ngntaggccg   120
cagatcagaa ccaccacagn caatatcacc accntcnnct tatanattcg gaatctcatg   180
atagggctc  agcctctgtg cgagtggaga gaagtttgca ggcgagctga ggagcaattg   240
caggtgatat gatgtgctcg gctcannggg cnnnnnnnnn nnnnnnnnnn nntgccgggg   300
ctaattattg gcaaaacgag ctcttgttgt aaacattgat ccaactggnn ggnnnnnnat   360
ggngnnngnn nntgnnnnnn gggatgatgg ttgctcagag gcaggagaag agcaacgaat   420
acnatcctat aaaagataaa acataaataa acagtcttga ttatattctg ggtattaaan   480
nnnnngncag aacaaatata tgctttgnnn nntnncntgn nnncnnnngg nnnnnnnnnn   540
nnnnnggccn cnnnnngaga acttgtnnnn nntaagaag atattttatt cgnnctgctg   600
acttgctgga tgtcgggaaa tattctgcat ttgataagag gcggttaatt gcagatataa   660
ttggtagtga aaagggtcgt tgctatggtc accgtgaagc gagtacagca gcacangann   720
gtgtgccgtt ctcagttaat attgnttgaa tatggtaacc tgttttagtc ggtttaaagg   780
taagaaganc taaccnaaaa caacactgcn nnnngnggg gggnnnnnnn nnnnntact    840
tnnnnnnnnn nnnnnnnnna catcnncgnn nnnnnncaac                        880

<210> SEQ ID NO 12
<211> LENGTH: 875
<212> TYPE: DNA
<213> ORGANISM: Artificial Sequence
<220> FEATURE:
<223> OTHER INFORMATION: S. cerevisiae PCR reaction /DNA sequence
      standard
<220> FEATURE:
<221> NAME/KEY: misc_feature
<222> LOCATION: (5)..(5)
<223> OTHER INFORMATION: n is unknown
<220> FEATURE:
<221> NAME/KEY: misc_feature
<222> LOCATION: (8)..(8)
<223> OTHER INFORMATION: n is unknown
<220> FEATURE:
<221> NAME/KEY: misc_feature
<222> LOCATION: (10)..(10)
<223> OTHER INFORMATION: n is unknown
<220> FEATURE:
<221> NAME/KEY: misc_feature
<222> LOCATION: (69)..(69)
<223> OTHER INFORMATION: n is unknown
<220> FEATURE:
<221> NAME/KEY: misc_feature
<222> LOCATION: (71)..(71)
<223> OTHER INFORMATION: n is unknown
<220> FEATURE:
<221> NAME/KEY: misc_feature
<222> LOCATION: (98)..(98)
<223> OTHER INFORMATION: n is unknown
<220> FEATURE:
<221> NAME/KEY: misc_feature
<222> LOCATION: (101)..(101)
<223> OTHER INFORMATION: n is unknown
<220> FEATURE:
<221> NAME/KEY: misc_feature
<222> LOCATION: (118)..(118)
<223> OTHER INFORMATION: n is unknown
<220> FEATURE:
```

```
<221> NAME/KEY: misc_feature
<222> LOCATION: (130)..(130)
<223> OTHER INFORMATION: n is unknown
<220> FEATURE:
<221> NAME/KEY: misc_feature
<222> LOCATION: (144)..(144)
<223> OTHER INFORMATION: n is unknown
<220> FEATURE:
<221> NAME/KEY: misc_feature
<222> LOCATION: (147)..(148)
<223> OTHER INFORMATION: n is unknown
<220> FEATURE:
<221> NAME/KEY: misc_feature
<222> LOCATION: (255)..(257)
<223> OTHER INFORMATION: n is unknown
<220> FEATURE:
<221> NAME/KEY: misc_feature
<222> LOCATION: (263)..(280)
<223> OTHER INFORMATION: n is unknown
<220> FEATURE:
<221> NAME/KEY: misc_feature
<222> LOCATION: (282)..(283)
<223> OTHER INFORMATION: n is unknown
<220> FEATURE:
<221> NAME/KEY: misc_feature
<222> LOCATION: (338)..(341)
<223> OTHER INFORMATION: n is unknown
<220> FEATURE:
<221> NAME/KEY: misc_feature
<222> LOCATION: (343)..(348)
<223> OTHER INFORMATION: n is unknown
<220> FEATURE:
<221> NAME/KEY: misc_feature
<222> LOCATION: (350)..(350)
<223> OTHER INFORMATION: n is unknown
<220> FEATURE:
<221> NAME/KEY: misc_feature
<222> LOCATION: (353)..(353)
<223> OTHER INFORMATION: n is unknown
<220> FEATURE:
<221> NAME/KEY: misc_feature
<222> LOCATION: (355)..(361)
<223> OTHER INFORMATION: n is unknown
<220> FEATURE:
<221> NAME/KEY: misc_feature
<222> LOCATION: (365)..(370)
<223> OTHER INFORMATION: n is unknown
<220> FEATURE:
<221> NAME/KEY: misc_feature
<222> LOCATION: (373)..(373)
<223> OTHER INFORMATION: n is unknown
<220> FEATURE:
<221> NAME/KEY: misc_feature
<222> LOCATION: (421)..(421)
<223> OTHER INFORMATION: n is unknown
<220> FEATURE:
<221> NAME/KEY: misc_feature
<222> LOCATION: (470)..(475)
<223> OTHER INFORMATION: n is unknown
<220> FEATURE:
<221> NAME/KEY: misc_feature
<222> LOCATION: (499)..(505)
<223> OTHER INFORMATION: n is unknown
<220> FEATURE:
<221> NAME/KEY: misc_feature
<222> LOCATION: (507)..(509)
<223> OTHER INFORMATION: n is unknown
<220> FEATURE:
<221> NAME/KEY: misc_feature
<222> LOCATION: (516)..(519)
<223> OTHER INFORMATION: n is unknown
<220> FEATURE:
<221> NAME/KEY: misc_feature
<222> LOCATION: (521)..(535)
<223> OTHER INFORMATION: n is unknown
<220> FEATURE:
<221> NAME/KEY: misc_feature
<222> LOCATION: (540)..(546)
<223> OTHER INFORMATION: n is unknown
<220> FEATURE:
```

```
<221> NAME/KEY: misc_feature
<222> LOCATION: (557)..(563)
<223> OTHER INFORMATION: n is unknown
<220> FEATURE:
<221> NAME/KEY: misc_feature
<222> LOCATION: (583)..(583)
<223> OTHER INFORMATION: n is unknown
<220> FEATURE:
<221> NAME/KEY: misc_feature
<222> LOCATION: (707)..(707)
<223> OTHER INFORMATION: n is unknown
<220> FEATURE:
<221> NAME/KEY: misc_feature
<222> LOCATION: (709)..(710)
<223> OTHER INFORMATION: n is unknown
<220> FEATURE:
<221> NAME/KEY: misc_feature
<222> LOCATION: (712)..(712)
<223> OTHER INFORMATION: n is unknown
<220> FEATURE:
<221> NAME/KEY: misc_feature
<222> LOCATION: (728)..(733)
<223> OTHER INFORMATION: n is unknown
<220> FEATURE:
<221> NAME/KEY: misc_feature
<222> LOCATION: (771)..(771)
<223> OTHER INFORMATION: n is unknown
<220> FEATURE:
<221> NAME/KEY: misc_feature
<222> LOCATION: (801)..(801)
<223> OTHER INFORMATION: n is unknown
<220> FEATURE:
<221> NAME/KEY: misc_feature
<222> LOCATION: (804)..(804)
<223> OTHER INFORMATION: n is unknown
<220> FEATURE:
<221> NAME/KEY: misc_feature
<222> LOCATION: (806)..(806)
<223> OTHER INFORMATION: n is unknown
<220> FEATURE:
<221> NAME/KEY: misc_feature
<222> LOCATION: (808)..(808)
<223> OTHER INFORMATION: n is unknown
<220> FEATURE:
<221> NAME/KEY: misc_feature
<222> LOCATION: (810)..(811)
<223> OTHER INFORMATION: n is unknown
<220> FEATURE:
<221> NAME/KEY: misc_feature
<222> LOCATION: (814)..(827)
<223> OTHER INFORMATION: n is unknown
<220> FEATURE:
<221> NAME/KEY: misc_feature
<222> LOCATION: (834)..(847)
<223> OTHER INFORMATION: n is unknown
<220> FEATURE:
<221> NAME/KEY: misc_feature
<222> LOCATION: (850)..(850)
<223> OTHER INFORMATION: n is unknown
<220> FEATURE:
<221> NAME/KEY: misc_feature
<222> LOCATION: (864)..(869)
<223> OTHER INFORMATION: n is unknown
<220> FEATURE:
<221> NAME/KEY: misc_feature
<222> LOCATION: (872)..(872)
<223> OTHER INFORMATION: n is unknown

<400> SEQUENCE: 12
gttgntcncn gctgacaatg ctgctgctgc ttctcctcac tgtctccact tccttgaaca      60
atgcgccgnc ntgcttcttt tgcctcccgc tgctccanag ngctaggccg cagatcanaa     120
ccaccacagn caatatcacc accntcnnct tatagattcg gaatctcatg atagggctc      180 agcctctgtg cgagtggaga gaagtttgca ggcgagctga ggagcaattg caggtgatat     240
gatgtgctcg gctcnnnggg cgnnnnnnnn nnnnnnnnnn cnngccgggg ctaattattg     300
```

```
gcaaaacgag ctcttgttgt aaacattgat ccaactgnnn ngnnnnnnan ggngnnnnnn   360
ngtgnnnnnn ggnatgatgg ttgctcagag gcaggagaag agcaacgaat acgatcctat   420
naaagataaa acataaataa acagtcttga ttatattctg ggtattaaan nnnnngtcag   480
aacaaatata tgctttgtnn nnnnncnnnc cttctnnnng nnnnnnnnnn nnnnnggccn   540
nnnnnngaga acttgtnnnn nnntaagaag atattttatt cgntctgctg acttgctgga   600
tgtcgggaaa tattctgcat ttgataagag gcggttaatt gcagatataa ttggtagtga   660
aaagggtcgt tgctatggtc accgtgaagc gagtacagca gcacaanann gngtgccgtt   720
ctcagttnnn nnngtttgaa tatggtaacc tgttttagtc ggtttaaagg naagaagatc   780
taaccaaaaa caacactgca ntgncngngn nggnnnnnnn nnnnnnntac ttannnnnnn   840
nnnnnnnggn gtaaacatca acgnnnnnnt cnacc                             875
```

<210> SEQ ID NO 13
<211> LENGTH: 817
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (2)..(2)
<223> OTHER INFORMATION: n is unknown
<220> FEATURE:
<221> NAME/KEY: misc_feature
<222> LOCATION: (5)..(5)
<223> OTHER INFORMATION: n is unknown
<220> FEATURE:
<221> NAME/KEY: misc_feature
<222> LOCATION: (12)..(12)
<223> OTHER INFORMATION: n is unknown
<220> FEATURE:
<221> NAME/KEY: misc_feature
<222> LOCATION: (41)..(41)
<223> OTHER INFORMATION: n is unknown
<220> FEATURE:
<221> NAME/KEY: misc_feature
<222> LOCATION: (46)..(46)
<223> OTHER INFORMATION: n is unknown
<220> FEATURE:
<221> NAME/KEY: misc_feature
<222> LOCATION: (215)..(217)
<223> OTHER INFORMATION: n is unknown
<220> FEATURE:
<221> NAME/KEY: misc_feature
<222> LOCATION: (221)..(221)
<223> OTHER INFORMATION: n is unknown
<220> FEATURE:
<221> NAME/KEY: misc_feature
<222> LOCATION: (226)..(226)
<223> OTHER INFORMATION: n is unknown
<220> FEATURE:
<221> NAME/KEY: misc_feature
<222> LOCATION: (347)..(349)
<223> OTHER INFORMATION: n is unknown
<220> FEATURE:
<221> NAME/KEY: misc_feature
<222> LOCATION: (351)..(352)
<223> OTHER INFORMATION: n is unknown
<220> FEATURE:
<221> NAME/KEY: misc_feature
<222> LOCATION: (356)..(356)
<223> OTHER INFORMATION: n is unknown
<220> FEATURE:
<221> NAME/KEY: misc_feature
<222> LOCATION: (358)..(365)
<223> OTHER INFORMATION: n is unknown
<220> FEATURE:
<221> NAME/KEY: misc_feature
<222> LOCATION: (531)..(540)
<223> OTHER INFORMATION: n is unknown
<220> FEATURE:

<221> NAME/KEY: misc_feature
<222> LOCATION: (548)..(553)
<223> OTHER INFORMATION: n is unknown
<220> FEATURE:
<221> NAME/KEY: misc_feature
<222> LOCATION: (795)..(795)
<223> OTHER INFORMATION: n is unknown

<400> SEQUENCE: 13

```
gntangttgc tnctactgct gacaatgctg ctgctgcttc ncctcnctgt ctccacttcc      60
ttgaacaatg cgccgtcatg cttcttttgc ctcccgctgc tccagaaagc taggccgcag     120
atcagaacca ccacagtcaa tatcaccacc ttcctcttat agattcggaa tcaattgcag     180
gtgatatgat gtgctcggct caagaagcgg gcccnnngag naggangtcg tgtcatgata     240
ggggctcagc ctctgtgcga gtggagagaa gtttgcaggc gagctgagga gcccggggct     300
aattattggc aaaacgagct cttgttgtaa acattgatcc aactggnnng nnactnannn     360
nnnnncaata ttccataagg catgatggtt gctcagaggc aggagaagag caacgaatac     420
gatcctataa aagataaaac ataaataaac agtcttgatt atattctggg tattaaagcc     480
acaatcagaa caaatatatg ctttgtatct tttcttgcct tcttcattac nnnnnnnnnn     540
cgcgggcnnn nnnaagagaa cttgtggtaa gataagaaga tattttattc gttctgctga     600
cttgctggat gtcgggaaat attctgcatt tgataagagg cggttaattg cagatataat     660
tggtagtgaa aagggtcgtt gctatggtca ccgtgaagcg agtacagcag cacaagaatg     720
tgtgccgttc tcagttaata ttgtttgaat atggtaacct gttttagtcg gtttaaaggt     780
aagaagatct aaccnaaaac aacactgcag tgactga                              817
```

<210> SEQ ID NO 14
<211> LENGTH: 880
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (2)..(2)
<223> OTHER INFORMATION: n is unknown
<220> FEATURE:
<221> NAME/KEY: misc_feature
<222> LOCATION: (4)..(5)
<223> OTHER INFORMATION: n is unknown
<220> FEATURE:
<221> NAME/KEY: misc_feature
<222> LOCATION: (49)..(49)
<223> OTHER INFORMATION: n is unknown
<220> FEATURE:
<221> NAME/KEY: misc_feature
<222> LOCATION: (54)..(54)
<223> OTHER INFORMATION: n is unknown
<220> FEATURE:
<221> NAME/KEY: misc_feature
<222> LOCATION: (277)..(277)
<223> OTHER INFORMATION: n is unknown
<220> FEATURE:
<221> NAME/KEY: misc_feature
<222> LOCATION: (279)..(283)
<223> OTHER INFORMATION: n is unknown
<220> FEATURE:
<221> NAME/KEY: misc_feature
<222> LOCATION: (285)..(286)
<223> OTHER INFORMATION: n is unknown
<220> FEATURE:
<221> NAME/KEY: misc_feature
<222> LOCATION: (349)..(350)
<223> OTHER INFORMATION: n is unknown
<220> FEATURE:
<221> NAME/KEY: misc_feature
<222> LOCATION: (356)..(356)

```
<223> OTHER INFORMATION: n is unknown
<220> FEATURE:
<221> NAME/KEY: misc_feature
<222> LOCATION: (358)..(364)
<223> OTHER INFORMATION: n is unknown
<220> FEATURE:
<221> NAME/KEY: misc_feature
<222> LOCATION: (528)..(533)
<223> OTHER INFORMATION: n is unknown
<220> FEATURE:
<221> NAME/KEY: misc_feature
<222> LOCATION: (539)..(542)
<223> OTHER INFORMATION: n is unknown
<220> FEATURE:
<221> NAME/KEY: misc_feature
<222> LOCATION: (545)..(545)
<223> OTHER INFORMATION: n is unknown
<220> FEATURE:
<221> NAME/KEY: misc_feature
<222> LOCATION: (799)..(810)
<223> OTHER INFORMATION: n is unknown
<220> FEATURE:
<221> NAME/KEY: misc_feature
<222> LOCATION: (819)..(819)
<223> OTHER INFORMATION: n is unknown
<220> FEATURE:
<221> NAME/KEY: misc_feature
<222> LOCATION: (826)..(827)
<223> OTHER INFORMATION: n is unknown
<220> FEATURE:
<221> NAME/KEY: misc_feature
<222> LOCATION: (829)..(829)
<223> OTHER INFORMATION: n is unknown
<220> FEATURE:
<221> NAME/KEY: misc_feature
<222> LOCATION: (854)..(855)
<223> OTHER INFORMATION: n is unknown
<220> FEATURE:
<221> NAME/KEY: misc_feature
<222> LOCATION: (865)..(865)
<223> OTHER INFORMATION: n is unknown
<220> FEATURE:
<221> NAME/KEY: misc_feature
<222> LOCATION: (873)..(873)
<223> OTHER INFORMATION: n is unknown
<220> FEATURE:
<221> NAME/KEY: misc_feature
<222> LOCATION: (879)..(880)
<223> OTHER INFORMATION: n is unknown

<400> SEQUENCE: 14
gntnnctgtt aatgttgcta ctactgctga caatgctgct gctgcttcnc ctcnctgtct    60
ccacttcctt gaacaatgcg ccgtcatgct tcttttgcct cccgctgctc cagaaagcta   120
ggccgcagat cagaaccacc acagtcaata tcaccacctt cctcttatag attcggaatc   180
tcatgatagg ggctcagcct ctgtgcgagt ggagagaagt ttgcaggcga gctgaggagc   240
aattgcaggt gatatgatgt gctcggctca agaagcngnn nnngnnagga agaagtcgtg   300
ccggggctaa ttattggcaa aacgagctct tgttgtaaac attgatccnn ctggantnnn   360
nnnnatggcg aatcaatatt ccataaggca tgatggttgc tcagaggcag gagaagagca   420
acgaatacga tcctataaaa gataaaacat aaataaacag tcttgattat attctgggta   480
ttaaagccac aatcagaaca aatatatgct ttgtatcttt tcttgccnnn nnngttacnn   540
nntgnttccg cggccacatt aagagaactt gtggtaagat aagaagatat tttattcgtt   600
ctgctgactt gctggatgtc gggaaatatt ctgcatttga taagaggcgg ttaattgcag   660
atataattgg tagtgaaaag ggtcgttgct atggtcaccg tgaagcgagt acagcagcac   720
aagaatgtgt gccgttctca gttaatattg tttgaatatg gtaacctgtt ttagtcggtt   780
taaaggtaag aagatctann nnnnnnnnnn cactgcagng actganngna gtatttattt   840
```

```
ttttacttaa tctnnatttt ggtgnaaaca tcnacggcnn                              880
```

```
<210> SEQ ID NO 15
<211> LENGTH: 879
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (2)..(2)
<223> OTHER INFORMATION: n is unknown
<220> FEATURE:
<221> NAME/KEY: misc_feature
<222> LOCATION: (4)..(6)
<223> OTHER INFORMATION: n is unknown
<220> FEATURE:
<221> NAME/KEY: misc_feature
<222> LOCATION: (11)..(11)
<223> OTHER INFORMATION: n is unknown
<220> FEATURE:
<221> NAME/KEY: misc_feature
<222> LOCATION: (15)..(16)
<223> OTHER INFORMATION: n is unknown
<220> FEATURE:
<221> NAME/KEY: misc_feature
<222> LOCATION: (35)..(36)
<223> OTHER INFORMATION: n is unknown
<220> FEATURE:
<221> NAME/KEY: misc_feature
<222> LOCATION: (38)..(40)
<223> OTHER INFORMATION: n is unknown
<220> FEATURE:
<221> NAME/KEY: misc_feature
<222> LOCATION: (42)..(42)
<223> OTHER INFORMATION: n is unknown
<220> FEATURE:
<221> NAME/KEY: misc_feature
<222> LOCATION: (47)..(47)
<223> OTHER INFORMATION: n is unknown
<220> FEATURE:
<221> NAME/KEY: misc_feature
<222> LOCATION: (149)..(149)
<223> OTHER INFORMATION: n is unknown
<220> FEATURE:
<221> NAME/KEY: misc_feature
<222> LOCATION: (215)..(215)
<223> OTHER INFORMATION: n is unknown
<220> FEATURE:
<221> NAME/KEY: misc_feature
<222> LOCATION: (217)..(222)
<223> OTHER INFORMATION: n is unknown
<220> FEATURE:
<221> NAME/KEY: misc_feature
<222> LOCATION: (229)..(229)
<223> OTHER INFORMATION: n is unknown
<220> FEATURE:
<221> NAME/KEY: misc_feature
<222> LOCATION: (289)..(294)
<223> OTHER INFORMATION: n is unknown
<220> FEATURE:
<221> NAME/KEY: misc_feature
<222> LOCATION: (329)..(342)
<223> OTHER INFORMATION: n is unknown
<220> FEATURE:
<221> NAME/KEY: misc_feature
<222> LOCATION: (344)..(355)
<223> OTHER INFORMATION: n is unknown
<220> FEATURE:
<221> NAME/KEY: misc_feature
<222> LOCATION: (358)..(361)
<223> OTHER INFORMATION: n is unknown
<220> FEATURE:
<221> NAME/KEY: misc_feature
<222> LOCATION: (364)..(368)
<223> OTHER INFORMATION: n is unknown
<220> FEATURE:
<221> NAME/KEY: misc_feature
<222> LOCATION: (378)..(378)
```

```
<223> OTHER INFORMATION: n is unknown
<220> FEATURE:
<221> NAME/KEY: misc_feature
<222> LOCATION: (381)..(382)
<223> OTHER INFORMATION: n is unknown
<220> FEATURE:
<221> NAME/KEY: misc_feature
<222> LOCATION: (405)..(411)
<223> OTHER INFORMATION: n is unknown
<220> FEATURE:
<221> NAME/KEY: misc_feature
<222> LOCATION: (414)..(422)
<223> OTHER INFORMATION: n is unknown
<220> FEATURE:
<221> NAME/KEY: misc_feature
<222> LOCATION: (515)..(519)
<223> OTHER INFORMATION: n is unknown
<220> FEATURE:
<221> NAME/KEY: misc_feature
<222> LOCATION: (530)..(535)
<223> OTHER INFORMATION: n is unknown
<220> FEATURE:
<221> NAME/KEY: misc_feature
<222> LOCATION: (633)..(639)
<223> OTHER INFORMATION: n is unknown
<220> FEATURE:
<221> NAME/KEY: misc_feature
<222> LOCATION: (655)..(655)
<223> OTHER INFORMATION: n is unknown
<220> FEATURE:
<221> NAME/KEY: misc_feature
<222> LOCATION: (725)..(725)
<223> OTHER INFORMATION: n is unknown
<220> FEATURE:
<221> NAME/KEY: misc_feature
<222> LOCATION: (735)..(740)
<223> OTHER INFORMATION: n is unknown
<220> FEATURE:
<221> NAME/KEY: misc_feature
<222> LOCATION: (755)..(758)
<223> OTHER INFORMATION: n is unknown
<220> FEATURE:
<221> NAME/KEY: misc_feature
<222> LOCATION: (779)..(789)
<223> OTHER INFORMATION: n is unknown
<220> FEATURE:
<221> NAME/KEY: misc_feature
<222> LOCATION: (797)..(797)
<223> OTHER INFORMATION: n is unknown
<220> FEATURE:
<221> NAME/KEY: misc_feature
<222> LOCATION: (813)..(813)
<223> OTHER INFORMATION: n is unknown
<220> FEATURE:
<221> NAME/KEY: misc_feature
<222> LOCATION: (820)..(821)
<223> OTHER INFORMATION: n is unknown
<220> FEATURE:
<221> NAME/KEY: misc_feature
<222> LOCATION: (837)..(840)
<223> OTHER INFORMATION: n is unknown
<220> FEATURE:
<221> NAME/KEY: misc_feature
<222> LOCATION: (842)..(846)
<223> OTHER INFORMATION: n is unknown
<220> FEATURE:
<221> NAME/KEY: misc_feature
<222> LOCATION: (850)..(850)
<223> OTHER INFORMATION: n is unknown
<220> FEATURE:
<221> NAME/KEY: misc_feature
<222> LOCATION: (852)..(852)
<223> OTHER INFORMATION: n is unknown

<400> SEQUENCE: 15
cngnnntgtt nctcnnctgc tgacaatgct gctgnngnnn cncctcnctg tctccacttc    60
cttgaacaat gcgccgtcat gcttcttttg cctcccgctg ctccagaaag ctaggccgca   120
```

```
gatcagaacc accacagtca atatcaccnc cttcctctta tagattcgga atctcatgat      180
aggggctcag cctctgtgcg agtggagaga agttngnnnn nnagctgang agcaattgca      240
ggtgatatga tgtgctcggc tcaagaagcg ggcccggaga ggaagaagnn nnnncggggg      300
ctaattattg gcaaaacgag ctcttgttnn nnnnnnnnnn nngnnnnnnn nnnnnacnnn      360
nggnnnnnca atattccnta nngcatgatg gttgctcaga ggcannnnnn nagnnnnnnn      420
nncgatccta taaagataaa aacataaata aacagtcttg attatattct gggtattaaa      480
gccacaatca gaacaaatat atgctttgta tcttnnnnng ccttcttcan nnnnnactgc      540
ttccgcggcc acattaagag aacttgtggt aagataagaa gatattttat tcgttctgct      600
gacttgctgg atgtcgggaa atattctgca ttnnnnnnna ggcggttaat tgcanatata      660
attggtagtg aaaagggtcg ttgctatggt caccgtgaag cgagtacagc agcacaagaa      720
tgtgngccgt tctcnnnnnn tattgtttga atatnnnnac ctgttttagt cggtttaann      780
nnnnnnnnnt ctaaccnaaa acaacactgc agngactgan ngtagtattt attttttnnnn      840 cnnnnncttn antttggtgt aaacatcaac ggcgcactt                             879
```

<210> SEQ ID NO 16
<211> LENGTH: 879
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (2)..(2)
<223> OTHER INFORMATION: n is unknown
<220> FEATURE:
<221> NAME/KEY: misc_feature
<222> LOCATION: (4)..(7)
<223> OTHER INFORMATION: n is unknown
<220> FEATURE:
<221> NAME/KEY: misc_feature
<222> LOCATION: (14)..(14)
<223> OTHER INFORMATION: n is unknown
<220> FEATURE:
<221> NAME/KEY: misc_feature
<222> LOCATION: (36)..(37)
<223> OTHER INFORMATION: n is unknown
<220> FEATURE:
<221> NAME/KEY: misc_feature
<222> LOCATION: (39)..(41)
<223> OTHER INFORMATION: n is unknown
<220> FEATURE:
<221> NAME/KEY: misc_feature
<222> LOCATION: (43)..(43)
<223> OTHER INFORMATION: n is unknown
<220> FEATURE:
<221> NAME/KEY: misc_feature
<222> LOCATION: (48)..(48)
<223> OTHER INFORMATION: n is unknown
<220> FEATURE:
<221> NAME/KEY: misc_feature
<222> LOCATION: (216)..(223)
<223> OTHER INFORMATION: n is unknown
<220> FEATURE:
<221> NAME/KEY: misc_feature
<222> LOCATION: (230)..(230)
<223> OTHER INFORMATION: n is unknown
<220> FEATURE:
<221> NAME/KEY: misc_feature
<222> LOCATION: (233)..(233)
<223> OTHER INFORMATION: n is unknown
<220> FEATURE:
<221> NAME/KEY: misc_feature
<222> LOCATION: (280)..(280)
<223> OTHER INFORMATION: n is unknown
<220> FEATURE:
<221> NAME/KEY: misc_feature
<222> LOCATION: (282)..(282)

```
<223> OTHER INFORMATION: n is unknown
<220> FEATURE:
<221> NAME/KEY: misc_feature
<222> LOCATION: (286)..(286)
<223> OTHER INFORMATION: n is unknown
<220> FEATURE:
<221> NAME/KEY: misc_feature
<222> LOCATION: (291)..(295)
<223> OTHER INFORMATION: n is unknown
<220> FEATURE:
<221> NAME/KEY: misc_feature
<222> LOCATION: (297)..(298)
<223> OTHER INFORMATION: n is unknown
<220> FEATURE:
<221> NAME/KEY: misc_feature
<222> LOCATION: (301)..(303)
<223> OTHER INFORMATION: n is unknown
<220> FEATURE:
<221> NAME/KEY: misc_feature
<222> LOCATION: (306)..(311)
<223> OTHER INFORMATION: n is unknown
<220> FEATURE:
<221> NAME/KEY: misc_feature
<222> LOCATION: (313)..(314)
<223> OTHER INFORMATION: n is unknown
<220> FEATURE:
<221> NAME/KEY: misc_feature
<222> LOCATION: (316)..(316)
<223> OTHER INFORMATION: n is unknown
<220> FEATURE:
<221> NAME/KEY: misc_feature
<222> LOCATION: (324)..(324)
<223> OTHER INFORMATION: n is unknown
<220> FEATURE:
<221> NAME/KEY: misc_feature
<222> LOCATION: (328)..(328)
<223> OTHER INFORMATION: n is unknown
<220> FEATURE:
<221> NAME/KEY: misc_feature
<222> LOCATION: (353)..(357)
<223> OTHER INFORMATION: n is unknown
<220> FEATURE:
<221> NAME/KEY: misc_feature
<222> LOCATION: (359)..(359)
<223> OTHER INFORMATION: n is unknown
<220> FEATURE:
<221> NAME/KEY: misc_feature
<222> LOCATION: (388)..(401)
<223> OTHER INFORMATION: n is unknown
<220> FEATURE:
<221> NAME/KEY: misc_feature
<222> LOCATION: (403)..(412)
<223> OTHER INFORMATION: n is unknown
<220> FEATURE:
<221> NAME/KEY: misc_feature
<222> LOCATION: (416)..(421)
<223> OTHER INFORMATION: n is unknown
<220> FEATURE:
<221> NAME/KEY: misc_feature
<222> LOCATION: (514)..(518)
<223> OTHER INFORMATION: n is unknown
<220> FEATURE:
<221> NAME/KEY: misc_feature
<222> LOCATION: (530)..(536)
<223> OTHER INFORMATION: n is unknown
<220> FEATURE:
<221> NAME/KEY: misc_feature
<222> LOCATION: (548)..(549)
<223> OTHER INFORMATION: n is unknown
<220> FEATURE:
<221> NAME/KEY: misc_feature
<222> LOCATION: (623)..(623)
<223> OTHER INFORMATION: n is unknown
<220> FEATURE:
<221> NAME/KEY: misc_feature
<222> LOCATION: (632)..(633)
<223> OTHER INFORMATION: n is unknown
<220> FEATURE:
<221> NAME/KEY: misc_feature
<222> LOCATION: (635)..(638)
```

```
<223> OTHER INFORMATION: n is unknown
<220> FEATURE:
<221> NAME/KEY: misc_feature
<222> LOCATION: (654)..(654)
<223> OTHER INFORMATION: n is unknown
<220> FEATURE:
<221> NAME/KEY: misc_feature
<222> LOCATION: (677)..(677)
<223> OTHER INFORMATION: n is unknown
<220> FEATURE:
<221> NAME/KEY: misc_feature
<222> LOCATION: (679)..(680)
<223> OTHER INFORMATION: n is unknown
<220> FEATURE:
<221> NAME/KEY: misc_feature
<222> LOCATION: (723)..(723)
<223> OTHER INFORMATION: n is unknown
<220> FEATURE:
<221> NAME/KEY: misc_feature
<222> LOCATION: (733)..(738)
<223> OTHER INFORMATION: n is unknown
<220> FEATURE:
<221> NAME/KEY: misc_feature
<222> LOCATION: (754)..(756)
<223> OTHER INFORMATION: n is unknown
<220> FEATURE:
<221> NAME/KEY: misc_feature
<222> LOCATION: (762)..(762)
<223> OTHER INFORMATION: n is unknown
<220> FEATURE:
<221> NAME/KEY: misc_feature
<222> LOCATION: (777)..(787)
<223> OTHER INFORMATION: n is unknown
<220> FEATURE:
<221> NAME/KEY: misc_feature
<222> LOCATION: (794)..(795)
<223> OTHER INFORMATION: n is unknown
<220> FEATURE:
<221> NAME/KEY: misc_feature
<222> LOCATION: (809)..(809)
<223> OTHER INFORMATION: n is unknown
<220> FEATURE:
<221> NAME/KEY: misc_feature
<222> LOCATION: (811)..(811)
<223> OTHER INFORMATION: n is unknown
<220> FEATURE:
<221> NAME/KEY: misc_feature
<222> LOCATION: (818)..(818)
<223> OTHER INFORMATION: n is unknown
<220> FEATURE:
<221> NAME/KEY: misc_feature
<222> LOCATION: (821)..(824)
<223> OTHER INFORMATION: n is unknown
<220> FEATURE:
<221> NAME/KEY: misc_feature
<222> LOCATION: (839)..(849)
<223> OTHER INFORMATION: n is unknown
<220> FEATURE:
<221> NAME/KEY: misc_feature
<222> LOCATION: (878)..(879)
<223> OTHER INFORMATION: n is unknown

<400> SEQUENCE: 16
cngnnnngtt gctnctactg ctgacaatgc tgctgnngnn ncncctcnct gtctccactt      60
ccttgaacaa tgcgccgtca tgcttctttt gcctcccgct gctccagaaa gctaggccgc     120
agatcagaac caccacagtc aatatcacca ccttcctctt atagattcgg aatctcatga    180 tagggctca gcctctgtgc gagtggagag aagttnnnnn nnnagctgan gancaattgc     240
aggtgatatg atgtgctcgg ctcaagaagc gggcccggan angaanaagt nnnnncnngg    300
nnnctnnnnn ngnncnatat tccntaangc atgatggttg ctcagaggca ggnnnnnanc    360
taattattgg caaaacgagc tcttgttnnn nnnnnnnnnn ngnnnnnnnn nncaannnnn    420
ncgatcctat aaaagataaa acataaataa acagtcttga ttatattctg ggtattaaag    480
```

```
ccacaatcag aacaaatata tgctttgtat cttnnnnngc cttcttcatn nnnnnntgct    540
tccgcggnna cattaagaga acttgtggta agataagaag atattttatt cgttctgctg    600
acttgctgga tgtcgggaaa tantctgcat tnnannnnag gcggttaatt gcanatataa    660
ttggtagtga aaagggncnn tgctatggtc accgtgaagc gagtacagca gacaagaatg    720
tgngccgttc tcnnnnnnta ttgtttgaat atgnnnacct gntttagtcg gtttaannnn    780
nnnnnnntct aacnnaaaac aacactgcng ngactgantg nnnnatttat tttttttacnn    840 nnnnnnnnnt ttggtgtaaa catcaacggc gcacttcnn                          879
```

<210> SEQ ID NO 17
<211> LENGTH: 878
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (2)..(2)
<223> OTHER INFORMATION: n is unknown
<220> FEATURE:
<221> NAME/KEY: misc_feature
<222> LOCATION: (4)..(5)
<223> OTHER INFORMATION: n is unknown
<220> FEATURE:
<221> NAME/KEY: misc_feature
<222> LOCATION: (7)..(7)
<223> OTHER INFORMATION: n is unknown
<220> FEATURE:
<221> NAME/KEY: misc_feature
<222> LOCATION: (11)..(12)
<223> OTHER INFORMATION: n is unknown
<220> FEATURE:
<221> NAME/KEY: misc_feature
<222> LOCATION: (15)..(17)
<223> OTHER INFORMATION: n is unknown
<220> FEATURE:
<221> NAME/KEY: misc_feature
<222> LOCATION: (35)..(35)
<223> OTHER INFORMATION: n is unknown
<220> FEATURE:
<221> NAME/KEY: misc_feature
<222> LOCATION: (41)..(41)
<223> OTHER INFORMATION: n is unknown
<220> FEATURE:
<221> NAME/KEY: misc_feature
<222> LOCATION: (46)..(46)
<223> OTHER INFORMATION: n is unknown
<220> FEATURE:
<221> NAME/KEY: misc_feature
<222> LOCATION: (125)..(125)
<223> OTHER INFORMATION: n is unknown
<220> FEATURE:
<221> NAME/KEY: misc_feature
<222> LOCATION: (214)..(218)
<223> OTHER INFORMATION: n is unknown
<220> FEATURE:
<221> NAME/KEY: misc_feature
<222> LOCATION: (220)..(221)
<223> OTHER INFORMATION: n is unknown
<220> FEATURE:
<221> NAME/KEY: misc_feature
<222> LOCATION: (228)..(228)
<223> OTHER INFORMATION: n is unknown
<220> FEATURE:
<221> NAME/KEY: misc_feature
<222> LOCATION: (231)..(231)
<223> OTHER INFORMATION: n is unknown
<220> FEATURE:
<221> NAME/KEY: misc_feature
<222> LOCATION: (279)..(284)
<223> OTHER INFORMATION: n is unknown
<220> FEATURE:
<221> NAME/KEY: misc_feature
<222> LOCATION: (288)..(299)

```
-continued

<223> OTHER INFORMATION: n is unknown
<220> FEATURE:
<221> NAME/KEY: misc_feature
<222> LOCATION: (327)..(340)
<223> OTHER INFORMATION: n is unknown
<220> FEATURE:
<221> NAME/KEY: misc_feature
<222> LOCATION: (342)..(352)
<223> OTHER INFORMATION: n is unknown
<220> FEATURE:
<221> NAME/KEY: misc_feature
<222> LOCATION: (357)..(358)
<223> OTHER INFORMATION: n is unknown
<220> FEATURE:
<221> NAME/KEY: misc_feature
<222> LOCATION: (360)..(361)
<223> OTHER INFORMATION: n is unknown
<220> FEATURE:
<221> NAME/KEY: misc_feature
<222> LOCATION: (363)..(364)
<223> OTHER INFORMATION: n is unknown
<220> FEATURE:
<221> NAME/KEY: misc_feature
<222> LOCATION: (374)..(374)
<223> OTHER INFORMATION: n is unknown
<220> FEATURE:
<221> NAME/KEY: misc_feature
<222> LOCATION: (377)..(378)
<223> OTHER INFORMATION: n is unknown
<220> FEATURE:
<221> NAME/KEY: misc_feature
<222> LOCATION: (402)..(407)
<223> OTHER INFORMATION: n is unknown
<220> FEATURE:
<221> NAME/KEY: misc_feature
<222> LOCATION: (414)..(415)
<223> OTHER INFORMATION: n is unknown
<220> FEATURE:
<221> NAME/KEY: misc_feature
<222> LOCATION: (417)..(418)
<223> OTHER INFORMATION: n is unknown
<220> FEATURE:
<221> NAME/KEY: misc_feature
<222> LOCATION: (420)..(420)
<223> OTHER INFORMATION: n is unknown
<220> FEATURE:
<221> NAME/KEY: misc_feature
<222> LOCATION: (511)..(515)
<223> OTHER INFORMATION: n is unknown
<220> FEATURE:
<221> NAME/KEY: misc_feature
<222> LOCATION: (526)..(531)
<223> OTHER INFORMATION: n is unknown
<220> FEATURE:
<221> NAME/KEY: misc_feature
<222> LOCATION: (533)..(534)
<223> OTHER INFORMATION: n is unknown
<220> FEATURE:
<221> NAME/KEY: misc_feature
<222> LOCATION: (538)..(542)
<223> OTHER INFORMATION: n is unknown
<220> FEATURE:
<221> NAME/KEY: misc_feature
<222> LOCATION: (620)..(620)
<223> OTHER INFORMATION: n is unknown
<220> FEATURE:
<221> NAME/KEY: misc_feature
<222> LOCATION: (630)..(635)
<223> OTHER INFORMATION: n is unknown
<220> FEATURE:
<221> NAME/KEY: misc_feature
<222> LOCATION: (651)..(651)
<223> OTHER INFORMATION: n is unknown
<220> FEATURE:
<221> NAME/KEY: misc_feature
<222> LOCATION: (719)..(719)
<223> OTHER INFORMATION: n is unknown
<220> FEATURE:
<221> NAME/KEY: misc_feature
<222> LOCATION: (731)..(731)
```

```
<223> OTHER INFORMATION: n is unknown
<220> FEATURE:
<221> NAME/KEY: misc_feature
<222> LOCATION: (733)..(736)
<223> OTHER INFORMATION: n is unknown
<220> FEATURE:
<221> NAME/KEY: misc_feature
<222> LOCATION: (753)..(753)
<223> OTHER INFORMATION: n is unknown
<220> FEATURE:
<221> NAME/KEY: misc_feature
<222> LOCATION: (770)..(770)
<223> OTHER INFORMATION: n is unknown
<220> FEATURE:
<221> NAME/KEY: misc_feature
<222> LOCATION: (775)..(785)
<223> OTHER INFORMATION: n is unknown
<220> FEATURE:
<221> NAME/KEY: misc_feature
<222> LOCATION: (806)..(807)
<223> OTHER INFORMATION: n is unknown
<220> FEATURE:
<221> NAME/KEY: misc_feature
<222> LOCATION: (809)..(809)
<223> OTHER INFORMATION: n is unknown
<220> FEATURE:
<221> NAME/KEY: misc_feature
<222> LOCATION: (816)..(816)
<223> OTHER INFORMATION: n is unknown
<220> FEATURE:
<221> NAME/KEY: misc_feature
<222> LOCATION: (832)..(841)
<223> OTHER INFORMATION: n is unknown
<220> FEATURE:
<221> NAME/KEY: misc_feature
<222> LOCATION: (855)..(855)
<223> OTHER INFORMATION: n is unknown
<220> FEATURE:
<221> NAME/KEY: misc_feature
<222> LOCATION: (863)..(863)
<223> OTHER INFORMATION: n is unknown

<400> SEQUENCE: 17
cngnnangtt nntcnnngct gacaatgctg ctgcngcttc ncctcnctgt ctccacttcc      60
ttgaacaatg cgccgtcatg cttcttttgc ctcccgctgc tccagaaagc taggccgcag     120
atcanaacca ccacagtcaa tatcaccacc ttcctcttat agattcggaa tctcatgata     180
ggggctcagc ctctgtgcga gtggagagaa gttnnnnngn nagctganga ncaattgcag     240
gtgatatgat gtgctcggct caagaagcgg gcccggagnn nnnnaagnnn nnnnnnnnnt     300
aattattggc aaaacgagct cttgttnnnn nnnnnnnnnn gnnnnnnnnn nnactanngn     360
ngnncaatat tccntanngc atgatggttg ctcagaggca gnnnnnnagc aacnnanncn     420
atcctataaa agataaaaca taaataaaca gtcttgatta tattctgggt attaaagcca     480
caatcagaac aaatatatgc tttgtatctt nnnnngcctt cttcannnnn nanngctnnn     540
nnggccacat taagagaact tgtggtaaga taagaagata ttttattcgt tctgctgact     600
tgctggatgt cgggaaatan tctgcatttn nnnnnaggcg gttaattgca natataattg     660
gtagtgaaaa gggtcgttgc tatggtcacc gtgaagcgag tacagcagca caagaatgng     720
tgccgttctc ngnnnntatt gtttgaatat ggnaacctgt tttagtcggn ttaannnnnn     780
nnnnntctaa ccaaaaacaa cactgnngng actgantgta gtatttattt tnnnnnnnnn     840
ncttaatttt ggtgnaaaca tcnacggcgc acttcaac                            878

<210> SEQ ID NO 18
<211> LENGTH: 869
<212> TYPE: DNA
<213> ORGANISM: Artificial Sequence
<220> FEATURE:
```

```
<223> OTHER INFORMATION: S. enterica PCR reaction /DNA sequence standard
<220> FEATURE:
<221> NAME/KEY: misc_feature
<222> LOCATION: (4)..(5)
<223> OTHER INFORMATION: n is unknown
<220> FEATURE:
<221> NAME/KEY: misc_feature
<222> LOCATION: (8)..(10)
<223> OTHER INFORMATION: n is unknown
<220> FEATURE:
<221> NAME/KEY: misc_feature
<222> LOCATION: (28)..(28)
<223> OTHER INFORMATION: n is unknown
<220> FEATURE:
<221> NAME/KEY: misc_feature
<222> LOCATION: (39)..(39)
<223> OTHER INFORMATION: n is unknown
<220> FEATURE:
<221> NAME/KEY: misc_feature
<222> LOCATION: (118)..(118)
<223> OTHER INFORMATION: n is unknown
<220> FEATURE:
<221> NAME/KEY: misc_feature
<222> LOCATION: (207)..(213)
<223> OTHER INFORMATION: n is unknown
<220> FEATURE:
<221> NAME/KEY: misc_feature
<222> LOCATION: (267)..(267)
<223> OTHER INFORMATION: n is unknown
<220> FEATURE:
<221> NAME/KEY: misc_feature
<222> LOCATION: (270)..(271)
<223> OTHER INFORMATION: n is unknown
<220> FEATURE:
<221> NAME/KEY: misc_feature
<222> LOCATION: (281)..(292)
<223> OTHER INFORMATION: n is unknown
<220> FEATURE:
<221> NAME/KEY: misc_feature
<222> LOCATION: (323)..(333)
<223> OTHER INFORMATION: n is unknown
<220> FEATURE:
<221> NAME/KEY: misc_feature
<222> LOCATION: (335)..(345)
<223> OTHER INFORMATION: n is unknown
<220> FEATURE:
<221> NAME/KEY: misc_feature
<222> LOCATION: (349)..(352)
<223> OTHER INFORMATION: n is unknown
<220> FEATURE:
<221> NAME/KEY: misc_feature
<222> LOCATION: (354)..(354)
<223> OTHER INFORMATION: n is unknown
<220> FEATURE:
<221> NAME/KEY: misc_feature
<222> LOCATION: (356)..(357)
<223> OTHER INFORMATION: n is unknown
<220> FEATURE:
<221> NAME/KEY: misc_feature
<222> LOCATION: (367)..(367)
<223> OTHER INFORMATION: n is unknown
<220> FEATURE:
<221> NAME/KEY: misc_feature
<222> LOCATION: (370)..(371)
<223> OTHER INFORMATION: n is unknown
<220> FEATURE:
<221> NAME/KEY: misc_feature
<222> LOCATION: (395)..(400)
<223> OTHER INFORMATION: n is unknown
<220> FEATURE:
<221> NAME/KEY: misc_feature
<222> LOCATION: (406)..(408)
<223> OTHER INFORMATION: n is unknown
<220> FEATURE:
<221> NAME/KEY: misc_feature
<222> LOCATION: (410)..(411)
<223> OTHER INFORMATION: n is unknown
<220> FEATURE:
<221> NAME/KEY: misc_feature
<222> LOCATION: (504)..(508)
```

```
<223> OTHER INFORMATION: n is unknown
<220> FEATURE:
<221> NAME/KEY: misc_feature
<222> LOCATION: (520)..(526)
<223> OTHER INFORMATION: n is unknown
<220> FEATURE:
<221> NAME/KEY: misc_feature
<222> LOCATION: (529)..(529)
<223> OTHER INFORMATION: n is unknown
<220> FEATURE:
<221> NAME/KEY: misc_feature
<222> LOCATION: (538)..(538)
<223> OTHER INFORMATION: n is unknown
<220> FEATURE:
<221> NAME/KEY: misc_feature
<222> LOCATION: (623)..(628)
<223> OTHER INFORMATION: n is unknown
<220> FEATURE:
<221> NAME/KEY: misc_feature
<222> LOCATION: (724)..(729)
<223> OTHER INFORMATION: n is unknown
<220> FEATURE:
<221> NAME/KEY: misc_feature
<222> LOCATION: (746)..(746)
<223> OTHER INFORMATION: n is unknown
<220> FEATURE:
<221> NAME/KEY: misc_feature
<222> LOCATION: (769)..(769)
<223> OTHER INFORMATION: n is unknown
<220> FEATURE:
<221> NAME/KEY: misc_feature
<222> LOCATION: (771)..(777)
<223> OTHER INFORMATION: n is unknown
<220> FEATURE:
<221> NAME/KEY: misc_feature
<222> LOCATION: (785)..(785)
<223> OTHER INFORMATION: n is unknown
<220> FEATURE:
<221> NAME/KEY: misc_feature
<222> LOCATION: (805)..(805)
<223> OTHER INFORMATION: n is unknown
<220> FEATURE:
<221> NAME/KEY: misc_feature
<222> LOCATION: (808)..(812)
<223> OTHER INFORMATION: n is unknown
<220> FEATURE:
<221> NAME/KEY: misc_feature
<222> LOCATION: (816)..(816)
<223> OTHER INFORMATION: n is unknown
<220> FEATURE:
<221> NAME/KEY: misc_feature
<222> LOCATION: (830)..(841)
<223> OTHER INFORMATION: n is unknown
<220> FEATURE:
<221> NAME/KEY: misc_feature
<222> LOCATION: (849)..(849)
<223> OTHER INFORMATION: n is unknown

<400> SEQUENCE: 18
gttnntcnnn gctgacaatg ctgctgcngc ttctcctcnc tgtctccact tccttgaaca      60
atgcgccgtc atgcttcttt tgcctcccgc tgctccagaa agctaggccg cagatcanaa     120
ccaccacagt caatatcacc accttcctct tatagattcg gaatctcatg ataggggctc     180
agcctctgtg cgagtggaga gaagttnnnn nnngagctga ggagcaattg caggtgatat     240
gatgtgctcg gctcaagaag cgggccnggn naggaagaag nnnnnnnnnn nntaattatt     300
ggcaaaacga gctcttgttg tannnnnnnn nnngnnnnnn nnnnactnn  nngngnncaa     360 tattccntan ngcatgatgg ttgctcagag gcagnnnnnn agcaannnan ncgatccctat    420 aaaagataaa acataaataa acagtcttga ttatattctg ggtattaaag ccacaatcag     480
aacaaatata tgctttgtat cttnnnnngc cttcttcatn nnnnnntgnt tccgcggnca     540
cattaagaga acttgtggta agataagaag atatttatt  cgttctgctg acttgctgga    600
```

```
tgtcgggaaa tattctgcat ttnnnnnnag gcggttaatt gcagatataa ttggtagtga     660
aaagggtcgt tgctatggtc accgtgaagc gagtacagca gcacaagaat gtgtgccgtt     720
ctcnnnnnnt attgtttgaa tatggnaacc tgttttagtc ggtttaaang nnnnnnntct     780
aaccnaaaac aacactgcag tgacngannn nngtanttat tttttactn nnnnnnnnnn     840 ntttggtgna aacatcaacg gcgcacttc                                      869
```

```
<210> SEQ ID NO 19
<211> LENGTH: 874
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (7)..(7)
<223> OTHER INFORMATION: n is unknown
<220> FEATURE:
<221> NAME/KEY: misc_feature
<222> LOCATION: (18)..(18)
<223> OTHER INFORMATION: n is unknown
<220> FEATURE:
<221> NAME/KEY: misc_feature
<222> LOCATION: (41)..(41)
<223> OTHER INFORMATION: n is unknown
<220> FEATURE:
<221> NAME/KEY: misc_feature
<222> LOCATION: (209)..(209)
<223> OTHER INFORMATION: n is unknown
<220> FEATURE:
<221> NAME/KEY: misc_feature
<222> LOCATION: (269)..(269)
<223> OTHER INFORMATION: n is unknown
<220> FEATURE:
<221> NAME/KEY: misc_feature
<222> LOCATION: (271)..(274)
<223> OTHER INFORMATION: n is unknown
<220> FEATURE:
<221> NAME/KEY: misc_feature
<222> LOCATION: (276)..(278)
<223> OTHER INFORMATION: n is unknown
<220> FEATURE:
<221> NAME/KEY: misc_feature
<222> LOCATION: (285)..(286)
<223> OTHER INFORMATION: n is unknown
<220> FEATURE:
<221> NAME/KEY: misc_feature
<222> LOCATION: (288)..(288)
<223> OTHER INFORMATION: n is unknown
<220> FEATURE:
<221> NAME/KEY: misc_feature
<222> LOCATION: (291)..(291)
<223> OTHER INFORMATION: n is unknown
<220> FEATURE:
<221> NAME/KEY: misc_feature
<222> LOCATION: (325)..(335)
<223> OTHER INFORMATION: n is unknown
<220> FEATURE:
<221> NAME/KEY: misc_feature
<222> LOCATION: (337)..(347)
<223> OTHER INFORMATION: n is unknown
<220> FEATURE:
<221> NAME/KEY: misc_feature
<222> LOCATION: (351)..(352)
<223> OTHER INFORMATION: n is unknown
<220> FEATURE:
<221> NAME/KEY: misc_feature
<222> LOCATION: (354)..(357)
<223> OTHER INFORMATION: n is unknown
<220> FEATURE:
<221> NAME/KEY: misc_feature
<222> LOCATION: (361)..(361)
<223> OTHER INFORMATION: n is unknown
<220> FEATURE:
<221> NAME/KEY: misc_feature
<222> LOCATION: (369)..(369)
```

-continued

```
<223> OTHER INFORMATION: n is unknown
<220> FEATURE:
<221> NAME/KEY: misc_feature
<222> LOCATION: (373)..(373)
<223> OTHER INFORMATION: n is unknown
<220> FEATURE:
<221> NAME/KEY: misc_feature
<222> LOCATION: (396)..(396)
<223> OTHER INFORMATION: n is unknown
<220> FEATURE:
<221> NAME/KEY: misc_feature
<222> LOCATION: (398)..(401)
<223> OTHER INFORMATION: n is unknown
<220> FEATURE:
<221> NAME/KEY: misc_feature
<222> LOCATION: (408)..(408)
<223> OTHER INFORMATION: n is unknown
<220> FEATURE:
<221> NAME/KEY: misc_feature
<222> LOCATION: (411)..(411)
<223> OTHER INFORMATION: n is unknown
<220> FEATURE:
<221> NAME/KEY: misc_feature
<222> LOCATION: (506)..(506)
<223> OTHER INFORMATION: n is unknown
<220> FEATURE:
<221> NAME/KEY: misc_feature
<222> LOCATION: (508)..(509)
<223> OTHER INFORMATION: n is unknown
<220> FEATURE:
<221> NAME/KEY: misc_feature
<222> LOCATION: (521)..(528)
<223> OTHER INFORMATION: n is unknown
<220> FEATURE:
<221> NAME/KEY: misc_feature
<222> LOCATION: (530)..(530)
<223> OTHER INFORMATION: n is unknown
<220> FEATURE:
<221> NAME/KEY: misc_feature
<222> LOCATION: (538)..(541)
<223> OTHER INFORMATION: n is unknown
<220> FEATURE:
<221> NAME/KEY: misc_feature
<222> LOCATION: (624)..(628)
<223> OTHER INFORMATION: n is unknown
<220> FEATURE:
<221> NAME/KEY: misc_feature
<222> LOCATION: (725)..(730)
<223> OTHER INFORMATION: n is unknown
<220> FEATURE:
<221> NAME/KEY: misc_feature
<222> LOCATION: (769)..(779)
<223> OTHER INFORMATION: n is unknown
<220> FEATURE:
<221> NAME/KEY: misc_feature
<222> LOCATION: (803)..(803)
<223> OTHER INFORMATION: n is unknown
<220> FEATURE:
<221> NAME/KEY: misc_feature
<222> LOCATION: (806)..(808)
<223> OTHER INFORMATION: n is unknown
<220> FEATURE:
<221> NAME/KEY: misc_feature
<222> LOCATION: (811)..(813)
<223> OTHER INFORMATION: n is unknown
<220> FEATURE:
<221> NAME/KEY: misc_feature
<222> LOCATION: (828)..(838)
<223> OTHER INFORMATION: n is unknown
<220> FEATURE:
<221> NAME/KEY: misc_feature
<222> LOCATION: (850)..(850)
<223> OTHER INFORMATION: n is unknown
<220> FEATURE:
<221> NAME/KEY: misc_feature
<222> LOCATION: (852)..(852)
<223> OTHER INFORMATION: n is unknown
<220> FEATURE:
<221> NAME/KEY: misc_feature
<222> LOCATION: (860)..(860)
```

<223> OTHER INFORMATION: n is unknown
<220> FEATURE:
<221> NAME/KEY: misc_feature
<222> LOCATION: (870)..(870)
<223> OTHER INFORMATION: n is unknown
<220> FEATURE:
<221> NAME/KEY: misc_feature
<222> LOCATION: (872)..(874)
<223> OTHER INFORMATION: n is unknown

<400> SEQUENCE: 19

| | | | | | |
|---|---|---|---|---|---|
| gttgctncta | ctgctganaa | tgctgctgct | gcttctcctc | nctgtctcca | cttccttgaa | 60 |
| caatgcgccg | tcatgcttct | tttgcctccc | gctgctccag | aaagctaggc | cgcagatcag | 120 |
| aaccaccaca | gtcaatatca | ccaccttcct | cttatagatt | cggaatctca | tgatagggc | 180 |
| tcagcctctg | tgcgagtgga | gagaagttng | caggcgagct | gaggagcaat | tgcaggtgat | 240 |
| atgatgtgct | cggctcaaga | agcgggccng | nnnngnnnga | agtcnngncg | nggctaatta | 300 |
| ttggcaaaac | gagctcttgt | tgtannnnnn | nnnngnnnn | nnnnnncta | nngnnnatc | 360 |
| natattccnt | aangcatgat | ggttgctcag | aggcangnnn | nagcaacnaa | nacgatccta | 420 |
| taaaagataa | aacataaata | aacagtcttg | attatattct | gggtattaaa | gccacaatca | 480 |
| gaacaaatat | atgctttgta | tctttncnng | ccttcttcat | nnnnnnnngn | ttccgcgnnn | 540 |
| ncattaagag | aacttgtggt | aagataagaa | gatatttat | tcgttctgct | gacttgctgg | 600 |
| atgtcgggaa | atattctgca | tttnnnnnga | ggcggttaat | tgcagatata | attggtagtg | 660 |
| aaaagggtcg | ttgctatggt | caccgtgaag | cgagtacagc | agcacaagaa | tgtgtgccgt | 720 |
| tctcnnnnnn | tattgtttga | atatggtaac | ctgttttagt | cggtttaann | nnnnnnnnt | 780 |
| ctaaccaaaa | acaacactgc | agnggnnngg | nnngtagtat | ttatttnnn | nnnnnnnct | 840 |
| taattttggn | gnaaacatcn | acggcgcacn | tnnn | | | 874 |

<210> SEQ ID NO 20
<211> LENGTH: 868
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (2)..(2)
<223> OTHER INFORMATION: n is unknown
<220> FEATURE:
<221> NAME/KEY: misc_feature
<222> LOCATION: (5)..(5)
<223> OTHER INFORMATION: n is unknown
<220> FEATURE:
<221> NAME/KEY: misc_feature
<222> LOCATION: (7)..(7)
<223> OTHER INFORMATION: n is unknown
<220> FEATURE:
<221> NAME/KEY: misc_feature
<222> LOCATION: (9)..(10)
<223> OTHER INFORMATION: n is unknown
<220> FEATURE:
<221> NAME/KEY: misc_feature
<222> LOCATION: (13)..(14)
<223> OTHER INFORMATION: n is unknown
<220> FEATURE:
<221> NAME/KEY: misc_feature
<222> LOCATION: (18)..(18)
<223> OTHER INFORMATION: n is unknown
<220> FEATURE:
<221> NAME/KEY: misc_feature
<222> LOCATION: (30)..(32)
<223> OTHER INFORMATION: n is unknown
<220> FEATURE:
<221> NAME/KEY: misc_feature
<222> LOCATION: (34)..(36)

```
<223> OTHER INFORMATION: n is unknown
<220> FEATURE:
<221> NAME/KEY: misc_feature
<222> LOCATION: (103)..(103)
<223> OTHER INFORMATION: n is unknown
<220> FEATURE:
<221> NAME/KEY: misc_feature
<222> LOCATION: (105)..(105)
<223> OTHER INFORMATION: n is unknown
<220> FEATURE:
<221> NAME/KEY: misc_feature
<222> LOCATION: (107)..(108)
<223> OTHER INFORMATION: n is unknown
<220> FEATURE:
<221> NAME/KEY: misc_feature
<222> LOCATION: (130)..(132)
<223> OTHER INFORMATION: n is unknown
<220> FEATURE:
<221> NAME/KEY: misc_feature
<222> LOCATION: (135)..(135)
<223> OTHER INFORMATION: n is unknown
<220> FEATURE:
<221> NAME/KEY: misc_feature
<222> LOCATION: (138)..(138)
<223> OTHER INFORMATION: n is unknown
<220> FEATURE:
<221> NAME/KEY: misc_feature
<222> LOCATION: (174)..(175)
<223> OTHER INFORMATION: n is unknown
<220> FEATURE:
<221> NAME/KEY: misc_feature
<222> LOCATION: (178)..(179)
<223> OTHER INFORMATION: n is unknown
<220> FEATURE:
<221> NAME/KEY: misc_feature
<222> LOCATION: (218)..(218)
<223> OTHER INFORMATION: n is unknown
<220> FEATURE:
<221> NAME/KEY: misc_feature
<222> LOCATION: (224)..(224)
<223> OTHER INFORMATION: n is unknown
<220> FEATURE:
<221> NAME/KEY: misc_feature
<222> LOCATION: (232)..(232)
<223> OTHER INFORMATION: n is unknown
<220> FEATURE:
<221> NAME/KEY: misc_feature
<222> LOCATION: (234)..(239)
<223> OTHER INFORMATION: n is unknown
<220> FEATURE:
<221> NAME/KEY: misc_feature
<222> LOCATION: (265)..(265)
<223> OTHER INFORMATION: n is unknown
<220> FEATURE:
<221> NAME/KEY: misc_feature
<222> LOCATION: (267)..(271)
<223> OTHER INFORMATION: n is unknown
<220> FEATURE:
<221> NAME/KEY: misc_feature
<222> LOCATION: (273)..(274)
<223> OTHER INFORMATION: n is unknown
<220> FEATURE:
<221> NAME/KEY: misc_feature
<222> LOCATION: (328)..(330)
<223> OTHER INFORMATION: n is unknown
<220> FEATURE:
<221> NAME/KEY: misc_feature
<222> LOCATION: (341)..(351)
<223> OTHER INFORMATION: n is unknown
<220> FEATURE:
<221> NAME/KEY: misc_feature
<222> LOCATION: (517)..(523)
<223> OTHER INFORMATION: n is unknown
<220> FEATURE:
<221> NAME/KEY: misc_feature
<222> LOCATION: (525)..(525)
<223> OTHER INFORMATION: n is unknown
<220> FEATURE:
<221> NAME/KEY: misc_feature
<222> LOCATION: (527)..(527)
```

```
<223> OTHER INFORMATION: n is unknown
<220> FEATURE:
<221> NAME/KEY: misc_feature
<222> LOCATION: (529)..(529)
<223> OTHER INFORMATION: n is unknown
<220> FEATURE:
<221> NAME/KEY: misc_feature
<222> LOCATION: (552)..(552)
<223> OTHER INFORMATION: n is unknown
<220> FEATURE:
<221> NAME/KEY: misc_feature
<222> LOCATION: (554)..(554)
<223> OTHER INFORMATION: n is unknown
<220> FEATURE:
<221> NAME/KEY: misc_feature
<222> LOCATION: (662)..(662)
<223> OTHER INFORMATION: n is unknown
<220> FEATURE:
<221> NAME/KEY: misc_feature
<222> LOCATION: (664)..(665)
<223> OTHER INFORMATION: n is unknown
<220> FEATURE:
<221> NAME/KEY: misc_feature
<222> LOCATION: (686)..(686)
<223> OTHER INFORMATION: n is unknown
<220> FEATURE:
<221> NAME/KEY: misc_feature
<222> LOCATION: (795)..(798)
<223> OTHER INFORMATION: n is unknown
<220> FEATURE:
<221> NAME/KEY: misc_feature
<222> LOCATION: (800)..(802)
<223> OTHER INFORMATION: n is unknown
<220> FEATURE:
<221> NAME/KEY: misc_feature
<222> LOCATION: (811)..(815)
<223> OTHER INFORMATION: n is unknown
<220> FEATURE:
<221> NAME/KEY: misc_feature
<222> LOCATION: (817)..(821)
<223> OTHER INFORMATION: n is unknown
<220> FEATURE:
<221> NAME/KEY: misc_feature
<222> LOCATION: (827)..(827)
<223> OTHER INFORMATION: n is unknown
<220> FEATURE:
<221> NAME/KEY: misc_feature
<222> LOCATION: (833)..(833)
<223> OTHER INFORMATION: n is unknown
<220> FEATURE:
<221> NAME/KEY: misc_feature
<222> LOCATION: (836)..(836)
<223> OTHER INFORMATION: n is unknown
<220> FEATURE:
<221> NAME/KEY: misc_feature
<222> LOCATION: (845)..(845)
<223> OTHER INFORMATION: n is unknown

<400> SEQUENCE: 20
gntcncngnn gannatgntg ctgctgcttn nngnnnctgt ctccacttcc ttgaacaatg      60
cgccgtcatg cttcttttgc ctcccgctgc tccagaaagc tangncnnag atcagaacca    120
ccacagtcan nntcnccncc ttcctcttat agattcggaa tctcatgata gggnntcnnc    180
ctctgtgcga gtggagagaa gtttgcaggc gagctganga gcanttgcag gngnnnnnnt    240
gtgctcggct caagaagcgg gcccngnnnn nannaagtcg tgccggggct aattattggc    300
aaaacgagct cttgttgtaa acattgannn gggggggggg nnnnnnnnnn natcaatatt    360
ccataaggca tgatggttgc tcagaggcag gagaagagca acgaatacga tcctataaaa    420
gataaaacat aaataaacag tcttgattat attctgggta ttaaagccac aatcagaaca    480
aatatatgct ttgtatcttt tcttgccttc ttcattnnnn nnngntncng cggccacatt    540
aagagaactt gngntaagat aagaagatat tttattcgtt ctgctgactt gctggatgtc    600
```

-continued

```
gggaaatatt ctgcatttga taagaggcgg ttaattgcag atataattgg tagtgaaaag      660
gngnnttgct atggtcaccg tgaagngagt acagcagcac aagaatgtgt gccgttctca      720
gttaatattg tttgaatatg gtaacctgtt ttagtcggtt taaaggtaag aagatctaac      780
caaaaacaac actgnnnngn nngattgtag nnnnnannnn ntttacntaa tcntantttt      840
ggtgnaaaca tcaacggcgc acttcaac                                         868
```

```
<210> SEQ ID NO 21
<211> LENGTH: 876
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (2)..(3)
<223> OTHER INFORMATION: n is unknown
<220> FEATURE:
<221> NAME/KEY: misc_feature
<222> LOCATION: (8)..(8)
<223> OTHER INFORMATION: n is unknown
<220> FEATURE:
<221> NAME/KEY: misc_feature
<222> LOCATION: (14)..(14)
<223> OTHER INFORMATION: n is unknown
<220> FEATURE:
<221> NAME/KEY: misc_feature
<222> LOCATION: (16)..(16)
<223> OTHER INFORMATION: n is unknown
<220> FEATURE:
<221> NAME/KEY: misc_feature
<222> LOCATION: (21)..(21)
<223> OTHER INFORMATION: n is unknown
<220> FEATURE:
<221> NAME/KEY: misc_feature
<222> LOCATION: (37)..(43)
<223> OTHER INFORMATION: n is unknown
<220> FEATURE:
<221> NAME/KEY: misc_feature
<222> LOCATION: (68)..(68)
<223> OTHER INFORMATION: n is unknown
<220> FEATURE:
<221> NAME/KEY: misc_feature
<222> LOCATION: (110)..(110)
<223> OTHER INFORMATION: n is unknown
<220> FEATURE:
<221> NAME/KEY: misc_feature
<222> LOCATION: (112)..(115)
<223> OTHER INFORMATION: n is unknown
<220> FEATURE:
<221> NAME/KEY: misc_feature
<222> LOCATION: (134)..(134)
<223> OTHER INFORMATION: n is unknown
<220> FEATURE:
<221> NAME/KEY: misc_feature
<222> LOCATION: (136)..(139)
<223> OTHER INFORMATION: n is unknown
<220> FEATURE:
<221> NAME/KEY: misc_feature
<222> LOCATION: (141)..(141)
<223> OTHER INFORMATION: n is unknown
<220> FEATURE:
<221> NAME/KEY: misc_feature
<222> LOCATION: (145)..(145)
<223> OTHER INFORMATION: n is unknown
<220> FEATURE:
<221> NAME/KEY: misc_feature
<222> LOCATION: (181)..(182)
<223> OTHER INFORMATION: n is unknown
<220> FEATURE:
<221> NAME/KEY: misc_feature
<222> LOCATION: (185)..(186)
<223> OTHER INFORMATION: n is unknown
<220> FEATURE:
<221> NAME/KEY: misc_feature
<222> LOCATION: (218)..(218)
```

-continued

```
<223> OTHER INFORMATION: n is unknown
<220> FEATURE:
<221> NAME/KEY: misc_feature
<222> LOCATION: (225)..(225)
<223> OTHER INFORMATION: n is unknown
<220> FEATURE:
<221> NAME/KEY: misc_feature
<222> LOCATION: (231)..(231)
<223> OTHER INFORMATION: n is unknown
<220> FEATURE:
<221> NAME/KEY: misc_feature
<222> LOCATION: (239)..(239)
<223> OTHER INFORMATION: n is unknown
<220> FEATURE:
<221> NAME/KEY: misc_feature
<222> LOCATION: (241)..(243)
<223> OTHER INFORMATION: n is unknown
<220> FEATURE:
<221> NAME/KEY: misc_feature
<222> LOCATION: (245)..(246)
<223> OTHER INFORMATION: n is unknown
<220> FEATURE:
<221> NAME/KEY: misc_feature
<222> LOCATION: (263)..(263)
<223> OTHER INFORMATION: n is unknown
<220> FEATURE:
<221> NAME/KEY: misc_feature
<222> LOCATION: (269)..(269)
<223> OTHER INFORMATION: n is unknown
<220> FEATURE:
<221> NAME/KEY: misc_feature
<222> LOCATION: (275)..(275)
<223> OTHER INFORMATION: n is unknown
<220> FEATURE:
<221> NAME/KEY: misc_feature
<222> LOCATION: (334)..(359)
<223> OTHER INFORMATION: n is unknown
<220> FEATURE:
<221> NAME/KEY: misc_feature
<222> LOCATION: (522)..(522)
<223> OTHER INFORMATION: n is unknown
<220> FEATURE:
<221> NAME/KEY: misc_feature
<222> LOCATION: (560)..(560)
<223> OTHER INFORMATION: n is unknown
<220> FEATURE:
<221> NAME/KEY: misc_feature
<222> LOCATION: (562)..(562)
<223> OTHER INFORMATION: n is unknown
<220> FEATURE:
<221> NAME/KEY: misc_feature
<222> LOCATION: (670)..(670)
<223> OTHER INFORMATION: n is unknown
<220> FEATURE:
<221> NAME/KEY: misc_feature
<222> LOCATION: (694)..(694)
<223> OTHER INFORMATION: n is unknown
<220> FEATURE:
<221> NAME/KEY: misc_feature
<222> LOCATION: (801)..(801)
<223> OTHER INFORMATION: n is unknown
<220> FEATURE:
<221> NAME/KEY: misc_feature
<222> LOCATION: (816)..(817)
<223> OTHER INFORMATION: n is unknown
<220> FEATURE:
<221> NAME/KEY: misc_feature
<222> LOCATION: (819)..(827)
<223> OTHER INFORMATION: n is unknown
<220> FEATURE:
<221> NAME/KEY: misc_feature
<222> LOCATION: (835)..(836)
<223> OTHER INFORMATION: n is unknown
<220> FEATURE:
<221> NAME/KEY: misc_feature
<222> LOCATION: (838)..(838)
<223> OTHER INFORMATION: n is unknown
<220> FEATURE:
<221> NAME/KEY: misc_feature
<222> LOCATION: (862)..(862)
```

<223> OTHER INFORMATION: n is unknown

<400> SEQUENCE: 21

```
tnngttgntc tacngntgac natgctgctg ctgcttnnnn nnnctgtctc cacttccttg      60
aacaatgngc cgtcatgctt cttttgcctc ccgctgctcc agaaagctan gnnnnagatc     120
agaaccacca cagncnnnnt naccnccttc ctcttataga ttcggaatct catgataggg     180
nntcnncctc tgtgcgagtg gagagaagtt tgcaggcnag ctgangagca nttgcaggng     240
nnngnntgtg ctcggctcaa gangcgggnc cgganaggaa gaagtcgtgc cggggctaat     300
tattggcaaa acgagctctt gttgtaaaca ttgnnnnnnn nnnnnnnnnn nnnnnnnnna     360
tcaatattcc ataaggcatg atggttgctc agaggcagga gaagagcaac gaatacgatc     420
ctataaaaga taaacataa ataaacagtc ttgattatat tctgggtatt aaagccacaa      480
tcagaacaaa tatatgcttt gtatcttttc ttgccttctt cnttaccaac tgcttccgcg     540
gccacattaa gagaacttgn gntaagataa gaagatattt tattcgttct gctgacttgc     600
tggatgtcgg gaaatattct gcatttgata agaggcggtt aattgcagat ataattggta    660
gtgaaaaggn gcgttgctat ggtcaccgtg aagngagtac agcagcacaa gaatgtgtgc    720
cgttctcagt taatattgtt tgaatatggt aacctgtttt agtcggttta aaggtaagaa     780
gatctaacca aaacaacac ngcagtgact gattgnngnn nnnnnntttt tttanntnat      840
cttaattttg gtgtaaacat cnacggcgca cttcaa                              876
```

<210> SEQ ID NO 22
<211> LENGTH: 880
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (2)..(2)
<223> OTHER INFORMATION: n is unknown
<220> FEATURE:
<221> NAME/KEY: misc_feature
<222> LOCATION: (17)..(17)
<223> OTHER INFORMATION: n is unknown
<220> FEATURE:
<221> NAME/KEY: misc_feature
<222> LOCATION: (24)..(24)
<223> OTHER INFORMATION: n is unknown
<220> FEATURE:
<221> NAME/KEY: misc_feature
<222> LOCATION: (41)..(42)
<223> OTHER INFORMATION: n is unknown
<220> FEATURE:
<221> NAME/KEY: misc_feature
<222> LOCATION: (44)..(46)
<223> OTHER INFORMATION: n is unknown
<220> FEATURE:
<221> NAME/KEY: misc_feature
<222> LOCATION: (71)..(71)
<223> OTHER INFORMATION: n is unknown
<220> FEATURE:
<221> NAME/KEY: misc_feature
<222> LOCATION: (115)..(115)
<223> OTHER INFORMATION: n is unknown
<220> FEATURE:
<221> NAME/KEY: misc_feature
<222> LOCATION: (117)..(118)
<223> OTHER INFORMATION: n is unknown
<220> FEATURE:
<221> NAME/KEY: misc_feature
<222> LOCATION: (137)..(137)
<223> OTHER INFORMATION: n is unknown
<220> FEATURE:
<221> NAME/KEY: misc_feature
<222> LOCATION: (139)..(140)

-continued

```
<223> OTHER INFORMATION: n is unknown
<220> FEATURE:
<221> NAME/KEY: misc_feature
<222> LOCATION: (145)..(145)
<223> OTHER INFORMATION: n is unknown
<220> FEATURE:
<221> NAME/KEY: misc_feature
<222> LOCATION: (148)..(148)
<223> OTHER INFORMATION: n is unknown
<220> FEATURE:
<221> NAME/KEY: misc_feature
<222> LOCATION: (184)..(185)
<223> OTHER INFORMATION: n is unknown
<220> FEATURE:
<221> NAME/KEY: misc_feature
<222> LOCATION: (188)..(189)
<223> OTHER INFORMATION: n is unknown
<220> FEATURE:
<221> NAME/KEY: misc_feature
<222> LOCATION: (228)..(228)
<223> OTHER INFORMATION: n is unknown
<220> FEATURE:
<221> NAME/KEY: misc_feature
<222> LOCATION: (244)..(248)
<223> OTHER INFORMATION: n is unknown
<220> FEATURE:
<221> NAME/KEY: misc_feature
<222> LOCATION: (328)..(328)
<223> OTHER INFORMATION: n is unknown
<220> FEATURE:
<221> NAME/KEY: misc_feature
<222> LOCATION: (333)..(333)
<223> OTHER INFORMATION: n is unknown
<220> FEATURE:
<221> NAME/KEY: misc_feature
<222> LOCATION: (335)..(335)
<223> OTHER INFORMATION: n is unknown
<220> FEATURE:
<221> NAME/KEY: misc_feature
<222> LOCATION: (337)..(339)
<223> OTHER INFORMATION: n is unknown
<220> FEATURE:
<221> NAME/KEY: misc_feature
<222> LOCATION: (348)..(362)
<223> OTHER INFORMATION: n is unknown
<220> FEATURE:
<221> NAME/KEY: misc_feature
<222> LOCATION: (563)..(563)
<223> OTHER INFORMATION: n is unknown
<220> FEATURE:
<221> NAME/KEY: misc_feature
<222> LOCATION: (673)..(676)
<223> OTHER INFORMATION: n is unknown
<220> FEATURE:
<221> NAME/KEY: misc_feature
<222> LOCATION: (770)..(770)
<223> OTHER INFORMATION: n is unknown
<220> FEATURE:
<221> NAME/KEY: misc_feature
<222> LOCATION: (792)..(793)
<223> OTHER INFORMATION: n is unknown
<220> FEATURE:
<221> NAME/KEY: misc_feature
<222> LOCATION: (797)..(798)
<223> OTHER INFORMATION: n is unknown
<220> FEATURE:
<221> NAME/KEY: misc_feature
<222> LOCATION: (809)..(810)
<223> OTHER INFORMATION: n is unknown
<220> FEATURE:
<221> NAME/KEY: misc_feature
<222> LOCATION: (816)..(824)
<223> OTHER INFORMATION: n is unknown
<220> FEATURE:
<221> NAME/KEY: misc_feature
<222> LOCATION: (828)..(833)
<223> OTHER INFORMATION: n is unknown
<220> FEATURE:
<221> NAME/KEY: misc_feature
<222> LOCATION: (870)..(870)
```

<223> OTHER INFORMATION: n is unknown
<220> FEATURE:
<221> NAME/KEY: misc_feature
<222> LOCATION: (880)..(880)
<223> OTHER INFORMATION: n is unknown

<400> SEQUENCE: 22

```
cngttatgtt gctctcngct gacnatgctg ctgctgcttc nngnnnctgt ctccacttcc      60
ttgaacaatg ngccgtcatg cttcttttgc ctcccgctgc tccagaaagc taggncnnag     120
atcagaacca ccacagncnn tatcnccncc ttcctcttat agattcggaa tctcatgata     180
gggnntcnnc ctctgtgcga gtggagagaa gtttgcaggc gagctganga gcaattgcag     240
gtgnnnnnat gtgctcggct caagaagcgg gcccggagag gaagaagtcg tgccggggct     300
aattattggc aaaacgagct cttgttgnaa acntngnnng gggggggnnn nnnnnnnnnn     360
nnatcaatat tccataaggc atgatggttg ctcagaggca ggagaagagc aacgaatacg     420
atcctataaa agataaaaca taaataaaca gtcttgatta tattctgggt attaaagcca     480
caatcagaac aaatatatgc tttgtatctt ttcttgcctt cttcattacc aactgcttcc     540
gcggccacat taagagaact tgnggtaaga taagaagata ttttattcgt tctgctgact     600
tgctggatgt cgggaaatat tctgcatttg ataagaggcg gttaattgca gatataattg     660
gtagtgaaaa ggnnnnttgc tatggtcacc gtgaagcgag tacagcagca caagaatgtg     720
tgccgttctc agttaatatt gtttgaatat ggtaacctgt tttagtcggn ttaaaggtaa     780
gaagatctaa cnnaaannca acactgcann gactgnnnnn nnnnattnnn nnnttttttac     840
ttaatcttaa ttttggtgta aacatcaacn ggcgcacttn                           880
```

<210> SEQ ID NO 23
<211> LENGTH: 868
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (5)..(5)
<223> OTHER INFORMATION: n is unknown
<220> FEATURE:
<221> NAME/KEY: misc_feature
<222> LOCATION: (8)..(10)
<223> OTHER INFORMATION: n is unknown
<220> FEATURE:
<221> NAME/KEY: misc_feature
<222> LOCATION: (17)..(17)
<223> OTHER INFORMATION: n is unknown
<220> FEATURE:
<221> NAME/KEY: misc_feature
<222> LOCATION: (33)..(35)
<223> OTHER INFORMATION: n is unknown
<220> FEATURE:
<221> NAME/KEY: misc_feature
<222> LOCATION: (37)..(39)
<223> OTHER INFORMATION: n is unknown
<220> FEATURE:
<221> NAME/KEY: misc_feature
<222> LOCATION: (61)..(61)
<223> OTHER INFORMATION: n is unknown
<220> FEATURE:
<221> NAME/KEY: misc_feature
<222> LOCATION: (106)..(106)
<223> OTHER INFORMATION: n is unknown
<220> FEATURE:
<221> NAME/KEY: misc_feature
<222> LOCATION: (108)..(108)
<223> OTHER INFORMATION: n is unknown
<220> FEATURE:
<221> NAME/KEY: misc_feature
<222> LOCATION: (110)..(111)

```
<223> OTHER INFORMATION: n is unknown
<220> FEATURE:
<221> NAME/KEY: misc_feature
<222> LOCATION: (130)..(130)
<223> OTHER INFORMATION: n is unknown
<220> FEATURE:
<221> NAME/KEY: misc_feature
<222> LOCATION: (132)..(135)
<223> OTHER INFORMATION: n is unknown
<220> FEATURE:
<221> NAME/KEY: misc_feature
<222> LOCATION: (138)..(138)
<223> OTHER INFORMATION: n is unknown
<220> FEATURE:
<221> NAME/KEY: misc_feature
<222> LOCATION: (141)..(141)
<223> OTHER INFORMATION: n is unknown
<220> FEATURE:
<221> NAME/KEY: misc_feature
<222> LOCATION: (178)..(178)
<223> OTHER INFORMATION: n is unknown
<220> FEATURE:
<221> NAME/KEY: misc_feature
<222> LOCATION: (181)..(182)
<223> OTHER INFORMATION: n is unknown
<220> FEATURE:
<221> NAME/KEY: misc_feature
<222> LOCATION: (227)..(227)
<223> OTHER INFORMATION: n is unknown
<220> FEATURE:
<221> NAME/KEY: misc_feature
<222> LOCATION: (237)..(241)
<223> OTHER INFORMATION: n is unknown
<220> FEATURE:
<221> NAME/KEY: misc_feature
<222> LOCATION: (328)..(328)
<223> OTHER INFORMATION: n is unknown
<220> FEATURE:
<221> NAME/KEY: misc_feature
<222> LOCATION: (330)..(355)
<223> OTHER INFORMATION: n is unknown
<220> FEATURE:
<221> NAME/KEY: misc_feature
<222> LOCATION: (357)..(358)
<223> OTHER INFORMATION: n is unknown
<220> FEATURE:
<221> NAME/KEY: misc_feature
<222> LOCATION: (521)..(527)
<223> OTHER INFORMATION: n is unknown
<220> FEATURE:
<221> NAME/KEY: misc_feature
<222> LOCATION: (667)..(670)
<223> OTHER INFORMATION: n is unknown
<220> FEATURE:
<221> NAME/KEY: misc_feature
<222> LOCATION: (773)..(773)
<223> OTHER INFORMATION: n is unknown
<220> FEATURE:
<221> NAME/KEY: misc_feature
<222> LOCATION: (803)..(803)
<223> OTHER INFORMATION: n is unknown
<220> FEATURE:
<221> NAME/KEY: misc_feature
<222> LOCATION: (827)..(835)
<223> OTHER INFORMATION: n is unknown
<220> FEATURE:
<221> NAME/KEY: misc_feature
<222> LOCATION: (838)..(839)
<223> OTHER INFORMATION: n is unknown
<220> FEATURE:
<221> NAME/KEY: misc_feature
<222> LOCATION: (867)..(868)
<223> OTHER INFORMATION: n is unknown

<400> SEQUENCE: 23
gttgntcnnn gctgacnatg ctgctgctgc ttnnngnnnc tgtctccact tccttgaaca      60
ntgcgccgtc atgcttcttt tgcctcccgc tgctccagaa agctangncn nagatcagaa     120
```

```
ccaccacagn cnnnntcncc nccttcctct tatagattcg gaatctcatg ataggggntc    180
nncctctgtg cgagtggaga gaagtttgca ggcgagctga ggagcanttg caggtgnnnn    240
natgtgctcg gctcaagaag cgggcccgga gaggaagaag tcgtgccggg gctaattatt    300
ggcaaaacga gctcttgttg taaacatngn nnnnnnnnnn nnnnnnnnnn nnnnngnnca    360
atattccata aggcatgatg gttgctcaga ggcaggagaa gagcaacgaa tacgatccta    420
taaaagataa aacataaata aacagtcttg attatattct gggtattaaa gccacaatca    480
gaacaaatat atgctttgta tcttttcttg ccttcttcat nnnnnnntgc ttccgcggcc    540
acattaagag aacttggggt aagataagaa gatattttat tcgttctgct gacttgctgg    600
atgtcgggaa atattctgca tttgataaga ggcggttaat tgcagatata attggtagtg    660
aaaaggnnnn ttgctatggt caccgtgaag cgagtacagc agcacaagaa tgtgtgccgt    720
tctcagttaa tattgtttga atatggtaac ctgtttagt cggtttaaag gtnagaagat     780
ctaaccaaaa acaacactgc agngactgat tgtagtattt attttnnnn nnnnnctnna    840 ttttggtgta aacatcaacg gcgcacnn                                       868
```

```
<210> SEQ ID NO 24
<211> LENGTH: 877
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (2)..(2)
<223> OTHER INFORMATION: n is unknown
<220> FEATURE:
<221> NAME/KEY: misc_feature
<222> LOCATION: (4)..(5)
<223> OTHER INFORMATION: n is unknown
<220> FEATURE:
<221> NAME/KEY: misc_feature
<222> LOCATION: (7)..(7)
<223> OTHER INFORMATION: n is unknown
<220> FEATURE:
<221> NAME/KEY: misc_feature
<222> LOCATION: (12)..(12)
<223> OTHER INFORMATION: n is unknown
<220> FEATURE:
<221> NAME/KEY: misc_feature
<222> LOCATION: (15)..(17)
<223> OTHER INFORMATION: n is unknown
<220> FEATURE:
<221> NAME/KEY: misc_feature
<222> LOCATION: (23)..(25)
<223> OTHER INFORMATION: n is unknown
<220> FEATURE:
<221> NAME/KEY: misc_feature
<222> LOCATION: (40)..(41)
<223> OTHER INFORMATION: n is unknown
<220> FEATURE:
<221> NAME/KEY: misc_feature
<222> LOCATION: (44)..(45)
<223> OTHER INFORMATION: n is unknown
<220> FEATURE:
<221> NAME/KEY: misc_feature
<222> LOCATION: (138)..(138)
<223> OTHER INFORMATION: n is unknown
<220> FEATURE:
<221> NAME/KEY: misc_feature
<222> LOCATION: (147)..(147)
<223> OTHER INFORMATION: n is unknown
<220> FEATURE:
<221> NAME/KEY: misc_feature
<222> LOCATION: (188)..(188)
<223> OTHER INFORMATION: n is unknown
<220> FEATURE:
<221> NAME/KEY: misc_feature
<222> LOCATION: (243)..(249)
```

```
<223> OTHER INFORMATION: n is unknown
<220> FEATURE:
<221> NAME/KEY: misc_feature
<222> LOCATION: (273)..(274)
<223> OTHER INFORMATION: n is unknown
<220> FEATURE:
<221> NAME/KEY: misc_feature
<222> LOCATION: (276)..(284)
<223> OTHER INFORMATION: n is unknown
<220> FEATURE:
<221> NAME/KEY: misc_feature
<222> LOCATION: (337)..(366)
<223> OTHER INFORMATION: n is unknown
<220> FEATURE:
<221> NAME/KEY: misc_feature
<222> LOCATION: (529)..(534)
<223> OTHER INFORMATION: n is unknown
<220> FEATURE:
<221> NAME/KEY: misc_feature
<222> LOCATION: (537)..(542)
<223> OTHER INFORMATION: n is unknown
<220> FEATURE:
<221> NAME/KEY: misc_feature
<222> LOCATION: (544)..(544)
<223> OTHER INFORMATION: n is unknown
<220> FEATURE:
<221> NAME/KEY: misc_feature
<222> LOCATION: (563)..(563)
<223> OTHER INFORMATION: n is unknown
<220> FEATURE:
<221> NAME/KEY: misc_feature
<222> LOCATION: (673)..(676)
<223> OTHER INFORMATION: n is unknown
<220> FEATURE:
<221> NAME/KEY: misc_feature
<222> LOCATION: (797)..(797)
<223> OTHER INFORMATION: n is unknown
<220> FEATURE:
<221> NAME/KEY: misc_feature
<222> LOCATION: (813)..(813)
<223> OTHER INFORMATION: n is unknown
<220> FEATURE:
<221> NAME/KEY: misc_feature
<222> LOCATION: (815)..(818)
<223> OTHER INFORMATION: n is unknown
<220> FEATURE:
<221> NAME/KEY: misc_feature
<222> LOCATION: (820)..(821)
<223> OTHER INFORMATION: n is unknown
<220> FEATURE:
<221> NAME/KEY: misc_feature
<222> LOCATION: (823)..(823)
<223> OTHER INFORMATION: n is unknown
<220> FEATURE:
<221> NAME/KEY: misc_feature
<222> LOCATION: (834)..(843)
<223> OTHER INFORMATION: n is unknown
<220> FEATURE:
<221> NAME/KEY: misc_feature
<222> LOCATION: (854)..(854)
<223> OTHER INFORMATION: n is unknown
<220> FEATURE:
<221> NAME/KEY: misc_feature
<222> LOCATION: (856)..(856)
<223> OTHER INFORMATION: n is unknown
<220> FEATURE:
<221> NAME/KEY: misc_feature
<222> LOCATION: (877)..(877)
<223> OTHER INFORMATION: n is unknown

<400> SEQUENCE: 24
cngnnangtt gntcnnngct gannngctgc tgctgcttcn ngtnnctgtc tccacttcct       60
tgaacaatgc gccgtcatgc ttcttttgcc tcccgctgct ccagaaagct aggccgcaga      120
tcagaaccac cacagtcnat atcaccncct tcctcttata gattcggaat ctcatgatag      180
gggctcancc tctgtgcgag tggagagaag tttgcaggcg agctgaggag caattgcagg      240
```

```
tgnnnnnnng tgctcggctc aagaagcggg ccnngnnnnn nnnnagtcgt gccgggcta      300 attattggca aaacgagctc ttgttgtaaa cattgannnn nnnnnnnnnn nnnnnnnnnn     360
nnnncnatat tccataaggc atgatggttg ctcagaggca ggagaagagc aacgaatacg     420
atcctataaa agataaaaca taaataaaca gtcttgatta tattctgggt attaaagcca     480
caatcagaac aaatatatgc tttgtatctt ttcttgcctt cttcattann nncngcnnnn     540
nngnccacat taagagaact tgnggtaaga taagaagata ttttattcgt tctgctgact     600
tgctggatgt cgggaaatat tctgcatttg ataagaggcg gttaattgca gatataattg     660
gtagtgaaaa ggnnnnttgc tatggtcacc gtgaagcgag tacagcagca caagaatgtg     720
tgccgttctc agttaatatt gtttgaatat ggtaacctgt tttagtcggt ttaaaggtaa     780
gaagatctaa ccaaaancaa cactgcagtg acngnnnngn ngnatttatt tttnnnnnnn     840
nnnttaattt tggngnaaac atcaacggcg cacttcn                              877

<210> SEQ ID NO 25
<211> LENGTH: 34
<212> TYPE: DNA
<213> ORGANISM: Artificial Sequence
<220> FEATURE:
<223> OTHER INFORMATION: Primer

<400> SEQUENCE: 25
atccggcata tctcgacatt cctgattaca atcc                                 34

<210> SEQ ID NO 26
<211> LENGTH: 852
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (1)..(7)
<223> OTHER INFORMATION: n is unknown
<220> FEATURE:
<221> NAME/KEY: misc_feature
<222> LOCATION: (55)..(55)
<223> OTHER INFORMATION: n is unknown
<220> FEATURE:
<221> NAME/KEY: misc_feature
<222> LOCATION: (60)..(60)
<223> OTHER INFORMATION: n is unknown
<220> FEATURE:
<221> NAME/KEY: misc_feature
<222> LOCATION: (363)..(372)
<223> OTHER INFORMATION: n is unknown
<220> FEATURE:
<221> NAME/KEY: misc_feature
<222> LOCATION: (375)..(387)
<223> OTHER INFORMATION: n is unknown
<220> FEATURE:
<221> NAME/KEY: misc_feature
<222> LOCATION: (568)..(569)
<223> OTHER INFORMATION: n is unknown
<220> FEATURE:
<221> NAME/KEY: misc_feature
<222> LOCATION: (757)..(757)
<223> OTHER INFORMATION: n is unknown
<220> FEATURE:
<221> NAME/KEY: misc_feature
<222> LOCATION: (785)..(785)
<223> OTHER INFORMATION: n is unknown
<220> FEATURE:
<221> NAME/KEY: misc_feature
<222> LOCATION: (808)..(808)
<223> OTHER INFORMATION: n is unknown
<220> FEATURE:
<221> NAME/KEY: misc_feature
<222> LOCATION: (834)..(834)
```

<223> OTHER INFORMATION: n is unknown
<220> FEATURE:
<221> NAME/KEY: misc_feature
<222> LOCATION: (839)..(839)
<223> OTHER INFORMATION: n is unknown
<220> FEATURE:
<221> NAME/KEY: misc_feature
<222> LOCATION: (848)..(849)
<223> OTHER INFORMATION: n is unknown

<400> SEQUENCE: 26

```
nnnnnnnatt actgttaatg ttgctactac tgctgacaat gctgctgctg cttcnectcn      60
ctgtctccac ttccttgaac aatgcgccgt catgcttctt ttgcctcccg ctgctccaga     120
aagctaggcc gcagatcaga accaccacag tcaatatcac caccttcctc ttatagattc     180
ggaatctcat gatagggggct cagcctctgt gcgagtggag agaagtttgc aggcgagctg     240
aggagcaatt gcaggtgata tgatgtgctc ggctcaagaa gcgggcccgg agaggaagaa     300
gtcgtgccgg ggctaattat tggcaaaacg agctcttgtt gtaaacattg atccaactgg     360
aannnnnnnn nnggnnnnnn nnnnnnncat aaggcatgat ggttgctcag aggcaggaga     420
agagcaacga atacgatcct ataaaagata aacataaat aaacagtctt gattatattc      480
tgggtattaa agccacaatc agaacaaata tatgctttgt atcttttctt gccttcttca     540
ttaccaactg cttccgcggc cacattanna gaacttgtgg taagataaga agatatttta     600
ttcgttctgc tgacttgctg gatgtcggga aatattctgc atttgataag aggcggttaa     660
ttgcagatat aattggtagt gaaaagggtc gttgctatgg tcaccgtgaa gcgagtacag     720
cagcacaaga atgtgtgccg ttctcagtta atattgnttg aatatggtaa cctgttttag     780
tcggnttaaa ggtaagaaga tctaaccnaa aacaacactg cagtgactga ttgnagtant     840
tatttttnna ct                                                         852
```

<210> SEQ ID NO 27
<211> LENGTH: 870
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (1)..(4)
<223> OTHER INFORMATION: n is unknown
<220> FEATURE:
<221> NAME/KEY: misc_feature
<222> LOCATION: (7)..(9)
<223> OTHER INFORMATION: n is unknown
<220> FEATURE:
<221> NAME/KEY: misc_feature
<222> LOCATION: (23)..(23)
<223> OTHER INFORMATION: n is unknown
<220> FEATURE:
<221> NAME/KEY: misc_feature
<222> LOCATION: (62)..(62)
<223> OTHER INFORMATION: n is unknown
<220> FEATURE:
<221> NAME/KEY: misc_feature
<222> LOCATION: (364)..(365)
<223> OTHER INFORMATION: n is unknown
<220> FEATURE:
<221> NAME/KEY: misc_feature
<222> LOCATION: (367)..(372)
<223> OTHER INFORMATION: n is unknown
<220> FEATURE:
<221> NAME/KEY: misc_feature
<222> LOCATION: (377)..(387)
<223> OTHER INFORMATION: n is unknown
<220> FEATURE:
<221> NAME/KEY: misc_feature
<222> LOCATION: (743)..(743)

```
<223> OTHER INFORMATION: n is unknown
<220> FEATURE:
<221> NAME/KEY: misc_feature
<222> LOCATION: (810)..(810)
<223> OTHER INFORMATION: n is unknown
<220> FEATURE:
<221> NAME/KEY: misc_feature
<222> LOCATION: (841)..(841)
<223> OTHER INFORMATION: n is unknown
<220> FEATURE:
<221> NAME/KEY: misc_feature
<222> LOCATION: (864)..(869)
<223> OTHER INFORMATION: n is unknown

<400> SEQUENCE: 27
nnnnttnnna ttactgttaa tgntgctact actgctgaca atgctgctgc tgcttctcct      60
cnctgtctcc acttccttga acaatgcgcc gtcatgcttc ttttgcctcc cgctgctcca     120
gaaagctagg ccgcagatca gaaccaccac agtcaatatc accaccttcc tcttatagat     180
tcggaatctc atgataggg ctcagcctct gtgcgagtgg agagaagttt gcaggcgagc      240
tgaggagcaa ttgcaggtga tatgatgtgc tcggctcaag aagcgggccc ggagaggaag     300
aagtcgtgcc ggggctaatt attggcaaaa cgagctcttg ttgtaaacat tgatccaact     360 ggannqnnnn nnatggnnnn nnnnnnntcc ataaggcatg atggttgctc agaggcagga     420
gaagagcaac gaatacgatc ctataaaaga taaaacataa ataaacagtc ttgattatat     480
tctgggtatt aaagccacaa tcagaacaaa tatatgcttt gtatcttttc ttgccttctt     540
cattaccaac tgcttccgcg gccacattaa gagaacttgt ggtaagataa gaagatattt     600
tattcgttct gctgacttgc tggatgtcgg gaaatattct gcatttgata agaggcggtt     660
aattgcagat ataattggta gtgaaaaggg tcgttgctat ggtcaccgtg aagcgagtac     720
agcagcacaa gaatgtgtgc cgntctcagt taatattgtt tgaatatggt aacctgtttt     780
agtcggttta aaggtaagaa gatctaaccn aaaacaacac tgcagtgact gattgtagta     840 nttattttt tacttaatct taannnnnng                                       870

<210> SEQ ID NO 28
<211> LENGTH: 851
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (1)..(2)
<223> OTHER INFORMATION: n is unknown
<220> FEATURE:
<221> NAME/KEY: misc_feature
<222> LOCATION: (4)..(7)
<223> OTHER INFORMATION: n is unknown
<220> FEATURE:
<221> NAME/KEY: misc_feature
<222> LOCATION: (62)..(62)
<223> OTHER INFORMATION: n is unknown
<220> FEATURE:
<221> NAME/KEY: misc_feature
<222> LOCATION: (300)..(300)
<223> OTHER INFORMATION: n is unknown
<220> FEATURE:
<221> NAME/KEY: misc_feature
<222> LOCATION: (304)..(304)
<223> OTHER INFORMATION: n is unknown
<220> FEATURE:
<221> NAME/KEY: misc_feature
<222> LOCATION: (365)..(373)
<223> OTHER INFORMATION: n is unknown
<220> FEATURE:
<221> NAME/KEY: misc_feature
<222> LOCATION: (376)..(386)
```

```
<223> OTHER INFORMATION: n is unknown
<220> FEATURE:
<221> NAME/KEY: misc_feature
<222> LOCATION: (553)..(553)
<223> OTHER INFORMATION: n is unknown
<220> FEATURE:
<221> NAME/KEY: misc_feature
<222> LOCATION: (562)..(562)
<223> OTHER INFORMATION: n is unknown
<220> FEATURE:
<221> NAME/KEY: misc_feature
<222> LOCATION: (566)..(566)
<223> OTHER INFORMATION: n is unknown
<220> FEATURE:
<221> NAME/KEY: misc_feature
<222> LOCATION: (759)..(759)
<223> OTHER INFORMATION: n is unknown
<220> FEATURE:
<221> NAME/KEY: misc_feature
<222> LOCATION: (836)..(836)
<223> OTHER INFORMATION: n is unknown
<220> FEATURE:
<221> NAME/KEY: misc_feature
<222> LOCATION: (844)..(848)
<223> OTHER INFORMATION: n is unknown
<220> FEATURE:
<221> NAME/KEY: misc_feature
<222> LOCATION: (850)..(851)
<223> OTHER INFORMATION: n is unknown

<400> SEQUENCE: 28
nngnnnntga ttactgttaa tgttgctact actgctgaca atgctgctgc tgcttctcct      60
cnctgtctcc acttccttga acaatgcgcc gtcatgcttc ttttgcctcc cgctgctcca     120
gaaagctagg ccgcagatca gaaccaccac agtcaatatc accaccttcc tcttatagat     180
tcggaatctc atgataggg ctcagcctct gtgcgagtgg agagaagttt gcaggcgagc      240
tgaggagcaa ttgcaggtga tatgatgtgc tcggctcaag aagcgggccc ggagaggaan     300
aagncgtgcc ggggctaatt attggcaaaa cgagctcttg ttgtaaacat tgatccaact     360
ggaannnnnn nnntgnnnnn nnnnnnttcc ataaggcatg atggttgctc agaggcagga     420
gaagagcaac gaatacgatc ctataaaaga taaaacataa ataaacagtc ttgattatat     480
tctgggtatt aaagccacaa tcagaacaaa tatatgcttt gtatcttttc ttgccttctt     540
cattaccaac tgnttccgcg gncacnttaa gagaacttgt ggtaagataa gagatatttt    600
tattcgttct gctgacttgc tggatgtcgg gaaatattct gcatttgata agaggcggtt    660
aattgcagat ataattggta gtgaaaaggg tcgttgctat ggtcaccgtg aagcgagtac    720
agcagcacaa gaatgtgtgc cgttctcagt taatattgnt tgaatatggt aacctgtttt    780
agtcggttta aaggtaagaa gatctaacca aaaacaacac tgcagtgact gattgnagta    840
tttnnnnntn n                                                         851

<210> SEQ ID NO 29
<211> LENGTH: 892
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (1)..(1)
<223> OTHER INFORMATION: n is unknown
<220> FEATURE:
<221> NAME/KEY: misc_feature
<222> LOCATION: (7)..(13)
<223> OTHER INFORMATION: n is unknown
<220> FEATURE:
<221> NAME/KEY: misc_feature
<222> LOCATION: (62)..(63)
```

```
<223> OTHER INFORMATION: n is unknown
<220> FEATURE:
<221> NAME/KEY: misc_feature
<222> LOCATION: (364)..(364)
<223> OTHER INFORMATION: n is unknown
<220> FEATURE:
<221> NAME/KEY: misc_feature
<222> LOCATION: (366)..(366)
<223> OTHER INFORMATION: n is unknown
<220> FEATURE:
<221> NAME/KEY: misc_feature
<222> LOCATION: (368)..(368)
<223> OTHER INFORMATION: n is unknown
<220> FEATURE:
<221> NAME/KEY: misc_feature
<222> LOCATION: (372)..(375)
<223> OTHER INFORMATION: n is unknown
<220> FEATURE:
<221> NAME/KEY: misc_feature
<222> LOCATION: (377)..(383)
<223> OTHER INFORMATION: n is unknown
<220> FEATURE:
<221> NAME/KEY: misc_feature
<222> LOCATION: (760)..(760)
<223> OTHER INFORMATION: n is unknown
<220> FEATURE:
<221> NAME/KEY: misc_feature
<222> LOCATION: (771)..(771)
<223> OTHER INFORMATION: n is unknown
<220> FEATURE:
<221> NAME/KEY: misc_feature
<222> LOCATION: (778)..(778)
<223> OTHER INFORMATION: n is unknown
<220> FEATURE:
<221> NAME/KEY: misc_feature
<222> LOCATION: (811)..(811)
<223> OTHER INFORMATION: n is unknown
<220> FEATURE:
<221> NAME/KEY: misc_feature
<222> LOCATION: (827)..(827)
<223> OTHER INFORMATION: n is unknown
<220> FEATURE:
<221> NAME/KEY: misc_feature
<222> LOCATION: (837)..(837)
<223> OTHER INFORMATION: n is unknown
<220> FEATURE:
<221> NAME/KEY: misc_feature
<222> LOCATION: (839)..(840)
<223> OTHER INFORMATION: n is unknown
<220> FEATURE:
<221> NAME/KEY: misc_feature
<222> LOCATION: (849)..(853)
<223> OTHER INFORMATION: n is unknown
<220> FEATURE:
<221> NAME/KEY: misc_feature
<222> LOCATION: (855)..(858)
<223> OTHER INFORMATION: n is unknown
<220> FEATURE:
<221> NAME/KEY: misc_feature
<222> LOCATION: (861)..(861)
<223> OTHER INFORMATION: n is unknown
<220> FEATURE:
<221> NAME/KEY: misc_feature
<222> LOCATION: (863)..(869)
<223> OTHER INFORMATION: n is unknown
<220> FEATURE:
<221> NAME/KEY: misc_feature
<222> LOCATION: (871)..(871)
<223> OTHER INFORMATION: n is unknown
<220> FEATURE:
<221> NAME/KEY: misc_feature
<222> LOCATION: (881)..(881)
<223> OTHER INFORMATION: n is unknown

<400> SEQUENCE: 29
nctggtnnnn nnnactgtta atgttgctac tactgctgac aatgctgctg ctgcttctcc     60
tnnctgtctc cacttccttg aacaatgcgc cgtcatgctt cttttgcctc ccgctgctcc    120
```

-continued

```
agaaagctag gccgcagatc agaaccacca cagtcaatat caccaccttc ctcttataga    180
ttcggaatct catgataggg gctcagcctc tgtgcgagtg gagagaagtt tgcaggcgag    240
ctgaggagca attgcaggtg atatgatgtg ctcggctcaa gaagcgggcc cggagaggaa    300
gaagtcgtgc cggggctaat tattggcaaa acgagctctt gttgtaaaca ttgatccaac    360
tggnangnca cnnnngnnnn nnnaatattc cataaggcat gatggttgct cagaggcagg    420
agaagagcaa cgaatacgat cctataaaag ataaaacata aataaacagt cttgattata    480
ttctgggtat taaagccaca atcagaacaa atatatgctt tgtatctttt cttgccttct    540
tcattaccaa ctgcttccgc ggccacatta agagaacttg tggtaagata agaagatatt    600
ttattcgttc tgctgacttg ctggatgtcg ggaaatattc tgcatttgat aagaggcggt    660
taattgcaga tataattggt agtgaaaagg gtcgttgcta tggtcaccgt gaagcgagta    720
cagcagcaca agaatgtgtg ccgttctcag ttaatattgn ttgaatatgg naacctgntt    780
tagtcggttt aaaggtaaga agatctaacc naaaacaaca ctgcagngac tgattgnann    840 atttattnn nnncnnnntc ntnnnnnnng ngtaaacatc nacggcgcac tt              892
```

<210> SEQ ID NO 30
<211> LENGTH: 892
<212> TYPE: DNA
<213> ORGANISM: Artificial Sequence
<220> FEATURE:
<223> OTHER INFORMATION: PCR reaction background/DNA sequence standard
<220> FEATURE:
<221> NAME/KEY: misc_feature
<222> LOCATION: (1)..(1)
<223> OTHER INFORMATION: n is unknown
<220> FEATURE:
<221> NAME/KEY: misc_feature
<222> LOCATION: (3)..(3)
<223> OTHER INFORMATION: n is unknown
<220> FEATURE:
<221> NAME/KEY: misc_feature
<222> LOCATION: (5)..(7)
<223> OTHER INFORMATION: n is unknown
<220> FEATURE:
<221> NAME/KEY: misc_feature
<222> LOCATION: (12)..(12)
<223> OTHER INFORMATION: n is unknown
<220> FEATURE:
<221> NAME/KEY: misc_feature
<222> LOCATION: (63)..(63)
<223> OTHER INFORMATION: n is unknown
<220> FEATURE:
<221> NAME/KEY: misc_feature
<222> LOCATION: (375)..(375)
<223> OTHER INFORMATION: n is unknown
<220> FEATURE:
<221> NAME/KEY: misc_feature
<222> LOCATION: (378)..(384)
<223> OTHER INFORMATION: n is unknown
<220> FEATURE:
<221> NAME/KEY: misc_feature
<222> LOCATION: (737)..(737)
<223> OTHER INFORMATION: n is unknown
<220> FEATURE:
<221> NAME/KEY: misc_feature
<222> LOCATION: (771)..(771)
<223> OTHER INFORMATION: n is unknown
<220> FEATURE:
<221> NAME/KEY: misc_feature
<222> LOCATION: (778)..(778)
<223> OTHER INFORMATION: n is unknown
<220> FEATURE:
<221> NAME/KEY: misc_feature
<222> LOCATION: (855)..(859)
<223> OTHER INFORMATION: n is unknown
<220> FEATURE:
<221> NAME/KEY: misc_feature
<222> LOCATION: (865)..(871)

```
<223> OTHER INFORMATION: n is unknown
<220> FEATURE:
<221> NAME/KEY: misc_feature
<222> LOCATION: (873)..(873)
<223> OTHER INFORMATION: n is unknown
<220> FEATURE:
<221> NAME/KEY: misc_feature
<222> LOCATION: (875)..(875)
<223> OTHER INFORMATION: n is unknown
<220> FEATURE:
<221> NAME/KEY: misc_feature
<222> LOCATION: (878)..(878)
<223> OTHER INFORMATION: n is unknown

<400> SEQUENCE: 30
ncngnnnatg antactgtta atgttgctac tactgctgac aatgctgctg ctgcttctcc      60
tcnctgtctc cacttccttg aacaatgcgc cgtcatgctt cttttgcctc ccgctgctcc     120
agaaagctag gccgcagatc agaaccacca cagtcaatat caccaccttc ctcttataga     180
ttcggaatct catgataggg gctcagcctc tgtgcgagtg gagagaagtt tgcaggcgag     240
ctgaggagca attgcaggtg atatgatgtg ctcggctcaa gaagcgggcc cggagaggaa     300
gaagtcgtgc cggggctaat tattggcaaa acgagctctt gttgtaaaca ttgatccaac     360
tggaatgtca ctaanggnnn nnnnatattc cataaggcat gatggttgct cagaggcagg     420
agaagagcaa cgaatacgat cctataaaag ataaaacata aataaacagt cttgattata     480
ttctgggtat aaagccaca atcagaacaa atatatgctt tgtatctttt cttgccttct      540
tcattaccaa ctgcttccgc ggccacatta agagaacttg tggtaagata agaagatatt     600
ttattcgttc tgctgacttg ctggatgtcg ggaaatattc tgcatttgat aagaggcggt     660
taattgcaga tataattggt agtgaaaagg gtcgttgcta tggtcaccgt gaagcgagta     720
cagcagcaca agaatgngtg ccgttctcag ttaatattgt ttgaatatgg naacctgntt     780
tagtcggttt aaaggtaaga agatctaacc aaaaacaaca ctgcagtgac tgattgtagt     840
atttattttt ttacnnnnnc ttaannnnnn ngnanacntc aacggcgcac tt             892

<210> SEQ ID NO 31
<211> LENGTH: 839
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (1)..(1)
<223> OTHER INFORMATION: n is unknown
<220> FEATURE:
<221> NAME/KEY: misc_feature
<222> LOCATION: (4)..(4)
<223> OTHER INFORMATION: n is unknown
<220> FEATURE:
<221> NAME/KEY: misc_feature
<222> LOCATION: (6)..(12)
<223> OTHER INFORMATION: n is unknown
<220> FEATURE:
<221> NAME/KEY: misc_feature
<222> LOCATION: (63)..(64)
<223> OTHER INFORMATION: n is unknown
<220> FEATURE:
<221> NAME/KEY: misc_feature
<222> LOCATION: (752)..(753)
<223> OTHER INFORMATION: n is unknown
<220> FEATURE:
<221> NAME/KEY: misc_feature
<222> LOCATION: (755)..(762)
<223> OTHER INFORMATION: n is unknown
<220> FEATURE:
<221> NAME/KEY: misc_feature
<222> LOCATION: (778)..(778)
```

```
<223> OTHER INFORMATION: n is unknown
<220> FEATURE:
<221> NAME/KEY: misc_feature
<222> LOCATION: (817)..(822)
<223> OTHER INFORMATION: n is unknown
<220> FEATURE:
<221> NAME/KEY: misc_feature
<222> LOCATION: (837)..(838)
<223> OTHER INFORMATION: n is unknown

<400> SEQUENCE: 31
nccngnnnnn nntactgtta atgttgctac tactgctgac aatgctgctg ctgcttctcc    60
tcnntgtctc cacttccttg aacaatgcgc cgtcatgctt cttttgcctc ccgctgctcc   120
agaaagctag gccgcagatc agaaccacca cagtcaatat caccaccttc ctcttataga   180
ttcggaatct catgataggg gctcagcctc tgtgcgagtg gagagaagtt tgcaggcgag   240
ctgaggagca attgcaggtg atatgatgtg ctcggctcaa gaagcgggcc cggagaggaa   300
gaagtcgtgc cggggctaat tattggcaaa acgagctctt gttgtaaaca ttgatccaac   360
tggaatgtca ctaatggcga atcaatattc cataaggcat gatggttgct cagaggcagg   420
agaagagcaa cgaatacgat cctataaaag ataaaacata aataaacagt cttgattata   480
ttctgggtat taaagccaca atcagaacaa atatatgctt tgtatctttt cttgccttct   540
tcattaccaa ctgcttccgc ggccacatta agagaacttg tggtaagata agaagatatt   600
ttattcgttc tgctgacttg ctggatgtcg ggaaatattc tgcatttgat aagaggcggt   660
taattgcaga tataattggt agtgaaaagg gtcgttgcta tggtcaccgt gaagcgagta   720
cagcagcaca agaatgtgtg ccgttctcag tnngnnnnnn nngaatatgg taacctgntt   780
tagtcggttt aaaggtaaga agatctaacc aaaaacnnnn nngcagtgac tgattgnng    839

<210> SEQ ID NO 32
<211> LENGTH: 807
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (15)..(17)
<223> OTHER INFORMATION: n is unknown
<220> FEATURE:
<221> NAME/KEY: misc_feature
<222> LOCATION: (19)..(22)
<223> OTHER INFORMATION: n is unknown
<220> FEATURE:
<221> NAME/KEY: misc_feature
<222> LOCATION: (51)..(51)
<223> OTHER INFORMATION: n is unknown
<220> FEATURE:
<221> NAME/KEY: misc_feature
<222> LOCATION: (739)..(750)
<223> OTHER INFORMATION: n is unknown
<220> FEATURE:
<221> NAME/KEY: misc_feature
<222> LOCATION: (766)..(766)
<223> OTHER INFORMATION: n is unknown
<220> FEATURE:
<221> NAME/KEY: misc_feature
<222> LOCATION: (776)..(776)
<223> OTHER INFORMATION: n is unknown
<220> FEATURE:
<221> NAME/KEY: misc_feature
<222> LOCATION: (784)..(784)
<223> OTHER INFORMATION: n is unknown
<220> FEATURE:
<221> NAME/KEY: misc_feature
<222> LOCATION: (792)..(792)
<223> OTHER INFORMATION: n is unknown
<220> FEATURE:
```

<221> NAME/KEY: misc_feature
<222> LOCATION: (805)..(807)
<223> OTHER INFORMATION: n is unknown

<400> SEQUENCE: 32

```
tactgttaat gttgnnncnn nngctgacaa tgctgctgct gcttctcctc nctgtctcca      60
cttccttgaa caatgcgccg tcatgcttct tttgcctccc gctgctccag aaagctaggc     120
cgcagatcag aaccaccaca gtcaatatca ccaccttcct cttatagatt cggaatctca     180
tgatagggc tcagcctctg tgcgagtgga gagaagtttg caggcgagct gaggagcaat      240
tgcaggtgat atgatgtgct cggctcaaga agcgggcccg gagaggaaga agtcgtgccg     300
gggctaatta ttggcaaaac gagctcttgt tgtaaacatt gatccaactg gaatgtcact     360
aatggcgaat caatattcca taaggcatga tggttgctca gaggcaggag aagagcaacg     420
aatacgatcc tataaaagat aaaacataaa taaacagtct tgattatatt ctgggtatta     480
aagccacaat cagaacaaat atatgctttg tatcttttct tgccttcttc attaccaact     540
gcttccgcgg ccacattaag agaacttgtg gtaagataag aagatatttt attcgttctg     600
ctgacttgct ggatgtcggg aaatattctg catttgataa gaggcggtta attgcagata     660
taattggtag tgaaaagggt cgttgctatg gtcaccgtga agcgagtaca gcagcacaag     720
aatgtgtgcc gttctcagnn nnnnnnnnnn gaatatggta acctgnttta gtcggnttaa     780
aggnaagaag anctaaccaa aaacnnn                                         807
```

<210> SEQ ID NO 33
<211> LENGTH: 865
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (1)..(3)
<223> OTHER INFORMATION: n is unknown
<220> FEATURE:
<221> NAME/KEY: misc_feature
<222> LOCATION: (6)..(6)
<223> OTHER INFORMATION: n is unknown
<220> FEATURE:
<221> NAME/KEY: misc_feature
<222> LOCATION: (10)..(10)
<223> OTHER INFORMATION: n is unknown
<220> FEATURE:
<221> NAME/KEY: misc_feature
<222> LOCATION: (15)..(15)
<223> OTHER INFORMATION: n is unknown
<220> FEATURE:
<221> NAME/KEY: misc_feature
<222> LOCATION: (69)..(70)
<223> OTHER INFORMATION: n is unknown
<220> FEATURE:
<221> NAME/KEY: misc_feature
<222> LOCATION: (758)..(769)
<223> OTHER INFORMATION: n is unknown
<220> FEATURE:
<221> NAME/KEY: misc_feature
<222> LOCATION: (823)..(828)
<223> OTHER INFORMATION: n is unknown
<220> FEATURE:
<221> NAME/KEY: misc_feature
<222> LOCATION: (841)..(842)
<223> OTHER INFORMATION: n is unknown
<220> FEATURE:
<221> NAME/KEY: misc_feature
<222> LOCATION: (844)..(844)
<223> OTHER INFORMATION: n is unknown

<400> SEQUENCE: 33

```
nnngcngccn ggttntgatt actgttaatg ttgctactac tgctgacaat gctgctgctg    60
cttctcctnn ctgtctccac ttccttgaac aatgcgccgt catgcttctt ttgcctcccg   120
ctgctccaga aagctaggcc gcagatcaga accaccacag tcaatatcac caccttcctc   180
ttatagattc ggaatctcat gatagggct cagcctctgt gcgagtggag agaagtttgc    240
aggcgagctg aggagcaatt gcaggtgata tgatgtgctc ggctcaagaa gcgggcccgg   300
agaggaagaa gtcgtgccgg ggctaattat tggcaaaacg agctcttgtt gtaaacattg   360
atccaactgg aatgtcacta atggcgaatc aatattccat aaggcatgat ggttgctcag   420
aggcaggaga agagcaacga atacgatcct ataaaagata aaacataaat aaacagtctt   480
gattatattc tgggtattaa agccacaatc agaacaaata tatgctttgt atcttttctt   540
gccttcttca ttaccaactg cttccgcggc cacattaaga gaacttgtgg taagataaga   600 agatattta ttcgttctgc tgacttgctg gatgtcggga aatattctgc atttgataag    660
aggcggttaa ttgcagatat aattggtagt gaaaagggtc gttgctatgg tcaccgtgaa   720
gcgagtacag cagcacaaga atgtgtgccg ttctcagnnn nnnnnnnng aatatggtaa    780 cctgttttag tcggtttaaa ggtaagaaga tctaaccaaa aannnnnntg cagtgactga   840
nngnagtatt tattttttta cttaa                                         865

<210> SEQ ID NO 34
<211> LENGTH: 818
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (1)..(3)
<223> OTHER INFORMATION: n is unknown
<220> FEATURE:
<221> NAME/KEY: misc_feature
<222> LOCATION: (10)..(10)
<223> OTHER INFORMATION: n is unknown
<220> FEATURE:
<221> NAME/KEY: misc_feature
<222> LOCATION: (14)..(14)
<223> OTHER INFORMATION: n is unknown
<220> FEATURE:
<221> NAME/KEY: misc_feature
<222> LOCATION: (20)..(24)
<223> OTHER INFORMATION: n is unknown
<220> FEATURE:
<221> NAME/KEY: misc_feature
<222> LOCATION: (62)..(62)
<223> OTHER INFORMATION: n is unknown
<220> FEATURE:
<221> NAME/KEY: misc_feature
<222> LOCATION: (64)..(65)
<223> OTHER INFORMATION: n is unknown
<220> FEATURE:
<221> NAME/KEY: misc_feature
<222> LOCATION: (753)..(755)
<223> OTHER INFORMATION: n is unknown
<220> FEATURE:
<221> NAME/KEY: misc_feature
<222> LOCATION: (757)..(757)
<223> OTHER INFORMATION: n is unknown
<220> FEATURE:
<221> NAME/KEY: misc_feature
<222> LOCATION: (759)..(764)
<223> OTHER INFORMATION: n is unknown
<220> FEATURE:
<221> NAME/KEY: misc_feature
<222> LOCATION: (794)..(794)
<223> OTHER INFORMATION: n is unknown
<220> FEATURE:
<221> NAME/KEY: misc_feature
<222> LOCATION: (796)..(799)
```

```
<223> OTHER INFORMATION: n is unknown
<220> FEATURE:
<221> NAME/KEY: misc_feature
<222> LOCATION: (813)..(814)
<223> OTHER INFORMATION: n is unknown

<400> SEQUENCE: 34
nnnctggttn tgantactgn nnnngttgct actactgctg acaatgctgc tgctgcttct      60
cntnnctgtc tccacttcct tgaacaatgc gccgtcatgc ttcttttgcc tcccgctgct     120
ccagaaagct aggccgcaga tcagaaccac cacagtcaat atcaccacct tcctcttata     180
gattcggaat ctcatgatag gggctcagcc tctgtgcgag tggagagaag tttgcaggcg     240
agctgaggag caattgcagg tgatatgatg tgctcggctc aagaagcggg cccggagagg     300
aagaagtcgt gccggggcta attattggca aaacgagctc ttgttgtaaa cattgatcca     360
actggaatgt cactaatggc gaatcaatat tccataaggc atgatggttg ctcagaggca     420
ggagaagagc aacgaatacg atcctataaa agataaaaca taaataaaca gtcttgatta     480
tattctgggt attaaagcca caatcagaac aaatatatgc tttgtatctt tcttgccttt     540
cttcattacc aactgcttcc gcggccacat taagagaact tgtggtaaga taagaagata     600
ttttattcgt tctgctgact tgctggatgt cgggaaatat tctgcatttg ataagaggcg     660
gttaattgca gatataattg gtagtgaaaa gggtcgttgc tatggtcacc gtgaagcgag     720
tacagcagca caagaatgtg tgccgttctc agnnngnann nnnngaatat ggtaacctgt     780
tttagtcggt ttanannnna gaagatctaa ccnnaaaa                             818

<210> SEQ ID NO 35
<211> LENGTH: 822
<212> TYPE: DNA
<213> ORGANISM: Artificial Sequence
<220> FEATURE:
<223> OTHER INFORMATION: S. aureus PCR reaction /DNA sequence standard
<220> FEATURE:
<221> NAME/KEY: misc_feature
<222> LOCATION: (1)..(4)
<223> OTHER INFORMATION: n is unknown
<220> FEATURE:
<221> NAME/KEY: misc_feature
<222> LOCATION: (11)..(11)
<223> OTHER INFORMATION: n is unknown
<220> FEATURE:
<221> NAME/KEY: misc_feature
<222> LOCATION: (15)..(15)
<223> OTHER INFORMATION: n is unknown
<220> FEATURE:
<221> NAME/KEY: misc_feature
<222> LOCATION: (25)..(25)
<223> OTHER INFORMATION: n is unknown
<220> FEATURE:
<221> NAME/KEY: misc_feature
<222> LOCATION: (66)..(66)
<223> OTHER INFORMATION: n is unknown
<220> FEATURE:
<221> NAME/KEY: misc_feature
<222> LOCATION: (353)..(353)
<223> OTHER INFORMATION: n is unknown
<220> FEATURE:
<221> NAME/KEY: misc_feature
<222> LOCATION: (357)..(357)
<223> OTHER INFORMATION: n is unknown
<220> FEATURE:
<221> NAME/KEY: misc_feature
<222> LOCATION: (359)..(359)
<223> OTHER INFORMATION: n is unknown
<220> FEATURE:
<221> NAME/KEY: misc_feature
<222> LOCATION: (754)..(765)
<223> OTHER INFORMATION: n is unknown
<220> FEATURE:
```

<221> NAME/KEY: misc_feature
<222> LOCATION: (781)..(781)
<223> OTHER INFORMATION: n is unknown
<220> FEATURE:
<221> NAME/KEY: misc_feature
<222> LOCATION: (791)..(791)
<223> OTHER INFORMATION: n is unknown
<220> FEATURE:
<221> NAME/KEY: misc_feature
<222> LOCATION: (817)..(817)
<223> OTHER INFORMATION: n is unknown
<220> FEATURE:
<221> NAME/KEY: misc_feature
<222> LOCATION: (821)..(822)
<223> OTHER INFORMATION: n is unknown

<400> SEQUENCE: 35

```
nnnnctggtt ntgantactg ttaangttgc tactactgct gacaatgctg ctgctgcttc      60
tcctcnctgt ctccacttcc ttgaacaatg cgccgtcatg cttcttttgc ctcccgctgc     120
tccagaaagc taggccgcag atcagaacca ccacagtcaa tatcaccacc ttcctcttat     180
agattcggaa tctcatgata ggggctcagc ctctgtgcga gtggagagaa gtttgcaggc     240
gagctgagga gcaattgcag gtgatatgat gtgctcggct caagaagcgg gcccggagag     300
gaagaagtcg tgccggggct aattattggc aaaacgagct cttgttgtaa acnttgntnc     360
aactggaatg tcactaatgg cgaatcaata ttccataagg catgatggtt gctcagaggc     420
aggagaagag caacgaatac gatcctataa aagataaaac ataaataaac agtcttgatt     480
atattctggg tattaaagcc acaatcagaa caaatatatg ctttgtatct tttcttgcct     540
tcttcattac caactgcttc cgcggccaca ttaagagaac ttgtggtaag ataagaagat     600
attttattcg ttctgctgac ttgctggatg tcgggaaata ttctgcattt gataagaggc     660
ggttaattgc agatataatt ggtagtgaaa agggtcgttg ctatggtcac cgtgaagcga     720
gtacagcagc acaagaatgt gtgccgttct cagnnnnnnn nnnnngaata tggtaacctg     780
ntttagtcgg nttaaaggta agaagatcta accaaanaca nn                        822
```

<210> SEQ ID NO 36
<211> LENGTH: 844
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (1)..(1)
<223> OTHER INFORMATION: n is unknown
<220> FEATURE:
<221> NAME/KEY: misc_feature
<222> LOCATION: (4)..(4)
<223> OTHER INFORMATION: n is unknown
<220> FEATURE:
<221> NAME/KEY: misc_feature
<222> LOCATION: (16)..(20)
<223> OTHER INFORMATION: n is unknown
<220> FEATURE:
<221> NAME/KEY: misc_feature
<222> LOCATION: (59)..(59)
<223> OTHER INFORMATION: n is unknown
<220> FEATURE:
<221> NAME/KEY: misc_feature
<222> LOCATION: (371)..(380)
<223> OTHER INFORMATION: n is unknown
<220> FEATURE:
<221> NAME/KEY: misc_feature
<222> LOCATION: (498)..(509)
<223> OTHER INFORMATION: n is unknown
<220> FEATURE:
<221> NAME/KEY: misc_feature
<222> LOCATION: (511)..(511)

-continued

```
<223> OTHER INFORMATION: n is unknown
<220> FEATURE:
<221> NAME/KEY: misc_feature
<222> LOCATION: (526)..(529)
<223> OTHER INFORMATION: n is unknown
<220> FEATURE:
<221> NAME/KEY: misc_feature
<222> LOCATION: (588)..(588)
<223> OTHER INFORMATION: n is unknown
<220> FEATURE:
<221> NAME/KEY: misc_feature
<222> LOCATION: (591)..(591)
<223> OTHER INFORMATION: n is unknown
<220> FEATURE:
<221> NAME/KEY: misc_feature
<222> LOCATION: (603)..(609)
<223> OTHER INFORMATION: n is unknown
<220> FEATURE:
<221> NAME/KEY: misc_feature
<222> LOCATION: (674)..(685)
<223> OTHER INFORMATION: n is unknown
<220> FEATURE:
<221> NAME/KEY: misc_feature
<222> LOCATION: (716)..(718)
<223> OTHER INFORMATION: n is unknown
<220> FEATURE:
<221> NAME/KEY: misc_feature
<222> LOCATION: (721)..(726)
<223> OTHER INFORMATION: n is unknown
<220> FEATURE:
<221> NAME/KEY: misc_feature
<222> LOCATION: (730)..(730)
<223> OTHER INFORMATION: n is unknown
<220> FEATURE:
<221> NAME/KEY: misc_feature
<222> LOCATION: (733)..(733)
<223> OTHER INFORMATION: n is unknown
<220> FEATURE:
<221> NAME/KEY: misc_feature
<222> LOCATION: (735)..(735)
<223> OTHER INFORMATION: n is unknown
<220> FEATURE:
<221> NAME/KEY: misc_feature
<222> LOCATION: (738)..(739)
<223> OTHER INFORMATION: n is unknown
<220> FEATURE:
<221> NAME/KEY: misc_feature
<222> LOCATION: (741)..(749)
<223> OTHER INFORMATION: n is unknown
<220> FEATURE:
<221> NAME/KEY: misc_feature
<222> LOCATION: (756)..(756)
<223> OTHER INFORMATION: n is unknown
<220> FEATURE:
<221> NAME/KEY: misc_feature
<222> LOCATION: (767)..(769)
<223> OTHER INFORMATION: n is unknown
<220> FEATURE:
<221> NAME/KEY: misc_feature
<222> LOCATION: (774)..(774)
<223> OTHER INFORMATION: n is unknown
<220> FEATURE:
<221> NAME/KEY: misc_feature
<222> LOCATION: (784)..(784)
<223> OTHER INFORMATION: n is unknown
<220> FEATURE:
<221> NAME/KEY: misc_feature
<222> LOCATION: (807)..(807)
<223> OTHER INFORMATION: n is unknown
<220> FEATURE:
<221> NAME/KEY: misc_feature
<222> LOCATION: (836)..(836)
<223> OTHER INFORMATION: n is unknown
<220> FEATURE:
<221> NAME/KEY: misc_feature
<222> LOCATION: (838)..(844)
<223> OTHER INFORMATION: n is unknown

<400> SEQUENCE: 36
```

```
nttntgatta ctgttnnnnn tgctactact gctgacaatg ctgctgctgc ttctcctcnc      60
tgtctccact tccttgaaca atgcgccgtc atgcttcttt tgcctcccgc tgctccagaa     120
agctaggccg cagatcagaa ccaccacagt caatatcacc accttcctct tatagattcg     180
gaatctcatg atagggctc agcctctgtg cgagtggaga aagtttgca ggcgagctga      240
ggagcaattg caggtgatat gatgtgctcg gctcaagaag cgggcccgga gaggaagaag     300
tcgtgccggg gctaattatt ggcaaaacga gctcttgttg taaacattga tccaactgga     360
atgtcactaa nnnnnnnnnn atattccata aggcatgatg gttgctcaga ggcaggagaa     420
gagcaacgaa tacgatccta taaaagataa aacataaata aacagtcttg attatattct     480
gggtattaaa gccacaannn nnnnnnnnnt ntgctttgta tctttnnnng ccttcttcat     540
taccaactgc ttccgcggcc acattaagag aacttgtggt aagataanaa natattttat     600
tcnnnnnnnt gacttgctgg atgtcgggaa atattctgca tttgataaga ggcggttaat     660
tgcagatata attnnnnnnn nnnnnggtcg ttgctatggt caccgtgaag cgagtnnngc     720
nnnnnnagan tgngnggnng nnnnnnnnna tattgnttga atatggnnnc ctgntttagt     780
cggnttaaag gtaagaagat ctaaccnaaa acaacactgc agtgactgat tgtagnannn     840
nnnn                                                                  844
```

<210> SEQ ID NO 37
<211> LENGTH: 851
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (1)..(6)
<223> OTHER INFORMATION: n is unknown
<220> FEATURE:
<221> NAME/KEY: misc_feature
<222> LOCATION: (11)..(11)
<223> OTHER INFORMATION: n is unknown
<220> FEATURE:
<221> NAME/KEY: misc_feature
<222> LOCATION: (65)..(66)
<223> OTHER INFORMATION: n is unknown
<220> FEATURE:
<221> NAME/KEY: misc_feature
<222> LOCATION: (378)..(388)
<223> OTHER INFORMATION: n is unknown
<220> FEATURE:
<221> NAME/KEY: misc_feature
<222> LOCATION: (504)..(516)
<223> OTHER INFORMATION: n is unknown
<220> FEATURE:
<221> NAME/KEY: misc_feature
<222> LOCATION: (532)..(536)
<223> OTHER INFORMATION: n is unknown
<220> FEATURE:
<221> NAME/KEY: misc_feature
<222> LOCATION: (538)..(538)
<223> OTHER INFORMATION: n is unknown
<220> FEATURE:
<221> NAME/KEY: misc_feature
<222> LOCATION: (540)..(540)
<223> OTHER INFORMATION: n is unknown
<220> FEATURE:
<221> NAME/KEY: misc_feature
<222> LOCATION: (610)..(616)
<223> OTHER INFORMATION: n is unknown
<220> FEATURE:
<221> NAME/KEY: misc_feature
<222> LOCATION: (683)..(692)
<223> OTHER INFORMATION: n is unknown
<220> FEATURE:
<221> NAME/KEY: misc_feature
<222> LOCATION: (694)..(694)

```
<223> OTHER INFORMATION: n is unknown
<220> FEATURE:
<221> NAME/KEY: misc_feature
<222> LOCATION: (744)..(755)
<223> OTHER INFORMATION: n is unknown
<220> FEATURE:
<221> NAME/KEY: misc_feature
<222> LOCATION: (763)..(763)
<223> OTHER INFORMATION: n is unknown
<220> FEATURE:
<221> NAME/KEY: misc_feature
<222> LOCATION: (814)..(814)
<223> OTHER INFORMATION: n is unknown
<220> FEATURE:
<221> NAME/KEY: misc_feature
<222> LOCATION: (820)..(820)
<223> OTHER INFORMATION: n is unknown
<220> FEATURE:
<221> NAME/KEY: misc_feature
<222> LOCATION: (840)..(840)
<223> OTHER INFORMATION: n is unknown
<220> FEATURE:
<221> NAME/KEY: misc_feature
<222> LOCATION: (846)..(851)
<223> OTHER INFORMATION: n is unknown

<400> SEQUENCE: 37
nnnnnnggtt ntgattactg ttaatgttgc tactactgct gacaatgctg ctgctgcttc      60
tcctnnctgt ctccacttcc ttgaacaatg cgccgtcatg cttcttttgc ctcccgctgc     120
tccagaaagc taggccgcag atcagaacca ccacagtcaa tatcaccacc ttcctcttat    180
agattcggaa tctcatgata ggggctcagc ctctgtgcga gtggagagaa gtttgcaggc    240
gagctgagga gcaattgcag gtgatatgat gtgctcggct caagaagcgg gcccggagag    300
gaagaagtcg tgccggggct aattattggc aaaacgagct cttgttgtaa acattgatcc    360
aactggaatg tcactaannn nnnnnnnnta ttccataagg catgatggtt gctcagaggc    420
aggagaagag caacgaatac gatcctataa aagataaaac ataaataaac agtcttgatt    480
atattctggg tattaaagcc acannnnnnn nnnnnntatg ctttgtatct tnnnnngncn    540
tcttcattac caactgcttc cgcggccaca ttaagagaac ttgtggtaag ataagaagat    600
attttattcn nnnnnntgac ttgctggatg tcgggaaata ttctgcattt gataagaggc    660
ggttaattgc agatataatt ggnnnnnnnn nngntcgttg ctatggtcac cgtgaagcga    720
gtacagcagc acaagaatgt gtgnnnnnnn nnnnnaatat tgnttgaata tggtaacctg    780
ttttagtcgg tttaaaggta agaagatcta accnaaaacn acactgcagt gactgattgn    840
agtatnnnnn n                                                         851

<210> SEQ ID NO 38
<211> LENGTH: 890
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (4)..(7)
<223> OTHER INFORMATION: n is unknown
<220> FEATURE:
<221> NAME/KEY: misc_feature
<222> LOCATION: (18)..(21)
<223> OTHER INFORMATION: n is unknown
<220> FEATURE:
<221> NAME/KEY: misc_feature
<222> LOCATION: (61)..(62)
<223> OTHER INFORMATION: n is unknown
<220> FEATURE:
<221> NAME/KEY: misc_feature
<222> LOCATION: (374)..(381)
```

```
<223> OTHER INFORMATION: n is unknown
<220> FEATURE:
<221> NAME/KEY: misc_feature
<222> LOCATION: (383)..(383)
<223> OTHER INFORMATION: n is unknown
<220> FEATURE:
<221> NAME/KEY: misc_feature
<222> LOCATION: (416)..(416)
<223> OTHER INFORMATION: n is unknown
<220> FEATURE:
<221> NAME/KEY: misc_feature
<222> LOCATION: (499)..(507)
<223> OTHER INFORMATION: n is unknown
<220> FEATURE:
<221> NAME/KEY: misc_feature
<222> LOCATION: (510)..(511)
<223> OTHER INFORMATION: n is unknown
<220> FEATURE:
<221> NAME/KEY: misc_feature
<222> LOCATION: (527)..(531)
<223> OTHER INFORMATION: n is unknown
<220> FEATURE:
<221> NAME/KEY: misc_feature
<222> LOCATION: (533)..(533)
<223> OTHER INFORMATION: n is unknown
<220> FEATURE:
<221> NAME/KEY: misc_feature
<222> LOCATION: (605)..(611)
<223> OTHER INFORMATION: n is unknown
<220> FEATURE:
<221> NAME/KEY: misc_feature
<222> LOCATION: (678)..(679)
<223> OTHER INFORMATION: n is unknown
<220> FEATURE:
<221> NAME/KEY: misc_feature
<222> LOCATION: (682)..(687)
<223> OTHER INFORMATION: n is unknown
<220> FEATURE:
<221> NAME/KEY: misc_feature
<222> LOCATION: (689)..(690)
<223> OTHER INFORMATION: n is unknown
<220> FEATURE:
<221> NAME/KEY: misc_feature
<222> LOCATION: (720)..(721)
<223> OTHER INFORMATION: n is unknown
<220> FEATURE:
<221> NAME/KEY: misc_feature
<222> LOCATION: (739)..(749)
<223> OTHER INFORMATION: n is unknown
<220> FEATURE:
<221> NAME/KEY: misc_feature
<222> LOCATION: (756)..(756)
<223> OTHER INFORMATION: n is unknown
<220> FEATURE:
<221> NAME/KEY: misc_feature
<222> LOCATION: (786)..(786)
<223> OTHER INFORMATION: n is unknown
<220> FEATURE:
<221> NAME/KEY: misc_feature
<222> LOCATION: (829)..(835)
<223> OTHER INFORMATION: n is unknown
<220> FEATURE:
<221> NAME/KEY: misc_feature
<222> LOCATION: (841)..(846)
<223> OTHER INFORMATION: n is unknown
<220> FEATURE:
<221> NAME/KEY: misc_feature
<222> LOCATION: (856)..(860)
<223> OTHER INFORMATION: n is unknown
<220> FEATURE:
<221> NAME/KEY: misc_feature
<222> LOCATION: (865)..(865)
<223> OTHER INFORMATION: n is unknown
<220> FEATURE:
<221> NAME/KEY: misc_feature
<222> LOCATION: (880)..(880)
<223> OTHER INFORMATION: n is unknown

<400> SEQUENCE: 38
```

```
ctgnnnntga ttactgtnnn ngttgctact actgctgaca atgctgctgc tgcttctcct    60
nnctgtctcc acttccttga acaatgcgcc gtcatgcttc ttttgcctcc cgctgctcca   120
gaaagctagg ccgcagatca gaaccaccac agtcaatatc accaccttcc tcttatagat   180
tcggaatctc atgatagggg ctcagcctct gtgcgagtgg agagaagttt gcaggcgagc   240
tgaggagcaa ttgcaggtga tatgatgtgc tcggctcaag aagcgggccc ggagaggaag   300
aagtcgtgcc ggggctaatt attggcaaaa cgagctcttg ttgtaaacat tgatccaact   360
ggaatgtcac taannnnnnn nantattcca taaggcatga tggttgctca gaggcnggag   420
aagagcaacg aatacgatcc tataaaagat aaaacataaa taaacagtct tgattatatt   480
ctgggtatta aagccacann nnnnnnngan ntatgctttg tatcttnnnn ngncttcttc   540
attaccaact gcttccgcgg ccacattaag agaacttgtg gtaagataag aagatatttt   600
attcnnnnnn ntgacttgct ggatgtcggg aaatattctg catttgataa gaggcggtta   660
attgcagata taattggnng tnnnnnngnn cgttgctatg gtcaccgtga agcgagtacn   720
ncagcacaag aatgtgtgnn nnnnnnnnt aatatngttt gaatatggta acctgtttta   780
gtcggnttaa aggtaagaag atctaaccaa aaacaacact gcagtgacnn nnnnnagtat   840
nnnnnntttt acttannnnn aattntggtg taaacatcan cggcgcactt              890
```

<210> SEQ ID NO 39
<211> LENGTH: 875
<212> TYPE: DNA
<213> ORGANISM: Artificial Sequence
<220> FEATURE:
<223> OTHER INFORMATION: S. enterica PCR reaction /DNA sequence standard
<220> FEATURE:
<221> NAME/KEY: misc_feature
<222> LOCATION: (1)..(6)
<223> OTHER INFORMATION: n is unknown
<220> FEATURE:
<221> NAME/KEY: misc_feature
<222> LOCATION: (13)..(13)
<223> OTHER INFORMATION: n is unknown
<220> FEATURE:
<221> NAME/KEY: misc_feature
<222> LOCATION: (18)..(18)
<223> OTHER INFORMATION: n is unknown
<220> FEATURE:
<221> NAME/KEY: misc_feature
<222> LOCATION: (68)..(69)
<223> OTHER INFORMATION: n is unknown
<220> FEATURE:
<221> NAME/KEY: misc_feature
<222> LOCATION: (381)..(388)
<223> OTHER INFORMATION: n is unknown
<220> FEATURE:
<221> NAME/KEY: misc_feature
<222> LOCATION: (507)..(507)
<223> OTHER INFORMATION: n is unknown
<220> FEATURE:
<221> NAME/KEY: misc_feature
<222> LOCATION: (509)..(509)
<223> OTHER INFORMATION: n is unknown
<220> FEATURE:
<221> NAME/KEY: misc_feature
<222> LOCATION: (511)..(515)
<223> OTHER INFORMATION: n is unknown
<220> FEATURE:
<221> NAME/KEY: misc_feature
<222> LOCATION: (517)..(518)
<223> OTHER INFORMATION: n is unknown
<220> FEATURE:
<221> NAME/KEY: misc_feature
<222> LOCATION: (534)..(540)
<223> OTHER INFORMATION: n is unknown
<220> FEATURE:
<221> NAME/KEY: misc_feature
<222> LOCATION: (597)..(597)

```
<223> OTHER INFORMATION: n is unknown
<220> FEATURE:
<221> NAME/KEY: misc_feature
<222> LOCATION: (599)..(600)
<223> OTHER INFORMATION: n is unknown
<220> FEATURE:
<221> NAME/KEY: misc_feature
<222> LOCATION: (602)..(603)
<223> OTHER INFORMATION: n is unknown
<220> FEATURE:
<221> NAME/KEY: misc_feature
<222> LOCATION: (613)..(616)
<223> OTHER INFORMATION: n is unknown
<220> FEATURE:
<221> NAME/KEY: misc_feature
<222> LOCATION: (618)..(618)
<223> OTHER INFORMATION: n is unknown
<220> FEATURE:
<221> NAME/KEY: misc_feature
<222> LOCATION: (665)..(665)
<223> OTHER INFORMATION: n is unknown
<220> FEATURE:
<221> NAME/KEY: misc_feature
<222> LOCATION: (685)..(686)
<223> OTHER INFORMATION: n is unknown
<220> FEATURE:
<221> NAME/KEY: misc_feature
<222> LOCATION: (689)..(694)
<223> OTHER INFORMATION: n is unknown
<220> FEATURE:
<221> NAME/KEY: misc_feature
<222> LOCATION: (746)..(747)
<223> OTHER INFORMATION: n is unknown
<220> FEATURE:
<221> NAME/KEY: misc_feature
<222> LOCATION: (749)..(756)
<223> OTHER INFORMATION: n is unknown
<220> FEATURE:
<221> NAME/KEY: misc_feature
<222> LOCATION: (847)..(853)
<223> OTHER INFORMATION: n is unknown

<400> SEQUENCE: 39
nnnnnncctg gtnatganta ctgttaatgt tgctactact gctgacaatg ctgctgctgc        60
ttctcctnnc tgtctccact tccttgaaca atgcgccgtc atgcttcttt tgcctcccgc       120
tgctccagaa agctaggccg cagatcagaa ccaccacagt caatatcacc accttcctct       180
tatagattcg gaatctcatg atagggctc agcctctgtg cgagtggaga gaagtttgca       240
ggcgagctga ggagcaattg caggtgatat gatgtgctcg gctcaagaag cgggcccgga       300
gaggaagaag tcgtgccggg gctaattatt ggcaaaacga gctcttgttg taaacattga       360
tccaactgga atgtcactaa nnnnnnnnaa tattccataa ggcatgatgg ttgctcagag       420
gcaggagaag agcaacgaat acgatcctat aaaagataaa acataaataa acagtcttga       480
ttatattctg ggtattaaag ccacaangng nnnnnannta tgctttgtat cttnnnnnnn       540
cttcttcatt accaactgct tccgcggcca cattaagaga acttgtggta agataanann       600
annttttatt cgnnnngntg acttgctgga tgtcggaaaa tattctgcat ttgataagag       660
gcggntaatt gcagatataa ttggnngtnn nnnnggtcgt tgctatggtc accgtgaagc       720
gagtacagca gcacaagaat gtgtgnngnn nnnnnntaat attgtttgaa tatggtaacc       780
tgttttagtc ggtttaaagg taagaagatc taaccaaaaa caacactgca gtgactgatt       840
gtagtannnn nnntttttact taatcttaat tttgg                                875

<210> SEQ ID NO 40
<211> LENGTH: 838
<212> TYPE: DNA
<213> ORGANISM: Artificial Sequence
<220> FEATURE:
```

```
<223> OTHER INFORMATION: S. enterica PCR reaction /DNA sequence standard
<220> FEATURE:
<221> NAME/KEY: misc_feature
<222> LOCATION: (1)..(5)
<223> OTHER INFORMATION: n is unknown
<220> FEATURE:
<221> NAME/KEY: misc_feature
<222> LOCATION: (9)..(9)
<223> OTHER INFORMATION: n is unknown
<220> FEATURE:
<221> NAME/KEY: misc_feature
<222> LOCATION: (58)..(58)
<223> OTHER INFORMATION: n is unknown
<220> FEATURE:
<221> NAME/KEY: misc_feature
<222> LOCATION: (370)..(378)
<223> OTHER INFORMATION: n is unknown
<220> FEATURE:
<221> NAME/KEY: misc_feature
<222> LOCATION: (496)..(504)
<223> OTHER INFORMATION: n is unknown
<220> FEATURE:
<221> NAME/KEY: misc_feature
<222> LOCATION: (507)..(508)
<223> OTHER INFORMATION: n is unknown
<220> FEATURE:
<221> NAME/KEY: misc_feature
<222> LOCATION: (530)..(530)
<223> OTHER INFORMATION: n is unknown
<220> FEATURE:
<221> NAME/KEY: misc_feature
<222> LOCATION: (603)..(604)
<223> OTHER INFORMATION: n is unknown
<220> FEATURE:
<221> NAME/KEY: misc_feature
<222> LOCATION: (606)..(608)
<223> OTHER INFORMATION: n is unknown
<220> FEATURE:
<221> NAME/KEY: misc_feature
<222> LOCATION: (675)..(676)
<223> OTHER INFORMATION: n is unknown
<220> FEATURE:
<221> NAME/KEY: misc_feature
<222> LOCATION: (679)..(684)
<223> OTHER INFORMATION: n is unknown
<220> FEATURE:
<221> NAME/KEY: misc_feature
<222> LOCATION: (735)..(746)
<223> OTHER INFORMATION: n is unknown
<220> FEATURE:
<221> NAME/KEY: misc_feature
<222> LOCATION: (806)..(806)
<223> OTHER INFORMATION: n is unknown
<220> FEATURE:
<221> NAME/KEY: misc_feature
<222> LOCATION: (832)..(833)
<223> OTHER INFORMATION: n is unknown
<220> FEATURE:
<221> NAME/KEY: misc_feature
<222> LOCATION: (835)..(835)
<223> OTHER INFORMATION: n is unknown
<220> FEATURE:
<221> NAME/KEY: misc_feature
<222> LOCATION: (837)..(838)
<223> OTHER INFORMATION: n is unknown

<400> SEQUENCE: 40
nnnnnattnc tgttaatgtt gctactactg ctgacaatgc tgctgctgct tctcctcnct      60
gtctccactt ccttgaacaa tgcgccgtca tgcttctttt gcctcccgct gctccagaaa     120
gctaggccgc agatcagaac caccacagtc aatatcacca ccttcctctt atagattcgg     180
aatctcatga tagggctca gcctctgtgc gagtggagag aagtttgcag gcgagctgag      240
gagcaattgc aggtgatatg atgtgctcgg ctcaagaagc gggcccggag aggaagaagt     300
cgtgccgggg ctaattattg gcaaaacgag ctcttgttgt aaacattgat ccaactggaa     360
```

```
tgtcactaan nnnnnnnnaa tattccataa ggcatgatgg ttgctcagag gcaggagaag    420
agcaacgaat acgatcctat aaaagataaa acataaataa acagtcttga ttatattctg    480
ggtattaaag ccacannnnn nnnngannta tgctttgtat cttttcttgn cttcttcatt    540
accaactgct tccgcggcca cattaagaga acttgtggta agataagaag atattttatt    600
cgnncnnntg acttgctgga tgtcgggaaa tattctgcat ttgataagag gcggttaatt    660
gcagatataa ttggnngtnn nnnnggtcgt tgctatggtc accgtgaagc gagtacagca    720
gcacaagaat gtgtnnnnnn nnnnnntaat attgttgaa tatggtaacc tgttttagtc    780
ggtttaaagg taagaagatc taaccnaaaa caacactgca gtgactgatt gnngnann    838
```

```
<210> SEQ ID NO 41
<211> LENGTH: 865
<212> TYPE: DNA
<213> ORGANISM: Artificial Sequence
<220> FEATURE:
<223> OTHER INFORMATION: S. cerevisiae PCR reaction /DNA sequence
      standard
<220> FEATURE:
<221> NAME/KEY: misc_feature
<222> LOCATION: (1)..(5)
<223> OTHER INFORMATION: n is unknown
<220> FEATURE:
<221> NAME/KEY: misc_feature
<222> LOCATION: (8)..(9)
<223> OTHER INFORMATION: n is unknown
<220> FEATURE:
<221> NAME/KEY: misc_feature
<222> LOCATION: (15)..(15)
<223> OTHER INFORMATION: n is unknown
<220> FEATURE:
<221> NAME/KEY: misc_feature
<222> LOCATION: (24)..(24)
<223> OTHER INFORMATION: n is unknown
<220> FEATURE:
<221> NAME/KEY: misc_feature
<222> LOCATION: (58)..(59)
<223> OTHER INFORMATION: n is unknown
<220> FEATURE:
<221> NAME/KEY: misc_feature
<222> LOCATION: (244)..(246)
<223> OTHER INFORMATION: n is unknown
<220> FEATURE:
<221> NAME/KEY: misc_feature
<222> LOCATION: (347)..(355)
<223> OTHER INFORMATION: n is unknown
<220> FEATURE:
<221> NAME/KEY: misc_feature
<222> LOCATION: (359)..(359)
<223> OTHER INFORMATION: n is unknown
<220> FEATURE:
<221> NAME/KEY: misc_feature
<222> LOCATION: (378)..(381)
<223> OTHER INFORMATION: n is unknown
<220> FEATURE:
<221> NAME/KEY: misc_feature
<222> LOCATION: (383)..(387)
<223> OTHER INFORMATION: n is unknown
<220> FEATURE:
<221> NAME/KEY: misc_feature
<222> LOCATION: (393)..(394)
<223> OTHER INFORMATION: n is unknown
<220> FEATURE:
<221> NAME/KEY: misc_feature
<222> LOCATION: (424)..(426)
<223> OTHER INFORMATION: n is unknown
<220> FEATURE:
<221> NAME/KEY: misc_feature
<222> LOCATION: (428)..(428)
<223> OTHER INFORMATION: n is unknown
<220> FEATURE:
<221> NAME/KEY: misc_feature
<222> LOCATION: (433)..(437)
<223> OTHER INFORMATION: n is unknown
```

```
<220> FEATURE:
<221> NAME/KEY: misc_feature
<222> LOCATION: (493)..(493)
<223> OTHER INFORMATION: n is unknown
<220> FEATURE:
<221> NAME/KEY: misc_feature
<222> LOCATION: (499)..(500)
<223> OTHER INFORMATION: n is unknown
<220> FEATURE:
<221> NAME/KEY: misc_feature
<222> LOCATION: (502)..(503)
<223> OTHER INFORMATION: n is unknown
<220> FEATURE:
<221> NAME/KEY: misc_feature
<222> LOCATION: (533)..(550)
<223> OTHER INFORMATION: n is unknown
<220> FEATURE:
<221> NAME/KEY: misc_feature
<222> LOCATION: (602)..(608)
<223> OTHER INFORMATION: n is unknown
<220> FEATURE:
<221> NAME/KEY: misc_feature
<222> LOCATION: (611)..(616)
<223> OTHER INFORMATION: n is unknown
<220> FEATURE:
<221> NAME/KEY: misc_feature
<222> LOCATION: (659)..(659)
<223> OTHER INFORMATION: n is unknown
<220> FEATURE:
<221> NAME/KEY: misc_feature
<222> LOCATION: (674)..(684)
<223> OTHER INFORMATION: n is unknown
<220> FEATURE:
<221> NAME/KEY: misc_feature
<222> LOCATION: (720)..(728)
<223> OTHER INFORMATION: n is unknown
<220> FEATURE:
<221> NAME/KEY: misc_feature
<222> LOCATION: (799)..(799)
<223> OTHER INFORMATION: n is unknown
<220> FEATURE:
<221> NAME/KEY: misc_feature
<222> LOCATION: (832)..(832)
<223> OTHER INFORMATION: n is unknown
<220> FEATURE:
<221> NAME/KEY: misc_feature
<222> LOCATION: (835)..(835)
<223> OTHER INFORMATION: n is unknown
<220> FEATURE:
<221> NAME/KEY: misc_feature
<222> LOCATION: (837)..(837)
<223> OTHER INFORMATION: n is unknown
<220> FEATURE:
<221> NAME/KEY: misc_feature
<222> LOCATION: (860)..(860)
<223> OTHER INFORMATION: n is unknown
<220> FEATURE:
<221> NAME/KEY: misc_feature
<222> LOCATION: (863)..(864)
<223> OTHER INFORMATION: n is unknown

<400> SEQUENCE: 41
nnnnnatnnc tgttnatgtt gctnctactg ctgacaatgc tgctgctgct tctcctcnnt      60
gtctccactt ccttgaacaa tgcgccgtca tgcttctttt gcctcccgct gctccagaaa     120
gctaggccgc agatcagaac caccacagtc aatatcacca ccttcctctt atagattcgg     180
aatctcatga taggggctca gcctctgtgc gagtggagag aagtttgcag gcgagctgag     240
gagnnnttgc aggtgatatg atgtgctcgg ctcaagaagc gggcccggag aggaagaagt     300
cgtgccgggg ctaattattg gcaaaacgag ctcttgttgt aaacatnnnn nnnnntgna     360 tgtcactaat ggcgaatnnn nannnnntaa ggnntgatgg ttgctcagag gcaggagaag     420
agcnnngnat acnnnnntat aaaagataaa acataaataa acagtcttga ttatattctg     480
ggtattaaag ccncaatcnn annaaatata tgctttgtat cttttcttgc ctnnnnnnnn     540
```

```
nnnnnnnnnn tccgcggcca cattaagaga acttgtggta agataagaag atattttatt    600
cnnnnnnntg nnnnnntgga tgtcgggaaa tattctgcat ttgataagag gcggttaant    660
gcagatataa ttgnnnnnnn nnnnggtcgt tgctatggtc accgtgaagc gagtacagcn    720
nnnnnnnnat gtgtgccgtt ctcagttaat attgtttgaa tatggtaacc tgttttagtc    780
ggtttaaagg taagaaganc taaccaaaaa caacactgca gtgactgatt gnagnantta    840 ttttttact taatcttaan ttnng                                            865
```

```
<210> SEQ ID NO 42
<211> LENGTH: 888
<212> TYPE: DNA
<213> ORGANISM: Artificial Sequence
<220> FEATURE:
<223> OTHER INFORMATION: S. cerevisiae PCR reaction /DNA sequence
      standard
<220> FEATURE:
<221> NAME/KEY: misc_feature
<222> LOCATION: (1)..(1)
<223> OTHER INFORMATION: n is unknown
<220> FEATURE:
<221> NAME/KEY: misc_feature
<222> LOCATION: (4)..(5)
<223> OTHER INFORMATION: n is unknown
<220> FEATURE:
<221> NAME/KEY: misc_feature
<222> LOCATION: (19)..(20)
<223> OTHER INFORMATION: n is unknown
<220> FEATURE:
<221> NAME/KEY: misc_feature
<222> LOCATION: (22)..(23)
<223> OTHER INFORMATION: n is unknown
<220> FEATURE:
<221> NAME/KEY: misc_feature
<222> LOCATION: (25)..(25)
<223> OTHER INFORMATION: n is unknown
<220> FEATURE:
<221> NAME/KEY: misc_feature
<222> LOCATION: (58)..(59)
<223> OTHER INFORMATION: n is unknown
<220> FEATURE:
<221> NAME/KEY: misc_feature
<222> LOCATION: (348)..(357)
<223> OTHER INFORMATION: n is unknown
<220> FEATURE:
<221> NAME/KEY: misc_feature
<222> LOCATION: (380)..(386)
<223> OTHER INFORMATION: n is unknown
<220> FEATURE:
<221> NAME/KEY: misc_feature
<222> LOCATION: (388)..(388)
<223> OTHER INFORMATION: n is unknown
<220> FEATURE:
<221> NAME/KEY: misc_feature
<222> LOCATION: (394)..(396)
<223> OTHER INFORMATION: n is unknown
<220> FEATURE:
<221> NAME/KEY: misc_feature
<222> LOCATION: (398)..(398)
<223> OTHER INFORMATION: n is unknown
<220> FEATURE:
<221> NAME/KEY: misc_feature
<222> LOCATION: (425)..(427)
<223> OTHER INFORMATION: n is unknown
<220> FEATURE:
<221> NAME/KEY: misc_feature
<222> LOCATION: (429)..(429)
<223> OTHER INFORMATION: n is unknown
<220> FEATURE:
<221> NAME/KEY: misc_feature
<222> LOCATION: (435)..(438)
<223> OTHER INFORMATION: n is unknown
<220> FEATURE:
<221> NAME/KEY: misc_feature
<222> LOCATION: (534)..(551)
```

```
<223> OTHER INFORMATION: n is unknown
<220> FEATURE:
<221> NAME/KEY: misc_feature
<222> LOCATION: (580)..(580)
<223> OTHER INFORMATION: n is unknown
<220> FEATURE:
<221> NAME/KEY: misc_feature
<222> LOCATION: (603)..(609)
<223> OTHER INFORMATION: n is unknown
<220> FEATURE:
<221> NAME/KEY: misc_feature
<222> LOCATION: (611)..(617)
<223> OTHER INFORMATION: n is unknown
<220> FEATURE:
<221> NAME/KEY: misc_feature
<222> LOCATION: (660)..(660)
<223> OTHER INFORMATION: n is unknown
<220> FEATURE:
<221> NAME/KEY: misc_feature
<222> LOCATION: (718)..(720)
<223> OTHER INFORMATION: n is unknown
<220> FEATURE:
<221> NAME/KEY: misc_feature
<222> LOCATION: (722)..(729)
<223> OTHER INFORMATION: n is unknown
<220> FEATURE:
<221> NAME/KEY: misc_feature
<222> LOCATION: (797)..(798)
<223> OTHER INFORMATION: n is unknown
<220> FEATURE:
<221> NAME/KEY: misc_feature
<222> LOCATION: (800)..(801)
<223> OTHER INFORMATION: n is unknown
<220> FEATURE:
<221> NAME/KEY: misc_feature
<222> LOCATION: (831)..(831)
<223> OTHER INFORMATION: n is unknown
<220> FEATURE:
<221> NAME/KEY: misc_feature
<222> LOCATION: (833)..(833)
<223> OTHER INFORMATION: n is unknown
<220> FEATURE:
<221> NAME/KEY: misc_feature
<222> LOCATION: (864)..(864)
<223> OTHER INFORMATION: n is unknown
<220> FEATURE:
<221> NAME/KEY: misc_feature
<222> LOCATION: (866)..(867)
<223> OTHER INFORMATION: n is unknown
<220> FEATURE:
<221> NAME/KEY: misc_feature
<222> LOCATION: (869)..(869)
<223> OTHER INFORMATION: n is unknown
<220> FEATURE:
<221> NAME/KEY: misc_feature
<222> LOCATION: (878)..(878)
<223> OTHER INFORMATION: n is unknown
<220> FEATURE:
<221> NAME/KEY: misc_feature
<222> LOCATION: (882)..(884)
<223> OTHER INFORMATION: n is unknown
<220> FEATURE:
<221> NAME/KEY: misc_feature
<222> LOCATION: (886)..(886)
<223> OTHER INFORMATION: n is unknown

<400> SEQUENCE: 42
nttnngatta ctgttaatnn tnntnctact gctgacaatg ctgctgctgc ttctcctnnc    60
tgtctccact tccttgaaca atgcgccgtc atgcttcttt tgcctcccgc tgctccagaa   120
agctaggccg cagatcagaa ccaccacagt caatatcacc accttcctct tatagattcg   180
gaatctcatg atagggggctc agcctctgtg cgagtggaga gaagtttgca ggcgagctga   240
ggagcaattg caggtgatat gatgtgctcg gctcaagaag cgggcccgga gaggaagaag   300
tcgtgccggg gctaattatt ggcaaaacga gctcttgttg taaacatnnn nnnnnnngga   360
```

```
atgtcactaa tggcgaatcn nnnnnncnta aggnnngntg gttgctcaga ggcaggagaa      420
gagcnnngna tacgnnnnta taaaagataa aacataaata aacagtcttg attatattct      480
gggtattaaa gccacaatca gaacaaatat atgctttgta tcttttcttg cctnnnnnnn      540
nnnnnnnnnn ntccgcggcc acattaagag aacttgtggn aagataagaa gatattttat      600
tcnnnnnnnt nnnnnnntgg atgtcgggaa atattctgca tttgataaga ggcggttaan      660
tgcagatata attggtagtg aaaagggtcg ttgctatggt caccgtgaag cgagtacnnn      720
gnnnnnnnna tgtgtgccgt tctcagttaa tattgtttga atatggtaac ctgttttagt      780
cggtttaaag gtaagannan ntaaccaaaa acaacactgc agtgactgat ngnagtattt      840
atttttttac ttaatcttaa tttngnngna aacatcancg gnnngntt               888
```

<210> SEQ ID NO 43
<211> LENGTH: 695
<212> TYPE: DNA
<213> ORGANISM: Artificial Sequence
<220> FEATURE:
<223> OTHER INFORMATION: S. cerevisiae PCR reaction /DNA sequence
      standard
<220> FEATURE:
<221> NAME/KEY: misc_feature
<222> LOCATION: (1)..(3)
<223> OTHER INFORMATION: n is unknown
<220> FEATURE:
<221> NAME/KEY: misc_feature
<222> LOCATION: (6)..(7)
<223> OTHER INFORMATION: n is unknown
<220> FEATURE:
<221> NAME/KEY: misc_feature
<222> LOCATION: (13)..(13)
<223> OTHER INFORMATION: n is unknown
<220> FEATURE:
<221> NAME/KEY: misc_feature
<222> LOCATION: (16)..(16)
<223> OTHER INFORMATION: n is unknown
<220> FEATURE:
<221> NAME/KEY: misc_feature
<222> LOCATION: (71)..(71)
<223> OTHER INFORMATION: n is unknown
<220> FEATURE:
<221> NAME/KEY: misc_feature
<222> LOCATION: (259)..(259)
<223> OTHER INFORMATION: n is unknown
<220> FEATURE:
<221> NAME/KEY: misc_feature
<222> LOCATION: (360)..(372)
<223> OTHER INFORMATION: n is unknown
<220> FEATURE:
<221> NAME/KEY: misc_feature
<222> LOCATION: (374)..(374)
<223> OTHER INFORMATION: n is unknown
<220> FEATURE:
<221> NAME/KEY: misc_feature
<222> LOCATION: (390)..(394)
<223> OTHER INFORMATION: n is unknown
<220> FEATURE:
<221> NAME/KEY: misc_feature
<222> LOCATION: (396)..(400)
<223> OTHER INFORMATION: n is unknown
<220> FEATURE:
<221> NAME/KEY: misc_feature
<222> LOCATION: (406)..(407)
<223> OTHER INFORMATION: n is unknown
<220> FEATURE:
<221> NAME/KEY: misc_feature
<222> LOCATION: (436)..(439)
<223> OTHER INFORMATION: n is unknown
<220> FEATURE:
<221> NAME/KEY: misc_feature
<222> LOCATION: (441)..(441)
<223> OTHER INFORMATION: n is unknown
<220> FEATURE:
<221> NAME/KEY: misc_feature

```
<222> LOCATION: (446)..(451)
<223> OTHER INFORMATION: n is unknown
<220> FEATURE:
<221> NAME/KEY: misc_feature
<222> LOCATION: (546)..(563)
<223> OTHER INFORMATION: n is unknown
<220> FEATURE:
<221> NAME/KEY: misc_feature
<222> LOCATION: (616)..(621)
<223> OTHER INFORMATION: n is unknown
<220> FEATURE:
<221> NAME/KEY: misc_feature
<222> LOCATION: (624)..(629)
<223> OTHER INFORMATION: n is unknown
<220> FEATURE:
<221> NAME/KEY: misc_feature
<222> LOCATION: (663)..(663)
<223> OTHER INFORMATION: n is unknown
<220> FEATURE:
<221> NAME/KEY: misc_feature
<222> LOCATION: (668)..(668)
<223> OTHER INFORMATION: n is unknown
<220> FEATURE:
<221> NAME/KEY: misc_feature
<222> LOCATION: (672)..(672)
<223> OTHER INFORMATION: n is unknown
<220> FEATURE:
<221> NAME/KEY: misc_feature
<222> LOCATION: (675)..(675)
<223> OTHER INFORMATION: n is unknown
<220> FEATURE:
<221> NAME/KEY: misc_feature
<222> LOCATION: (677)..(677)
<223> OTHER INFORMATION: n is unknown
<220> FEATURE:
<221> NAME/KEY: misc_feature
<222> LOCATION: (682)..(682)
<223> OTHER INFORMATION: n is unknown
<220> FEATURE:
<221> NAME/KEY: misc_feature
<222> LOCATION: (688)..(689)
<223> OTHER INFORMATION: n is unknown
<220> FEATURE:
<221> NAME/KEY: misc_feature
<222> LOCATION: (691)..(691)
<223> OTHER INFORMATION: n is unknown

<400> SEQUENCE: 43
nnntgnngcc tgnttntgat tactgttaat gttgctacta ctgctgacaa tgctgctgct    60
gcttctcctc nctgtctcca cttccttgaa caatgcgccg tcatgcttct tttgcctccc   120
gctgctccag aaagctaggc cgcagatcag aaccaccaca gtcaatatca ccaccttcct   180
cttatagatt cggaatctca tgatagggggc tcagcctctg tgcgagtgga gagaagtttg   240
caggcgagct gaggagcant tgcaggtgat atgatgtgct cggctcaaga agcgggcccg   300
gagaggaaga agtcgtgccg gggctaatta ttggcaaaac gagctcttgt tgtaaacatn   360
nnnnnnnnnn nnangtcact aatggcgaan nnnnannnnn taaggnntga tggttgctca   420
gaggcaggag aagagnnnng natacnnnnn nataaaagat aaaacataaa taaacagtct   480
tgattatatt ctgggtatta aagccacaat cagaacaaat atatgctttg tatcttttct   540
tgcctnnnnn nnnnnnnnnn nnntccgcgg ccacattaag agaacttgtg gtaagataag   600
aagatatttt attcgnnnnn ntgnnnnnnt ggatgtcggg aaatattctg catttgataa   660
gangcggnta antgnanata tnattggnng ngaaa                              695

<210> SEQ ID NO 44
<211> LENGTH: 873
<212> TYPE: DNA
<213> ORGANISM: Artificial Sequence
<220> FEATURE:
<223> OTHER INFORMATION: S. cerevisiae PCR reaction /DNA sequence
```

```
                standard
<220> FEATURE:
<221> NAME/KEY: misc_feature
<222> LOCATION: (9)..(9)
<223> OTHER INFORMATION: n is unknown
<220> FEATURE:
<221> NAME/KEY: misc_feature
<222> LOCATION: (12)..(12)
<223> OTHER INFORMATION: n is unknown
<220> FEATURE:
<221> NAME/KEY: misc_feature
<222> LOCATION: (18)..(18)
<223> OTHER INFORMATION: n is unknown
<220> FEATURE:
<221> NAME/KEY: misc_feature
<222> LOCATION: (20)..(22)
<223> OTHER INFORMATION: n is unknown
<220> FEATURE:
<221> NAME/KEY: misc_feature
<222> LOCATION: (24)..(24)
<223> OTHER INFORMATION: n is unknown
<220> FEATURE:
<221> NAME/KEY: misc_feature
<222> LOCATION: (63)..(63)
<223> OTHER INFORMATION: n is unknown
<220> FEATURE:
<221> NAME/KEY: misc_feature
<222> LOCATION: (350)..(350)
<223> OTHER INFORMATION: n is unknown
<220> FEATURE:
<221> NAME/KEY: misc_feature
<222> LOCATION: (352)..(361)
<223> OTHER INFORMATION: n is unknown
<220> FEATURE:
<221> NAME/KEY: misc_feature
<222> LOCATION: (383)..(392)
<223> OTHER INFORMATION: n is unknown
<220> FEATURE:
<221> NAME/KEY: misc_feature
<222> LOCATION: (438)..(443)
<223> OTHER INFORMATION: n is unknown
<220> FEATURE:
<221> NAME/KEY: misc_feature
<222> LOCATION: (539)..(555)
<223> OTHER INFORMATION: n is unknown
<220> FEATURE:
<221> NAME/KEY: misc_feature
<222> LOCATION: (583)..(583)
<223> OTHER INFORMATION: n is unknown
<220> FEATURE:
<221> NAME/KEY: misc_feature
<222> LOCATION: (607)..(613)
<223> OTHER INFORMATION: n is unknown
<220> FEATURE:
<221> NAME/KEY: misc_feature
<222> LOCATION: (616)..(621)
<223> OTHER INFORMATION: n is unknown
<220> FEATURE:
<221> NAME/KEY: misc_feature
<222> LOCATION: (722)..(733)
<223> OTHER INFORMATION: n is unknown
<220> FEATURE:
<221> NAME/KEY: misc_feature
<222> LOCATION: (760)..(761)
<223> OTHER INFORMATION: n is unknown
<220> FEATURE:
<221> NAME/KEY: misc_feature
<222> LOCATION: (788)..(788)
<223> OTHER INFORMATION: n is unknown
<220> FEATURE:
<221> NAME/KEY: misc_feature
<222> LOCATION: (827)..(827)
<223> OTHER INFORMATION: n is unknown
<220> FEATURE:
<221> NAME/KEY: misc_feature
<222> LOCATION: (837)..(837)
<223> OTHER INFORMATION: n is unknown
<220> FEATURE:
<221> NAME/KEY: misc_feature
<222> LOCATION: (873)..(873)
```

<223> OTHER INFORMATION: n is unknown

<400> SEQUENCE: 44

```
cctggttang antactgntn nngntgctac tactgctgac aatgctgctg ctgcttctcc    60
tcnctgtctc cacttccttg aacaatgcgc cgtcatgctt cttttgcctc ccgctgctcc   120
agaaagctag gccgcagatc agaaccacca cagtcaatat caccaccttc ctcttataga   180
ttcggaatct catgataggg gctcagcctc tgtgcgagtg gagagaagtt tgcaggcgag   240
ctgaggagca attgcaggtg atatgatgtg ctcggctcaa gaagcgggcc cggagaggaa   300
gaagtcgtgc cggggctaat tattggcaaa acgagctctt gttgtaaacn tnnnnnnnnn   360
nggaatgtca ctaatggcga atnnnnnnnn nntaaggcat gatggttgct cagaggcagg   420
agaagagcaa cgaatacnnn nnnataaaag ataaaacata aataaacagt cttgattata   480
ttctgggtat taaagccaca atcagaacaa atatatgctt tgtatctttt cttgccttnn   540
nnnnnnnnnn nnnntccgc ggccacatta agagaacttg tgntaagata agaagatatt   600
ttattcnnnn nnntgnnnnn ntggatgtcg ggaaatattc tgcatttgat aagaggcggt   660
taattgcaga tataattggt agtgaaaagg gtcgttgcta tggtcaccgt gaagcgagta   720
cnnnnnnnnn nnnatgtgtg ccgttctcag ttaatattgn ntgaatatgg taacctgttt   780
tagtcggntt aaaggtaaga agatctaacc aaaaacaaca ctgcagngac tgattgnagt   840
atttattttt ttacttaatc ttaattttgg ggn                               873
```

<210> SEQ ID NO 45
<211> LENGTH: 862
<212> TYPE: DNA
<213> ORGANISM: Artificial Sequence
<220> FEATURE:
<223> OTHER INFORMATION: S. cerevisiae PCR reaction /DNA sequence
    standard
<220> FEATURE:
<221> NAME/KEY: misc_feature
<222> LOCATION: (5)..(9)
<223> OTHER INFORMATION: n is unknown
<220> FEATURE:
<221> NAME/KEY: misc_feature
<222> LOCATION: (63)..(63)
<223> OTHER INFORMATION: n is unknown
<220> FEATURE:
<221> NAME/KEY: misc_feature
<222> LOCATION: (352)..(361)
<223> OTHER INFORMATION: n is unknown
<220> FEATURE:
<221> NAME/KEY: misc_feature
<222> LOCATION: (382)..(392)
<223> OTHER INFORMATION: n is unknown
<220> FEATURE:
<221> NAME/KEY: misc_feature
<222> LOCATION: (398)..(398)
<223> OTHER INFORMATION: n is unknown
<220> FEATURE:
<221> NAME/KEY: misc_feature
<222> LOCATION: (440)..(440)
<223> OTHER INFORMATION: n is unknown
<220> FEATURE:
<221> NAME/KEY: misc_feature
<222> LOCATION: (443)..(444)
<223> OTHER INFORMATION: n is unknown
<220> FEATURE:
<221> NAME/KEY: misc_feature
<222> LOCATION: (539)..(555)
<223> OTHER INFORMATION: n is unknown
<220> FEATURE:
<221> NAME/KEY: misc_feature
<222> LOCATION: (608)..(613)
<223> OTHER INFORMATION: n is unknown
<220> FEATURE:
<221> NAME/KEY: misc_feature

```
<222> LOCATION: (616)..(621)
<223> OTHER INFORMATION: n is unknown
<220> FEATURE:
<221> NAME/KEY: misc_feature
<222> LOCATION: (662)..(664)
<223> OTHER INFORMATION: n is unknown
<220> FEATURE:
<221> NAME/KEY: misc_feature
<222> LOCATION: (667)..(667)
<223> OTHER INFORMATION: n is unknown
<220> FEATURE:
<221> NAME/KEY: misc_feature
<222> LOCATION: (725)..(725)
<223> OTHER INFORMATION: n is unknown
<220> FEATURE:
<221> NAME/KEY: misc_feature
<222> LOCATION: (727)..(733)
<223> OTHER INFORMATION: n is unknown
<220> FEATURE:
<221> NAME/KEY: misc_feature
<222> LOCATION: (768)..(768)
<223> OTHER INFORMATION: n is unknown
<220> FEATURE:
<221> NAME/KEY: misc_feature
<222> LOCATION: (771)..(776)
<223> OTHER INFORMATION: n is unknown
<220> FEATURE:
<221> NAME/KEY: misc_feature
<222> LOCATION: (827)..(827)
<223> OTHER INFORMATION: n is unknown
<220> FEATURE:
<221> NAME/KEY: misc_feature
<222> LOCATION: (850)..(857)
<223> OTHER INFORMATION: n is unknown

<400> SEQUENCE: 45
cctgnnnnng attactgtta atgttgctac tactgctgac aatgctgctg ctgcttctcc      60
tcnctgtctc cacttccttg aacaatgcgc cgtcatgctt cttttgcctc ccgctgctcc     120
agaaagctag gccgcagatc agaaccacca cagtcaatat caccaccttc ctcttataga     180
ttcggaatct catgataggg gctcagcctc tgtgcgagtg gagagaagtt tgcaggcgag     240
ctgaggagca attgcaggtg atatgatgtg ctcggctcaa gaagcgggcc cggagaggaa     300
gaagtcgtgc cggggctaat tattggcaaa acgagctctt gttgtaaaca tnnnnnnnnn     360
nggaatgtca ctaatggcga annnnnnnnn nntaaggnat gatggttgct cagaggcagg     420
agaagagcaa cgaatacgan gcnntaaaag ataaaacata aataaacagt cttgattata     480
ttctgggtat taaagccaca atcagaacaa atatatgctt tgtatctttt cttgccttnn     540
nnnnnnnnnn nnnntccgc ggccacatta agagaacttg tggtaagata agaagatatt     600
ttattcgnnn nnntgnnnnn ntggatgtcg ggaaatattc tgcatttgat aagaggcggt     660
tnnntgnaga tataattggt agtgaaaagg gtcgttgcta tggtcaccgt gaagcgagta     720
cagcngnnnn nnnatgtgtg ccgttctcag ttaatattgt ttgaatangg nnnnnngttt     780
tagtcggttt aaaggtaaga agatctaacc aaaaacaaca ctgcagngac tgattgtagt     840
atttattttn nnnnnnnatc tt                                              862

<210> SEQ ID NO 46
<211> LENGTH: 867
<212> TYPE: DNA
<213> ORGANISM: Artificial Sequence
<220> FEATURE:
<223> OTHER INFORMATION: S. aureus PCR reaction /DNA sequence standard
      consensus sequence
<220> FEATURE:
<221> NAME/KEY: misc_feature
<222> LOCATION: (10)..(10)
<223> OTHER INFORMATION: n is unknown
<220> FEATURE:
```

```
<221> NAME/KEY: misc_feature
<222> LOCATION: (17)..(17)
<223> OTHER INFORMATION: n is unknown
<220> FEATURE:
<221> NAME/KEY: misc_feature
<222> LOCATION: (33)..(35)
<223> OTHER INFORMATION: n is unknown
<220> FEATURE:
<221> NAME/KEY: misc_feature
<222> LOCATION: (37)..(39)
<223> OTHER INFORMATION: n is unknown
<220> FEATURE:
<221> NAME/KEY: misc_feature
<222> LOCATION: (64)..(64)
<223> OTHER INFORMATION: n is unknown
<220> FEATURE:
<221> NAME/KEY: misc_feature
<222> LOCATION: (106)..(106)
<223> OTHER INFORMATION: n is unknown
<220> FEATURE:
<221> NAME/KEY: misc_feature
<222> LOCATION: (108)..(108)
<223> OTHER INFORMATION: n is unknown
<220> FEATURE:
<221> NAME/KEY: misc_feature
<222> LOCATION: (110)..(111)
<223> OTHER INFORMATION: n is unknown
<220> FEATURE:
<221> NAME/KEY: misc_feature
<222> LOCATION: (130)..(130)
<223> OTHER INFORMATION: n is unknown
<220> FEATURE:
<221> NAME/KEY: misc_feature
<222> LOCATION: (132)..(133)
<223> OTHER INFORMATION: n is unknown
<220> FEATURE:
<221> NAME/KEY: misc_feature
<222> LOCATION: (135)..(135)
<223> OTHER INFORMATION: n is unknown
<220> FEATURE:
<221> NAME/KEY: misc_feature
<222> LOCATION: (138)..(138)
<223> OTHER INFORMATION: n is unknown
<220> FEATURE:
<221> NAME/KEY: misc_feature
<222> LOCATION: (141)..(141)
<223> OTHER INFORMATION: n is unknown
<220> FEATURE:
<221> NAME/KEY: misc_feature
<222> LOCATION: (177)..(178)
<223> OTHER INFORMATION: n is unknown
<220> FEATURE:
<221> NAME/KEY: misc_feature
<222> LOCATION: (181)..(182)
<223> OTHER INFORMATION: n is unknown
<220> FEATURE:
<221> NAME/KEY: misc_feature
<222> LOCATION: (221)..(221)
<223> OTHER INFORMATION: n is unknown
<220> FEATURE:
<221> NAME/KEY: misc_feature
<222> LOCATION: (227)..(227)
<223> OTHER INFORMATION: n is unknown
<220> FEATURE:
<221> NAME/KEY: misc_feature
<222> LOCATION: (237)..(241)
<223> OTHER INFORMATION: n is unknown
<220> FEATURE:
<221> NAME/KEY: misc_feature
<222> LOCATION: (328)..(328)
<223> OTHER INFORMATION: n is unknown
<220> FEATURE:
<221> NAME/KEY: misc_feature
<222> LOCATION: (330)..(355)
<223> OTHER INFORMATION: n is unknown
<220> FEATURE:
<221> NAME/KEY: misc_feature
<222> LOCATION: (556)..(556)
<223> OTHER INFORMATION: n is unknown
<220> FEATURE:
```

```
<221> NAME/KEY: misc_feature
<222> LOCATION: (666)..(669)
<223> OTHER INFORMATION: n is unknown
<220> FEATURE:
<221> NAME/KEY: misc_feature
<222> LOCATION: (763)..(763)
<223> OTHER INFORMATION: n is unknown
<220> FEATURE:
<221> NAME/KEY: misc_feature
<222> LOCATION: (802)..(802)
<223> OTHER INFORMATION: n is unknown
<220> FEATURE:
<221> NAME/KEY: misc_feature
<222> LOCATION: (812)..(813)
<223> OTHER INFORMATION: n is unknown
<220> FEATURE:
<221> NAME/KEY: misc_feature
<222> LOCATION: (815)..(816)
<223> OTHER INFORMATION: n is unknown
<220> FEATURE:
<221> NAME/KEY: misc_feature
<222> LOCATION: (819)..(823)
<223> OTHER INFORMATION: n is unknown

<400> SEQUENCE: 46
gttgctctcn gctgacnatg ctgctgctgc ttnnngnnnc tgtctccact tccttgaaca      60
atgngccgtc atgcttcttt tgcctcccgc tgctccagaa agctangncn nagatcagaa     120
ccaccacagn cnntntcncc nccttcctct tatagattcg gaatctcatg atagggnntc     180
nncctctgtg cgagtggaga gaagtttgca ggcgagctga ngagcanttg caggtgnnnn     240
natgtgctcg gctcaagaag cgggcccgga gaggaagaag tcgtgccggg gctaattatt     300
ggcaaaacga gctcttgttg taaacatngn nnnnnnnnnn nnnnnnnnnn nnnnnatcaa     360
tattccataa ggcatgatgg ttgctcagag gcaggagaag agcaacgaat acgatcctat     420
aaaagataaa acataaataa acagtcttga ttatattctg ggtattaaag ccacaatcag     480
aacaaatata tgctttgtat cttttcttgc cttcttcatt accaactgct tccgcggcca     540
cattaagaga acttgnggta agataagaag atattttatt cgttctgctg acttgctgga     600
tgtcgggaaa tattctgcat ttgataagag gcggttaatt gcagatataa ttggtagtga     660
aaaggnnnnt tgctatggtc accgtgaagc gagtacagca gcacaagaat gtgtgccgtt     720
ctcagttaat attgtttgaa tatggtaacc tgttttagtc ggnttaaagg taagaagatc     780
taaccaaaaa caacactgca gngactgatt gnngnnttnn nnnttttta cttaatctta      840 attttggtgt aaacatcaac ggcgcac                                         867

<210> SEQ ID NO 47
<211> LENGTH: 819
<212> TYPE: DNA
<213> ORGANISM: Artificial Sequence
<220> FEATURE:
<223> OTHER INFORMATION: S. aureus PCR reaction /DNA sequence standard
      consensus sequence
<220> FEATURE:
<221> NAME/KEY: misc_feature
<222> LOCATION: (1)..(3)
<223> OTHER INFORMATION: n is unknown
<220> FEATURE:
<221> NAME/KEY: misc_feature
<222> LOCATION: (10)..(10)
<223> OTHER INFORMATION: n is unknown
<220> FEATURE:
<221> NAME/KEY: misc_feature
<222> LOCATION: (14)..(14)
<223> OTHER INFORMATION: n is unknown
<220> FEATURE:
<221> NAME/KEY: misc_feature
<222> LOCATION: (24)..(24)
<223> OTHER INFORMATION: n is unknown
```

```
<220> FEATURE:
<221> NAME/KEY: misc_feature
<222> LOCATION: (64)..(65)
<223> OTHER INFORMATION: n is unknown
<220> FEATURE:
<221> NAME/KEY: misc_feature
<222> LOCATION: (753)..(764)
<223> OTHER INFORMATION: n is unknown
<220> FEATURE:
<221> NAME/KEY: misc_feature
<222> LOCATION: (818)..(819)
<223> OTHER INFORMATION: n is unknown

<400> SEQUENCE: 47
nnnctggttn tgantactgt taangttgct actactgctg acaatgctgc tgctgcttct    60
cctnnctgtc tccacttcct tgaacaatgc gccgtcatgc ttcttttgcc tcccgctgct   120
ccagaaagct aggccgcaga tcagaaccac cacagtcaat atcaccacct tcctcttata   180
gattcggaat ctcatgatag gggctcagcc tctgtgcgag tggagagaag tttgcaggcg   240
agctgaggag caattgcagg tgatatgatg tgctcggctc aagaagcggg cccggagagg   300
aagaagtcgt gccggggcta attattggca aaacgagctc ttgttgtaaa cattgatcca   360
actggaatgt cactaatggc gaatcaatat tccataaggc atgatggttg ctcagaggca   420
ggagaagagc aacgaatacg atcctataaa agataaaaca taaataaaca gtcttgatta   480
tattctgggt attaaagcca caatcagaac aaatatatgc tttgtatctt ttcttgcctt   540
cttcattacc aactgcttcc gcggccacat taagagaact tgtggtaaga taagaagata   600
ttttattcgt tctgctgact tgctggatgt cgggaaatat tctgcatttg ataagaggcg   660
gttaattgca gatataattg gtagtgaaaa gggtcgttgc tatggtcacc gtgaagcgag   720
tacagcagca caagaatgtg tgccgttctc agnnnnnnnn nnnngaatat ggtaacctgt   780
tttagtcggt ttaaaggtaa gaagatctaa ccaaaaann                          819

<210> SEQ ID NO 48
<211> LENGTH: 887
<212> TYPE: DNA
<213> ORGANISM: Artificial Sequence
<220> FEATURE:
<223> OTHER INFORMATION: S. cerevisiae PCR reaction /DNA sequence
      standard consensus sequence
<220> FEATURE:
<221> NAME/KEY: misc_feature
<222> LOCATION: (4)..(4)
<223> OTHER INFORMATION: n is unknown
<220> FEATURE:
<221> NAME/KEY: misc_feature
<222> LOCATION: (44)..(44)
<223> OTHER INFORMATION: n is unknown
<220> FEATURE:
<221> NAME/KEY: misc_feature
<222> LOCATION: (49)..(49)
<223> OTHER INFORMATION: n is unknown
<220> FEATURE:
<221> NAME/KEY: misc_feature
<222> LOCATION: (79)..(79)
<223> OTHER INFORMATION: n is unknown
<220> FEATURE:
<221> NAME/KEY: misc_feature
<222> LOCATION: (81)..(81)
<223> OTHER INFORMATION: n is unknown
<220> FEATURE:
<221> NAME/KEY: misc_feature
<222> LOCATION: (107)..(107)
<223> OTHER INFORMATION: n is unknown
<220> FEATURE:
<221> NAME/KEY: misc_feature
<222> LOCATION: (111)..(111)
<223> OTHER INFORMATION: n is unknown
<220> FEATURE:
```

```
<221> NAME/KEY: misc_feature
<222> LOCATION: (113)..(113)
<223> OTHER INFORMATION: n is unknown
<220> FEATURE:
<221> NAME/KEY: misc_feature
<222> LOCATION: (140)..(140)
<223> OTHER INFORMATION: n is unknown
<220> FEATURE:
<221> NAME/KEY: misc_feature
<222> LOCATION: (154)..(154)
<223> OTHER INFORMATION: n is unknown
<220> FEATURE:
<221> NAME/KEY: misc_feature
<222> LOCATION: (157)..(158)
<223> OTHER INFORMATION: n is unknown
<220> FEATURE:
<221> NAME/KEY: misc_feature
<222> LOCATION: (266)..(267)
<223> OTHER INFORMATION: n is unknown
<220> FEATURE:
<221> NAME/KEY: misc_feature
<222> LOCATION: (271)..(292)
<223> OTHER INFORMATION: n is unknown
<220> FEATURE:
<221> NAME/KEY: misc_feature
<222> LOCATION: (349)..(350)
<223> OTHER INFORMATION: n is unknown
<220> FEATURE:
<221> NAME/KEY: misc_feature
<222> LOCATION: (353)..(358)
<223> OTHER INFORMATION: n is unknown
<220> FEATURE:
<221> NAME/KEY: misc_feature
<222> LOCATION: (363)..(363)
<223> OTHER INFORMATION: n is unknown
<220> FEATURE:
<221> NAME/KEY: misc_feature
<222> LOCATION: (365)..(367)
<223> OTHER INFORMATION: n is unknown
<220> FEATURE:
<221> NAME/KEY: misc_feature
<222> LOCATION: (369)..(372)
<223> OTHER INFORMATION: n is unknown
<220> FEATURE:
<221> NAME/KEY: misc_feature
<222> LOCATION: (375)..(375)
<223> OTHER INFORMATION: n is unknown
<220> FEATURE:
<221> NAME/KEY: misc_feature
<222> LOCATION: (377)..(380)
<223> OTHER INFORMATION: n is unknown
<220> FEATURE:
<221> NAME/KEY: misc_feature
<222> LOCATION: (480)..(481)
<223> OTHER INFORMATION: n is unknown
<220> FEATURE:
<221> NAME/KEY: misc_feature
<222> LOCATION: (483)..(485)
<223> OTHER INFORMATION: n is unknown
<220> FEATURE:
<221> NAME/KEY: misc_feature
<222> LOCATION: (487)..(487)
<223> OTHER INFORMATION: n is unknown
<220> FEATURE:
<221> NAME/KEY: misc_feature
<222> LOCATION: (508)..(515)
<223> OTHER INFORMATION: n is unknown
<220> FEATURE:
<221> NAME/KEY: misc_feature
<222> LOCATION: (517)..(517)
<223> OTHER INFORMATION: n is unknown
<220> FEATURE:
<221> NAME/KEY: misc_feature
<222> LOCATION: (520)..(520)
<223> OTHER INFORMATION: n is unknown
<220> FEATURE:
<221> NAME/KEY: misc_feature
<222> LOCATION: (522)..(523)
<223> OTHER INFORMATION: n is unknown
<220> FEATURE:
```

```
<221> NAME/KEY: misc_feature
<222> LOCATION: (525)..(545)
<223> OTHER INFORMATION: n is unknown
<220> FEATURE:
<221> NAME/KEY: misc_feature
<222> LOCATION: (552)..(556)
<223> OTHER INFORMATION: n is unknown
<220> FEATURE:
<221> NAME/KEY: misc_feature
<222> LOCATION: (567)..(573)
<223> OTHER INFORMATION: n is unknown
<220> FEATURE:
<221> NAME/KEY: misc_feature
<222> LOCATION: (593)..(593)
<223> OTHER INFORMATION: n is unknown
<220> FEATURE:
<221> NAME/KEY: misc_feature
<222> LOCATION: (719)..(720)
<223> OTHER INFORMATION: n is unknown
<220> FEATURE:
<221> NAME/KEY: misc_feature
<222> LOCATION: (745)..(746)
<223> OTHER INFORMATION: n is unknown
<220> FEATURE:
<221> NAME/KEY: misc_feature
<222> LOCATION: (763)..(763)
<223> OTHER INFORMATION: n is unknown
<220> FEATURE:
<221> NAME/KEY: misc_feature
<222> LOCATION: (789)..(789)
<223> OTHER INFORMATION: n is unknown
<220> FEATURE:
<221> NAME/KEY: misc_feature
<222> LOCATION: (810)..(815)
<223> OTHER INFORMATION: n is unknown
<220> FEATURE:
<221> NAME/KEY: misc_feature
<222> LOCATION: (817)..(819)
<223> OTHER INFORMATION: n is unknown
<220> FEATURE:
<221> NAME/KEY: misc_feature
<222> LOCATION: (825)..(836)
<223> OTHER INFORMATION: n is unknown
<220> FEATURE:
<221> NAME/KEY: misc_feature
<222> LOCATION: (841)..(849)
<223> OTHER INFORMATION: n is unknown
<220> FEATURE:
<221> NAME/KEY: misc_feature
<222> LOCATION: (852)..(854)
<223> OTHER INFORMATION: n is unknown
<220> FEATURE:
<221> NAME/KEY: misc_feature
<222> LOCATION: (857)..(857)
<223> OTHER INFORMATION: n is unknown
<220> FEATURE:
<221> NAME/KEY: misc_feature
<222> LOCATION: (859)..(859)
<223> OTHER INFORMATION: n is unknown
<220> FEATURE:
<221> NAME/KEY: misc_feature
<222> LOCATION: (867)..(867)
<223> OTHER INFORMATION: n is unknown
<220> FEATURE:
<221> NAME/KEY: misc_feature
<222> LOCATION: (871)..(878)
<223> OTHER INFORMATION: n is unknown
<220> FEATURE:
<221> NAME/KEY: misc_feature
<222> LOCATION: (887)..(887)
<223> OTHER INFORMATION: n is unknown

<400> SEQUENCE: 48
ctgntaatgt tgctactact gctgacaatg ctgctgctgc ttcncctcnc tgtctccact      60
tccttgaaca atgcgccgnc ntgcttcttt tgcctcccgc tgctccngag ngntaggccg     120
cagatcagaa ccaccacagn caatatcacc accntcnnct tatagattcg gaatctcatg    180
```

```
atagggctc agcctctgtg cgagtggaga gaagtttgca ggcgagctga ggagcaattg    240
caggtgatat gatgtgctcg gctcannggg nnnnnnnnnn nnnnnnnnnn nntgccggg     300 ctaattattg gcaaaacgag ctcttgttgt aaacattgat ccaactggnn ggnnnnnnat    360
ggngnnngnn nntgncnnnn ggcatgatgg ttgctcagag gcaggagaag agcaacgaat    420
acgatcctat aaaagataaa acataaataa acagtcttga ttatattctg ggtattaaan    480
ncnnngncag aacaaatata tgctttgnnn nnnnncntgn cnncnnnnnn nnnnnnnnnn    540
nnnnnggcca cnnnnngaga acttgtnnnn nnntaagaag atattttatt cgntctgctg    600
acttgctgga tgtcgggaaa tattctgcat ttgataagag gcggttaatt gcagatataa    660
ttggtagtga aaagggtcgt tgctatggtc accgtgaagc gagtacagca gcacaagann    720
gtgtgccgtt ctcagttaat attgnntgaa tatggtaacc tgntttagtc ggtttaaagg    780
taagaaganc taaccaaaaa caacactgcn nnnnngnnng ggggnnnnnn nnnnnntact    840
nnnnnnnnnt tnnnggngna aacatcnacg nnnnnnnnca accaatn                 887
```

```
<210> SEQ ID NO 49
<211> LENGTH: 687
<212> TYPE: DNA
<213> ORGANISM: Artificial Sequence
<220> FEATURE:
<223> OTHER INFORMATION: S. cerevisiae PCR reaction /DNA sequence
      standard consensus sequence
<220> FEATURE:
<221> NAME/KEY: misc_feature
<222> LOCATION: (5)..(9)
<223> OTHER INFORMATION: n is unknown
<220> FEATURE:
<221> NAME/KEY: misc_feature
<222> LOCATION: (63)..(63)
<223> OTHER INFORMATION: n is unknown
<220> FEATURE:
<221> NAME/KEY: misc_feature
<222> LOCATION: (251)..(251)
<223> OTHER INFORMATION: n is unknown
<220> FEATURE:
<221> NAME/KEY: misc_feature
<222> LOCATION: (352)..(361)
<223> OTHER INFORMATION: n is unknown
<220> FEATURE:
<221> NAME/KEY: misc_feature
<222> LOCATION: (364)..(364)
<223> OTHER INFORMATION: n is unknown
<220> FEATURE:
<221> NAME/KEY: misc_feature
<222> LOCATION: (382)..(386)
<223> OTHER INFORMATION: n is unknown
<220> FEATURE:
<221> NAME/KEY: misc_feature
<222> LOCATION: (388)..(392)
<223> OTHER INFORMATION: n is unknown
<220> FEATURE:
<221> NAME/KEY: misc_feature
<222> LOCATION: (398)..(399)
<223> OTHER INFORMATION: n is unknown
<220> FEATURE:
<221> NAME/KEY: misc_feature
<222> LOCATION: (429)..(431)
<223> OTHER INFORMATION: n is unknown
<220> FEATURE:
<221> NAME/KEY: misc_feature
<222> LOCATION: (433)..(433)
<223> OTHER INFORMATION: n is unknown
<220> FEATURE:
<221> NAME/KEY: misc_feature
<222> LOCATION: (438)..(443)
<223> OTHER INFORMATION: n is unknown
<220> FEATURE:
<221> NAME/KEY: misc_feature
<222> LOCATION: (538)..(555)
<223> OTHER INFORMATION: n is unknown
```

<220> FEATURE:
<221> NAME/KEY: misc_feature
<222> LOCATION: (608)..(613)
<223> OTHER INFORMATION: n is unknown
<220> FEATURE:
<221> NAME/KEY: misc_feature
<222> LOCATION: (616)..(621)
<223> OTHER INFORMATION: n is unknown
<220> FEATURE:
<221> NAME/KEY: misc_feature
<222> LOCATION: (664)..(664)
<223> OTHER INFORMATION: n is unknown
<220> FEATURE:
<221> NAME/KEY: misc_feature
<222> LOCATION: (667)..(667)
<223> OTHER INFORMATION: n is unknown
<220> FEATURE:
<221> NAME/KEY: misc_feature
<222> LOCATION: (680)..(681)
<223> OTHER INFORMATION: n is unknown
<220> FEATURE:
<221> NAME/KEY: misc_feature
<222> LOCATION: (683)..(683)
<223> OTHER INFORMATION: n is unknown

<400> SEQUENCE: 49

```
cctgnnnnng attactgtta atgttgctac tactgctgac aatgctgctg ctgcttctcc      60
tcnctgtctc cacttccttg aacaatgcgc cgtcatgctt cttttgcctc ccgctgctcc     120
agaaagctag gccgcagatc agaaccacca cagtcaatat caccaccttc ctcttataga    180
ttcggaatct catgataggg gctcagcctc tgtgcgagtg gagagaagtt tgcaggcgag    240
ctgaggagca nttgcaggtg atatgatgtg ctcggctcaa gaagcgggcc cggagaggaa    300
gaagtcgtgc cggggctaat tattggcaaa acgagctctt gttgtaaaca tnnnnnnnnn    360
nggnatgtca ctaatggcga annnnnannn nntaaggnnt gatggttgct cagaggcagg    420
agaagagcnn ngnatacnnn nnnataaaag ataaaacata aataaacagt cttgattata    480
ttctgggtat taaagccaca atcagaacaa atatatgctt tgtatctttt cttgcctnnn    540
nnnnnnnnnn nnnntccgc ggccacatta agagaacttg tggtaagata agaagatatt    600
ttattcgnnn nnntgnnnnn ntggatgtcg ggaaatattc tgcatttgat aagaggcggt    660
taantgnaga tataattggn ngngaaa                                         687
```

<210> SEQ ID NO 50
<211> LENGTH: 859
<212> TYPE: DNA
<213> ORGANISM: Artificial Sequence
<220> FEATURE:
<223> OTHER INFORMATION: S. enterica PCR reaction /DNA sequence standard
      consensus sequence
<220> FEATURE:
<221> NAME/KEY: misc_feature
<222> LOCATION: (18)..(18)
<223> OTHER INFORMATION: n is unknown
<220> FEATURE:
<221> NAME/KEY: misc_feature
<222> LOCATION: (29)..(29)
<223> OTHER INFORMATION: n is unknown
<220> FEATURE:
<221> NAME/KEY: misc_feature
<222> LOCATION: (108)..(108)
<223> OTHER INFORMATION: n is unknown
<220> FEATURE:
<221> NAME/KEY: misc_feature
<222> LOCATION: (197)..(203)
<223> OTHER INFORMATION: n is unknown
<220> FEATURE:
<221> NAME/KEY: misc_feature
<222> LOCATION: (257)..(257)
<223> OTHER INFORMATION: n is unknown
<220> FEATURE:

```
<221> NAME/KEY: misc_feature
<222> LOCATION: (260)..(262)
<223> OTHER INFORMATION: n is unknown
<220> FEATURE:
<221> NAME/KEY: misc_feature
<222> LOCATION: (264)..(266)
<223> OTHER INFORMATION: n is unknown
<220> FEATURE:
<221> NAME/KEY: misc_feature
<222> LOCATION: (271)..(282)
<223> OTHER INFORMATION: n is unknown
<220> FEATURE:
<221> NAME/KEY: misc_feature
<222> LOCATION: (313)..(323)
<223> OTHER INFORMATION: n is unknown
<220> FEATURE:
<221> NAME/KEY: misc_feature
<222> LOCATION: (325)..(335)
<223> OTHER INFORMATION: n is unknown
<220> FEATURE:
<221> NAME/KEY: misc_feature
<222> LOCATION: (339)..(344)
<223> OTHER INFORMATION: n is unknown
<220> FEATURE:
<221> NAME/KEY: misc_feature
<222> LOCATION: (346)..(347)
<223> OTHER INFORMATION: n is unknown
<220> FEATURE:
<221> NAME/KEY: misc_feature
<222> LOCATION: (357)..(357)
<223> OTHER INFORMATION: n is unknown
<220> FEATURE:
<221> NAME/KEY: misc_feature
<222> LOCATION: (360)..(361)
<223> OTHER INFORMATION: n is unknown
<220> FEATURE:
<221> NAME/KEY: misc_feature
<222> LOCATION: (385)..(390)
<223> OTHER INFORMATION: n is unknown
<220> FEATURE:
<221> NAME/KEY: misc_feature
<222> LOCATION: (396)..(398)
<223> OTHER INFORMATION: n is unknown
<220> FEATURE:
<221> NAME/KEY: misc_feature
<222> LOCATION: (400)..(401)
<223> OTHER INFORMATION: n is unknown
<220> FEATURE:
<221> NAME/KEY: misc_feature
<222> LOCATION: (494)..(498)
<223> OTHER INFORMATION: n is unknown
<220> FEATURE:
<221> NAME/KEY: misc_feature
<222> LOCATION: (510)..(517)
<223> OTHER INFORMATION: n is unknown
<220> FEATURE:
<221> NAME/KEY: misc_feature
<222> LOCATION: (519)..(519)
<223> OTHER INFORMATION: n is unknown
<220> FEATURE:
<221> NAME/KEY: misc_feature
<222> LOCATION: (528)..(528)
<223> OTHER INFORMATION: n is unknown
<220> FEATURE:
<221> NAME/KEY: misc_feature
<222> LOCATION: (613)..(618)
<223> OTHER INFORMATION: n is unknown
<220> FEATURE:
<221> NAME/KEY: misc_feature
<222> LOCATION: (714)..(719)
<223> OTHER INFORMATION: n is unknown
<220> FEATURE:
<221> NAME/KEY: misc_feature
<222> LOCATION: (736)..(736)
<223> OTHER INFORMATION: n is unknown
<220> FEATURE:
<221> NAME/KEY: misc_feature
<222> LOCATION: (759)..(768)
<223> OTHER INFORMATION: n is unknown
<220> FEATURE:
```

<221> NAME/KEY: misc_feature
<222> LOCATION: (776)..(776)
<223> OTHER INFORMATION: n is unknown
<220> FEATURE:
<221> NAME/KEY: misc_feature
<222> LOCATION: (792)..(792)
<223> OTHER INFORMATION: n is unknown
<220> FEATURE:
<221> NAME/KEY: misc_feature
<222> LOCATION: (796)..(796)
<223> OTHER INFORMATION: n is unknown
<220> FEATURE:
<221> NAME/KEY: misc_feature
<222> LOCATION: (799)..(800)
<223> OTHER INFORMATION: n is unknown
<220> FEATURE:
<221> NAME/KEY: misc_feature
<222> LOCATION: (815)..(825)
<223> OTHER INFORMATION: n is unknown
<220> FEATURE:
<221> NAME/KEY: misc_feature
<222> LOCATION: (839)..(839)
<223> OTHER INFORMATION: n is unknown
<220> FEATURE:
<221> NAME/KEY: misc_feature
<222> LOCATION: (847)..(847)
<223> OTHER INFORMATION: n is unknown

<400> SEQUENCE: 50

| | | | | | |
|---|---|---|---|---|---|
| gctgacaatg | ctgctgcngc | ttctcctcnc | tgtctccact | tccttgaaca | atgcgccgtc | 60 |
| atgcttcttt | tgcctcccgc | tgctccagaa | agctaggccg | cagatcanaa | ccaccacagt | 120 |
| caatatcacc | accttcctct | tatagattcg | gaatctcatg | ataggggctc | agcctctgtg | 180 |
| cgagtggaga | gaagttnnnn | nnngagctga | ggagcaattg | caggtgatat | gatgtgctcg | 240 |
| gctcaagaag | cgggccnggn | nngnnngaag | nnnnnnnnnn | nntaattatt | ggcaaaacga | 300 |
| gctcttgttg | tannnnnnn | nnngnnnnnn | nnnnnactnn | nnnngnncaa | tattccntan | 360 |
| ngcatgatgg | ttgctcagag | gcagnnnnnn | agcaannnan | ncgatcctat | aaaagataaa | 420 |
| acataaataa | acagtcttga | ttatattctg | ggtattaaag | ccacaatcag | aacaaatata | 480 |
| tgctttgtat | cttnnnnngc | cttcttcatn | nnnnnnngnt | tccgcggnca | cattaagaga | 540 |
| acttgtggta | agataagaag | atattttatt | cgttctgctg | acttgctgga | tgtcgggaaa | 600 |
| tattctgcat | ttnnnnnnag | gcggttaatt | gcagatataa | ttggtagtga | aaagggtcgt | 660 |
| tgctatggtc | accgtgaagc | gagtacagca | gcacaagaat | gtgtgccgtt | ctcnnnnnnt | 720 |
| attgtttgaa | tatggnaacc | tgttttagtc | ggtttaaann | nnnnnnnntc | taaccnaaaa | 780 |
| caacactgca | gngacngann | gtagtattta | ttttnnnnnn | nnnncttaa | ttttggtgna | 840 |
| aacatcnacg | gcgcacttc | | | | | 859 |

<210> SEQ ID NO 51
<211> LENGTH: 843
<212> TYPE: DNA
<213> ORGANISM: Artificial Sequence
<220> FEATURE:
<223> OTHER INFORMATION: S. enterica PCR reaction /DNA sequence standard consensus sequence
<220> FEATURE:
<221> NAME/KEY: misc_feature
<222> LOCATION: (1)..(1)
<223> OTHER INFORMATION: n is unknown
<220> FEATURE:
<221> NAME/KEY: misc_feature
<222> LOCATION: (4)..(4)
<223> OTHER INFORMATION: n is unknown
<220> FEATURE:
<221> NAME/KEY: misc_feature
<222> LOCATION: (16)..(18)
<223> OTHER INFORMATION: n is unknown

```
<220> FEATURE:
<221> NAME/KEY: misc_feature
<222> LOCATION: (58)..(59)
<223> OTHER INFORMATION: n is unknown
<220> FEATURE:
<221> NAME/KEY: misc_feature
<222> LOCATION: (371)..(380)
<223> OTHER INFORMATION: n is unknown
<220> FEATURE:
<221> NAME/KEY: misc_feature
<222> LOCATION: (496)..(508)
<223> OTHER INFORMATION: n is unknown
<220> FEATURE:
<221> NAME/KEY: misc_feature
<222> LOCATION: (524)..(528)
<223> OTHER INFORMATION: n is unknown
<220> FEATURE:
<221> NAME/KEY: misc_feature
<222> LOCATION: (530)..(530)
<223> OTHER INFORMATION: n is unknown
<220> FEATURE:
<221> NAME/KEY: misc_feature
<222> LOCATION: (602)..(608)
<223> OTHER INFORMATION: n is unknown
<220> FEATURE:
<221> NAME/KEY: misc_feature
<222> LOCATION: (675)..(684)
<223> OTHER INFORMATION: n is unknown
<220> FEATURE:
<221> NAME/KEY: misc_feature
<222> LOCATION: (686)..(686)
<223> OTHER INFORMATION: n is unknown
<220> FEATURE:
<221> NAME/KEY: misc_feature
<222> LOCATION: (717)..(717)
<223> OTHER INFORMATION: n is unknown
<220> FEATURE:
<221> NAME/KEY: misc_feature
<222> LOCATION: (736)..(747)
<223> OTHER INFORMATION: n is unknown
<220> FEATURE:
<221> NAME/KEY: misc_feature
<222> LOCATION: (755)..(755)
<223> OTHER INFORMATION: n is unknown
<220> FEATURE:
<221> NAME/KEY: misc_feature
<222> LOCATION: (783)..(783)
<223> OTHER INFORMATION: n is unknown
<220> FEATURE:
<221> NAME/KEY: misc_feature
<222> LOCATION: (806)..(806)
<223> OTHER INFORMATION: n is unknown
<220> FEATURE:
<221> NAME/KEY: misc_feature
<222> LOCATION: (832)..(832)
<223> OTHER INFORMATION: n is unknown
<220> FEATURE:
<221> NAME/KEY: misc_feature
<222> LOCATION: (838)..(843)
<223> OTHER INFORMATION: n is unknown

<400> SEQUENCE: 51
nttntgatta ctgttnnngt tgctactact gctgacaatg ctgctgctgc ttctcctnnc      60
tgtctccact tccttgaaca atgcgccgtc atgcttcttt tgcctcccgc tgctccagaa     120
agctaggccg cagatcagaa ccaccacagt caatatcacc accttcctct tatagattcg    180
gaatctcatg atagggggctc agcctctgtg cgagtggaga gaagtttgca ggcgagctga   240
ggagcaattg caggtgatat gatgtgctcg gctcaagaag cgggcccgga gaggaagaag   300
tcgtgccggg gctaattatt ggcaaaacga gctcttgttg taaacattga tccaactgga   360
atgtcactaa nnnnnnnnnn tattccataa ggcatgatgg ttgctcagag gcaggagaag   420
agcaacgaat acgatcctat aaaagataaa acataaataa acagtcttga ttatattctg   480
ggtattaaag ccacannnnn nnnnnnnnta tgctttgtat cttnnnnngn cttcttcatt    540
```

-continued

```
accaactgct tccgcggcca cattaagaga acttgtggta agataagaag atattttatt    600
cnnnnnnntg acttgctgga tgtcgggaaa tattctgcat ttgataagag gcggttaatt    660
gcagatataa ttggnnnnnn nnnngntcgt tgctatggtc accgtgaagc gagtacngca    720
gcacaagaat gtgtgnnnnn nnnnnnnaat attgnttgaa tatggtaacc tgttttagtc    780
ggnttaaagg taagaagatc taaccnaaaa caacactgca gtgactgatt gnagtatnnn    840 nnn                                                                  843
```

GENETIC FINGERPRINTING AND IDENTIFICATION METHOD

CROSS-REFERENCE TO RELATED APPLICATION

This application claims the benefit of U.S. Provisional Application No. 61/235,999, filed Aug. 21, 2009, which is incorporated by reference herein in its entirety.

FIELD OF THE INVENTION

This invention relates to the field of molecular biology and more specifically to methods for molecular fingerprinting for the characterization and identification of organisms.

BACKGROUND OF THE INVENTION

Central to the field of microbiology is the ability to positively identify microorganisms at the level of genus, species, or serotype. Correct identification is not only an essential tool in the laboratory, but it plays a significant role in the control of microbial contamination in the processing of food stuffs, the production of agricultural products, and the monitoring of environmental media, such as ground water. Of greatest concern is the detection and control of pathogenic microorganisms. Typically, pathogen identification has relied on methods for distinguishing phenotypic aspects, such as growth or motility characteristics, and for immunological and serological characteristics. Selective growth procedures and immunological methods are the traditional methods of choice for bacterial identification and these can be effective for the presumptive detection of a large number of species within a particular genus. However, these methods are time consuming and are subject to error. Selective growth methods require culturing and subculturing in selective media, followed by subjective analysis by an experienced investigator. Immunological detection (e.g., ELISA) is more rapid and specific, however, it still requires growth of a significant population of organisms and isolation of the relevant antigens. For these reasons, interest has turned to detection of bacterial pathogens based on nucleic acid sequence.

Nucleic acid polymorphism provides a means to identify species, serotypes, strains, varieties, breeds, or individuals based on differences in their genetic make up. Nucleic acid polymorphism can be caused by nucleotide substitution, insertion, or deletion. The ability to determine genetic polymorphism has widespread application in areas such as genome mapping, genetic linkage studies, medical diagnosis, epidemiological studies, forensics, and agriculture. Several methods have been developed to compare homogenous segments of DNA to determine if polymorphism exists.

One method for determining genetic polymorphism uses primers of an arbitrary sequence to amplify DNA by the polymerase chain reaction (PCR) (Williams et al., Nucleic Acids Res. 18:6531-35 (1990); U.S. Pat. No. 5,126,239, incorporated herein by reference). Because the primers are not designed to amplify a specific sequence, the technique is called random amplification of polymorphic DNA (RAPD) or arbitrarily primed PCR (APPCR). The primers used are at least seven nucleotides in length. Under the proper conditions, differences as small as a single nucleotide can affect the binding of the primer to the template DNA, thus resulting in differences in the distribution of amplification products produced between genomes.

Another method for identifying and mapping genetic polymorphisms has been termed amplified fragment length polymorphism (AFLP; U.S. Pat. No. 5,874,215, incorporated herein by reference). AFLP combines the use of restriction enzymes with the use of PCR. Briefly, restriction fragments are produced by the digestion of genomic DNA with a single or a pair of restriction enzymes. If a pair of enzymes is used, enzymes are paired based on differences in the frequency of restriction sites in the genome, such that one of the restriction enzymes is a "frequent cutter" while the remaining enzyme is a "rare cutter." The use of two enzymes results in the production of single and double digestion fragments. Next, double stranded synthetic oligonucleotide adaptors of 10-30 bases are ligated onto the fragments generated. Primers are then designed based on the sequence of the adapters and the restriction site. When pairs of restriction enzymes are used, nucleotides extending into the restriction sites are added to the 3' end of the primers such that only fragments generated due to the action of both enzymes (double cut fragments) are amplified. Using this method, any polymorphism present at or near the restriction site will affect the binding of the primer and thus the distribution of the amplification products. In addition, any differences in the nucleotide sequence in the area flanked by the primers will also be detected. AFLP allows for the simultaneous co-amplification of multiple fragments.

A further method is Direct Linear Analysis (DLA), which analyzes individual DNA molecules bound with sequence-specific tags (see Chan et al., Genome Res. 14:1137-46 (2004); U.S. Pat. No. 6,263,286, incorporated herein by reference). The method is intended to identify repetitive information in DNA, which is moved past at least one station, at which labelled units of DNA interact with the station to produce a DNA-dependent impulse. Because the extended objects are similar, or preferably identical, and comprise a similar, or preferably identical, pattern of labelled units, a characteristic signature of interactions is repeated as each extended object moves past a station or a plurality of stations. This repetitive information is extracted from the overall raw data by means of an autocorrelation function and is then used to determine structural information about the DNA.

Another method is amplification of repetitive elements (REP-PCR). This technique is based on families of repetitive DNA sequences present throughout the genome of diverse bacterial species (reviewed by Versalovic et al., Methods Mol. Cell. Biol. 5:25-40 (1994)). Repetitive extragenic palindromic (REP) sequences are thought to play an important role in the organization of the bacterial genome. Genomic organization is believed to be shaped by selection and the differential dispersion of these elements within the genome of closely related bacterial strains can be used to discriminate between strains (see, e.g., Louws et al., Appl. Environ. Micro. 60:2286-95 (1994)). REP-PCR utilizes oligonucleotide primers complementary to these repetitive sequences to amplify the variably sized DNA fragments lying between them. The resulting products are separated by electrophoresis to establish the DNA "fingerprint" for each strain.

The output data of these fingerprinting systems generally is measured by assigning band sizes, though these assignments are somewhat imprecise depending on the sizing ladder used for the comparison. In addition, the output data can be difficult to compare between laboratories and often relies on the use of expensive proprietary software programs (such as BioNumerics, Applied Maths, Austin, Tex.) to handle the data.

SUMMARY OF THE INVENTION

Applicants have solved the aforementioned problems by embedding the fingerprint bands from any amplification based fingerprinting method within a DNA sequence so that small differences in size are resolvable. Fingerprint output is provided in a text file format that can then be analyzed by powerful, freeware bioinformatics tools.

One aspect is for a method of identifying an organism in a sample comprising: (a) providing a sample comprising said organism, said organism comprising at least one nucleic acid; (b) combining said sample or the at least one nucleic acid therefrom with an amplification mix comprising at least one labeled oligonucleotide primer; (c) generating at least one labeled amplification product from the at least one nucleic acid of said organism using a nucleotide amplification technique employing said at least one labeled oligonucleotide primer; (d) combining said at least one labeled amplification product with products of a DNA sequencing reaction to create a separation mix; and (e) separating said separation mix on the basis of oligonucleotide length in a fluorescent DNA sequencing instrument to generate a sequence embedded fingerprint pattern for said organism.

In some aspects, the method comprises after step (e) the further steps of: (f) comparing said sequence embedded fingerprint pattern for said organism to a database containing sequence embedded fingerprint patterns for known organisms; and (g) identifying said organism as a function of said comparison to said database.

Another aspect is for an isolated polynucleotide comprising the nucleic acid sequence set forth in SEQ ID NO:1, SEQ ID NO:2, SEQ ID NO:3, SEQ ID NO:4, or SEQ ID NO:5.

Other objects and advantages will become apparent to those skilled in the art upon reference to the detailed description that hereinafter follows.

SUMMARY OF THE SEQUENCES

SEQ ID NOs:1-4 and 25 are the nucleotide sequences of oligonucleotide primers useful in the present invention. Each primer can be employed alone or in conjunction with one or more other primers. For example, SEQ ID NOs:1-4 can be employed together to create the FB1 D1 primer mix, while SEQ ID NO:25 can be employed alone as the FP5 primer.

SEQ ID NOS:5-7, 13, and 14 are the nucleotide sequences resulting from operating the method of the present invention with negative control PCR reactions obtained using the FB1 D1 primer set.

SEQ ID NOS:8-12 are the nucleotide sequences resulting from operating the method of the present invention with PCR reactions obtained using the FB1 D1 primer set and *Saccharomyces cerevisiae* DNA.

SEQ ID NOS:15-19 are the nucleotide sequences resulting from operating the method of the present invention with PCR reactions obtained using the FB1 D1 primer set and *Salmonella enterica* DNA.

SEQ ID NOS:20-24 are the nucleotide sequences resulting from operating the method of the present invention with PCR reactions obtained using the FB1 D1 primer set and *Staphylococcus aureus* DNA.

SEQ ID NOS:26-30 are the nucleotide sequences resulting from operating the method of the present invention with negative control PCR reactions obtained using the FP5 primer.

SEQ ID NOS:31-35 are the nucleotide sequences resulting from operating the method of the present invention with PCR reactions obtained using the FP5 primer and *Staphylococcus aureus* DNA.

SEQ ID NOS:36-40 are the nucleotide sequences resulting from operating the method of the present invention with PCR reactions obtained using the FP5 primer and *Salmonella enterica* DNA.

SEQ ID NOS:41-45 are the nucleotide sequences resulting from operating the method of the present invention with PCR reactions obtained using the FP5 primer and *Saccharomyces cerevisiae* DNA.

SEQ ID NO:46 is the consensus nucleotide sequence obtained from a sequence comparison of SEQ ID NOS:21-23.

SEQ ID NO:47 is the consensus nucleotide sequence obtained from a sequence comparison of SEQ ID NOS:33-35.

SEQ ID NO:48 is the consensus nucleotide sequence obtained from a sequence comparison of SEQ ID NOS:9-11.

SEQ ID NO:49 is the consensus nucleotide sequence obtained from a sequence comparison of SEQ ID NOS:41, 43, and 45.

SEQ ID NO:50 is the consensus nucleotide sequence obtained from a sequence comparison of SEQ ID NOS:17-19.

SEQ ID NO:51 is the consensus nucleotide sequence obtained from a sequence comparison of SEQ ID NOS:36-38.

The sequences conform with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

DETAILED DESCRIPTION

Figure 1A:
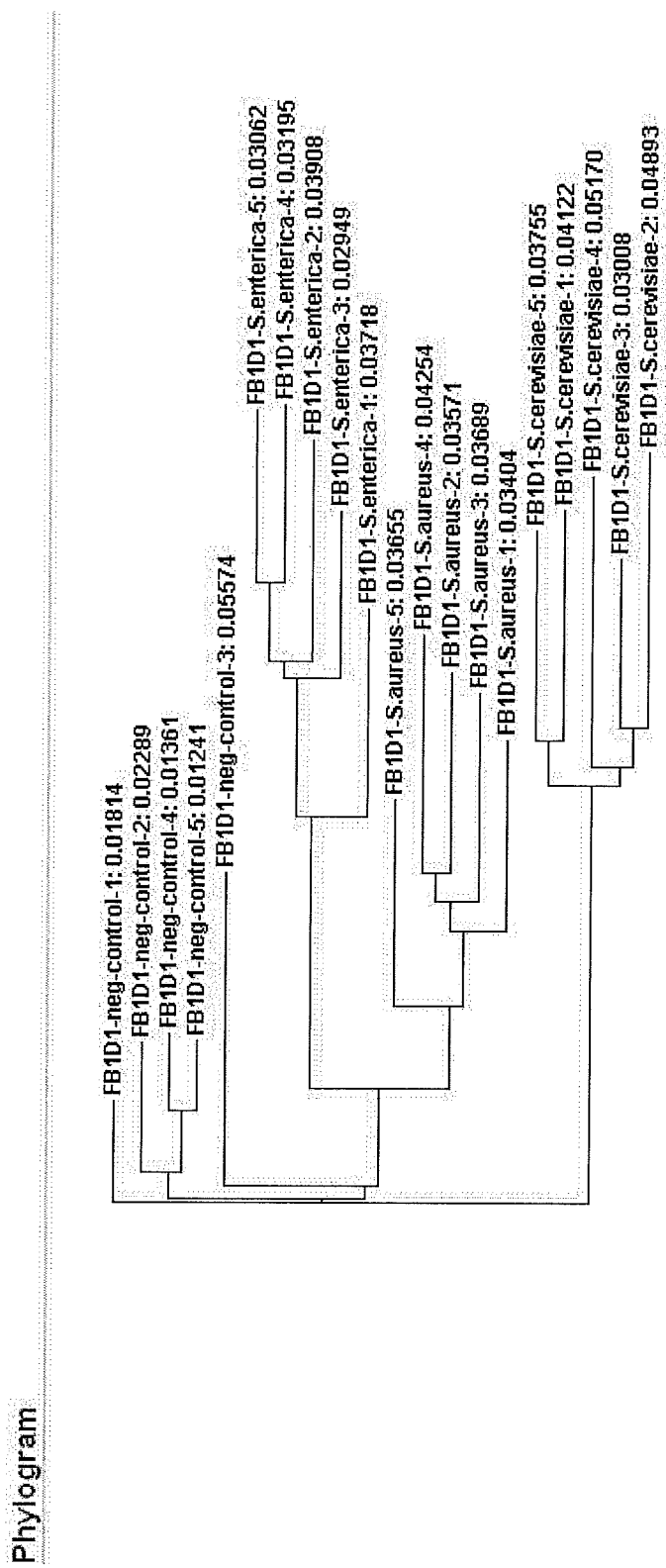
FIG. 1A shows a phylogram generated from a Clustal W alignment of all sequence reads from primer mix FB1 D1 of Example 1.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The term "comprising" is intended to include embodiments encompassed by the terms "consisting essentially of" and "consisting of." Similarly, the term "consisting essentially of" is intended to include embodiments encompassed by the term "consisting of."

The term "oligonucleotide" as used herein refers to a molecule comprised of two or more deoxyribonucleotides or ribonucleotides.

The term "primer" as used herein refers to an oligonucleotide of any arbitrary sequence, whether occurring naturally, as in a purified restriction digest, or produced synthetically, that is capable of acting as a point of initiation of synthesis when placed under conditions in which synthesis of a primer extension product which is complementary to a nucleic acid strand is induced, i.e., in the presence of nucleotides and an agent for polymerization such as DNA polymerase and at a suitable temperature and pH. It is preferable that primers are sequences that do not form a secondary structure by base pairing with other copies of the primer or sequences that form a "hair pin" configuration. The sequence conveniently can be generated by computer or selected at random from a gene bank. The primer is preferably single stranded for maximum efficiency in amplification, but may alternatively be double stranded. If double stranded, the primer is first treated to separate its strands before being used to prepare extension products. Preferably, the primer is an oligodeoxyribonucleotide.

In the present disclosure, primers used for amplification based fingerprint methods are labelled with a fluor. Following generation of the fingerprint products by amplification, the fingerprint amplicons are comingled with the product of a previously performed DNA sequencing reaction. The comingled products are then run to produce a DNA sequence from a fluorescent DNA sequencing instrument. The sequence output is perturbed at positions where the fingerprint products are migrating with like-sized DNA sequencing fragments. The perturbations result in an altered DNA sequence output from the instrument. These alterations are reproducible, and comparison of the output sequences can be used to characterize and/or identify the organism whose DNA was subject to the fingerprinting method.

The nucleic acids to be analyzed by a process described herein may be DNA or RNA, and the DNA or RNA may be double stranded or single stranded. Any source of nucleic acid, in purified or nonpurified form, can be utilized as the starting nucleic acid. For example, the nucleic acid may be from a natural DNA or RNA from any source, including virus, bacteria, and higher organisms such as plants, animals, and microbes or from cloned DNA or RNA. Additionally, the nucleic acid may constitute the entire nucleic acid or may be a fraction of a complex mixture of nucleic acids. Preferably, the nucleic acid is deoxyribonucleic acid.

Processes described herein are applicable to any nucleic acid-containing starting material, including foods and allied products, vaccines and milk infected with a virus or a bacterium, whole blood, blood serum, buffy coat, urine, feces, liquor cerebrospinalis, sperm, saliva, tissues, and cell cultures (such as mammalian cell cultures and bacterial cultures). The processes are also applicable to relatively pure input materials, such as the product of a PCR or the product to be purified further of another process for recovering nucleic acids.

The step of generating an amplified nucleic acid product can be performed by, for example, RAPD PCR, AFLP PCR, REP-PCR, or DLA. Using RAPD as an example, the choice of nucleic acid polymerase used in the extension reaction, depends on the nature of the template. For DNA template strands, suitable commercially available DNA polymerase includes DNA polymerase obtained from the thermophilic bacterium *Thermus aquaticus* (Taq polymerase) or other thermostable polymerases. Structural variants and modified forms of this and other DNA polymerases would also be expected to be useful in the process of the present invention. For RNA templates, reverse transcriptase is an example of a DNA polymerase that would also be expected to be useful. In the presence of the nucleoside triphosphate substrates, natural or analogues, the polymerase extends the length of the primer in the 3' direction. The sequence of the extension product will generally be complementary to the corresponding sequence of the template strand.

The nucleoside triphosphate substrates are employed as described in PCR Protocols, A Guide to Methods and Applications, M. A. Innis, D. H. Gelfand, J.- J. Sninsky and T. J. White, eds. pp. 3-12, Academic Press (1989), which is incorporated by reference, and U.S. Pat. Nos. 4,683,195 and 4,683,202, both incorporated by reference. The substrates can be modified for a variety of experimental purposes in ways known to those skilled in the art. As an example, at least one of the natural nucleoside triphosphate substrates may be replaced by a mobility-shifting analogue as taught in U.S. Pat. No. 4,879,214, which is incorporated by reference.

Specifically, U.S. Pat. No. 4,683,202 to Mullis is directed to a process for amplifying any desired specific nucleic acid sequence contained in a nucleic acid or mixture thereof. The process of Mullis comprises treating separate complementary strands of the nucleic acid with a molar excess of two oligonucleotide primers, and extending the primers to form complementary primer extension products, which act as templates for synthesizing the desired nucleic acid sequence. The primers of Mullis are designed to be sufficiently complementary to different strands of each specific sequence to be amplified. The steps of the reaction may be carried out stepwise or simultaneously and can be repeated as often as desired.

In one embodiment, at least one primer of greater than seven nucleotides is provided. Primers can be synthesized by standard techniques known to those skilled in the art. In some embodiments, at least one primer of nine to ten nucleotides in length is employed. Conveniently, one primer is employed. The at least one primer is labelled, preferably with a fluorophore, which can be, for example, dR6G, dR110, dTAMRA, dROX, VIC, NED, PET, LIZ, 6-FAM, TAMRA, DyeMer488/615, DyeMer488/630, PE-TexasRed, ECD, Alexa Fluor 610RPE, FITC, Oregon Green 488, or Qdot525. Other fluorophores can also be employed.

In some embodiments, a nucleic acid is contacted with at least one oligonucleotide primer as described herein. The extension product is dissociated from the complementary random nucleic acid on which it was synthesized to produce a single-stranded molecule; and the random nucleic acid segment is amplified by contacting the single-stranded extension product with a primer from above under conditions as, for example, disclosed in PCR Protocols and U.S. Pat. No. 4,683,202 such that an amplification extension product is synthesized using the single strand produced (i.e., the dissociated extension product) as a template.

The comingled products are then run to produce a DNA sequence from a fluorescent DNA sequencing instrument. The sequence output is perturbed at positions where the fingerprint products are migrating with like-sized DNA sequencing fragments. The perturbations result in an altered DNA sequence output from the instrument. These alterations are reproducible, and comparison of the output sequences can be used to characterize and/or identify the organism whose DNA was subject to the fingerprinting method using powerful freeware sequence analysis tools such as BLAST and Clustal W.

A process disclosed herein can be used to construct a nucleic acid 'fingerprint'. Such fingerprints are specific to individual organisms and can be applied to problems of identification or distinguishing of individual organisms. Such a fingerprint would be constructed using multiple polymorphisms generated by different primers and detected by the present invention, just as the polymorphisms are used to create a fingerprint in Jeffreys, A. J., "Individual-Specific 'Fingerprints' of Human DNA", Nature 316:76-79 (1985), which is incorporated herein by reference. That is, genomes are compared for the presence of absence of polymorphisms.

In some embodiments, the steps of generating amplification products and producing an amplification profile after mixing the amplifications products with the oligonucleotide size ladder can be repeated at different stringency conditions as compared to that of a first pass through the process to generate a different amplification profile as compared to that generated by the first pass. Multiple repetitions are of course possible.

EXAMPLES

The present invention is further defined in the following Examples. It should be understood that these Examples, while indicating preferred embodiments of the invention, are given by way of illustration only. From the above discussion and these Examples, one skilled in the art can ascertain the preferred features of this invention, and without departing from the spirit and scope thereof, can make various changes and modification of the invention to adapt it to various uses and conditions.

Example 1

The hypothesis that labeled amplification based fingerprinting products could be detected and reproducibly placed within a DNA sequence by means of the invention was tested using Random amplification of polymorphic DNA (RAPD) fingerprinting to generate the fingerprinting products. PCR was performed using a mix of four primers labeled at the 5' end with a FAM fluor, collectively known as primer mix FB1D1 and single primer FP5 (see Table 1).

TABLE 1

Primers

FB1D1 primer mix 1. 5' FAM-CGCTTCGCGTTTTAAAAACCGACATGAGTACAATAC (SEQ ID NO: 1)

2. 5' FAM-CGCTTCGCGTTTTAAAAACCGACATGAGTACAATCC (SEQ ID NO: 2)

3. 5' FAM-CGCTTCGCGTTTTAAAAACCGACATGAGTACAATGC (SEQ ID NO: 3)

4. 5' FAM-CGCTTCGCGTTTTAAAAACCGACATGAGTACAATTC (SEQ ID NO: 4)

FP5 primer 5. 5' FAM-ATCCGGCATATCTCGACATTCCTGATTACAATCC (SEQ ID NO: 25)

For primer mix FB1 D1, each primer was present in the reaction at 0.25 µM concentration in the presence of other components necessary for performing polymerase chain reaction (nucleotides, polymerase, buffer) in a total reaction volume of 30 µl; for single primer FP5, it was present in the reaction at 0.1 µM concentration in a total reaction volume of 30 µl, in the presence of the other components required by polymerase chain reaction.

Reactions were run either with or without (negative controls) the addition of purified microbial DNA from three diverse organisms (one yeast, one gram positive bacterium and one gram negative bacterium (Table 2)) at a concentration of 30 ng per reaction. Five replicates each were run for the negative control and each of the microbial DNA's.

TABLE 2

Microbial species analyzed

1. *Salmonella enterica* (serovar Minnesota) MR595 ATCC 49284D

2. *Staphylococcus aureus* Mu3 ATCC 700698D-5

3. *Saccharomyces cerevisiae* S288C ATCC 204508D-5

PCR was carried out using a 2 minute hold at 95° C. followed by 10 cycles of 15 seconds at 95° C., 5 minutes at 40° C. and 1 minute at 70° C., followed by 30 cycles of 95° C. for 15 seconds and 3 minutes at 70° C.

PCR reaction products were cleaned up as appropriate for DNA sequence reactions prior to loading on a capillary electrophoresis sequence apparatus, at which time the PCR products are recovered in a 15 µl volume of $H_2O$.

A 2 µl aliquot of the PCR product is then added to 20 µl of deionized water. A commercial sequence standard (hsp 60, Applied Biosystems, Foster City, Calif.) is prepared as follows. A 1 µl aliquot of the sequence standard is mixed with 9 µl of formamide (HiDi, Applied Biosystems). 1.5 µl of the diluted PCR product is then added to the 10 μl sequence standard/formamide solution. Samples are then mixed, denatured as for a standard sequencing reaction and loaded on to an Applied Biosystems 3730 DNA sequencer and run using standard DNA sequencing conditions. The output sequence files are then analyzed using standard DNA sequence analysis tools.

Figure 1B:
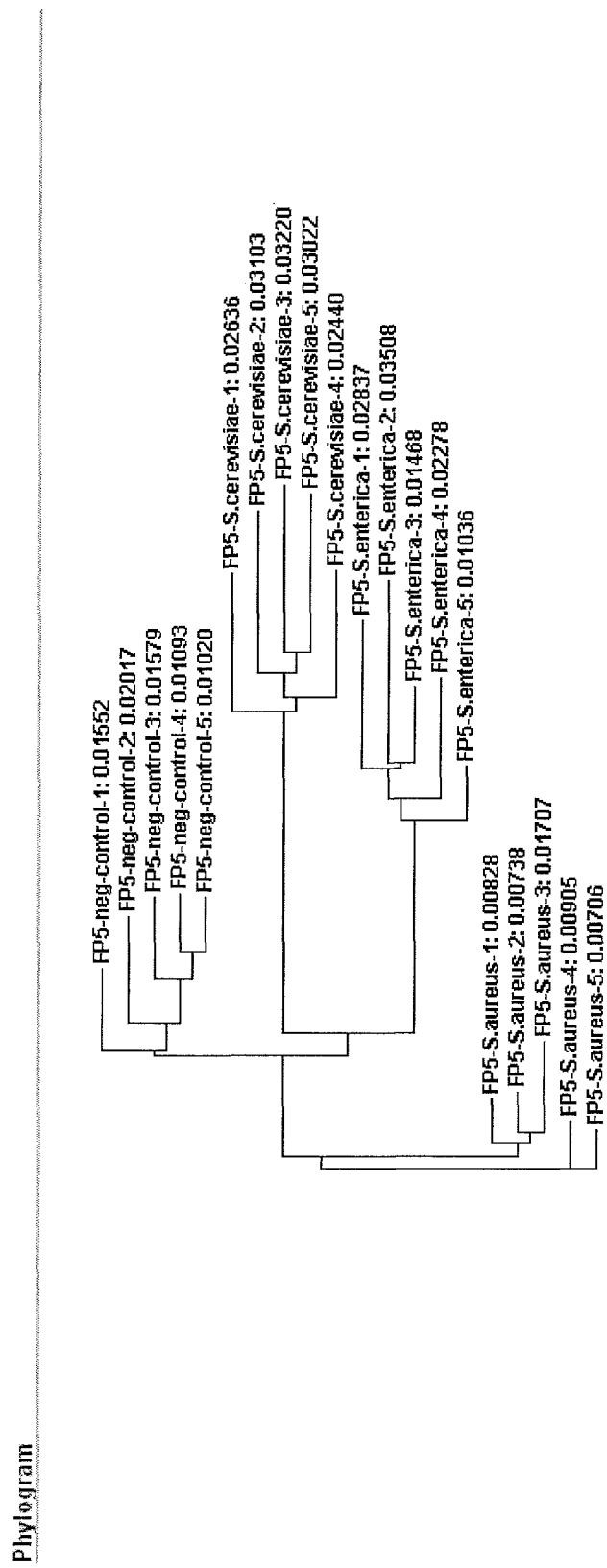
FIG. 1B shows a phylogram generated from a Clustal W alignment of all sequence reads from single primer FP5 of Example 1.

In order to test the ability of this invention to characterize an organism as belonging to a group (characterization) the sequences were examined using the Clustal W program (European Bioinformatics Institute web server). Two sets of alignments of sequences produced from primer mix FB1 D1 and single primer FP5 of Example 1 are shown in Tables 3A and 3B and the resulting phylograms are shown in FIGS. 1A and 1B. As hypothesized, the perturbations of the sequence due to the comingling of the PCR products from the RAPD fingerprinting reaction were detected as changes in the sequence output from the instrument. Clustal W alignments show that the replicate samples from a single organism cluster together and are separate from the clusters for non-identical microorganisms.

TABLE 3A

CLUSTAL 2.0.11 multiple sequence alignment of all sequence reads from primer mix FB1D1 of Example 1.

```
SEQ ID NO: 5   FB1D1-neg-control-4   -------------GTTGNT-CNNCTGCTGACAATGCTGCTGCTGCTTCNCCTCNCTGTCT   46
SEQ ID NO: 6   FB1D1-neg-control-5   --------------------TCNCNGCTGACAATGCTGCTGCTGCTTCNCCTCNNNGTCT   40
SEQ ID NO: 7   FB1D1-neg-control-2   --------GTNNNGTTGCTACTACTGCTGACAATGCTGCTGCTGCTTCTCCTCNNTGTCT   52
SEQ ID NO: 8   FB1D1-S. cerevisiae-5 ------------TGTTGCTACTACTGCTGACAATGCTGCTGCTGCTTCTCCTCACTGTCT   48
SEQ ID NO: 9   FB1D1-S. cerevisiae-1 -----CTGNTAATGTTGCTACTACTGCTGACAATGCTGCTGCTGCTTCTCCTCACTGTCT   55
SEQ ID NO: 10  FB1D1-S. cerevisiae-3 ----NCNGNNNNNGNTGCTACTACTGCTGACAATGCTGCTGCTTCTCCTCNCTGTCT     56
SEQ ID NO: 11  FB1D1-S. cerevisiae-2 -----CTGTTAATGTTGCTACTACTGCTGACAATGCTGCTGCTGCTTCNCCTCNCTGTCT   55
SEQ ID NO: 12  FB1D1-S. cerevisiae-4 -------------GTTGNT--CNCNGCTGACAATGCTGCTGCTGCTTCTCCTCACTGTCT   45
SEQ ID NO: 13  FB1D1-neg-control-1   --------GNTANGTTGCTNCTACTGCTGACAATGCTGCTGCTGCTTCNCCTCNCTGTCT   52
SEQ ID NO: 14  FB1D1-neg-control-3   GNTNNCTGTTAATGTTGCTACTACTGCTGACAATGCTGCTGCTGCTTCNCCTCNCTGTCT   60
SEQ ID NO: 15  FB1D1-S. enterica-5   ------CNGNNNTGTTNCTCNN-CTGCTGACAATGCTGCTGNNGNNNCNCCTCNCTGTCT   53
SEQ ID NO: 16  FB1D1-S. enterica-4   ------CNGNNNNGTTGCTNCTACTGCTGACAATGCTGCTGNNGNNNCNCCTCNCTGTCT   54
SEQ ID NO: 17  FB1D1-S. enterica-2   ------CNGNNANGTTNNTCNN--NGCTGACAATGCTGCTGCNGCTTCNCCTCNCTGTCT   52
SEQ ID NO: 18  FB1D1-S. enterica-3   -------------GTTNNTCNN--NGCTGACAATGCTGCTGCNGCTTCNCCTCNCTGTCT   45
SEQ ID NO: 19  FB1D1-S. enterica-1   -------------GTTGCTNCTACTGCTGANAATGCTGCTGCTTCTCCTCNCTGTCT     47
SEQ ID NO: 20  FB1D1-S. aureus-4     ----------------GNTCNC--NGNNGANNATGNTGCTGCTGCTTNNNGNNNCTGTCT   42
SEQ ID NO: 21  FB1D1-S. aureus-2     ---------TNNGTTGNTCTAC--NGNTGACNATGCTGCTGCTGCTTNNNNNNNNCTGTCT  49
SEQ ID NO: 22  FB1D1-S. aureus-3     ------CNGTTATGTTGCTCTC--NGCTGACNATGCTGCTGCTGCTTCNNGNNNCTGTCT   52
SEQ ID NO: 23  FB1D1-S. aureus-1     -------------GTTGNTCNN--NGCTGACNATGCTGCTGCTGCTTNNNGNNNCTGTCT   45
SEQ ID NO: 24  FB1D1-S. aureus-5     ------CNGNNANGTTGNTCNN--NGCTGANNN-GCTGCTGCTGCTTCNNGTNNCTGTCT   51
                                                 *  **    * *****   *               ****

FB1D1-neg-control-4    CCACTTCCTTGAACAATGCGCCGTCATGCTTCTTTTGCCTCCCGCTGCTCCAGAAAGCTA   106
FB1D1-neg-control-5    CCACTTCCTTGAACAATGCGCCGTCATGCTTCTTTTGCCTCCCGCTGCTCCAGAAAGCTA   100
FB1D1-neg-control-2    CCACTTCCTTGAACAATGCGCCGTCATGCTTCTTTTGCCTCCCGCTGCTCCAGAAAGCTA   112
FB1D1-S. cerevisiae-5  CCACTTCCTTGAACAATGCGCCGNCNTGCTTCTTTTGCCTCCCGCTGCTCCNGAGNGNTA   108
FB1D1-S. cerevisiae-1  CCACTTCCTTGAACAATGCGCCGNCNTGCTTCTTTTGCCTCCCGCTGCTCCNGAGNGCTA   115
FB1D1-S. cerevisiae-3  CCACTTCCTTGAACAATGCGCCGTCNTGCTTCTTTTGCCTCCCGCTGCTCCNNANNGNTA   116
FB1D1-S. cerevisiae-2  CCACTTCCTTGAACAATGCGCCGNCNTGCTTCTTTTGCCTCCCGCTGCTCCNGAGNGNTA   115
FB1D1-S. cerevisiae-4  CCACTTCCTTGAACAATGCGCCGNCNTGCTTCTTTTGCCTCCCGCTGCTCCANAGNGCTA   105
FB1D1-neg-control-1    CCACTTCCTTGAACAATGCGCCGTCATGCTTCTTTTGCCTCCCGCTGCTCCAGAAAGCTA   112
FB1D1-neg-control-3    CCACTTCCTTGAACAATGCGCCGTCATGCTTCTTTTGCCTCCCGCTGCTCCAGAAAGCTA   120
FB1D1-S. enterica-5    CCACTTCCTTGAACAATGCGCCGTCATGCTTCTTTTGCCTCCCGCTGCTCCAGAAAGCTA   113
FB1D1-S. enterica-4    CCACTTCCTTGAACAATGCGCCGTCATGCTTCTTTTGCCTCCCGCTGCTCCAGAAAGCTA   114
FB1D1-S. enterica-2    CCACTTCCTTGAACAATGCGCCGTCATGCTTCTTTTGCCTCCCGCTGCTCCAGAAAGCTA   112
FB1D1-S. enterica-3    CCACTTCCTTGAACAATGCGCCGTCATGCTTCTTTTGCCTCCCGCTGCTCCAGAAAGCTA   105
FB1D1-S. enterica-1    CCACTTCCTTGAACAATGCGCCGTCATGCTTCTTTTGCCTCCCGCTGCTCCAGAAAGCTA   107
FB1D1-S. aureus-4      CCACTTCCTTGAACAATGCGCCGTCATGCTTCTTTTGCCTCCCGCTGCTCCAGAAAGCTA   102
FB1D1-S. aureus-2      CCACTTCCTTGAACAATGNGCCGTCATGCTTCTTTTGCCTCCCGCTGCTCCAGAAAGCTA   109
FB1D1-S. aureus-3      CCACTTCCTTGAACAATGNGCCGTCATGCTTCTTTTGCCTCCCGCTGCTCCAGAAAGCTA   112
FB1D1-S. aureus-1      CCACTTCCTTGAACAANTGCGCCGTCATGCTTCTTTTGCCTCCCGCTGCTCCAGAAAGCTA  105
FB1D1-S. aureus-5      CCACTTCCTTGAACAATGCGCCGTCATGCTTCTTTTGCCTCCCGCTGCTCCAGAAAGCTA   111
                       ************** ** **** * *********************** *  *  * **

FB1D1-neg-control-4    GGCCGCAGATCAGAACCACCACAGTCAATATCACCACCTTCCTCTTATAGATTCGGAATC   166
FB1D1-neg-control-5    GGCCGCAGATCAGAACCACCACAGTCAATATCACCACCTTCCTCTTATAGATTCGGAATC   160
FB1D1-neg-control-2    GGCCGCAGATCAGAACCACCACAGTCAATATCACCACCTTCCTCTTATAGATTCGGAATC   172
FB1D1-S. cerevisiae-5  GGCCGCAGATCANAACCACCACAGTCAATATCACCACCTTCNTCTTATAGATTCGGAATC   168
FB1D1-S. cerevisiae-1  GGCCGCAGATCAGAACCACCACAGNCAATATCACCACCNNCNNCTTATAGATTCGGAATC   175
FB1D1-S. cerevisiae-3  GGCCGCAGATCAGAACCACCACAGTCAATATCACCACCTTCCTCTTATAGATTCGGAATC   176
FB1D1-S. cerevisiae-2  GGCCGCAGATCAGAACCACCACAGNCAATATCACCACCNNCNNCTTATANATTCGGAATC   175
FB1D1-S. cerevisiae-4  GGCCGCAGATCANAACCACCACAGNCAATATCACCACCNTCNNCTTATAGATTCGGAATC   165
FB1D1-neg-control-1    GGCCGCAGATCAGAACCACCACAGTCAATATCACCACCTTCCTCTTATAGATTCGGAATC   172
FB1D1-neg-control-3    GGCCGCAGATCAGAACCACCACAGTCAATATCACCACCTTCCTCTTATAGATTCGGAATC   180
FB1D1-S. enterica-5    GGCCGCAGATCAGAACCACCACAGTCAATATCACCNCCTTCCTCTTATAGATTCGGAATC   173
FB1D1-S. enterica-4    GGCCGCAGATCAGAACCACCACAGTCAATATCACCACCTTCCTCTTATAGATTCGGAATC   174
FB1D1-S. enterica-2    GGCCGCAGATCANAACCACCACAGTCAATATCACCACCTTCCTCTTATAGATTCGGAATC   172
FB1D1-S. enterica-3    GGCCGCAGATCANAACCACCACAGTCAATATCACCACCTTCCTCTTATAGATTCGGAATC   165
FB1D1-S. enterica-1    GGCCGCAGATCAGAACCACCACAGTCAATATCACCACCTTCCTCTTATAGATTCGGAATC   167
FB1D1-S. aureus-4      NGNCNNAGATCAGAACCACCACAGTCANNNTCNCCNCCTTCCTCTTATAGATTCGGAATC   162
FB1D1-S. aureus-2      NGNNNNAGATCAGAACCACCACAGAGNCNNNNTNACCNCCTTCCTCTTATAGATTCGGAATC 169
FB1D1-S. aureus-3      GGNCNNAGATCAGAACCACCACAGNCNNTATCNCCNCCTTCCTCTTATAGATTCGGAATC   172
```

TABLE 3A -continued

CLUSTAL 2.0.11 multiple sequence alignment of all sequence reads from primer mix FB1D1 of Example 1.

```
FB1D1-S. aureus-1        NGNCNNAGATCAGAACCAGCACAGNCNNNNTCNCCNCCTTCCTCTTATAGATTCGGAATC   165
FB1D1-S. aureus-5        GGCCGCAGATCAGAACCACCACAGTCNATATCACCNCCTTCCTCTTATAGATTCGGAATC   171
                               ****** ********** *    *  ** **  *   ****** **********

FB1D1-neg-control-4      TCATGATAGGGGCTCAGCCTCTGTGCGAGTGGAGAGAAGTTTGCAGGCGAGCTGAGGAGC   226
FB1D1-neg-control-5      TCATGATAGGGGCTCAGCCTCTGTGCGAGTGGAGAGAAGTTTGCAGGCGAGCTGAGGAGC   220
FB1D1-neg-control-2      TCATGATAGGGGCTCAGCCTCTGTGCGAGTGGAGAGAAGTTTGCAGGCGAGCTGAGGAGC   232
FB1D1-S. cerevisiae-5    TCATGATAGGGGCTCAGCCTCTGTGCGAGTGGAGAGAAGTTTGCAGGCGAGCTGAGGAGC   228
FB1D1-S. cerevisiae-1    TCATGATAGGGGCTCAGCCTCTGTGCGAGTGGAGAGAAGTTTGCAGGCGAGCTGAGGAGC   235
FB1D1-S. cerevisiae-3    TCATGATAGGGGCTCAGCCTCTGTGCGAGTGGAGAGAAGTTTGCAGGCGAGCTGAGGAGC   236
FB1D1-S. cerevisiae-2    TCATGATAGGGGCTCAGCCTCTGTGCGAGTGGAGAGAAGTTTGCAGGCGAGCTGAGGAGC   235
FB1D1-S. cerevisiae-4    TCATGATAGGGGCTCAGCCTCTGTGCGAGTGGAGAGAAGTTTGCAGGCGAGCTGAGGAGC   225
FB1D1-neg-control-1      TCATGATAGGGGCTCAGCCTCTGTGCGAGTGGAGAGAAGTTTGCAGGCGAGCTGAGGAGC   232
FB1D1-neg-control-3      TCATGATAGGGGCTCAGCCTCTGTGCGAGTGGAGAGAAGTTTGCAGGCGAGCTGAGGAGC   240
FB1D1-S. enterica-5      TCATGATAGGGGCTCAGCCTCTGTGCGAGTGGAGAGAAGTTNGNNNNNNNAGCTGANGAGC  233
FB1D1-S. enterica-4      TCATGATAGGGGCTCAGCCTCTGTGCGAGTGGAGAGAAGTTNNNNNNNNAGCTGANGANC   234
FB1D1-S. enterica-2      TCATGATAGGGGCTCAGCCTCTGTGCGAGTGGAGAGAAGTTNNNNNGNNAGCTGANGANC   232
FB1D1-S. enterica-3      TCATGATAGGGGCTCAGCCTCTGTGCGAGTGGAGAGAAGTTNNNNNNNGAGCTGAGGAGC   225
FB1D1-S. enterica-1      TCATGATAGGGGCTCAGCCTCTGTGCGAGTGGAGAGAAGTTNGCAGGCGAGCTGAGGAGC   227
FS1D1-S. aureus-4        TCATGATAGGGNNTCNNCCTCTGTGCGAGTGGAGAGAAGTTTGCAGGCGAGCTGANGAGC   222
FB1D1-S. aureus-2        TCATGATAGGGNNTCNNCCTCTGTGCGAGTGGAGAGAAGTTTGCAGGCNAGCTGANGAGC   229
FB1D1-S. aureus-3        TCATGATAGGGNNTCNNCCTCTGTGCGAGTGGAGAGAAGTTTGCAGGCGAGCTGANGAGC   232
FB1D1-S. aureus-1        TCATGATAGGGGNTCNNCCTCTGTGCGAGTGGAGAGAAGTTTGCAGGCGAGCTGAGGAGC   225
FB1D1-S. aureus-5        TCATGATAGGGGCTCANCCTCTGTGCGAGTGGAGAGAAGTTTGCAGGCGAGCTGAGGAGC   231
                         **********  **  ************************          ****** ** *

FB1D1-neg-control-4      AATTGCAGGTGATATGATGTGCTCGGCTCAAGAAGCGGGCCCGNNNNGNNNNNNNNCGTG   286
FB1D1-neg-control-5      AATTGCAGGTGATATGATGTGCTCGGCTCAAGAAGCGGGCCCGGNNNNNNNNNNNNCGTG   280
FB1D1-neg-control-2      AATTGCAGGTGATATGATGTGCTCGGCTCAAGAAGCGGGCCCGGAGAGGAANANNTCGTG   292
FB1D1-S. cerevisiae-5    AATTGCAGGTGATATGATGTGCTCGGCTCNNNGGGCGNGGN-NNNNNNNNNANGNCNNG   287
FB1D1-S. cerevisiae-1    AATTGCNGGTGATATGATGTGCTCGGCTCNNNGGGNNNGGN-GNNNNNNNNANGNCNNG-   293
FB1D1-S. cerevisiae-3    AATTGCAGGTGATATGATGTGCTCGGCTCANGGGGNNNNNN-NNNNNNNNNNNNNNCNNG   295
FB1D1-S. cerevisiae-2    AATTGCAGGTGATATGATGTGCTCGGCTCANNGGGCNNNNN-NNNNNNNNNNNNNNNNTG   294
FB1D1-S. cerevisiae-4    AATTGCAGGTGATATGATGTGCTCGGCTCNNNGGGCGNNNN-NNNNNNNNNNNNNNCNNG   284
FB1D1-neg-control-1      AATTGCAGGTGATATGATGTGCTCGGCTCAAGAAGCGGGCCCNNNGAGNAGGANGTCGTG   292
FB1D1-neg-control-3      AATTGCAGGTGATATGATGTGCTCGGCTCAAGAAGCGNGNNNAGGAAGAAGTCGTG   300
FB1D1-S. enterica-5      AATTGCAGGTGATATGATGTGCTCGGCTCAAGAAGCGGGCCCGGAGAGGAAGAAGNNNNN   293
FB1D1-S. enterica-4      AATTGCAGGTGATATGATGTGCTCGGCTCAAGAAGCGGGCCCGGANANGAANAAGTNNNN   294
FB1D1-S. enterica-2      AATTGCAGGTGATATGATGTGCTCGGCTCAAGAAGCGGGCCCGGAGNNNNNAAGNNNNN   292
FB1D1-S. enterica-3      AATTGCAGGTGATATGATGTGCTCGGCTCAAGAAGCGGGCCNGGNNAGGAAGAAGNNNNN   285
FB1D1-S. enterica-1      AATTGCAGGTGATATGATGTGCTCGGCTCAAGAAGCGGGCCNGNNNNGNNNGAAGTCNNG   287
FB1D1-S. aureus-4        ANTTGCAGGNGNNNNNNTGTGCTCGGCTCAAGAAGCGGGCCCNGNNNNNANNAAGTCGTG   282
FB1D1-S. aureus-2        ANTTGCAGGNGNNNGNNTGTGCTCGGCTCAAGANGCGGGNCCGGANAGGAAGAAGTCGTG   289
FB1D1-S. aureus-3        AATTGCAGGNGNNNNATGTGCTCGGCTCAAGAAGCGGGCCCGGAGAGGAAGAAGTCGTG   292
FB1D1-S. aureus-1        ANTTGCAGGTGNNNNATGTGCTCGGCTCAAGAAGCGGGCCCGAGAGGAAGAAGTCGTG   285
FB1D1-S. aureus-5        AATTGCAGGTGNNNNNNNGTGCTCGGCTCAAGAAGCGGGCCNNGNNNNNNNNAGTCGTG   291
                          * ****  ** *       **********           *

FB1D1-neg-control-4      CCGGGG-CTAATTATTGGCAAAACGAGCTCTTGTTGTAAACATTGATCCAACTGGAATGN   345
FB1D1-neg-control-5      CCGGGG-CTAATTATTGGCAAAACGAGCTCTTGTTGTAAACATTGATCCAACTGGAANGN   339
FB1D1-neg-control-2      CCGGGG-CTAATTATTGGCAAAACGAGCTCTTGTTGTAAACATTGATCCAACTGGAATGN   351
FB1D1-S. cerevisiae-5    CCGGGG-CTAATTATTGGCAAAACGAGCTCTTGTTGTAAACATTGATCCCGGGNGATGN   346
FB1D1-S. cerevisiae-1    CCGGGG-CTAATTATTGGCAAAACGAGCTCTTGTTGTAAACATTGATCCNNNNGGNNNGT   352
FB1D1-S. cerevisiae-3    CCGGGG-CTAATTATTGGCAAAACGAGCTCTTGTTGTAAACATTGATCCAACTGGNNGGN   354
FB1D1-S. cerevisiae-2    CCGGGG-CTAATTATTGGCAAAACGAGCTCTTGTTGTAAACATTGATCCAACTGGNNGGN   353
FB1D1-S. cerevisiae-4    CCGGGG-CTAATTATTGGCAAAACGAGCTCTTGTTGTAAACATTGATCCAACTGNNNNGN   343
FB1D1-neg-control-1      CCGGGG-CTAATTATTGGCAAAACGAGCTCTTGTTGTAAACATTGATCCAACTGGNNNGN   351
FB1D1-neg-control-3      CCGGGG-CTAATTATTGGCAAAACGAGCTCTTGTTGTAAACATTGATCCNNCTGGANTNN   359
FB1D1-S. enterica-5      NCGGGGGCTAATTATTGGCAAAACGAGCTCTTGTTNNNNNNNNNNNNNGNNNNNNNNNN   353
FB1D1-S. enterica-4      NCNNGG-CTAATTATTGGCAAAACGAGCTCTTGTTNNNNNNNNNNNNNNGNNNNNNNNNN   353
FB1D1-S. enterica-2      NNNNNN-NTAATTATTGGCAAAACGAGCTCTTGTTNNNNNNNNNNNNNGNNNNNNNNNN   351
FB1D1-S. enterica-3      NNNNNN-NTAATTATTGGCAAAACGAGCTCTTGTTGTANNNNNNNNNNNGNNNNNNNNNN   344
FB1D1-S. enterica-1      NCGNGG-CTAATTATTGGCAAAACGAGCTCTTGTTGTANNNNNNNNNNNGNNNNNNNNNN   346
FB1D1-S. aureus-4        CCGGGG-CTAATTATTGGCAAAACGAGCTCTTGTTGTAAACATTGANNGGGGGGGGGN   341
FB1D1-S. aureus-2        CCGGGG-CTAATTATTGGCAAAACGAGCTCTTGTTGTAAACATTGANTGNNNNNNNNNN   348
FB1D1-S. aureus-3        CCGGGG-CTAATTATTGGCAAAACGAGCTCTTGTTGNAAACNTNGNNNGGGGGGGGNNNN   351
FB1D1-S. aureus-1        CCGGGG-CTAATTATTGGCAAAACGAGCTCTTGTTGTAAACATTGNNNNNNNNNNNNNN   344
FB1D1-S. aureus-5        CCGGGG-CTAATTATTGGCAAAACGAGCTCTTGTTGTAAACATTGANNNNNNNNNNNNNN   350
                                *************************

FB1D1-neg-control-4      CNCTAATNNNNNNNTCAATATTCCATAAGGCATGATGGTTGCTCAGAGGCAGGAGAAGAG   405
FB1D1-neg-control-5      CNCTAANNNNNNNAT-CAATATTCCATAAGGCATGATGGTTGCTCAGAGGCAGGAGAAGAG  398
FB1D1-neg-control-2      CNCTAANNNNNNNN-NAATATTCCATAAGGCATGATGGTTGCTCAGAGGCAGGAGAAGAG   410
FB1D1-S. cerevisiae-5    NNNNNANGNNNNNN-NNNNNNGNNNNNGGNATGATGGTTGCTCAGAGGCAGGAGAAGAG   405
FB1D1-S. cerevisiae-1    NNNNNNGGNGNNN-GANNNTGNNNNNGGNNNGGNATGATGGTTGCTCAGAGGCAGGAGAAGAG   411
FB1D1-S. cerevisiae-3    NNNNNATGGNGNNN-NNNNNTGCCNNNNNGCATGATGGTTGCTCAGAGGCAGGAGAAGAG   413
FB1D1-S. cerevisiae-2    NNNNNATGNGNNN-GNNNNTGNNNNNNGGGATGATGGTTGCTCAGAGGCAGGAGAAGAG   412
FB1D1-S. cerevisiae-4    NNNNNANGGNGNNN-NNNNNGTGNNNNNNNGGNATGATGGTTGCTCAGAGGCAGGAGAAGAG   402
```

TABLE 3A -continued

CLUSTAL 2.0.11 multiple sequence alignment of all sequence reads from primer mix FB1D1 of Example 1.

```
FB1D1-neg-control-1      NACTNANNNNNNNN-CAATATTCCATAAGGCATGATGGTTGCTCAGAGGCAGGAGAAGAG    410
FB1D1-neg-control-3      NNNNNATGGCGAAT-CAATATTCCATAAGGCATGATGGTTGCTCAGAGGCAGGAGAAGAG    418
FB1D1-S. enterica-5      NNACNNNNGGNNNNNCAATATTCCNTANNGCATGATGGTTGCTCAGAGGCANNNNNNNAG    413
FB1D1-S. enterica-4      NNNCTNNNNNNNGNNCNA-TATTCCNTAANGCATGATGGTTGCTCAGAGGCAGGNNNNNAN    412
FB1D1-S. enterica-2      NA--CTANNGNNGNNCAATATTCCNTANNGCATGATGGTTGCTCAGAGGCAGNNNNNNAG    409
FB1D1-S. enterica-3      NA--CTNNNNGNGNNCAATATTCCNTAANGCATGATGGTTGCTCAGAGGCAGNNNNNNAG    402
FB1D1-S. enterica-1      NC--TANNGNNNNATCNATATTCCNTAANGCATGATGGTTGCTCAGAGGCANGNNNNA-G    403
FB1D1-S. aureus-4        NNN-NNNNNNNA--TCAATATTCCATAAGGCATGATGGTTGCTCAGAGGCAGGAGAAGAG    398
FB1D1-S. aureus-2        NNN-NNNNNNNNA-TCAATATTCCATAAGGCATGATGGTTGCTCAGAGGCAGGAGAAGAG    406
FB1D1-S. aureus-3        NNN-NNNNNNNNA-TCAATATTCCATAAGGCATGATGGTTGCTCAGAGGCAGGAGAAGAG    409
FB1D1-S. aureus-1        NNN-NNNNNNNNGNNCCATAAGGCATGATGGTTGCTCAGAGGCAGGAGAAGAG           403
FB1D1-S. aureus-5        NNN-NNNNNNNNNNNCNATATTCCATAAGGCATGATGGTTGCTCAGAGGCAGGAGAAGAG    409
                                            *  ******************

FB1D1-neg-control-4      CAACGAATACGATCCTATAAAAGATAAAACATAAATAAACAGTCTTGATTATATTCTGGG    465
FB1D1-neg-control-5      CAACGAATACGATCCTATAAAAGATAAAACATAAATAAACAGTCTTGATTATATTCTGGG    458
FB1D1-neg-control-2      CAACGAATACGATCCTATAAAAGATAAAACATAAATAAACAGTCTTGATTATATTCTGGG    470
FB1D1-S. cerevisiae-5    CAACGAATACGATCCTATNAAAGATAAAACATAAATAAACAGTCTTGATTATATTCTGGG    465
FB1D1-S. cerevisiae-1    CAACGAATACGATCCTATAAAAGATAAAACATAAATAAACNGTCTTGATTATATTCTGGG    471
FB1D1-S. cerevisiae-3    CAACGAATACGATCCTATAAAAGATAAAACATAAATAAACAGTCTTGATTATATTCTGGG    473
FB1D1-S. cerevisiae-2    CAACGAATACNATCCTATAAAAGATAAAACATAAATAAACAGTCTTGATTATATTCTGGG    472
FB1D1-S. cerevisiae-4    CAACGAATACGATCCTATNAAAGATAAAACATAAATAAACAGTCTTGATTATATTCTGGG    462
FB1D1-neg-control-1      CAACGAATACGATCCTATAAAAGATAAAACATAAATAAACAGTCTTGATTATATTCTGGG    470
FB1D1-neg-control-3      CAACGAATACGATCCTATAAAAGATAAAACATAAATAAACAGTCTTGATTATATTCTGGG    478
FB1D1-S. enterica-5      NNNNNNNNNCGATCCTATAAAAGATAAAACATAAATAAACAGTCTTGATTATATTCTGGG    473
FB1D1-S. enterica-4      CAANNNNNNCGATCCTATAAAAGATAAAACATAAATAAACAGTCTTGATTATATTCTGGG    472
FB1D1-S. enterica-2      CAACNAANNCATCTATAAAAGATAAAACATAAATAAACAGTCTTGATTATATTCTGGG     469
FB1D1-S. enterica-3      CAANNNANNCGATCCTATAAAAGATAAAACATAAATAAACAGTCTTGATTATATTCTGGG    462
FB1D1-S. enterica-1      CAACNAANACGATCCTATAAAAGATAAAACATAAATAAACAGTCTTGATTATATTCTGGG    463
FB1D1-S. aureus-4        CAACGAATACGATCCTATAAAAGATAAAACATAAATAAACAGTCTTGATTATATTCTGGG    458
FB1D1-S. aureus-2        CAACGAATACGATCCTATAAAAGATAAAACATAAATAAACAGTCTTGATTATATTCTGGG    466
FB1D1-S. aureus-3        CAACGAATACGATCCTATAAAAGATAAAACATAAATAAACAGTCTTGATTATATTCTGGG    469
FB1D1-S. aureus-1        CAACGAATACGATCCTATAAAAGATAAAACATAAATAAACAGTCTTGATTATATTCTGGG    463
FB1D1-S. aureus-5        CAACGAATACGATCCTATAAAAGATAAAACATAAATAAACAGTCTTGATTATATTCTGGG    469
                                 * ******  ********************* *  ****************

FB1D1-neg-control-4      TATTAAAGCCACAATCAGAACAAATATATGCTTTGTATCTTTTCTTGCCTTCTTCAT-TA    524
FB1D1-neg-control-5      TATTAAAGCCACAATCAGAACAAATATATGCTTTGTATCTTTTCTTGCCTTCTTCAT-TA    517
FB1D1-neg-control-2      TATTAAAGCCACAATCAGAACAAATATATGCTTTGTATCTTTTCTTGCCTTCTTCAT-TA    529
FB1D1-S. cerevisiae-5    TATTAAANNCNCNGCAGAACAAATATATGCTTTGTNNNNNNNTNNNGNCNNTTNNNNNN-GN    524
FB1D1-S. cerevisiae-1    TATTAAANNCNNNGNNAGAACAAATATATGCTTTNNNNNNNNTCNNGNCNNNNNNNNN-NN    530
FB1D1-S. cerevisiae-3    TATTAAAGNCNCAGNCAGAACAAATATATGCTTTGTNNCTNNNCNTGCCTTCTTNNN-NN    532
FB1D1-S. cerevisiae-2    TATTAAANNNNNNGNCAGAACAAATATATGCTTTGNNNNNTNNCNTGNNNCNNNNG-GN    531
FB1D1-S. cerevisiae-4    TATTAAANNNNNNGTCAGAACAAATATATGCTTTGTNNNNNNCNNNCCTTCTNNNN-GN    521
FB1D1-neg-control-1      TATTAAAGCCACAATCAGAACAAATATATGCTTTGTATCTTTTCTTGCCTTCTTCATTAC    530
FB1D1-neg-control-3      TATTAAAGCCACAATCAGAACAAATATATGCTTTGTATCTTTTCTTGCCNNNNNNGT-TA    537
FB1D1-S. enterica-5      TATTAAAGCCACAATCAGAACAAATATATGCTTTGTATCTTNNNNGCCTTCTTCAN-NN    532
FB1D1-S. enterica-4      TATTAAAGCCACAATCAGAACAAATATATGCTTTGTATCTTNNNNGCCTTCTTCAT-NN    531
FB1D1-S. enterica-2      TATTAAAGCCACAATCAGAACAAATATATGCTTTGTATCTTNNNNGCCTTCTTCAN-NN    528
FB1D1-S. enterica-3      TATTAAAGCCACAATCAGAACAAATATATGCTTTGTATCTTNNNNNGCCTTCTTCAT-NN    521
FB1D1-S. enterica-1      TATTAAAGCCACAATCAGAACANATATATGCTTTGTATCTTTNCNNGCCTTCTTCAT-NN    522
FB1D1-S. aureus-4        TATTAAAGCCACAATCAGAACAAATATATGCTTTGTATCTTTTCTTGCCTTCTTCAT-TN    517
FB1D1-S. aureus-2        TATTAAAGCCACAATCAGAACAAATATATGCTTTGTATCTTTTCTTGCCTTCTTCNT-TA    525
FB1D1-S. aureus-3        TATTAAAGCCACAATCAGAACAAATATATGCTTTGTATCTTTTCTTGCCTTCTTCAT-TA    528
FB1D1-S. aureus-1        TATTAAAGCCACAATCAGAACAAATATATGCTTTGTATCTTTTCTTGCCTTCTTCAT-NN    522
FB1D1-S. aureus-5        TATTAAAGCCACAATCAGAACAAATATATGCTTTGTATCTTTTCTTGCCTTCTTCAT-TA    528
                         *******                  *****************

FB1D1-neg-control-4      CCAANNGNNTNNNCNNNNNNNNNNAGAGAACTTGTGGTAAGATAAGAAGATATTTTATTC    584
FB1D1-neg-control-5      CCNANNNNNNNNNNNNNNNNNNNTAAGAGAACTTGTGGTAAGATAAGAAGATATTTTATTC   577
FB1D1-neg-control-2      CCAACTGCTTNNNCGGCNCNTTNAGAGAACTTGTGGTAAGATAAGAAGATATTTTATTC    589
FB1D1-S. cerevisiae-5    NNNNNNNNNNNNNCGGCCANNNNNNNAGAGAACTTGTGNNNNNATAAGAAGATATTTTATTC   584
FB1D1-S. cerevisiae-1    NNNNNNNNNNNNNNGGCCACATTAAGAGAACTTGTNNNNNNNTAAGAAGATATTTTATTC  590
FB1D1-S. cerevisiae-3    NNNNNNNNNNNNNNGGCCACNNNNNAGAACTTGNGGNGNNATAAGAAGATATTTTATTC  592
FB1D1-S. cerevisiae-2    NNNNNNNNNNNNNGGCCNCNNNNNGAGAACTTGTNNNNNNNTAAGAAGATATTTTATTC  591
FB1D1-S. cerevisiae-4    NNNNNNNNNNNNNGGCCNCNNNNGAGAACTTGTNNNNNNNTAAGAAGATATTTTATTC   581
FB1D1-neg-control-1      NNNNNNNNNCGCGGGCNNNNNNAAGAGAACTTGTGGTAAGATAAGAAGATATTTTATTC   590
FB1D1-neg-control-3      CNNNNTGNTTCCGCGGCCACATTAAGAGAACTTGTGGTAAGATAAGAAGATATTTTATTC   597
FB1D1-S. enterica-5      NNNACTGCTTCCGCGGCCACATTAAGAGAACTTGTGGTAAGATAAGAAGATATTTTATTC  592
FB1D1-S. enterica-4      NNNNNTGCTTCCGCGGNNACATTAAGAGAACTTGTGGTAAGATAAGAAGATATTTTATTC  591
FB1D1-S. enterica-2      NNNANNGCTNNNNNGGCCACATTAAGAGAACTTGTGGTAAGATAAGAAGATATTTTATTC  588
FB1D1-S. enterica-3      NNNNNTGNTTCCGCGGNCACATTAAGAGAACTTGTGGTAAGATAAGAAGATATTTTATTC  581
FB1D1-S. enterica-1      NNNNNNGNTTCCGCGNNNCATTAAGAGAACTTGTGGTAAGATAAGAAGATATTTTATTC   582
FB1D1-S. aureus-4        NNNNNNGNTNCGCGGCCACATTAAGAGAACTTGNGNTAAGATAAGAAGATATTTTATTC   577
FB1D1-S. aureus-2        CCAACTGCTTCCGCGGCCACATTAAGAGAACTTGNGNTAAGATAAGAAGATATTTTATTC  585
FB1D1-S. aureus-3        CCAACTGCTTCCGCGGCCACATTAAGAGAACTTGNGGTAAGATAAGAAGATATTTTATTC  588
```

TABLE 3A -continued

CLUSTAL 2.0.11 multiple sequence alignment of all sequence reads from primer mix FB1D1 of Example 1.

```
FB1D1-S. aureus-1        NNNNNTGCTTCCGCGGCCACATTAAGAGAACTTGGGGTAAGATAAGAAGATATTTTATTC    582
FB1D1-S. aureus-5        NNNNCNGCNNNNNNGNCCACATTAAGAGAACTTGNGGTAAGATAAGAAGATATTTTATTC    588
                                *******        ******************

FB1D1-neg-control-4      GTTCTGCTGACTTGCTGGATGTCGGGAAATATTCTGCATTTGATAAGAGGCGGTTAATTG    644
FB1D1-neg-control-5      GTTCTGCTGACTTGCTGGATGTCGGGAAATATTCTGCATTTGATAAGAGGCGGTTAATTG    637
FB1D1-neg-control-2      GTTCTGCTGACTTGCTGGATGTCGGGAAATATTCTGCATTTGATAAGAGGCGGTTAATTG    649
FB1D1-S. cerevisiae-5    GNTCTGCTGACTTGCTGGATGTCGGGAAATATTCTGCATTTGATAAGAGGCGGTTAATTG    644
FB1D1-S. cerevisiae-1    GNTCTGCTGACTTGCTGGATGTCGGGAAATATTCTGCATTTGATAAGAGGCGGTTAATTG    650
FB1D1-S. cerevisiae-3    GNTCTGCTGACTTGCTGGATGTCGGGAAATATTCTGCATTTGATAAGAGGCGGTTAATTG    652
FB1D1-S. cerevisiae-2    GNNCTGCTGACTTGCTGGATGTCGGGAAATATTCTGCATTTGATAAGAGGCGGTTAATTG    651
FB1D1-S. cerevisiae-4    GNTCTGCTGACTTGCTGGATGTCGGGAAATATTCTGCATTTGATAAGAGGCGGTTAATTG    641
FB1D1-neg-control-1      GTTCTGCTGACTTGCTGGATGTCGGGAAATATTCTGCATTTGATAAGAGGCGGTTAATTG    650
FB1D1-neg-control-3      GTTCTGCTGACTTGCTGGATGTCGGGAAATATTCTGCATTTGATAAGAGGCGGTTAATTG    657
FB1D1-S. enterica-5      GTTCTGCTGACTTGCTGGATGTCGGGAAATATTCTGCATTNNNNNNNAGGCGGTTAATTG    652
FB1D1-S. enterica-4      GTTCTGCTGACTTGCTGGATGTCGGGAAATANTCTGCATTNNANNNNAGGCGGTTAATTG    651
FB1D1-S. enterica-2      GTTCTGCTGACTTGCTGGATGTCGGGAAATANTCTGCATTTNNNNNNAGGCGGTTAATTG    648
FB1D1-S. enterica-3      GTTCTGCTGACTTGCTGGATGTCGGGAAATATTCTGCATTTNNNNNAGGCGGTTAATTG     641
FB1D1-S. enterica-1      GTTCTGCTGACTTGCTGGATGTCGGGAAATATTCTGCATTTNNNNNGAGGCGGTTAATTG    642
FB1D1-S. aureus-4        GTTCTGCTGACTTGCTGGATGTCGGGAAATATTCTGCATTTGATAAGAGGCGGTTAATTG    637
FB1D1-S. aureus-2        GTTCTGCTGACTTGCTGGATGTCGGGAAATATTCTGCATTTGATAAGAGGCGGTTAATTG    645
FB1D1-S. aureus-3        GTTCTGCTGACTTGCTGGATGTCGGGAAATATTCTGCATTTGATAAGAGGCGGTTAATTG    648
FB1D1-S. aureus-1        GTTCTGCTGACTTGCTGGATGTCGGGAAATATTCTGCATTTGATAAGAGGCGGTTAATTG    642
FB1D1-S. aureus-5        GTTCTGCTGACTTGCTGGATGTCGGGAAATATTCTGCATTTGATAAGAGGCGGTTAATTG    648
                         * ****************************  ********        *************

FB1D1-neg-control-4      CAGATATAATTGGTAGTGAAAAGGGTCGTTGCTATGGTCACCGTGAAGCGAGTACAGCAG    704
FB1D1-neg-control-5      CAGATATAATTGGTAGTGAAAAGGGTCGTTGCTATGGTCACCGTGAAGCGAGTACAGCAG    697
FB1D1-neg-control-2      CAGATATAATTGGTAGTGAAAAGGGTCGTTGCTATGGTCACCGTGAAGCGAGTACAGCAG    709
FB1D1-S. cerevisiae-5    CAGATATAATTGGTAGTGAAAAGGGTCGTTGCTATGGTCACCGTGAAGCGAGTACAGCAG    704
FB1D1-S. cerevisiae-1    CAGATATAATTGGTAGTGAAAAGGGTCGTTGCTATGGTCACCGTGAAGCGAGTACAGCAG    710
FB1D1-S. cerevisiae-3    CAGATATAATTGGTAGTGAAAAGGGTCGTTGCTATGGTCACCGTGAAGCGAGTACAGCAG    712
FB1D1-S. cerevisiae-2    CAGATATAATTGGTAGTGAAAAGGGTCGTTGCTATGGTCACCGTGAAGCGAGTACAGCAG    711
FB1D1-S. cerevisiae-4    CAGATATAATTGGTAGTGAAAAGGGTCGTTGCTATGGTCACCGTGAAGCGAGTACAGCAG    701
FB1D1-neg-control-1      CAGATATAATTGGTAGTGAAAAGGGTCGTTGCTATGGTCACCGTGAAGCGAGTACAGCAG    710
FB1D1-neg-control-3      CAGATATAATTGGTAGTGAAAAGGGTCGTTGCTATGGTCACCGTGAAGCGAGTACAGCAG    717
FB1D1-S. enterica-5      CANATATAATTGGTAGTGAAAAGGGTCGTTGCTATGGTCACCGTGAAGCGAGTACAGCAG    712
FB1D1-S. enterica-4      CANATATAATTGGTAGTGAAAAGGGNCNNTGCTATGGTCACCGTGAAGCGAGTACAGCAG    711
FB1D1-S. enterica-2      CANATATAATTGGTAGTGAAAAGGGTCGTTGCTATGGTCACCGTGAAGCGAGTACAGCAG    708
FB1D1-S. enterica-3      CAGATATAATTGGTAGTGAAAAGGGTCGTTGCTATGGTCACCGTGAAGCGAGTACAGCAG    701
FB1D1-S. enterica-1      CAGATATAATTGGTAGTGAAAAGGGTCGTTGCTATGGTCACCGTGAAGCGAGTACAGCAG    702
FB1D1-S. aureus-4        CAGATATAATTGGTAGTGAAAAGGNGNNTTGCTATGGTCACCGTGAAGNGAGTACAGCAG    697
FB1D1-S. aureus-2        CAGATATAATTGGTAGTGAAAAGGNGCGTTGCTATGGTCACCGTGAAGNGAGTACAGCAG    705
FB1D1-S. aureus-3        CAGATATAATTGGTAGTGAAAAGGNNNNTTGCTATGGTCACCGTGAAGCGAGTACAGCAG    708
FB1D1-S. aureus-1        CAGATATAATTGGTAGTGAAAAGGNNNNTTGCTATGGTCACCGTGAAGCGAGTACAGCAG    702
FB1D1-S. aureus-5        CAGATATAATTGGTAGTGAAAAGGNNNNTTGCTATGGTCACCGTGAAGCGAGTACAGCAG    708
                         ** *******************       *******************  **********

FB1D1-neg-control-4      CACAAGAATGTGTGCCGTTCTCAGTTAATATTGTTTGAATATGGTAACCTGTTTTAGTCG    764
FB1D1-neg-control-5      CACAAGAATGTGTGCCGTTCTCAGTTAATATTGTTTGAATATGGTAACCTGTTTTAGTCG    757
FB1D1-neg-control-2      CACAAGAATGTGTGCCGTTCTCAGTTAATATTGTTTGAATATGGTAACCTGNTTTAGTCG    769
FB1D1-S. cerevisiae-5    CACAAGAATGTGTGCCGNTCTCAGTTAATATTGTTTGAATATGGNAACCTGTTTTAGTCG    764
FB1D1-S. cerevisiae-1    CACAAGAATGTGTGCCGTTCTCAGTTAATATTGTNTGAATATGGTAACCTGNTTTAGTCG    770
FB1D1-S. cerevisiae-3    CACAAGANNGTGTGCCGTTCTCAGTTAATATNGNNNGAATATGGTAACCTGNTTTAGTCG    772
FB1D1-S. cerevisiae-2    CACANGANNGTGTGCCGTTCTCAGTTAATATTGNTTGAATATGGTAACCTGTTTTAGTCG    771
FB1D1-S. cerevisiae-4    CACAANANNGNGTGCCGTTCTCAGTTNNNNNNGTTTGAATATGGTAACCTGTTTTAGTCG    761
FB1D1-neg-control-1      CACAAGAATGTGTGCCGTTCTCAGTTAATATTGTTTGAATATGGTAACCTGTTTTAGTCG    770
FB1D1-neg-control-3      CACAAGAATGTGTGCCGTTCTCAGTTAATATTGTTTGAATATGGTAACCTGTTTTAGTCG    777
FB1D1-S. enterica-5      CACAAGAATGTGNGCCGTTCTCNNNNNNTATTGTTTGAATATNNNNACCTGTTTTAGTCG    772
FB1D1-S. enterica-4      CACAAGAATGTGNGCCGTTCTCNNNNNNTATTGTTTGAATATGNNNACCTGNTTTAGTCG    771
FB1D1-S. enterica-2      CACAAGAATGTGNGCCGTTCTCNGNNNNTATTGTTTGAATATGGNAACCTGTTTTAGTCG    768
FB1D1-S. enterica-3      CACAAGAATGTGTGCCGTTCTCNNNNNNTATTGTTTGAATATGGNAACCTGTTTTAGTCG    761
FB1D1-S. enterica-1      CACAAGAATGTGTGCCGTTCTCNNNNNNTATTGTTTGAATATGGTAACCTGTTTTAGTCG    762
FB1D1-S. aureus-4        CACAAGAATGTGTGCCGTTCTCAGTTAATATTGTTTGAATATGGTAACCTGTTTTAGTCG    757
FB1D1-S. aureus-2        CACAAGAATGTGTGCCGTTCTCAGTTAATATTGTTTGAATATGGTAACCTGTTTTAGTCG    765
FB1D1-S. aureus-3        CACAAGAATGTGTGCCGTTCTCAGTTAATATTGTTTGAATATGGTAACCTGTTTTAGTCG    768
FB1D1-S. aureus-1        CACAAGAATGTGTGCCGTTCTCAGTTAATATTGTTTGAATATGGTAACCTGTTTTAGTCG    762
FB1D1-S. aureus-5        CACAAGAATGTGTGCCGTTCTCAGTTAATATTGTTTGAATATGGTAACCTGTTTTAGTCG    768
                         ****  *    * *   ***  ****           *  ******    *****  *******

FB1D1-neg-control-4      GTTTAAAGGTAAGAAGANCTAACCAAAAACAAC-ACTGCAGTGACTG--ANNGTAGTATT    821
FB1D1-neg-control-5      GTTTAAAGGNAAGAAGATCTAACCAAAAACAAC-ACTGCAGTGACTG--ATTG-------    807
FB1D1-neg-control-2      GTTTAAAGGTAAGAAGATCTAACCAAAAACAAC-ACTGCAGTGACTG--ATT--------    818
FB1D1-S. cerevisiae-5    GTTTAAAGGTAAGAAGATCTAACCNAAAACAAN-NNNNNNNGNCNNN--NNGNNGNNNNN    821
FB1D1-S. cerevisiae-1    GTTTAAAGGTAAGAAGATCTAACCAAAAACAAC-ACTGCNNGNCGN---NNNNNNGGNNN    827
FB1D1-S. cerevisiae-3    GTTTAAAGGTAAGAAGANCTAACCAAAAACAAC-ACTGCNNNNNNN---NNGGGGGNNNN    829
FB1D1-S. cerevisiae-2    GTTTAAAGGTAAGAAGANCTAACCNAAAACAAC-ACTGCNNNNNNGN--GGGGGGNNNNN    828
FB1D1-S. cerevisiae-4    GTTTAAAGGNAAGAAGATCTAACCAAAAACAAC-ACTGCANTGNCNG--NGNNGGGNNNN    818
```

TABLE 3A -continued

CLUSTAL 2.0.11 multiple sequence alignment of all sequence reads from primer mix FB1D1 of Example 1.

| | | |
|---|---|---|
| FB1D1-neg-control-1 | GTTTAAAGGTAAGAAGATCTAACCNAAAACAAC-ACTGCAGTGACTG--A---------- | 817 |
| FB1D1-neg-control-3 | GTTTAAAGGTAAGAAGATCTANNNNNNNNNNNCACTGCAGNGACTG--ANNGNAGTATT | 835 |
| FB1D1-S. enterica-5 | GTTTAANNNNNNNNNNNTCTAACCNAAAAC-AACACTGCAGNGACTG--ANNGTAGTATT | 829 |
| FB1D1-S. enterica-4 | GTTTAANNNNNNNNNNNTCTAACNNAAAAC-AACACTGCNGNGACTG--ANTGNNNNATT | 828 |
| FB1D1-S. enterica-2 | GNTTAANNNNNNNNNNNTCTAACCAAAAAC-AACACTGNNGNGACTG--ANTGTAGTATT | 825 |
| FB1D1-S. enterica-3 | GTTTAAANGNNNNNNNNT-CTAACCNAAAAC-AACACTGCAGTGACNG--ANNNNNGTANT | 817 |
| FB1D1-S. enterica-1 | GTTTAANNNNNNNNNNTCTAACCAAAAAC-AACACTGCAGNGGNNNGGNNNGTAGTATT | 821 |
| FB1D1-S. aureus-4 | GTTTAAAGGTAAGAAGATCTAACCAAAAAC-AACACTGNNNGNNNG--ATTGTAGNNNN | 814 |
| FB1D1-S. aureus-2 | GTTTAAAGGTAAGAAGATCTAACCAAAAAC-AACACNGCAGTGACTG--AfTGNNGNNNN | 822 |
| FB1D1-S. aureus-3 | GNTTAAAGGTAAGAAGATCTAACNNAAANNCAACACTGCANNGACTG--NNNNNNNNNAT | 826 |
| FB1D1-S. aureus-1 | GTTTAAAGGTNAGAAGATCTAACCAAAAAC-AACACTGCAGNGACTG--ATTGTAGTATT | 819 |
| FB1D1-S. aureus-5 | GTTTAAAGGTAAGAAGATCTAACCAAAANC-AACACTGCAGTGACNG--NNNNGNNGNAT | 825 |
| | * **** *** | |
| FB1D1-neg-control-4 | ------------------------------------------------------------ | |
| FB1D1-neg-control-5 | ------------------------------------------------------------ | |
| FB1D1-neg-control-2 | ------------------------------------------------------------ | |
| FB1D1-S. cerevisiae-5 | NNNNNNTT--A--CTTNNNNNNNATTTTGGNNGNA--AACATCAACGG-NNNNNNTCAAC | 874 |
| FB1D1-S. cerevisiae-1 | NNNNNNNNTTA--CTNNNNNNATTTTGGNN-TA--AACATCAACGG-NNNNNNNCANC | 881 |
| FB1D1-S. cerevisiae-3 | NNNNNNNTT-A--CTNNNNGNNNNTTNNNGGNGNA--AACATCNACGN-NNNNNNNCAAC | 883 |
| FB1D1-S. cerevisiae-2 | NNNNNNNNT-A--CTTNNNNNNNNNNNNNNNNN----ACATCNNCGN-NNNNNNNCAAC | 880 |
| FB1D1-S. cerevisiae-4 | NNNNNNNNNTA--CTTANNNNNNNNNNNNNGGNGTAAACATCAACGN-NNNNNTCNACC | 875 |
| FB1D1-neg-control-1 | ------------------------------------------------------------ | |
| FB1D1-neg-control-3 | TATTTTTTT-A--CTTAATCTNNATTTTGGTGNAA---ACATCNACGG-CNN-------- | 880 |
| FB1D1-S. enterica-5 | TATTTTTNNNN--CNNNNNCTTNANTTT-GGTGTA--AACATCAACGG-CGCACTT---- | 879 |
| FB1D1-S. enterica-4 | TATTTTTTTAC--NNNNNNNNNNTTT--GGTGTA--AACATCAACGG-CGCACTTCNN- | 880 |
| FB1D1-S. enterica-2 | TATTTTNNNNN--NNNNNCTTAATTTT--GGTGNA--AACATCNACGG-CGCACTTCAAC | 878 |
| FB1D1-S. enterica-3 | TATTTTTTTAC--TNNNNNNNNNNNTTTGGTGNA--AACATCAACGG-CGCACTTC--- | 869 |
| FB1D1-S. enterica-1 | TATTTTNNNNN--NNNNNNCTTAATTTT-GGNGNA--AACATCAACGG-CGCACNTNNN- | 874 |
| FB1D1-S. aureus-4 | NANNNNNTTT--ACNTAATCNTANTTTT-GGTGNA--AACATCAACGG-CGCACTTCAAC | 868 |
| FB1D1-S. aureus-2 | NNNNNTTTTTT-ANNTATCTTAATTTT-GGTGTA--AACATCAACGG-CGCACTTCAA- | 876 |
| FB1D1-S. aureus-3 | TNNNNNNTTTTTACTTAATCTTAATTTT-GGTGTA--AACATCAACNGGCGCACTTN--- | 880 |
| FB1D1-S. aureus-1 | TATTTTTNNN---NNNNNNCTNNATTTT-GGTGTA--AACATCAACGG-CGCACNN---- | 868 |
| FB1D1-S. aureus-5 | TTATTTTTNN--NNNNNNNNTTAATTTT-GGNGNA--AACATCAACGG-CGCACTTCN- | 877 |

TABLE 3B

CLUSTAL 2.0.11 multiple sequence alignment of all sequence reads from single primer FP5 of Example 1.

| | | | |
|---|---|---|---|
| SEQ ID NO: 26 | FP5-neg-control-4 | -----------NNNNNNNATTACTGTTAATGTTGCTACTACTGCTGACAATGCTGCTGCT | 49 |
| SEQ ID NO: 27 | FP5-neg-control-5 | ---------NNNNTTNNNATTACTGTTAATGNTGCTACTACTGCTGACAATGCTGCTGCT | 51 |
| SEQ ID NO: 28 | FP5-neg-control-3 | ---------NNGNNNNTGATTACTGTTAATGTTGCTACTACTGCTGACAATGCTGCTGCT | 51 |
| SEQ ID NO: 29 | FP5-neg-control-2 | --------NCTGGTNNNNNNNACTGTTAATGTTGCTACTACTGCTGACAATGCTGCTGCT | 52 |
| SEQ ID NO: 30 | FP5-neg-control-1 | --------NCNGNNNATGANTACTGTTAATGTTGCTACTACTGCTGACAATGCTGCTGCT | 52 |
| SEQ ID NO: 31 | FP5-S. aureus-4 | --------NCCGNNNNNNNNTACTGTTAATGTTGCTACTACTGCTGACAATGCTGCTGCT | 52 |
| SEQ ID NO: 32 | FP5-S. aureus-5 | --------------------TACTGTTAATGTTGNNNCNNNNGCTGACAATGCTGCTGCT | 40 |
| SEQ ID NO: 33 | FP5-S. aureus-2 | -NNNGCNGCCNGGTTNTGATTACTGTTAATGTTGCTACTACTGCTGACAATGCTGCTGCT | 59 |
| SEQ ID NO: 34 | FP5-S. aureus-3 | ------NNNCTGGTTNTGANTACTGNNNNNGTTGCTACTACTGCTGACAATGCTGCTGCT | 54 |
| SEQ ID NO: 35 | FP5-S. aureus-1 | -----NNNNCTGGTTNTGANTACTGTTAANGTTGCTACTACTGCTGACAATGCTGCTGCT | 55 |
| SEQ ID NO: 36 | FP5-S. enterica-2 | -----------NTTNTGATTACTGTTNNNNNTGCTACTACTGCTGACAATGCTGCTGCT | 48 |
| SEQ ID NO: 37 | FP5-S. enterica-3 | -----NNNNNNGGTTNTGATTACTGTTAATGTTGCTACTACTGCTGACAATGCTGCTGCT | 55 |
| SEQ ID NO: 38 | FP5-S. enterica-1 | ---------CTGNNNNTGATTACTGTTNNNNGTTGCTACTACTGCTGACAATGCTGCTGCT | 51 |
| SEQ ID NO: 39 | FP5-S. enterica-4 | --NNNNNNCCTGGTNATGANTACTGTTAATGTTGCTACTACTGCTGACAATGCTGCTGCT | 58 |
| SEQ ID NO: 40 | FP5-S. enterica-5 | -------------NNNNNATTNCTGTTAATGTTGCTACTACTGCTGACAATGCTGCTGCT | 47 |
| SEQ ID NO: 41 | FP5-S. cerevisiae-3 | -------------NNNNNATNNCTGTTNATGTTGCTNCTACTGCTGACAATGCTGCTGCT | 47 |
| SEQ ID NO: 42 | FP5-S. cerevisiae-5 | -------------NTTNNGATTACTGTTAATNNTNNTCTACTGCTGACAATGCTGCTGCT | 48 |
| SEQ ID NO: 43 | FP5-S. cerevisiae-2 | NNNNTGNNGCCTGNTTNTGATTACTGTTAATGTTGCTACTACTGCTGACAATGCTGCTGCT | 60 |
| SEQ ID NO: 44 | FP5-S. cerevisiae-4 | --------CCTGGTTANGANTACTGNTNNNGNTGCTACTACTGCTGACAATGCTGCTGCT | 52 |
| SEQ ID NO: 45 | FP5-S. cerevisiae-1 | --------CCTGNNNNGATTACTGTTAATGTTGCTACTACTGCTGACAATGCTGCTGCT | 52 |
| | | *** * * ***************** | |
| | FP5-neg-control-4 | GCTTCNCCTCNCTGTCTCCACTTCCTTGAACAATGCGCCGTCATGCTTCTTTTGCCTCCC | 109 |
| | FP5-neg-control-5 | GCTTCTCCTCNCTGTCTCCACTTCCTTGAACAATGCGCCGTCATGCTTCTTTTGCCTCCC | 111 |
| | FP5-neg-control-3 | GCTTCTCCTCNCTGTCTCCACTTCCTTGAACAATGCGCCGTCATGCTTCTTTTGCCTCCC | 111 |
| | FP5-neg-control-2 | GCTTCTCCTNNCTGTCTCCACTTCCTTGAACAATGCGCCGTCATGCTTCTTTTGCCTCCC | 112 |
| | FP5-neg-control-1 | GCTTCTCCTCNCTGTCTCCACTTCCTTGAACAATGCGCCGTCATGCTTCTTTTGCCTCCC | 112 |
| | FP5-S. aureus-4 | GCTTCTCCTCNNTGTCTCCACTTCCTTGAACAATGCGCCGTCATGCTTCTTTTGCCTCCC | 112 |
| | FP5-S. aureus-5 | GCTTCTCCTCNCTGTCTCCACTTCCTTGAACAATGCGCCGTCATGCTTCTTTTGCCTCCC | 100 |
| | FP5-S. aureus-2 | GCTTCTCCTNNCTGTCTCCACTTCCTTGAACAATGCGCCGTCATGCTTCTTTTGCCTCCC | 119 |
| | FP5-S. aureus-3 | GCTTCTCNTNNCTGTCTCCACTTCCTTGAACAATGCGCCGTCATGCTTCTTTTGCCTCCC | 114 |
| | FP5-S. aureus-1 | GCTTCTCCTCNCTGTCTCCACTTCCTTGAACAATGCGCCGTCATGCTTCTTTTGCCTCCC | 115 |
| | FP5-S. enterica-2 | GCTTCTCCTCNCTGTCTCCACTTCCTTGAACAATGCGCCGTCATGCTTCTTTTGCCTCCC | 108 |
| | FP5-S. enterica-3 | GCTTCTCCTNNCTGTCTCCACTTCCTTGAACAATGCGCCGTCATGCTTCTTTTGCCTCCC | 115 |
| | FP5-S. enterica-1 | GCTTCTCCTNNCTGTCTCCACTTCCTTGAACAATGCGCCGTCATGCTTCTTTTGCCTCCC | 111 |

TABLE 3B -continued

CLUSTAL 2.0.11 multiple sequence alignment of all sequence reads from single primer FP5 of Example 1.

```
FP5-S. enterica-4         GCTTCTCCTNNCTGTCTCCACTTCCTTGAACAATGCGCCGTCATGCTTTCTTTTGCCTCCC    118
FP5-S. enterica-5         GCTTCTCCTCNCTGTCTCCACTTCCTTGAACAATGCGCCGTCATGCTTCTTTTGCCTCCC    107
FP5-S. cerevisiae-3       GCTTCTCCTCNNTGTCTCCACTTCCTTGAACAATGCGCCGTCATGCTTCTTTTGCCTCCC    107
FP5-S. cerevisiae-5       GCTTCTCCTNNCTGTCTCCACTTCCTTGAACAATGCGCCGTCATGCTTCTTTTGCCTCCC    108
FP5-S. cerevisiae-2       GCTTCTCCTCNCTGTCTCCACTTCCTTGAACAATGCGCCGTCATGCTTCTTTTGCCTCCC    120
FP5-S. cerevisiae-4       GCTTCTCCTCNCTGTCTCCACTTCCTTGAACAATGCGCCGTCATGCTTCTTTTGCCTCCC    112
FP5-S. cerevisiae-1       GCTTCTCCTCNCTGTCTCCACTTCCTTGAACAATGCGCCGTCATGCTTCTTTTGCCTCCC    112
                          ***** *  *   *********************************************

FP5-neg-control-4         GCTGCTCCAGAAAGCTAGGCCGCAGATCAGAACCACCACAGTCAATATCACCACCTTCCT    169
FP5-neg-control-5         GCTGCTCCAGAAAGCTAGGCCGCAGATCAGAACCACCACAGTCAATATCACCACCTTCCT    171
FP5-neg-control-3         GCTGCTCCAGAAAGCTAGGCCGCAGATCAGAACCACCACAGTCAATATCACCACCTTCCT    171
FP5-neg-control-2         GCTGCTCCAGAAAGCTAGGCCGCAGATCAGAACCACCACAGTCAATATCACCACCTTCCT    172
FP5-neg-control-1         GCTGCTCCAGAAAGCTAGGCCGCAGATCAGAACCACCACAGTCAATATCACCACCTTCCT    172
FP5-S. aureus-4           GCTGCTCCAGAAAGCTAGGCCGCAGATCAGAACCACCACAGTCAATATCACCACCTTCCT    172
FP5-S. aureus-5           GCTGCTCCAGAAAGCTAGGCCGCAGATCAGAACCACCACAGTCAATATCACCACCTTCCT    160
FP5-S. aureus-2           GCTGCTCCAGAAAGCTAGGCCGCAGATCAGAACCACCACAGTCAATATCACCACCTTCCT    179
FP5-S. aureus-3           GCTGCTCCAGAAAGCTAGGCCGCAGATCAGAACCACCACAGTCAATATCACCACCTTCCT    174
FP5-S. aureus-1           GCTGCTCCAGAAAGCTAGGCCGCAGATCAGAACCACCACAGTCAATATCACCACCTTCCT    175
FP5-S. enterica-2         GCTGCTCCAGAAAGCTAGGCCGCAGATCAGAACCACCACAGTCAATATCACCACCTTCCT    168
FP5-S. enterica-3         GCTGCTCCAGAAAGCTAGGCCGCAGATCAGAACCACCACAGTCAATATCACCACCTTCCT    175
FP5-S. enterica-1         GCTGCTCCAGAAAGCTAGGCCGCAGATCAGAACCACCACAGTCAATATCACCACCTTCCT    171
FP5-S. enterica-4         GCTGCTCCAGAAAGCTAGGCCGCAGATCAGAACCACCACAGTCAATATCACCACCTTCCT    178
FP5-S. enterica-5         GCTGCTCCAGAAAGCTAGGCCGCAGATCAGAACCACCACAGTCAATATCACCACCTTCCT    167
FP5-S. cerevisiae-3       GCTGCTCCAGAAAGCTAGGCCGCAGATCAGAACCACCACAGTCAATATCACCACCTTCCT    167
FP5-S. cerevisiae-5       GCTGCTCCAGAAAGCTAGGCCGCAGATCAGAACCACCACAGTCAATATCACCACCTTCCT    168
FP5-S. cerevisiae-2       GCTGCTCCAGAAAGCTAGGCCGCAGATCAGAACCACCACAGTCAATATCACCACCTTCCT    180
FP5-S. cerevisiae-4       GCTGCTCCAGAAAGCTAGGCCGCAGATCAGAACCACCACAGTCAATATCACCACCTTCCT    172
FP5-S. cerevisiae-1       GCTGCTCCAGAAAGCTAGGCCGCAGATCAGAACCACCACAGTCAATATCACCACCTTCCT    172
                          ************************************************************

FP5-neg-control-4         CTTATAGATTCGGAATCTCATGATAGGGGCTCAGCCTCTGTGCGAGTGGAGAGAAGTTTG    229
FP5-neg-control-5         CTTATAGATTCGGAATCTCATGATAGGGGCTCAGCCTCTGTGCGAGTGGAGAGAAGTTTG    231
FP5-neg-control-3         CTTATAGATTCGGAATCTCATGATAGGGGCTCAGCCTCTGTGCGAGTGGAGAGAAGTTTG    231
FP5-neg-control-2         CTTATAGATTCGGAATCTCATGATAGGGGCTCAGCCTCTGTGCGAGTGGAGAGAAGTTTG    232
FP5-neg-control-1         CTTATAGATTCGGAATCTCATGATAGGGGCTCAGCCTCTGTGCGAGTGGAGAGAAGTTTG    232
FP5-S. aureus-4           CTTATAGATTCGGAATCTCATGATAGGGGCTCAGCCTCTGTGCGAGTGGAGAGAAGTTTG    232
FP5-S. aureus-5           CTTATAGATTCGGAATCTCATGATAGGGGCTCAGCCTCTGTGCGAGTGGAGAGAAGTTTG    220
FP5-S. aureus-2           CTTATAGATTCGGAATCTCATGATAGGGGCTCAGCCTCTGTGCGAGTGGAGAGAAGTTTG    239
FP5-S. aureus-3           CTTATAGATTCGGAATCTCATGATAGGGGCTCAGCCTCTGTGCGAGTGGAGAGAAGTTTG    234
FP5-S. aureus-1           CTTATAGATTCGGAATCTCATGATAGGGGCTCAGCCTCTGTGCGAGTGGAGAGAAGTTTG    235
FP5-S. enterica-2         CTTATAGATTCGGAATCTCATGATAGGGGCTCAGCCTCTGTGCGAGTGGAGAGAAGTTTG    228
FP5-S. enterica-3         CTTATAGATTCGGAATCTCATGATAGGGGCTCAGCCTCTGTGCGAGTGGAGAGAAGTTTG    235
FP5-S. enterica-1         CTTATAGATTCGGAATCTCATGATAGGGGCTCAGCCTCTGTGCGAGTGGAGAGAAGTTTG    231
FP5-S. enterica-4         CTTATAGATTCGGAATCTCATGATAGGGGCTCAGCCTCTGTGCGAGTGGAGAGAAGTTTG    238
FP5-S. enterica-5         CTTATAGATTCGGAATCTCATGATAGGGGCTCAGCCTCTGTGCGAGTGGAGAGAAGTTTG    227
FP5-S. cerevisiae-3       CTTATAGATTCGGAATCTCATGATAGGGGCTCAGCCTCTGTGCGAGTGGAGAGAAGTTTG    227
FP5-S. cerevisiae-5       CTTATAGATTCGGAATCTCATGATAGGGGCTCAGCCTCTGTGCGAGTGGAGAGAAGTTTG    228
FP5-S. cerevisiae-2       CTTATAGATTCGGAATCTCATGATAGGGGCTCAGCCTCTGTGCGAGTGGAGAGAAGTTTG    240
FP5-S. cerevisiae-4       CTTATAGATTCGGAATCTCATGATAGGGGCTCAGCCTCTGTGCGAGTGGAGAGAAGTTTG    232
FP5-S. cerevisiae-1       CTTATAGATTCGGAATCTCATGATAGGGGCTCAGCCTCTGTGCGAGTGGAGAGAAGTTTG    232
                          ************************************************************

FP5-neg-control-4         CAGGCGAGCTGAGGAGCAATTGCAGGTGATATGATGTGCTCGGCTCAAGAAGCGGGCCCG    289
FP5-neg-control-5         CAGGCGAGCTGAGGAGCAATTGCAGGTGATATGATGTGCTCGGCTCAAGAAGCGGGCCCG    291
FP5-neg-control-3         CAGGCGAGCTGAGGAGCAATTGCAGGTGATATGATGTGCTCGGCTCAAGAAGCGGGCCCG    291
FP5-neg-control-2         CAGGCGAGCTGAGGAGCAATTGCAGGTGATATGATGTGCTCGGCTCAAGAAGCGGGCCCG    292
FP5-neg-control-1         CAGGCGAGCTGAGGAGCAATTGCAGGTGATATGATGTGCTCGGCTCAAGAAGCGGGCCCG    292
FP5-S. aureus-4           CAGGCGAGCTGAGGAGCAATTGCAGGTGATATGATGTGCTCGGCTCAAGAAGCGGGCCCG    292
FP5-S. aureus-5           CAGGCGAGCTGAGGAGCAATTGCAGGTGATATGATGTGCTCGGCTCAAGAAGCGGGCCCG    280
FP5-S. aureus-2           CAGGCGAGCTGAGGAGCAATTGCAGGTGATATGATGTGCTCGGCTCAAGAAGCGGGCCCG    299
FP5-S. aureus-3           CAGGCGAGCTGAGGAGCAATTGCAGGTGATATGATGTGCTCGGCTCAAGAAGCGGGCCCG    294
FP5-S. aureus-1           CAGGCGAGCTGAGGAGCAATTGCAGGTGATATGATGTGCTCGGCTCAAGAAGCGGGCCCG    295
FP5-S. enterica-2         CAGGCGAGCTGAGGAGCAATTGCAGGTGATATGATGTGCTCGGCTCAAGAAGCGGGCCCG    288
FP5-S. enterica-3         CAGGCGAGCTGAGGAGCAATTGCAGGTGATATGATGTGCTCGGCTCAAGAAGCGGGCCCG    295
FP5-S. enterica-1         CAGGCGAGCTGAGGAGCAATTGCAGGTGATATGATGTGCTCGGCTCAAGAAGCGGGCCCG    291
FP5-S. enterica-4         CAGGCGAGCTGAGGAGCAATTGCAGGTGATATGATGTGCTCGGCTCAAGAAGCGGGCCCG    298
FP5-S. enterica-5         CAGGCGAGCTGAGGAGCAATTGCAGGTGATATGATGTGCTCGGCTCAAGAAGCGGGCCCG    287
FP5-S. cerevisiae-3       CAGGCGAGCTGAGGAGNNNTTGCAGGTGATATGATGTGCTCGGCTCAAGAAGCGGGCCCG    287
FP5-S. cerevisiae-5       CAGGCGAGCTGAGGAGCAATTGCAGGTGATATGATGTGCTCGGCTCAAGAAGCGGGCCCG    288
FP5-S. cerevisiae-2       CAGGCGAGCTGAGGAGCANTTGCAGGTGATATGATGTGCTCGGCTCAAGAAGCGGGCCCG    300
FP5-S. cerevisiae-4       CAGGCGAGCTGAGGAGCAATTGCAGGTGATATGATGTGCTCGGCTCAAGAAGCGGGCCCG    292
FP5-S. cerevisiae-1       CAGGCGAGCTGAGGAGCAATTGCAGGTGATATGATGTGCTCGGCTCAAGAAGCGGGCCCG    292
                          ****************   *****************************************

FP5-neg-control-4         GAGAGGAAGAAGTCGTGCCGGGGCTAATTATTGGCAAAACGAGCTCTTGTTGTAAACATT    349
FP5-neg-control-5         GAGAGGAAGAAGTCGTGCCGGGGCTAATTATTGGCAAAACGAGCTCTTGTTGTAAACATT    351
```

TABLE 3B -continued

CLUSTAL 2.0.11 multiple sequence alignment of all sequence reads from single primer FP5 of Example 1.

```
FP5-neg-control-3      GAGAGGAANAAGNCGTGCCGGGGCTAATTATTGGCAAAACGAGCTCTTGTTGTAAACATT  351
FP5-neg-control-2      GAGAGGAAGAAGTCGTGCCGGGGCTAATTATTGGCAAAACGAGCTCTTGTTGTAAACATT  352
FP5-neg-control-1      GAGAGGAAGAAGTCGTGCCGGGGCTAATTATTGGCAAAACGAGCTCTTGTTGTAAACATT  352
FP5-S. aureus-4        GAGAGGAAGAAGTCGTGCCGGGGCTAATTATTGGCAAAACGAGCTCTTGTTGTAAACATT  352
FP5-S. aureus-5        GAGAGGAAGAAGTCGTGCCGGGGCTAATTATTGGCAAAACGAGCTCTTGTTGTAAACATT  340
FP5-S. aureus-2        GAGAGGAAGAAGTCGTGCCGGGGCTAATTATTGGCAAAACGAGCTCTTGTTGTAAACATT  359
FP5-S. aureus-3        GAGAGGAAGAAGTCGTGCCGGGGCTAATTATTGGCAAAACGAGCTCTTGTTGTAAACATT  354
FP5-S. aureus-1        GAGAGGAAGAAGTCGTGCCGGGGCTAATTATTGGCAAAACGAGCTCTTGTTGTAAACNTT  355
FP5-S. enterica-2      GAGAGGAAGAAGTCGTGCCGGGGCTAATTATTGGCAAAACGAGCTCTTGTTGTAAACATT  348
FP5-S. enterica-3      GAGAGGAAGAAGTCGTGCCGGGGCTAATTATTGGCAAAACGAGCTCTTGTTGTAAACATT  355
FP5-S. enterica-1      GAGAGGAAGAAGTCGTGCCGGGGCTAATTATTGGCAAAACGAGCTCTTGTTGTAAACATT  351
FP5-S. enterica-4      GAGAGGAAGAAGTCGTGCCGGGGCTAATTATTGGCAAAACGAGCTCTTGTTGTAAACATT  358
FP5-S. enterica-5      GAGAGGAAGAAGTCGTGCCGGGGCTAATTATTGGCAAAACGAGCTCTTGTTGTAAACATT  347
FP5-S. cerevisiae-3    GAGAGGAAGAAGTCGTGCCGGGGCTAATTATTGGCAAAACGAGCTCTTGTTGTAAACATN  347
FP5-S. cerevisiae-5    GAGAGGAAGAAGTCGTGCCGGGGCTAATTATTGGCAAAACGAGCTCTTGTTGTAAACATN  348
FP5-S. cerevisiae-2    GAGAGGAAGAAGTCGTGCCGGGGCTAATTATTGGCAAAACGAGCTCTTGTTGTAAACATN  360
FP5-S. cerevisiae-4    GAGAGGAAGAAGTCGTGCCGGGGCTAATTATTGGCAAAACGAGCTCTTGTTGTAAACNTN  352
FP5-S. cerevisiae-1    GAGAGGAAGAAGTCGTGCCGGGGCTAATTATTGGCAAAACGAGCTCTTGTTGTAAACATN  352
                       ******** ***  *********************************************  *

FP-neg-control-4       GATCCAACTGGAANNNNNNNNNGGNNNNNNNNNNNNNNCATAAGGCATGATGGTTGCTCA  409
FP5-neg-control-5      GATCCAACTGGANNGNNNNNNNATGNNNNNNNNNNNNTCCATAAGGCATGATGGTTGCTCA  411
FP5-neg-control-3      GATCCAACTGGAANNNNNNNNNTGNNNNNNNNNNNTTCCATAAGGCATGATGGTTGCTCA  411
FP5-neg-control-2      GATCCAACTGGNANGNCACNNNNGNNNNNNMAATATTCCATAAGGCATGATGGTTGCTCA  412
FP5-neg-control-1      GATCCAACTGGAATGTCACTAANGGNNNNNNNATATTCCATAAGGCATGATGGTTGCTCA  412
FP5-S. aureus-4        GATCCAACTGGAATGTCACTAATGGCGAATCAATATTCCATAAGGCATGATGGTTGCTCA  412
FP5-S. aureus-5        GATCCAACTGGAATGTCACTAATGGCGAATCAATATTCCATAAGGCATGATGGTTGCTCA  400
FP5-S. aureus-2        GATCCAACTGGAATGTCACTAATGGCGAATCAATATTCCATAAGGCATGATGGTTGCTCA  419
FP5-S. aureus-3        GATCCAACTGGAATGTCACTAATGGCGAATCAATATTCCATAAGGCATGATGGTTGCTCA  414
FP5-S. aureus-1        GNTNCAACTGGAATGTCACTAATGGCGAATCAATATTCCATAAGGCATGATGGTTGCTCA  415
FP5-S. enterica-2      GATCCAACTGGAATGTCACTAANNNNNNNNNATATTCCATAAGGCATGATGGTTGCTCA  408
FP5-S. enterica-3      GATCCAACTGGAATGTCACTAANNNNNNNNNNTATTCCATAAGGCATGATGGTTGCTCA  415
FP5-S. enterica-1      GATCCAACTGGAATGTCACTAANNNNNNNAN-TATTCCATAAGGCATGATGGTTGCTCA  410
FP5-S. enterica-4      GATCCAACTGGAATGTCACTAANNNNNNNNAA-TATTCCATAAGGCATGATGGTTGCTCA  417
FP5-S. enterica-5      GATCCAACTGGAATGTCACTAANNNNNNNNNNAATATTCCATAAGGCATGATGGTTGCTCA  407
FP5-S. cerevisiae-3    NNNNNNNNTGGNATGTCACTAATGGCGAATNNNNANNNNTAAGGNNTGATGGTTGCTCA  407
FP5-S. cerevisiae-5    NNNNNNNNGGAATGTCACTAATGGCGAATCNNNNNNCNTAAGGNNNGNTGGTTGCTCA  408
FP5-S. cerevisiae-2    NNNNNNNNNNNNANGTCACTAATGGCGAANNNNNANNNNTAAGGNNTGATGGTTGCTCA  420
FP5-S. cerevisiae-4    NNNNNNNNGGAATGTCACTAATGGCGAATNNNNNNNNNNTAAGGNATGATGGTTGCTCA  412
FP5-S. cerevisiae-1    NNNNNNNNGGAATGTCACTAATGGCGAANNNNNNNNNNNTAAGGNATGATGGTTGCTCA  412
                                                                 *****    * **********

FP5-neg-control-4      GAGGCAGGAGAAGAGCAACGAATACGATCCTATAAAAGATAAAACATAAATAAACAGTCT  469
FP5-neg-control-5      GAGGCAGGAGAAGAGCAACGAATACGATCCTATAAAAGATAAAACATAAATAAACAGTCT  471
FP5-neg-control-3      GAGGCAGGAGAAGAGCAACGAATACGATCCTATAAAAGATAAAACATAAATAAACAGTCT  471
FP5-neg-control-2      GAGGCAGGAGAAGAGCAACGAATACGATCCTATAAAAGATAAAACATAAATAAACAGTCT  472
FP5-neg-control-1      GAGGCAGGAGAAGAGCAACGAATACGATCCTATAAAAGATAAAACATAAATAAACAGTCT  472
FP5-S. aureus-4        GAGGCAGGAGAAGAGCAACGAATACGATCCTATAAAAGATAAAACATAAATAAACAGTCT  472
FP5-S. aureus-5        GAGGCAGGAGAAGAGCAACGAATACGATCCTATAAAAGATAAAACATAAATAAACAGTCT  460
FP5-S. aureus-2        GAGGCAGGAGAAGAGCAACGAATACGATCCTATAAAAGATAAAACATAAATAAACAGTCT  479
FP5-S. aureus-3        GAGGCAGGAGAAGAGCAACGAATACGATCCTATAAAAGATAAAACATAAATAAACAGTCT  474
FP5-S. aureus-1        GAGGCAGGAGAAGAGCAACGAATACGATCCTATAAAAGATAAAACATAAATAAACAGTCT  475
FP5-S. enterica-2      GAGGCAGGAGAAGAGCAACGAATACGATCCTATAAAAGATAAAACATAAATAAACAGTCT  468
FP5-S. enterica-3      GAGGCAGGAGAAGAGCAACGAATACGATCCTATAAAAGATAAAACATAAATAAACAGTCT  475
FP5-S. enterica-1      GAGGCNGGAGAAGAGCAACGAATACGATCCTATAAAAGATAAAACATAAATAAACAGTCT  470
FP5-S. enterica-4      GAGGCAGGAGAAGAGCAACGAATACGATCCTATAAAAGATAAAACATAAATAAACAGTCT  477
FP5-S. enterica-5      GAGGCAGGAGAAGAGCAACGAATACGATCCTATAAAAGATAAAACATAAATAAACAGTCT  467
FP5-S. cerevisiae-3    GAGGCAGGAGAAGAGCNNNGNATACNNNNNTATAAAAGATAAAACATAAATAAACAGTCT  467
FP5-S. cerevisiae-5    GAGGCAGGAGAAGAGCNNNGNATACGNNNNTATAAAAGATAAAACATAAATAAACAGTCT  468
FP5-S. cerevisiae-2    GAGGCAGGAGAAGAGNNNNGNATACNNNNNNATAAAAGATAAAACATAAATAAACAGTCT  480
FP5-S. cerevisiae-4    GAGGCAGGAGAAGAGCAACGAATACNNNNNNATAAAAGATAAAACATAAATAAACAGTCT  472
FP5-S. cerevisiae-1    GAGGCAGGAGAAGAGCAACGAATACGANGCNNTAAAAGATAAAACATAAATAAACAGTCT  472
                       ****  ********     *  ****           ***************************

FP5-neg-control-4      TGATTATATTCTGGGTATTAAAGCCACAATCAGAACAAATATGCTTTGTATCTTTTCT   529
FP5-neg-control-5      TGATTATATTCTGGGTATTAAAGCCACAATCAGAACAAATATGCTTTGTATCTTTTCT   531
FP5-neg-control-3      TGATTATATTCTGGGTATTAAAGCCACAATCAGAACAAATATGCTTTGTATCTTTTCT   531
FP5-neg-control-2      TGATTATATTCTGGGTATTAAAGCCACAATCAGAACAAATATGCTTTGTATCTTTTCT   532
FP5-neg-control-1      TGATTATATTCTGGGTATTAAAGCCACAATCAGAACAAATATGCTTTGTATCTTTTCT   532
FP5-S. aureus-4        TGATTATATTCTGGGTATTAAAGCCACAATCAGAACAAATATGCTTTGTATCTTTTCT   532
FP5-S. aureus-5        TGATTATATTCTGGGTATTAAAGCCACAATCAGAACAAATATGCTTTGTATCTTTTCT   520
FP5-S. aureus2         TGATTATATTCTGGGTATTAAAGCCACAATCAGAACAAATATGCTTTGTATCTTTTCT   539
FP5-S. aureus-3        TGATTATATTCTGGGTATTAAAGCCACAATCAGAACAAATATGCTTTGTATCTTTTCT   534
FP5-S. aureus-1        TGATTATATTCTGGGTATTAAAGCCACAATCAGAACAAATATGCTTTGTATCTTTTCT   535
FP5-S. enterica-2      TGATTATATTCTGGGTATTAAAGCCACAANNNNNNNNNNNTNTGCTTTGTATCTTTNNN   528
FP5-S. enterica-3      TGATTATATTCTGGGTATTAAAGCCACANNNNNNNNNNNNNTATGCTTTGTATCTTNNN   535
FP5-S. enterica-1      TGATTATATTCTGGGTATTAAAGCCACANNNNNNNNNNGANNTATGCTTTGTATCTTNNNN  530
```

TABLE 3B -continued

CLUSTAL 2.0.11 multiple sequence alignment of all sequence reads from single primer FP5 of Example 1.

```
FP5-S. enterica-4      TGATTATATTCTGGGTATTAAAGCCACAANGNGNNNNNANNTATGCTTTGTATCTTNNNN  537
FP5-S. enterica-5      TGATTATATTCTGGGTATTAAAGCCACANNNNNNNNNGANNTATGCTTTGTATCTTTTCT  527
FP5-S. cerevisiae-3    TGATTATATTCTGGGTATTAAAGCCNCAATCNNANNAAATATATGCTTTGTATCTTTTCT  527
FP5-S. cerevisiae-5    TGATTATATTCTGGGTATTAAAGCCACAATCAGAACAAATATATGCTTTGTATCTTTTCT  528
FP5-S. cerevisiae-2    TGATTATATTCTGGGTATTAAAGCCACAATCAGAACAAATATATGCTTTGTATCTTTTCT  540
FP5-S. cerevisiae-4    TGATTATATTCTGGGTATTAAAGCCACAATCAGAACAAATATATGCTTTGTATCTTTTCT  532
FP5-S. cerevisiae-1    TGATTATATTCTGGGTATTAAAGCCACAATCAGAACAAATATATGCTTTGTATCTTTTCT  532
                       ***********************  **             * *************

FP5-neg-control-4      TGCCTTCTTCATTACCAACTGCTTCCGCGGCCACATTANNAGAACTTGTGGTAAGATAAG  589
FP5-neg-control-5      TGCCTTCTTCATTACCAACTGCTTCCGCGGCCACATTAAGAGAACTTGTGGTAAGATAAG  591
FP5-neg-control-3      TGCCTTCTTCATTACCAACTGNTTCCGCGGNCACNTTAAGAGAACTTGTGGTAAGATAAG  591
FP5-neg-control-2      TGCCTTCTTCATTACCAACTGCTTCCGCGGCCACATTAAGAGAACTTGTGGTAAGATAAG  592
FP5-neg-control-1      TGCCTTCTTCATTACCAACTGCTTCCGCGGCCACATTAAGAGAACTTGTGGTAAGATAAG  592
FP5-S. aureus-4        TGCCTTCTTCATTACCAACTGCTTCCGCGGCCACATTAAGAGAACTTGTGGTAAGATAAG  592
FP5-S. aureus-5        TGCCTTCTTCATTACCAACTGCTTCCGCGGCCACATTAAGAGAACTTGTGGTAAGATAAG  580
FP5-S. aureus-2        TGCCTTCTTCATTACCAACTGCTTCCGCGGCCACATTAAGAGAACTTGTGGTAAGATAAG  599
FP5-S. aureus-3        TGCCTTCTTCATTACCAACTGCTTCCGCGGCCACATTAAGAGAACTTGTGGTAAGATAAG  594
FP5-S. aureus-1        TGCCTTCTTCATTACCAACTGCTTCCGCGGCCACATTAAGAGAACTTGTGGTAAGATAAG  595
FP5-S. enterica-2      NGCCTTCTTCATTACCAACTGCTTCCGCGGCCACATTAAGAGAACTTGTGGTAAGATAAN  588
FP5-S. enterica-3      NGNCNTCTTCATTACCAACTGCTTCCGCGGCCACATTAAGAGAACTTGTGGTAAGATAAG  595
FP5-S. enterica-1      NGNCTTCTTCATTACCAACTGCTTCCGCGGCCACATTAAGAGAACTTGTGGTAAGATAAG  590
FP5-S. enterica-4      NNNCTTCTTCATTACCAACTGCTTCCGCGGCCACATTAAGAGAACTTGTGGTAAGATAAN  597
FP5-S. enterica-5      TGNCTTCTTCATTACCAACTGCTTCCGCGGCCACATTAAGAGAACTTGTGGTAAGATAAG  587
FP5-S. cerevisiae-3    TGCCTNNNNNNNNNNNNNNNNNNNTCCGCGGCCACATTAAGAGAACTTGTGGTAAGATAAG  587
FP5-S. cerevisiae-5    TGCCTNNNNNNNNNNNNNNNNNNNTCCGCGGCCACATTAAGAGAACTTGTGGNAAGATAAG  588
FP5-S. cerevisiae-2    TGCCTNNNNNNNNNNNNNNNNNNNTCCGCGGCCACATTAAGAGAACTTGTGGTAAGATAAG  600
FP5-S. cerevisiae-4    TGCCTTNNNNNNNNNNNNNNNNNNTCCGCGGCCACATTAAGAGAACTTGTGNTAAGATAAG  592
FP5-S. cerevisiae-1    TGCCTTNNNNNNNNNNNNNNNNNNTCCGCGGCCACATTAAGAGAACTTGTGGTAAGATAAG  592
                           *             ******  ***  ***  **********   *******

FP5-neg-control-4      AAGATATTTTATTCGTTCTGCTGACTTGCTGGATGTCGGGAAATATTCTGCATTTGATAA  649
FP5-neg-control-5      AAGATATTTTATTCGTTCTGCTGACTTGCTGGATGTCGGGAAATATTCTGCATTTGATAA  651
FP5-neg-control-3      AAGATATTTTATTCGTTCTGCTGACTTGCTGGATGTCGGGAAATATTCTGCATTTGATAA  651
FP5-neg-control-2      AAGATATTTTATTCGTTCTGCTGACTTGCTGGATGTCGGGAAATATTCTGCATTTGATAA  652
FP5-neg-control-1      AAGATATTTTATTCGTTCTGCTGACTTGCTGGATGTCGGGAAATATTCTGCATTTGATAA  652
FP5-S. aureus-4        AAGATATTTTATTCGTTCTGCTGACTTGCTGGATGTCGGGAAATATTCTGCATTTGATAA  652
FP5-S. aureus-5        AAGATATTTTATTCGTTCTGCTGACTTGCTGGATGTCGGGAAATATTCTGCATTTGATAA  640
FP5-S. aureus-2        AAGATATTTTATTCGTTCTGCTGACTTGCTGGATGTCGGGAAATATTCTGCATTTGATAA  659
FP5-S. aureus-3        AAGATATTTTATTCGTTCTGCTGACTTGCTGGATGTCGGGAAATATTCTGCATTTGATAA  654
FP5-S. aureus-1        AAGATATTTTATTCGTTCTGCTGACTTGCTGGATGTCGGGAAATATTCTGCATTTGATAA  655
FP5-S. enterica-2      AANATATTTTATTCNNNNNNNTGACTTGCTGGATGTCGGGAAATATTCTGCATTTGATAA  648
FP5-S. enterica-3      AAGATATTTTATTCNNNNNNNTGACTTGCTGGATGTCGGGAAATATTCTGCATTTGATAA  655
FP5-S. enterica-1      AAGATATTTTATTCNNNNNNNTGACTTGCTGGATGTCGGGAAATATTCTGCATTTGATAA  650
FP5-S. enterica-4      ANNANTTTTATTCGNNNNGNTGACTTGCTGGATGTCGGGAAATATTCTGCATTTGATAA  657
FP5-S. enterica-5      AAGATATTTTATTCGNNCNNNTGACTTGCTGGATGTCGGGAAATATTCTGCATTTGATAA  647
FP5-S. cerevisiae-3    AAGATATTTTATTCNNNNNNNNGNNNNNNTGGATGTCGGGAAATATTCTGCATTTGATAA  647
FP5-S. cerevisiae-5    AAGATATTTTATTCNNNNNNNTNNNNNNTGGATGTCGGGAAATATTCTGCATTTGATAA  648
FP5-S. cerevisiae-2    AAGATATTTTATTCGNNNNNNTGNNNNNNTGGATGTCGGGAAATATTCTGCATTTGATAA  660
FP5-S. cerevisiae-4    AAGATATTTTATTCNNNNNNNTGNNNNNNTGGATGTCGGGAAATATTCTGCATTTGATAA  652
FP5-S. cerevisiae-1    AAGATATTTTATTCGNNNNNNTGNNNNNNTGGATGTCGGGAAATATTCTGCATTTGATAA  652
                       *  * *******                  ***********************

FP5-neg-control-4      GAGGCGGTTAATTGCAGATATAATTGGTAGTGAAAAGGGTCGTTGCTATGGTCACCGTGA  709
FP5-neg-control-5      GAGGCGGTTAATTGCAGATATAATTGGTAGTGAAAAGGGTCGTTGCTATGGTCACCGTGA  711
FP5-neg-control-3      GAGGCGGTTAATTGCAGATATAATTGGTAGTGAAAAGGGTCGTTGCTATGGTCACCGTGA  711
FP5-neg-control-2      GAGGCGGTTAATTGCAGATATAATTGGTAGTGAAAAGGGTCGTTGCTATGGTCACCGTGA  712
FP5-neg-control-1      GAGGCGGTTAATTGCAGATATAATTGGTAGTGAAAAGGGTCGTTGCTATGGTCACCGTGA  712
FP5-S. aureus-4        GAGGCGGTTAATTGCAGATATAATTGGTAGTGAAAAGGGTCGTTGCTATGGTCACCGTGA  712
FP5-S. aureus-5        GAGGCGGTTAATTGCAGATATAATTGGTAGTGAAAAGGGTCGTTGCTATGGTCACCGTGA  700
FP5-S. aureus-2        GAGGCGGTTAATTGCAGATATAATTGGTAGTGAAAAGGGTCGTTGCTATGGTCACCGTGA  719
FP5-S. aureus-3        GAGGCGGTTAATTGCAGATATAATTGGTAGTGAAAAGGGTCGTTGCTATGGTCACCGTGA  714
FP5-S. aureus-1        GAGGCGGTTAATTGCAGATATAATTGGTAGTGAAAAGGGTCGTTGCTATGGTCACCGTGA  715
FP5-S. enterica-2      GAGGCGGTTAATTGCAGATATAATTNNNNNNNNNNNNGGTCGTTGCTATGGTCACCGTGA  708
FP5-S. enterica-3      GAGGCGGTTAATTGCAGATATAATTGGNNNNNNNNNGNTCGTTGCTATGGTCACCGTGA  715
FP5-S. enterica-1      GAGGCGGTTAATTGCAGATATAATTGGNGTNNNNNGNNCGTTGCTATGGTCACCGTGA  710
FP5-S. enterica-4      GAGGCGGNTAATTGCAGATATAATTGGNNGTNNNNNGGTCGTTGCTATGGTCACCGTGA  717
FP5-S. enterica-5      GAGGCGGTTAATTGCAGATATAATTGGNNGTNNNNNGGTCGTTGCTATGGTCACCGTGA  707
FP5-S. cerevisiae-3    GAGGCGGTTAANTGCAGATATAATTGNNNNNNNNNNGGTCGTTGCTATGGTCACCGTGA  707
FP5-S. cerevisiae-5    GAGGCGGTTAANTGCAGATATAATTGGTAGTGAAAAGGGTCGTTGCTATGGTCACCGTGA  708
FP5-S. cerevisiae-2    GANGCGGNTAANTGNANATATNATTGGNNGNGAAA-------------------------  695
FP5-S. cerevisiae-4    GAGGCGGTTAATTGCAGATATAATTGGTAGTGAAAAGGGTCGTTGCTATGGTCACCGTGA  712
FP5-S. cerevisiae-1    GAGGCGGTTNNNTGNAGATATAATTGGTAGTGAAAAGGGTCGTTGCTATGGTCACCGTGA  712
                       ** **** *   ** * **** ***

FP5-neg-control-4      AGCGAGTACAGCAGCACAAGAATGTGTGCCGTTCTCAGTTAATATTGNTTGAATATGGTA  769
FP5-neg-control-5      AGCGAGTACAGCAGCACAAGAATGTGTGCCGNTCTCAGTTAATATTGTTTGAATATGGTA  771
```

TABLE 3B -continued

CLUSTAL 2.0.11 multiple sequence alignment of all sequence reads from single primer FP5 of Example 1.

| | | |
|---|---|---|
| FP5-neg-control-3 | AGCGAGTACAGCAGCACAAGAATGTGTGCCGTTCTCAGTTAATATTGNTTGAATATGGTA | 771 |
| FP5-neg-control-2 | AGCGAGTACAGCAGCACAAGAATGTGTGCCGTTCTCAGTTAATATTGNTTGAATATGGNA | 772 |
| FP5-neg-control-1 | AGCGAGTACAGCAGCACAAGAATGNGTGCCGTTCTCAGTTAATATTGTTTGAATATGGNA | 772 |
| FP5-S. aureus-4 | AGCGAGTACAGCAGCACAAGAATGTGTGCCGTTCTCAGTNNGNNNNNNNNNGAATATGGTA | 772 |
| FP5-S. aureus-5 | AGCGAGTACAGCAGCACAAGAATGTGTGCCGTTCTCAGNNNNNNNNNNNNNGAATATGGTA | 760 |
| FP5-S. aureus-2 | AGCGAGTACAGCAGCACAAGAATGTGTGCCGTTCTCAGNNNNNNNNNNNNGAATATGGTA | 779 |
| FP5-S. aureus-3 | AGCGAGTACAGCAGCACAAGAATGTGTGCCGTTCTCAGNNNGNANNNNNGAATATGGTA | 774 |
| FP5-S. aureus-1 | AGCGAGTACAGCAGCACAAGAATGTGTGCCGTTCTCAGNNNNNNNNNNNNGAATATGGTA | 775 |
| FP5-S. enterica-2 | AGCGAGTNNNGCNNNNNNAGANTGNGNGGNNGNNNNNNNNNATATTGNTTGAATATGGNN | 768 |
| FP5-S. enterica-3 | AGCGAGTACAGCAGCACAAGAATGTGTGNNNNNNNNNNNNAATATTGNTTGAATATGGTA | 775 |
| FP5-S. enterica-1 | AGCGAGTACNNCAGCACAAGAATGTGTGNNNNNNNNNNNTAATATNGTTTGAATATGGTA | 770 |
| FP5-S. enterica-4 | AGCGAGTACAGCAGCACAAGAATGTGTGNNGNNNNNNTAATATTGTTTGAATATGGTA | 777 |
| FP5-S. enterica-5 | AGCGAGTACAGCAGCACAAGAATGTGTNNNNNNNNNNNTAATATTGTTTGAATATGGTA | 767 |
| FP5-S. cerevisiae-3 | AGCGAGTACAGCNNNNNNNNATGTGTGCCGTTCTCAGTTAATATTGTTTGAATATGGTA | 767 |
| FP5-S. cerevisiae-5 | AGCGAGTACNNNGNNNNNNNATGTGTGCCGTTCTCAGTTAATATTGTTTGAATATGGTA | 768 |
| FP5-S. cerevisiae-2 | ------------------------------------------------------------ | |
| FP5-S. cerevisiae-4 | AGCGAGTACNNNNNNNNNNNATGTGTGCCGTTCTCAGTTAATATTGNNTGAATATGGTA | 772 |
| FP5-S. cerevisiae-1 | AGCGAGTACAGCNGNNNNNNNATGTGTGCCGTTCTCAGTTAATATTGTTTGAATANGGNN | 772 |
| | | |
| FP5-neg-control-4 | ACCTGTTTTAGTCGGNTTAAAGGTAAGAAGATCTAACCNAAAACAACACTGCAGTGACTG | 829 |
| FP5-neg-control-5 | ACCTGTTTTAGTCGGTTTAAAGGTAAGAAGATCTAACCNAAAACAACACTGCAGTGACTG | 831 |
| FP5-neg-control-3 | ACCTGTTTTAGTCGGTTTAAAGGTAAGAAGATCTAACCAAAAACAACACTGCAGTGACTG | 831 |
| FP5-neg-control-2 | ACCTGNTTTAGTCGGTTTAAAGGTAAGAAGATCTAACCNAAAACAACACTGCAGNGACTG | 832 |
| FP5-neg-control-1 | ACCTGNTTTAGTCGGTTTAAAGGTAAGAAGATCTAACCAAAAACAACACTGCAGTGACTG | 832 |
| FP5-S. aureus-4 | ACCTGNTTTAGTCGGTTTAAAGGTAAGAAGATCTAACCAAAACACNNNNNNGCAGTGACTG | 832 |
| FP5-S. aureus-5 | ACCTGNTTAGTCGGNTTAAAGGNAAGAAGANCTAACCAAAAACNNN------------- | 807 |
| FP5-S. aureus-2 | ACCTGTTTTAGTCGGTTTAAAGGTAAGAAGATCTAACCAAAAANNNNNTGCAGTGACTG | 839 |
| FP5-S. aureus-3 | ACCTGTTTTAGTCGGTTTANANNNNAGAAGATCTAACCNNAAAA--------------- | 818 |
| FP5-S. aureus-1 | ACCTGNTTTAGTCGGNTTAAAGGTAAGAAGATCTAACCAAANACANN------------ | 822 |
| FP5-S. enterica-2 | NCCTGNTTTAGTCGGNTTAAAGGTAAGAAGATCTAACCNAAAACAACACTGCAGTGACTG | 828 |
| FP5-S. enterica-3 | ACCTGTTTTAGTCGGTTTAAAGGTAAGAAGATCTAACCNAAAACNACACTGCAGTGACTG | 835 |
| FP5-S. enterica-1 | ACCTGTTTTAGTCGGNTTAAAGGTAAGAAGATCTAACCAAAAACAACACTGCAGTGACNN | 830 |
| FP5-S. enterica-4 | ACCTGTTTTAGTCGGTTTAAAGGTAAGAAGATCTAACCAAAAACAACACTGCAGTGACTG | 837 |
| FP5-S. enterica-5 | ACCTGTTTTAGTCGGTTTAAAGGTAAGAAGATCTAACCNAAAACAACACTGCAGTGACTG | 827 |
| FP5-S. cerevisiae-3 | ACCTGTTTTAGTCGGTTTAAAGGTAAGAAGANCTAACCAAAAACAACACTGCAGTGACTG | 827 |
| FP5-S. cerevisiae-5 | ACCTGTTTTAGTCGGTTTAAAGGTAAGANNANNTAACCAAAAACAACACTGCAGTGACTG | 828 |
| FP5-S. cerevisiae-2 | ------------------------------------------------------------ | |
| FP5-S. cerevisiae-4 | ACCTGTTTTAGTCGGNTTAAAGGTAAGAAGATCTAACCAAAAACAACACTGCAGNGACTG | 832 |
| FP5-S. cerevisiae-1 | NNNNGTTTTAGTCGGTTTAAAGGTAAGAAGATCTAACCAAAAACAACACTGCAGNGACTG | 832 |
| | | |
| FP5-neg-control-4 | ATTGNAGTANTTATTTTTNNACT------------------------------------- | 852 |
| FP5-neg-control-5 | ATTGTAGTANTTATTTTTTTACTTAATCTTAANNNNNNG--------------------- | 870 |
| FP5-neg-control-3 | ATTGNAGTATTTNNNNNTNN---------------------------------------- | 851 |
| FP5-neg-control-2 | ATTGNANNATTTATTTNNNNNCNNNNTCNTNNNNNNNNGNGTAAACATCNACGGCGCACTT | 892 |
| FP5-neg-control-1 | ATTGTAGTATTTATTTTTTACNNNNNCTTAANNNNNNNGNANACNTCAACGGCGCACTT | 892 |
| FP5-S. aureus-4 | ATTGNNG----------------------------------------------------- | 839 |
| FP5-S. aureus-5 | ------------------------------------------------------------ | |
| FP5-S. aureus-2 | ANNGNAGTATTTATTTTTTTACTTAA---------------------------------- | 865 |
| FP5-S. aureus-3 | ------------------------------------------------------------ | |
| FP5-S. aureus-1 | ------------------------------------------------------------ | |
| FP5-S. enterica-2 | ATTGTAGNANNNNNNNN------------------------------------------- | 844 |
| FP5-S. enterica-3 | ATTGNAGTATNNNNNNN------------------------------------------- | 851 |
| FP5-S. enterica-1 | NNNNNAGTATNNNNNNTTTTACTTANNNNNAATTNTGGTGTAAACATCANCGGCGCACTT | 890 |
| FP5-S. enterica-4 | ATTGTAGTANNNNNNNTTTTACTTAATCTTAATTTTGG---------------------- | 875 |
| FP5-S. enterica-5 | ATTGNNGNANN------------------------------------------------- | 838 |
| FP5-S. cerevisiae-3 | ATTGNAGNANTTATTTTTTACTTAATCTTAANTTNNG---------------------- | 865 |
| FP5-S. cerevisiae-5 | ATNGNAGTATTTATTTTTTACTTAATCTTAATTTNGNNGNAAACATCANCGGNNNGNTT | 888 |
| FP5-S. cerevisiae-2 | ------------------------------------------------------------ | |
| FP5-S. cerevisiae-4 | ATTGNAGTATTTATTTTTTACTTAATCTTAATTTTGGGGN------------------- | 873 |
| FP5-S. cerevisiae-1 | ATTGTAGTATTTATTTTNNNNNNNATCTT------------------------------ | 862 |

In order to test the ability of the invention to provide a means of identification by comparison to a database, the first three sequence embedded fingerprints (Numbers 1-3) generated for each microorganism were used to produce a consensus fingerprint sequence for that organism (Tables 4-6). These consensus sequences were then used to create a BLAST database (NCBI BLAST web server). The fifth sequence embedded fingerprint (number 5) for each organism was used to query the database. The resultant blast scores (Tables 7-9) show that the comparison of BLAST program identifies each microorganisms sequence embedded fingerprint as belonging to the correct species (highest total score).

TABLE 4A

```
                    CLUSTAL 2.0.11 multiple sequence alignment
   First three Staphylococcus aureus MU3 sequence embedded fingerprints by primer mix FB1D1 were
                       aligned and used to generate a consensus sequence SEQ ID NO: 46 consensus        -------GTTGCTCT-CNGCTGACNATGCTGCTGCTGCTTNNNGNNNCTGTCTCCACTTC
SEQ ID NO: 22 FB1D1 S. aureus 3 CNGTTATGTTGCTCT-CNGCTGACNATGCTGCTGCTGCTTNNNGNNNCTGTCTCCACTTC  59
SEQ ID NO: 21 FB1D1 S. aureus 2 ----TNNGGTTGNTCTACNGNTGACNATGCTGCTGCTGCTTNNNNNNNCTGTCTCCACTTC 56
SEQ ID NO: 23 FB1D1 S. aureus 1 -------GTTGNTCN-NNGCTGACNATGCTGCTGCTGCTTNNNGNNNCTGTCTCCACTTC  52
                                **      *************  *************** consensus                      CTTGAACAATGNGCCGTCATGCTTCTTTTGCCTCCCGCTGCTCCAGAAAGCTANGNCNNA
FB1D1 S. aureus 3              CTTGAACAATGNGCCGTCATGCTTCTTTTGCCTCCCGCTGCTCCAGAAAGCTAGGNCNNA 119
FB1D1 S. aureus 2              CTTGAACAATGNGCCGTCATGCTTCTTTTGCCTCCCGCTGCTCCAGAAAGCTANGNNNNA 116
FB1D1 S. aureus 1              CTTGAACANTGNGCCGTCATGCTTCTTTTGCCTCCCGCTGCTCCAGAAAGCTANGNCNNA 112
                               ******  ********************************  *** consensus                      GATCAGAACCACCACAGNCNNTNTCNCCNCCTTCCTCTTATAGATTCGGAATCTCATGAT
FB1D1 S. aureus 3              GATCAGAACCACCACAGNCNNTATCNCCNCCTTCCTCTTATAGATTCGGAATCTCATGAT 179
FB1D1 S. aureus 2              GATCAGAACCACCACAGNCNNNNTNACCNCCTTCCTCTTATAGATTCGGAATCTCATGAT 176
FB1D1 S. aureus 1              GATCAGAACCACCACAGNCNNNNTCNCCNCCTTCCTCTTATAGATTCGGAATCTCATGAT 172
                               ******************   *  ************************************ consensus                      AGGGNNTCNNCCTCTGTGCGAGTGGAGAGAAGTTTGCAGGCGAGCTGANGAGCANTTGCA
FB1D1 S. aureus 3              AGGGNNTCNNCCTCTGTGCGAGTGGAGAGAAGTTTGCAGGCGAGCTGANGAGCAATTGCA 239
FB1D1 S. aureus 2              AGGGNNTCNNCCTCTGTGCGAGTGGAGAGAAGTTTGCAGGCNAGCTGANGAGCANTTGCA 236
FB1D1 S. aureus 1              AGGGGNTCNNCCTCTGTGCGAGTGGAGAGAAGTTTGCAGGCGAGCTGAGGAGCANTTGCA 232
                               **  **************************** ** * *** consensus                      GGTGNNNNNATGTGCTCGGCTCAAGAAGCGGGCCCGGAGAGGAAGAAGTCGTGCCGGGGC
FB1D1 S. aureus 3              GGTGNNNNNATGTGCTCGGCTCAAGAAGCGGGCCCGGAGAGGAAGAAGTCGTGCCGGGGC 299
FB1D1 S. aureus 2              GGGNGNNNGNNTGTGCTCGGCTCAAGANGCGGGNCCGGANAGGAAGAAGTCGTGCCGGGGC 296
FB1D1 S. aureus 1              GGTGNNNNNATGTGCTCGGCTCAAGAAGCGGGCCCGGAGAGGAAGAAGTCGTGCCGGGGC 292
                                ** * *************   * ******************** consensus                      TAATTATTGGCAAAACGAGCTCTTGTTGTAAACATNGNNNNNNNNNNNNNNNNNNNNNNN
FB1D1 S. aureus 3              TAATTATTGGCAAAACGAGCTCTTGTTGNAAACNTNGNNNGGGGGGGNNNNNNNNNNNN  359
FB1D1 S. aureus 2              TAATTATTGGCAAAACGAGCTCTTGTTGTAAACATTGNNNNNNNNNNNNNNNNNNNNNNN 356
FB1D1 S. aureus 1              TAATTATTGGCAAAACGAGCTCTTGTTGTAAACATNGNNNNNNNNNNNNNNNNNNNNNNN 352
                               **************************  *  * **           ********* consensus                      NNN-ATCAATATTCCATAAGGCATGATGGTTGCTCAGAGGCAGGAGAAGAGCAACGAATA
FB1D1 S. aureus 3              NNN-ATCAATATTCCATAAGGCATGATGGTTGCTCAGAGGCAGGAGAAGAGCAACGAATA 418
FB1D1 S. aureus 2              NNN-ATCAATATTCCATAAGGCATGATGGTTGCTCAGAGGCAGGAGAAGAGCAACGAATA 415
FB1D1 S. aureus 1              NNNGNNCAATATTCCATAAGGCATGATGGTTGCTCAGAGGCAGGAGAAGAGCAACGAATA 412
                               *    ************************************************** consensus                      CGATCCTATAAAAGATAAAACATAAATAAACAGTCTTGATTATATTCTGGGTATTAAAGC
FB1D1 S. aureus 3              CGATCCTATAAAAGATAAAACATAAATAAACAGTCTTGATTATATTCTGGGTATTAAAGC 478
FB1D1 S. aureus 2              CGATCCTATAAAAGATAAAACATAAATAAACAGTCTTGATTATATTCTGGGTATTAAAGC 475
FB1D1 S. aureus 1              CGATCCTATAAAAGATAAAACATAAATAAACAGTCTTGATTATATTCTGGGTATTAAAGC 472
                               ************************************************************ consensus                      CACAATCAGAACAAATATATGCTTTGTATCTTTTCTTGCCTTCTTCATTACCAACTGCTT
FB1D1 S. aureus 3              CACAATCAGAACAAATATATGCTTTGTATCTTTTCTTGCCTTCTTCATTACCAACTGCTT 538
FB1D1 S. aureus 2              CACAATCAGAACAAATATATGCTTTGTATCTTTTCTTGCCTTCTTCNTTACCAACTGCTT 535
FB1D1 S. aureus 1              CACAATCAGAACAAATATATGCTTTGTATCTTTTCTTGCCTTCTTCATNNNNNNNTGCTT 532
                               **********************************************  *      ***** consensus                      CCGCGGCCACATTAAGAGAACTTGNGGTAAGATAAGAAGATATTTTATTCGTTCTGCTGA
FB1D1 S. aureus 3              CCGCGGCCACATTAAGAGAACTTGNGGTAAGATAAGAAGATATTTTATTCGTTCTGCTGA 598
FB1D1 S. aureus 2              CCGCGGCCACATTAAGAGAACTTGNGNTAAGATAAGAAGATATTTTATTCGTTCTGCTGA 595
FB1D1 S. aureus 1              CCGCGGCCACATTAAGAGAACTTGGGGTAAGATAAGAAGATATTTTATTCGTTCTGCTGA 592
                               ************************ * ********************************* consensus                      CTTGCTGGATGTCGGGAAATATTCTGCATTTGATAAGAGGCGGTTAATTGCAGATATAAT
FB1D1 S. aureus 3              CTTGCTGGATGTCGGGAAATATTCTGCATTTGATAAGAGGCGGTTAATTGCAGATATAAT 658
FB1D1 S. aureus 2              CTTGCTGGATGTCGGGAAATATTCTGCATTTGATAAGAGGCGGTTAATTGCAGATATAAT 655
FB1D1 S. aureus 1              CTTGCTGGATGTCGGGAAATATTCTGCATTTGATAAGAGGCGGTTAATTGCAGATATAAT 652
                               ************************************************************ consensus                      TGGTAGTGAAAAGGNNNNNTTGCTATGGTCACCGTGAAGCGAGTACAGCAGCACAAGAATG
FB1D1 S. aureus 3              TGGTAGTGAAAAGGNNNNNTTGCTATGGTCACCGTGAAGCGAGTACAGCAGCACAAGAATG 718
FB1D1 S. aureus 2              TGGTAGTGAAAAGGNGCNTTGCTATGGTCACCGTGAAGNGAGTACAGGAGCACAAGAATG  715
FB1D1 S. aureus 1              TGGTAGTGAAAAGGNNNNTTGCTATGGTCACCGTGAAGCGAGTACAGCAGCACAAGAATG  712
                               ************    ***************** *** ******** consensus                      TGTGCCGTTCTCAGTTAATATTGTTTGAATATGGTAACCTGTTTTAGTCGGNTTAAAGGT
FB1D1 S. aureus 3              TGTGCCGTTCTCAGTTAATATTGTTTGAATATGGTAACCTGTTTTAGTCGGNTTAAAGGT 778
FB1D1 S. aureus 2              TGTGCCGTTCTCAGTTAATATTGTTTGAATATGGTAACCTGTTTTAGTCGGTTTAAAGGT 775
FB1D1 S. aureus 1              TGTGCCGTTCTCAGTTAATATTGTTTGAATATGGTAACCTGTTTTAGTCGGTTTAAAGGT 772
```

TABLE 4A -continued

CLUSTAL 2.0.11 multiple sequence alignment
First three *Staphylococcus aureus* MU3 sequence embedded fingerprints by primer mix FB1D1 were
aligned and used to generate a consensus sequence

```
consensus          AAGAAGATCTAACCAAAAAC-AACACTGCAGNGACTGATTGNNGNN-TTNNNNNTTTTTT
FB1D1 S. aureus 3  AAGAAGATCTAACNNAAANNCAACACTGCANNGACTGNNNNNNNNATTNNNNNNTTTTT 838
FB1D1 S. aureus 2  AAGAAGATCTAACCAAAAAC-AACACNGCAGTGACTGATTGNNGNN-NNNNNNNTTTTTT 833
FB1D1 S. aureus 1  NAGAAGATCTAACCAAAAAC-AACACTGCAGNGACTGATTGTAGTA---TTTATTTTTNN 828
                   ********** * *** * ***              * consensus          ACTTAATCTTAATTTTGGTGTAAACATCAACGG-CGCAC-----
FB1D1 S. aureus 3  ACTTAATCTTAATTTTGGTGTAAACATCAACNGGCGCACTTN--                 880
FB1D1 S. aureus 2  ANNNTATCTTAATTTTGGTGTAAACATCNACGG-CGCACTTCAA                 876
FB1D1 S. aureus 1  NNNNNNNCTNNATTTTGGTGTAAACATCAACGG-CGCACNN---                 868
                   **  ***************** ** * *****
```

TABLE 4B

CLUSTAL 2.0.11 multiple sequence alignment
First three *Staphylococcus aureus* MU3 sequence embedded fingerprints by primer
FP5 were aligned and used to generate a consensus sequence

```
SEQ ID NO: 47 Consensus       -----NNNCTGGTTNTGANTACTGTTAANGTTGCTACTACTGCTGACAATGCTGCTGCTG  55
SEQ ID NO: 33 FP5-S. aureus-2 NNNGCNGCCNGGTTNTGATTACTGTTAATGTTGCTACTACTGCTGACAATGCTGCTGCTG  60
SEQ ID NO: 35 FP5-S. aureus-1 ----NNNNCTGGTTNTGANTACTGTTAANGTTGCTACTACTGCTGACAATGCTGCTGCTG  56
SEQ ID NO: 34 FP5-S. aureus-3 -----NNNCTGGTTNTGANTACTGNNNNNGTTGCTACTACTGCTGACAATGCTGCTGCTG  55
                                   *  * ******* *****     ******************************

Consensus        CTTCTCCTNNCTGTCTCCACTTCCTTGAACAATGCGCCGTCATGCTTCTTTTGCCTCCCG 115
FP5-S. aureus-2  CTTCTCCTNNCTGTCTCCACTTCCTTGAACAATGCGCCGTCATGCTTCTTTTGCCTCCCG 120
FP5-S. aureus-1  CTTCTCCTCNCTGTCTCCACTTCCTTGAACAATGCGCCGTCATGCTTCTTTTGCCTCCCG 116
FP5-S. aureus-3  CTTCTCNTNNCTGTCTCCACTTCCTTGAACAATGCGCCGTCATGCTTCTTTTGCCTCCCG 115
                 ****** * *************************************************

Consensus        CTGCTCCAGAAAGCTAGGCCGCAGATCAGAACCACCACAGTCAATATCACCACCTTCCTC 175
FP5-S. aureus-2  CTGCTCCAGAAAGCTAGGCCGCAGATCAGAACCACCACAGTCAATATCACCACCTTCCTC 180
FP5-S. aureus-1  CTGCTCCAGAAAGCTAGGCCGCAGATCAGAACCACCACAGTCAATATCACCACCTTCCTC 176
FP5-S. aureus-3  CTGCTCCAGAAAGCTAGGCCGCAGATCAGAACCACCACAGTCAATATCACCACCTTCCTC 175
                 ************************************************************

Consensus        TTATAGATTCGGAATCTCATGATAGGGGCTCAGCCTCTGTGCGAGTGGAGAGAAGTTTGC 235
FP5-S. aureus-2  TTATAGATTCGGAATCTCATGATAGGGGCTCAGCCTCTGTGCGAGTGGAGAGAAGTTTGC 240
FP5-S. aureus-1  TTATAGATTCGGAATCTCATGATAGGGGCTCAGCCTCTGTGCGAGTGGAGAGAAGTTTGC 236
FP5-S. aureus-3  TTATAGATTCGGAATCTCATGATAGGGGCTCAGCCTCTGTGCGAGTGGAGAGAAGTTTGC 235
                 ************************************************************

Consensus        AGGCGAGCTGAGGAGCAATTGCAGGTGATATGATGTGCTCGGCTCAAGAAGCGGGCCCGG 295
FP5-S. aureus-2  AGGCGAGCTGAGGAGCAATTGCAGGTGATATGATGTGCTCGGCTCAAGAAGCGGGCCCGG 300
FP5-S. aureus-1  AGGCGAGCTGAGGAGCAATTGCAGGTGATATGATGTGCTCGGCTCAAGAAGCGGGCCCGG 296
FP5-S. aureus-3  AGGCGAGCTGAGGAGCAATTGCAGGTGATATGATGTGCTCGGCTCAAGAAGCGGGCCCGG 295
                 ************************************************************

Consensus        AGAGGAAGAAGTCGTGCCGGGGCTAATTATTGGCAAAACGAGCTCTTGTTGTAAACATTG 355
FP5-S. aureus-2  AGAGGAAGAAGTCGTGCCGGGGCTAATTATTGGCAAAACGAGCTCTTGTTGTAAACATTG 360
FP5-S. aureus-1  AGAGGAAGAAGTCGTGCCGGGGCTAATTATTGGCAAAACGAGCTCTTGTTGTAAACNTTG 356
FP5-S. aureus-3  AGAGGAAGAAGTCGTGCCGGGGCTAATTATTGGCAAAACGAGCTCTTGTTGTAAACATTG 355
                 ******************************************************** ***

Consensus        ATCCAACTGGAATGTCACTAATGGCGAATCAATATTCCATAAGGCATGATGGTTGCTCAG 415
FP5-S. aureus-2  ATCCAACTGGAATGTCACTAATGGCGAATCAATATTCCATAAGGCATGATGGTTGCTCAG 420
FP5-S. aureus-1  NTNCAACTGGAATGTCACTAATGGCGAATCAATATTCCATAAGGCATGATGGTTGCTCAG 416
FP5-S. aureus-3  ATCCAACTGGAATGTCACTAATGGCGAATCAATATTCCATAAGGCATGATGGTTGCTCAG 415
                  *  ********************************************************

Consensus        AGGCAGGAGAAGAGCAACGAATACGATCCTATAAAAGATAAAACATAAATAAACAGTCTT 475
FP5-S. aureus-2  AGGCAGGAGAAGAGCAACGAATACGATCCTATAAAAGATAAAACATAAATAAACAGTCTT 480
FP5-S. aureus-1  AGGCAGGAGAAGAGCAACGAATACGATCCTATAAAAGATAAAACATAAATAAACAGTCTT 476
FP5-S. aureus-3  AGGCAGGAGAAGAGCAACGAATACGATCCTATAAAAGATAAAACATAAATAAACAGTCTT 475
                 ************************************************************

Consensus        GATTATATTCTGGGTATTAAAGCCACAATCAGAACAAATATATGCTTTGTATCTTTTCTT 535
FP5-S. aureus-2  GATTATATTCTGGGTATTAAAGCCACAATCAGAACAAATATATGCTTTGTATCTTTTCTT 540
FP5-S. aureus-1  GATTATATTCTGGGTATTAAAGCCACAATCAGAACAAATATATGCTTTGTATCTTTTCTT 536
FP5-S. aureus-3  GATTATATTCTGGGTATTAAAGCCACAATCAGAACAAATATATGCTTTGTATCTTTTCTT 535
                 ************************************************************
```

TABLE 4B -continued

CLUSTAL 2.0.11 multiple sequence alignment
First three *Staphylococcus aureus* MU3 sequence embedded fingerprints by primer
FP5 were aligned and used to generate a consensus sequence

```
Consensus        GCCTTCTTCATTACCAACTGCTTCCGCGGCCACATTAAGAGAACTTGTGGTAAGATAAGA 595
FP5-S. aureus-2  GCCTTCTTCATTACCAACTGCTTCCGCGGCCACATTAAGAGAACTTGTGGTAAGATAAGA 600
FP5-S. aureus-1  GCCTTCTTCATTACCAACTGCTTCCGCGGCCACATTAAGAGAACTTGTGGTAAGATAAGA 596
FP5-S. aureus-3  GCCTTCTTCATTACCAACTGCTTCCGCGGCCACATTAAGAGAACTTGTGGTAAGATAAGA 595
                 ************************************************************

Consensus        AGATATTTTATTCGTTCTGCTGACTTGCTGGATGTCGGGAAATATTCTGCATTTGATAAG 655
FP5-S. aureus-2  AGATATTTTATTCGTTCTGCTGACTTGCTGGATGTCGGGAAATATTCTGCATTTGATAAG 660
FP5-S. aureus-1  AGATATTTTATTCGTTCTGCTGACTTGCTGGATGTCGGGAAATATTCTGCATTTGATAAG 656
FP5-S. aureus-3  AGATATTTTATTCGTTCTGCTGACTTGCTGGATGTCGGGAAATATTCTGCATTTGATAAG 655
                 ************************************************************

Consensus        AGGCGGTTAATTGCAGATATAATTGGTAGTGAAAAGGGTCGTTGCTATGGTCACCGTGAA 715
FP5-S. aureus-2  AGGCGGTTAATTGCAGATATAATTGGTAGTGAAAAGGGTCGTTGCTATGGTCACCGTGAA 720
FP5-S. aureus-1  AGGCGGTTAATTGCAGATATAATTGGTAGTGAAAAGGGTCGTTGCTATGGTCACCGTGAA 716
FP5-S. aureus-3  AGGCGGTTAATTGCAGATATAATTGGTAGTGAAAAGGGTCGTTGCTATGGTCACCGTGAA 715
                 ************************************************************

Consensus        GCGAGTACAGCAGCACAAGAATGTGTGCCGTTCTCAGNNNNNNNNNNNNNGAATATGGTAA 775
FP5-S. aureus-2  GCGAGTACAGCAGCACAAGAATGTGTGCCGTTCTCAGNNNNNNNNNNNNNGAATATGGTAA 780
FP5-S. aureus-1  GCGAGTACAGCAGCACAAGAATGTGTGCCGTTCTCAGNNNNNNNNNNNNNGAATATGGTAA 776
FP5-S. aureus-3  GCGAGTACAGGAGCACAAGAATGTGTGCCGTTCTCAGNNNNGNANNNNNNGAATATGGTAA 775
                 ********** ************************** * ****************

Consensus        CCTGTTTTAGTCGGTTTAAAGGTAAGAAGATCTAACCAAAAANN---------------- 819
FP5-S. aureus-2  CCTGTTTTAGTCGGTTTAAAGGTAAGAAGATCTAACCAAAAANNNNNTGCAGTGACTGA  840
FP5-S. aureus-1  CCTGNTTTAGTCGGNTTAAAGGTAAGAAGATCTAACCAAANACANN-------------  822
FP5-S. aureus-3  CCTGTTTTAGTCGGTTTANANNNNAGAAGATCTAACCNNAAAA----------------  818
                 **** ********* *** *   ************ * *
```

TABLE 5A

CLUSTAL 2.0.11 multiple sequence alignment
First Three *Saccharomyces cerevisiae* S288C sequence embedded fingerprints by primer mix
FB1D1 were aligned and used to generate a consensus sequence

```
SEQ ID NO: 48 Consensus        CTGNTAATGTTGCTACTACTGCTGACAATGCTGCTGCTGCTTCNCCTCNCTGTCTCCAC
SEQ ID NO: 10 FB1D1 S. cervisiae 3  NCNGNNNNNGNTGCTACTACTGCTGACAATGCTGCTGCTGCTTCTCCTCNCTGTCTCCAC  60
SEQ ID NO: 11 FB1D1 S. cervisiae 2  -CTGTTAATGTTGCTACTACTGCTGACAATGCTGCTGCTGCTTCNCCTCNCTGTCTCCAC  59
SEQ ID NO: 9  FB1D1 S. cervisiae 1  -CTGNTAATGTTGCTACTACTGCTGACAATGCTGCTGCTGCTTCTCCTCACTGTCTCCAC  59
                                    * *   * ******************************** **** **********

Consensus             TTCCTTGAACAATGCGCCGNCTGCTTCTTTTGCCTCCCGCTGCTCCNGAGNGNTAGGCC
FB1D1 S. cervisiae 3  TTCCTTGAACAATGCGCCGTCNTGCTTCTTTTGCCTCCCGCTGCTCCNNANNGNTAGGCC  120
FB1D1 S. cervisiae 2  TTCCTTGAACAATGCGCCGNCNTGCTTCTTTTGCCTCCCGCTGCTCCNGAGNGNTAGGCC  119
FB1D1 S. cervisiae 1  TTCCTTGAACAATGCGCCGNCNTGCTTCTTTTGCCTCCCGCTGCTCCNGAGNGCTAGGCC  119
                      *******************  ************************* * ** ******

Consensus             GCAGATCAGAACCACCACAGNCAATATCACCACCNTCNNCTTATAGATTCGGAATCTCAT
FB1D1 S. cervisiae 3  GCAGATCAGAACCACCACAGTCAATATCACCACCTTCCTCTTATAGATTCGGAATCTCAT  180
FB1D1 S. cervisiae 2  GCAGATCAGAACCACCACAGNCAATATCACCACCNTCNNCTTATANATTCGGAATCTCAT  179
FB1D1 S. cervisiae 1  GCAGATCAGAACCACCACAGNCAATATCACCACCNNCNNCTTATAGATTCGGAATCTCAT  179
                      ******************* *************  *  ****** **************

Consensus             GATAGGGGCTCAGCCTCTGTGCGAGTGGAGAGAAGTTTGCAGGCGAGCTGAGGAGCAATT
FB1D1 S. cervisiae 3  GATAGGGGCTCAGCCTCTGTGCGAGTGGAGAGAAGTTTGCAGGCGAGCTGAGGAGCAATT  240
FB1D1 S. cervisiae 2  GATAGGGGCTCAGCCTCTGTGCGAGTGGAGAGAAGTTTGCAGGCGAGCTGAGGAGCAATT  239
FB1D1 S. cervisiae 1  GATAGGGGCTCAGCCTCTGTGCGAGTGGAGAGAAGTTTGCAGGCGAGCTGAGGAGCAATT  239
                      ************************************************************

Consensus             GCAGGTGATATGATGTGCTCGGCTCANGGGNNNNNNNNNNNNNNNNNNNNNTGCCGGG
FB1D1 S. cervisiae 3  GCAGGTGATATGATGTGCTCGGCTCANGGGGNNNNNNNNNNNNNNNNNNNNNNGCCGGG  300
FB1D1 S. cervisiae 2  GCAGGTGATATGATGTGCTCGGCTCANGGGCNNNNNNNNNNNNNNNNNNNNNTGCCGGG  299
FB1D1 S. cervisiae 1  GCNGGTGATATGATGTGCTCGGCTCNNGGGGNNNNGGNGNNNNNNNNANGNCNN-GCCGGG  298
                      ** *********************  ***  ** * * ******* * * *   ******

Consensus             GCTAATTATTGGCAAAACGAGCTCTTGTTGTAAACATTGATCCAACTGGNNGGNNNNNNA
FB1D1 S. cervisiae 3  GCTAATTATTGGCAAAACGAGCTCTTGTTGTAAACATTGATCCAACTGGNNGGNNNNNNA  360
FB1D1 S. cervisiae 2  GCTAATTATTGGCAAAACGAGCTCTTGTTGTAAACATTGATCCAACTGGNNGGNNNNNNA  359
FB1D1 S. cervisiae 1  GCTAATTATTGGCAAAACGAGCTCTTGTTGTAAACATTGATCCNNNGGNNNGTNNNNNN  358
                      ******************************************   *** *   **** *
```

TABLE 5A -continued

CLUSTAL 2.0.11 multiple sequence alignment
First Three *Saccharomyces cerevisiae* S288C sequence embedded fingerprints by primer mix
FB1D1 were aligned and used to generate a consensus sequence

```
Consensus            TGGNGNNNGNNNNTGNCNNNNGGCATGATGGTTGCTCAGAGGCAGGAGAAGAGCAACGAA
FB1D1 S. cervisiae 3 TGGNGNNNNNNNNTGCCNNNNNGCATGATGGTTGCTCAGAGGCAGGAGAAGAGCAACGAA    420
FB1D1 S. cervisiae 2 TGGNGNNNGNNNNTGNNNNNNGGATGATGGTTGCTCAGAGGCAGGAGAAGAGCAACGAA     419
FB1D1 S. cervisiae 1 NGGNGNNNGANNNTGNNNNNNGGNATGATGGTTGCTCAGAGGCAGGAGAAGAGCAACGAA    418
                     ******  ****  ****  * **************************************

Consensus            TACGATCCTATAAAAGATAAAACATAAATAAACAGTCTTGATTATATTCTGGGTATTAAA
FB1D1 S. cervisiae 3 TACGATCCTATAAAAGATAAAACATAAATAAACAGTCTTGATTATATTCTGGGTATTAAA    480
FB1D1 S. cervisiae 2 TACNATCCTATAAAAGATAAAACATAAATAAACAGTCTTGATTATATTCTGGGTATTAAA    479
FB1D1 S. cervisiae 1 TACGATCCTATNAAAGATAAAACATAAATAAACNGTCTTGATTATATTCTGGGTATTAAA    478
                     *** ******* **************************************

Consensus            NNCNNNGNCAGAACAAATATATGCTTTGNNNNNNNNCNTGNCNNCNNNNNNNNNNNNNNN
FB1D1 S. cervisiae 3 GNCNCAGNCAGAACAAATATATGCTTTGTNNCTNNNCNTGCCTTCTTNNNNNNNNNNNNN    540
FB1D1 S. cervisiae 2 NNNNNNGNCAGAACAAATATATGCTTTGNNNNNTNNCNTGNNNNCNNNNGGNNNNNNNNN    539
FB1D1 S. cervisiae 1 NNCNNNGNNAGAACAAATATATGCTTTNNNNNNNNTCNNGNCNNNNNNNNNNNNNNNNNN    538
                      *  *  ** ****************    *    **  *  **       ** *********

Consensus            NNNNNNGGCCACNNNNNNGAGAACTTGTNNNNNNNTAAGAAGATATTTTATTCGNTCTGCT
FB1D1 S. cervisiae 3 NNNNNNGGCCACNNNNNNAGAACTTGNGGNGNNATAAGAAGATATTTTATTCGNTCTGCT    600
FB1D1 S. cervisiae 2 NNNNNNGGCCNCNNNNNGAGAACTTGTNNNNNNNTAAGAAGATATTTTATTCGNNCTGCT    599
FB1D1 S. cervisiae 1 NNNNNNGGCCACATTAAGAGAACTTGTNNNNNNNTAAGAAGATATTTTATTCGNTCTGCT    598
                     ********** *        *******  * ** ********************  *****

Consensus            GACTTGCTGGATGTCGGGAAATATTCTGCATTTGATAAGAGGCGGTTAATTGCAGATATA
FB1D1 S. cervisiae 3 GACTTGCTGGATGTCGGGAAATATTCTGCATTTGATAAGAGGCGGTTAATTGCAGATATA    660
FB1D1 S. cervisiae 2 GACTTGCTGGATGTCGGGAAATATTCTGCATTTGATAAGAGGCGGTTAATTGCAGATATA    659
FB1D1 S. cervisiae 1 GACTTGCTGGATGTCGGGAAATATTCTGCATTTGATAAGAGGCGGTTAATTGCAGATATA    658
                     ************************************************************

Consensus            ATTGGTAGTGAAAAGGGTCGTTGCTATGGTCACCGTGAAGCGAGTACAGCAGCACAAGAN
FB1D1 S. cervisiae 3 ATTGGTAGTGAAAAGGGTCGTTGCTATGGTCACCGTGAAGCGAGTACAGCAGCACAAGAN    720
FB1D1 S. cervisiae 2 ATTGGTAGTGAAAAGGGTCGTTGCTATGGTCACCGTGAAGCGAGTACAGCAGCACANGAN    719
FB1D1 S. cervisiae 1 ATTGGTAGTGAAAAGGGTCGTTGCTATGGTCACCGTGAAGCGAGTACAGCAGCACAAGAA    718
                     ********************************************************* **

Consensus            NGTGTGCCGTTCTCAGTTAATATTGNNTGAATATGGTAACCTGNTTTAGTCGGTTTAAAG
FB1D1 S. cervisiae 3 NGTGTGCCGTTCTCAGTTAATATNGNNNGAATATGGTAACCTGNTTTAGTCGGTTTAAAG    780
FB1D1 S. cervisiae 2 NGTGTGCCGTTCTCAGTTAATATTGNTTGAATATGGTAACCTGTTTTAGTCGGTTTAAAG    779
FB1D1 S. cervisiae 1 TGTGTGCCGTTCTCAGTTAATATTGTNTGAATATGGTAACCTGNTTTAGTCGGTTTAAAG    778
                      ******************** *   *************** **************

Consensus            GTAAGAAGANCTAACCAAAAACAACACTGCNNNNNNNGNNNGGGGGNNNNNNNNNNNNTAC
FB1D1 S. cervisiae 3 GTAAGAAGANCTAACCAAAAACAACACTGCNNNNNNNNNGGGGGNNNNNNNNNNNNNTTAC   840
FB1D1 S. cervisiae 2 GTAAGAAGANCTAACCNAAAACAACACTGCNNNNNNGNGGGGGGNNNNNNNNNNNNNNTAC   839
FB1D1 S. cervisiae 1 GTAAGAAGATCTAACCAAAAACAACACTGCNNGNCNGNNNNNNGGNNNNNNNNNNNNNTTA   838
                     ********* ****** *************   * *        **********  *

Consensus            TNNNNNNNNNNTTNNNGGNGNAAACATCNACGNNNNNNNNCAACCAATN
FB1D1 S. cervisiae 3 TNNNNGNNNNTTNNNGGNGNAAACATCNACGNNNNNNNNNCAACCNATNNN              890
FB1D1 S. cervisiae 2 TTNNNNNNNNNNNNNNNNNN--ACATCNNCGNNNNNNNNCAACCAATAN-              886
FB1D1 S. cervisiae 1 CTNNNNNNNNATTTTGGNNTAAACATCAACGGNNNNNNNCANCCANNN--              886
                      *** ****      *      *****  ** ********* **
```

TABLE 5B

CLUSTAL 2.0.11 multiple sequence alignment
First Three *Saccharomyces cerevisiae* S288C sequence embedded fingerprints by primer
FP5 were aligned and used to generate a consensus sequence

```
SEQ ID NO: 49 Consensus       --------CCTGNNNNNGATTACTGTTAATGTTGCTACTACTGCTGACAATGCTGCTGCT    52
SEQ ID NO: 45 FP5-S. cerevisiae-1 --------CCTGNNNNNGATTACTGTTAATGTTGCTACTACTGCTGACAATGCTGCTGCT    52
SEQ ID NO: 43 FP5-S. cerevisiae-2 NNNTGNNGCCTGNTTNTGATTACTGTTAATGTTGCTACTACTGCTGACAATGCTGCTGCT    60
SEQ ID NO: 41 FP5-S. cerevisiae-3 -------------NNNNNATNNCTGTTNATGTTGCTNCTACTGCTGACAATGCTGCTGCT    47
                                          * **  **** ******** ***************************

Consensus         GCTTCTCCTCNCTGTCTCCACTTCCTTGAACAATGCGCCGTCATGCTTCTTTTGCCTCCC    112
FP5-S. cerevisiae-1 GCTTCTCCTCNCTGTCTCCACTTCCTTGAACAATGCGCCGTCATGCTTCTTTTGCCTCCC   112
FP5-S. cerevisiae-2 GCTTCTCCTCNCTGTCTCCACTTCCTTGAACAATGCGCCGTCATGCTTCTTTTGCCTCCC   120
FP5-S. cerevisiae-3 GCTTCTCCTCNNTGTCTCCACTTCCTTGAACAATGCGCCGTCATGCTTCTTTTGCCTCCC   107
                  ********** ************************************************
```

TABLE 5B -continued

CLUSTAL 2.0.11 multiple sequence alignment
First Three *Saccharomyces cerevisiae* S288C sequence embedded fingerprints by primer
FP5 were aligned and used to generate a consensus sequence

```
Consensus              GCTGCTCCAGAAAGCTAGGCCGCAGATCAGAACCACCACAGTCAATATCACCACCTTCCT   172
FP5-S. cerevisiae-1    GCTGCTCCAGAAAGCTAGGCCGCAGATCAGAACCACCACAGTCAATATCACCACCTTCCT   172
FP5-S. cerevisiae-2    GCTGCTCCAGAAAGCTAGGCCGCAGATCAGAACCACCACAGTCAATATCACCACCTTCCT   180
FP5-S. cerevisiae-3    GCTGCTCCAGAAAGCTAGGCCGCAGATCAGAACCACCACAGTCAATATCACCACCTTCCT   167
                       ************************************************************

Consensus              CTTATAGATTCGGAATCTCATGATAGGGGCTCAGCCTCTGTGCGAGTGGAGAGAAGTTTG   232
FP5-S. cerevisiae-1    CTTATAGATTCGGAATCTCATGATAGGGGCTCAGCCTCTGTGCGAGTGGAGAGAAGTTTG   232
FP5-S. cerevisiae-2    CTTATAGATTCGGAATCTCATGATAGGGGCTCAGCCTCTGTGCGAGTGGAGAGAAGTTTG   240
FP5-S. cerevisiae-3    CTTATAGATTCGGAATCTCATGATAGGGGCTCAGCCTCTGTGCGAGTGGAGAGAAGTTTG   227
                       ************************************************************

Consensus              CAGGCGAGCTGAGGAGCANTTGCAGGTGATATGATGTGCTCGGCTCAAGAAGCGGGCCCG   292
FP5-S. cerevisiae-1    CAGGCGAGCTGAGGAGCAATTGCAGGTGATATGATGTGCTCGGCTCAAGAAGCGGGCCCG   292
FP5-S. cerevisiae-2    CAGGCGAGCTGAGGAGCANTTGCAGGTGATATGATGTGCTCGGCTCAAGAAGCGGGCCCG   300
FP5-S. cerevisiae-3    CAGGCGAGCTGAGGAGNNNTTGCAGGTGATATGATGTGCTCGGCTCAAGAAGCGGGCCCG   287
                       ****************   *****************************************

Consensus              GAGAGGAAGAAGTCGTGCCGGGGCTAATTATTGGCAAAACGAGCTCTTGTTGTAAACATN   352
FP5-S. cerevisiae-1    GAGAGGAAGAAGTCGTGCCGGGGCTAATTATTGGCAAAACGAGCTCTTGTTGTAAACATN   352
FP5-S. cerevisiae-2    GAGAGGAAGAAGTCGTGCCGGGGCTAATTATTGGCAAAACGAGCTCTTGTTGTAAACATN   360
FP5-S. cerevisiae-3    GAGAGGAAGAAGTCGTGCCGGGGCTAATTATTGGCAAAACGAGCTCTTGTTGTAAACATN   347
                       ************************************************************

Consensus              NNNNNNNNNNGGNATGTCACTAATGGCGAANNNNNANNNNNTAAGGNNTGATGGTTGCTCA   412
FP5-S. cerevisiae-1    NNNNNNNNNNGGAATGTCACTAATGGCGAANNNNNNNNNNNTAAGGNATGATGGTTGCTCA   412
FP5-S. cerevisiae-2    NNNNNNNNNNNNNANGTCACTAATGGCGAANNNNNANNNNNTAAGGNNTGATGGTTGCTCA   420
FP5-S. cerevisiae-3    NNNNNNNNTGGNATGTCACTAATGGCGAATNNNNANNNNNTAAGGNNTGATGGTTGCTCA   407
                       ********    * *************** ****  ********** *************

Consensus              GAGGCAGGAGAAGAGCNNNGNATACNNNNNNATAAAAGATAAAACATAAATAAACAGTCT   472
FP5-S. cerevisiae-1    GAGGCAGGAGAAGAGCAACGAATACGANGCNNTAAAAGATAAAACATAAATAAACAGTCT   472
FP5-S. cerevisiae-2    GAGGCAGGAGAAGAGNNNNGNATACNNNNNNATAAAAGATAAAACATAAATAAACAGTCT   480
FP5-S. cerevisiae-3    GAGGCAGGAGAAGAGCNNNGNATACNNNNNTATAAAAGATAAAACATAAATAAACAGTCT   467
                       ***************   ** ****     * ****************************

Consensus              TGATTATATTCTGGGTATTAAAGCCACAATCAGAACAAATATATGCTTTGTATCTTTTCT   532
FP5-S. cerevisiae-1    TGATTATATTCTGGGTATTAAAGCCACAATCAGAACAAATATATGCTTTGTATCTTTTCT   532
FP5-S. cerevisiae-2    TGATTATATTCTGGGTATTAAAGCCACAATCAGAACAAATATATGCTTTGTATCTTTTCT   540
FP5-S. cerevisiae-3    TGATTATATTCTGGGTATTAAAGCCNCAATCNNANNAAATATATGCTTTGTATCTTTTCT   527
                       ************************* ***** * * ************************

Consensus              TGCCTNNNNNNNNNNNNNNNNNNNTCCGCGGCCACATTAAGAGAACTTGTGGTAAGATAAG   592
FP5-S. cerevisiae-1    TGCCTNNNNNNNNNNNNNNNNNNNTCCGCGGCCACATTAAGAGAACTTGTGGTAAGATAAG   592
FP5-S. cerevisiae-2    TGCCTNNNNNNNNNNNNNNNNNNNTCCGCGGCCACATTAAGAGAACTTGTGGTAAGATAAG   600
FP5-S. cerevisiae-3    TGCCTNNNNNNNNNNNNNNNNNNNTCCGCGGCCACATTAAGAGAACTTGTGGTAAGATAAG   587
                       *****  *****************************************************

Consensus              AAGATATTTTATTCGNNNNNNTGNNNNNNTGGATGTCGGGAAATATTCTGCATTTGATAA   652
FP5-S. cerevisiae-1    AAGATATTTTATTCGNNNNNNTGNNNNNNTGGATGTCGGGAAATATTCTGCATTTGATAA   652
FP5-S. cerevisiae-2    AAGATATTTTATTCGNNNNNNTGNNNNNNTGGATGTCGGGAAATATTCTGCATTTGATAA   660
FP5-S. cerevisiae-3    AAGATATTTTATTCNNNNNNNTGNNNNNNTGGATGTCGGGAAATATTCTGCATTTGATAA   647
                       ************** ************* *******************************

Consensus              GAGGCGGTTAANTGNAGATATAATTGGNNGNGAAA------------------------   687
FP5-S. cerevisiae-1    GAGGCGGTTNNNTGNAGATATAATTGGTAGTGAAAAGGGTCGTTGCTATGGTCACCGTGA   712
FP5-S. cerevisiae-2    GANGCGGNTAANTGNANATATNATTGGNNGNGAAA------------------------   695
FP5-S. cerevisiae-3    GAGGCGGTTAANTGCAGATATAATTGNNNNNNNNNGGTCGTTGCTATGGTCACCGTGA   707
                       ** **** *  *** *  *** ****

Consensus              ------------------------------------------------------------
FP5-S. cerevisiae-1    AGCGAGTACAGCNGNNNNNNNATGTGTGCCGTTCTCAGTTAATATTGTTTGAATANGGNN   772
FP5-S. cerevisiae-2    ------------------------------------------------------------
FP5-S. cerevisiae-3    AGCGAGTACAGCNNNNNNNNNATGTGTGCCGTTCTCAGTTAATATTGTTTGAATATGGTA   767

Consensus              ------------------------------------------------------------
FP5-S. cerevisiae-1    NNNNGTTTTAGTCGGTTTAAAGGTAAGAAGATCTAACCAAAAGAACACTGCAGNGACTG   832
FP5-S. cerevisiae-2    ------------------------------------------------------------
FP5-S. cerevisiae-3    ACCTGTTTTAGTCGGTTTAAAGGTAAGAAGANCTAACCAAAAACAACACTGCAGTGACTG   827

Consensus              --------------------------------------
FP5-S. cerevisiae-1    ATTGTAGTATTTATTTTNNNNNNNNATCTT--------   862
FP5-S. cerevisiae-2    --------------------------------------
FP5-S. cerevisiae-3    ATTGNAGNANTTATTTTTTTACTTAATCTTAANTTNNG   865
```

TABLE 6A

CLUSTAL 2.0.11 multiple sequence alignment
First Three *Salmonella enterica* MR595 sequence embedded fingerprints by primer mix FB1D1 were aligned and used to generate a consensus sequence

```
SEQ ID NO: 50 Consensus                           GCTGACAATGCTGCTGCNGCTTCTCCTCNCTGTCTCCACTT
SEQ ID NO: 18 FB1D1 S. enterica 3    -------GTTNNTCNNN--GCTGACAATGCTGCTGCNGCTTCTCCTCNCTGTCTCCACTT    51
SEQ ID NO: 17 FB1D1 S. enterica 2    CNGNNANGTTNNTCNNN--GCTGACAATGCTGCTGCNGCTTCNCCTCNCTGTCTCCACTT    58
SEQ ID NO: 19 FB1D1 S. enterica 1    -------GTTGCTNCTACTGCTGANAATGCTGCTGCTGCTTCTCCTCNCTGTCTCCACTT    53
                                            ***  *      ***** *********** ***** *****************

Consensus                            CCTTGAACAATGCGCCGTCATGCTTCTTTTGCCTCCCGCTGCTCCAGAAAGCTAGGCCGC
FB1D1 S. enterica 3                  CCTTGAACAATGCGCCGTCATGCTTCTTTTGCCTCCCGCTGCTCCAGAAAGCTAGGCCGC   111
FB1D1 S. enterica 2                  CCTTGAACAATGCGCCGTCATGCTTCTTTTGCCTCCCGCTGCTCCAGAAAGCTAGGCCGC   118
FB1D1 S. enterica 1                  CCTTGAACAATGCGCCGTCATGCTTCTTTTGCCTCCCGCTGCTCCAGAAAGCTAGGCCGC   113
                                     ************************************************************

Consensus                            AGATCANAACCACCACAGTCAATATCACCACCTTCCTCTTATAGATTCGGAATCTCATGA
FB1D1 S. enterica 3                  AGATCANAACCACCACAGTCAATATCACCACCTTCCTCTTATAGATTCGGAATCTCATGA   171
FB1D1 S. enterica 2                  AGATCANAACCACCACAGTCAATATCACCACCTTCCTCTTATAGATTCGGAATCTCATGA   178
FB1D1 S. enterica 1                  AGATCAGAACCACCACAGTCAATATCACCACCTTCCTCTTATAGATTCGGAATCTCATGA   173
                                     ****** *****************************************************

Consensus                            TAGGGGCTCAGCCTCTGTGCGAGTGGAGAGAAGTTNNNNNNNGAGCTGAGGAGCAATTGC
FB1D1 S. enterica 3                  TAGGGGCTCAGCCTCTGTGCGAGTGGAGAGAAGTTNNNNNNNGAGCTGAGGAGCAATTGC   231
FB1D1 S. enterica 2                  TAGGGGCTCAGCCTCTGTGCGAGTGGAGAGAAGTTNNNNNGNNAGCTGANGANCAATTGC   238
FB1D1 S. enterica 1                  TAGGGGCTCAGCCTCTGTGCGAGTGGAGAGAAGTTNGCAGGCGAGCTGAGGAGCAATTGC   233
                                     ************************************       ****** ** *******

Consensus                            AGGTGATATGATGTGCTCGGCTCAAGAAGCGGGCCNGGNNNGNNNGAAGNNNNNNNNNNN
FB1D1 S. enterica 3                  AGGTGATATGATGTGCTCGGCTCAAGAAGCGGGCCNGGNNAGGAAGAAGNNNNNNNNNNN   291
FB1D1 S. enterica 2                  AGGTGATATGATGTGCTCGGCTCAAGAAGCGGGCCCGGAGNNNNNNAAGNNNNNNNNNNN   298
FB1D1 S. enterica 1                  AGGTGATATGATGTGCTCGGCTCAAGAAGCGGGCCNGNNNNGNNNGAAGTCNNGNCGNGG   293
                                      ********************************** *         ***  ** *  *

Consensus                            NTAATTATTGGCAAAACGAGCTCTTGTTGTANNNNNNNNNNNNGNNNNNNNNNNNACTNNN
FB1D1 S. enterica 3                  NTAATTATTGGCAAAACGAGCTCTTGTTGTANNNNNNNNNNNNGNNNNNNNNNNNACTNNN   351
FB1D1 S. enterica 2                  NTAATTATTGGCAAAACGAGCTCTTGTTNNNNNNNNNNNNNNNGNNNNNNNNNNNACTANN   358
FB1D1 S. enterica 1                  CTAATTATTGGCAAAACGAGCTCTTGTTGTANNNNNNNNNNNNGNNNNNNNNNNNCTANNG   353
                                      ***************************   ***********************    *

Consensus                            NNNGNNCAATATTCCNTANNGCATGATGGTTGCTCAGAGGCAGNNNNNNAGCAANNNANN
FB1D1 S. enterica 3                  NGNGNNCAATATTCCNTANNGCATGATGGTTGCTCAGAGGCAGNNNNNNAGCAANNNANN   411
FB1D1 S. enterica 2                  GNNGNNCAATATTCCNTANNGCATGATGGTTGCTCAGAGGCAGNNNNNNAGCAACNNANN   418
FB1D1 S. enterica 1                  NNNNATCNATATTCCNTAANGCATGATGGTTGCTCAGAGGCANGNNNN-AGCAACNAANA   412
                                       *   * ********** ***********************  ****  **** * **

Consensus                            CGATCCTATAAAAGATAAAACATAAATAAACAGTCTTGATTATATTCTGGGTATTAAAGC
FB1D1 S. enterica 3                  CGATCCTATAAAAGATAAAACATAAATAAACAGTCTTGATTATATTCTGGGTATTAAAGC   471
FB1D1 S. enterica 2                  CNATCCTATAAAAGATAAAACATAAATAAACAGTCTTGATTATATTCTGGGTATTAAAGC   478
FB1D1 S. enterica 1                  CGATCCTATAAAAGATAAAACATAAATAAACAGTCTTGATTATATTCTGGGTATTAAAGC   472
                                     * **********************************************************

Consensus                            CACAATCAGAACAAATATATGCTTTGTATCTTNNNNNGCCTTCTTCATNNNNNNNNNGNTT
FB1D1 S. enterica 3                  CACAATCAGAACAAATATATGCTTTGTATCTTNNNNNGCCTTCTTCATNNNNNNNNNTGNTT   531
FB1D1 S. enterica 2                  CACAATCAGAACAAATATATGCTTTGTATCTTNNNNNGCCTTCTTCANNNNNNNANNGCTN   538
FB1D1 S. enterica 1                  CACAATCAGAACAAATATATGCTTTGTATCTTTNCNNGCCTTCTTCATNNNNNNNNNGNTT   532
                                     ******************************** * ************ ***** * * *

Consensus                            CCGCGGNCACATTAAGAGAACTTGTGGTAAGATAAGAAGATATTTTATTCGTTCTGCTGA
FB1D1 S. enterica 3                  CCGCGGNCACATTAAGAGAACTTGTGGTAAGATAAGAAGATATTTTATTCGTTCTGCTGA   591
FB1D1 S. enterica 2                  NNNNGGCCACATTAAGAGAACTTGTGGTAAGATAAGAAGATATTTTATTCGTTCTGCTGA   598
FB1D1 S. enterica 1                  CCGCGNNNNCATTAAGAGAACTTGTGGTAAGATAAGAAGATATTTTATTCGTTCTGCTGA   592
                                         *    ***************************************************

Consensus                            CTTGCTGGATGTCGGGAAATATTCTGCATTTNNNNNNAGGCGGTTAATTGCAGATATAAT
FB1D1 S. enterica 3                  CTTGCTGGATGTCGGGAAATATTCTGCATTTNNNNNNAGGCGGTTAATTGCAGATATAAT   651
FB1D1 S. enterica 2                  CTTGCTGGATGTCGGGAAATANTCTGCATTTNNNNNNAGGCGGTTAATTGCANATATAAT   658
FB1D1 S. enterica 1                  CTTGCTGGATGTCGGGAAATATTCTGCATTTNNNNNGAGGCGGTTAATTGCAGATATAAT   652
                                     ********************* ************** *************** *******

Consensus                            TGGTAGTGAAAAGGGTCGTTGCTATGGTCACCGTGAAGCGAGTACAGCAGCACAAGAATG
FB1D1 S. enterica 3                  TGGTAGTGAAAAGGGTCGTTGCTATGGTCACCGTGAAGCGAGTACAGCAGCACAAGAATG   711
FB1D1 S. enterica 2                  TGGTAGTGAAAAGGGTCGTTGCTATGGTCACCGTGAAGCGAGTACAGCAGCACAAGAATG   718
FB1D1 S. enterica 1                  TGGTAGTGAAAAGGGTCGTTGCTATGGTCACCGTGAAGCGAGTACAGCAGCACAAGAATG   712
                                     ************************************************************
```

TABLE 6A-continued

CLUSTAL 2.0.11 multiple sequence alignment
First Three *Salmonella enterica* MR595 sequence embedded fingerprints by primer mix FB1D1 were aligned and used to generate a consensus sequence

```
Consensus              TGTGCCGTTCTCNNNNNNTATTGTTTGAATATGGNAACCTGTTTTAGTCGGTTTAAANNN
FB1D1 S. enterica 3    TGTGCCGTTCTCNNNNNNTATTGTTTGAATATGGNAACCTGTTTTAGTCGGTTTAAANGN     771
FB1D1 S. enterica 2    NGTGCCGTTCTCNGNNNNTATTGTTTGAATATGGNAACCTGTTTTAGTCGGNTTAANNNN     778
FB1D1 S. enterica 1    TGTGCCGTTCTCNNNNNNTATTGTTTGAATATGGTAACCTGTTTTAGTCGGTTTAANNNN     772
                       ************ ****************** ************** ****  * *

Consensus              NNNNNNNTCTAACCNAAAACAACACTGCAGNGACNG--ANNGTAGTATTTATTTTNNNNN
FB1D1 S. enterica 3    NNNNNNT-CTAACCNAAAACAACACTGCAGTGACNG--ANNNNNGTANTTATTTTTTTAC     828
FB1D1 S. enterica 2    NNNNNNNTCTAACCAAAAACAACACTGNNGNGACTG--ANTGTAGTATTTATTTTNNNNN     836
FB1D1 S. enterica 1    NNNNNNNTCTAACCAAAAACAACACTGCAGNGGNNNGGNNNGTAGTATTTATTTTNNNNN     832
                       ******  ****** ************   *  *     *   *** *******

Consensus              NNNNNNCTTAATTTT-GGTGNAAACATCNACGGCGCACTTC
FB1D1 S. enterica 3    TNNNNNNNNNNNNNTTTGGTGNAAACATCAACGGCGCACTTC--------              869
FB1D1 S. enterica 2    NNNNNN-CTTAATTTT-GGTGNAAACATCNACGGCGCACTTCAACCANNN              883
FB1D1 S. enterica 1    NNNNNNCTTAATTTT-GGNGNAAACATCNACGGCGCACNTNNN-----                874
                       ****          *  ** ********* ********* *
```

TABLE 6B

CLUSTAL 2.0.11 multiple sequence alignment
First Three *Salmonella enterica* MR595 sequence embedded fingerprints by primer FP5 were aligned and used to generate a consensus sequence

```
SEQ ID NO: 51 Consensus         ------GNTTNTGATTACTGTTNNNGTTGCTACTACTGCTGACAATGCTGCTGCTGCTTC    54
SEQ ID NO: 38 FP5-S. enterica-1 ----CTGNNNNTGATTACTGTTNNNNGTTGCTACTACTGCTGACAATGCTGCTGCTGCTTC    56
SEQ ID NO: 37 FP5-S. enterica-3 NNNNNNNGGTTNTGATTACTGTTAATGCTACTACTGCTGACAATGCTGCTGCTGCTTC    60
SEQ ID NO: 36 FP5-S. enterica-2 -------NTTNTGATTACTGTTNNNNNTGCTACTACTGCTGACAATGCTGCTGCTGCTTC    53
                                          **********    *******************************

Consensus          TCCTNNCTGTCTCCACTTCCTTGAACAATGCGCCGTCATGCTTCTTTTGCCTCCCGCTGC  114
FP5-S. enterica-1  TCCTNNCTGTCTCCACTTCCTTGAACAATGCGCCGTCATGCTTCTTTTGCCTCCCGCTGC  116
FP5-S. enterica-3  TCCTNNCTGTCTCCACTTCCTTGAACAATGCGCCGTCATGCTTCTTTTGCCTCCCGCTGC  120
FP5-S. enterica-2  TCCTCNCTGTCTCCACTTCCTTGAACAATGCGCCGTCATGCTTCTTTTGCCTCCCGCTGC  113
                   ****  ******************************************************

Consensus          TCCAGAAAGCTAGGCCGCAGATCAGAACCACCACAGTCAATATCACCACCTTCCTCTTAT  174
FP5-S. enterica-1  TCCAGAAAGCTAGGCCGCAGATCAGAACCACCACAGTCAATATCACCACCTTCCTCTTAT  176
FP5-S. enterica-3  TCCAGAAAGCTAGGCCGCAGATCAGAACCACCACAGTCAATATCACCACCTTCCTCTTAT  180
FP5-S. enterica-2  TCCAGAAAGCTAGGCCGCAGATCAGAACCACCACAGTCAATATCACCACCTTCCTCTTAT  173
                   ************************************************************

Consensus          AGATTCGGAATCTCATGATAGGGGCTCAGCCTCTGTGCGAGTGGAGAGAAGTTTGCAGGC  234
FP5-S. enterica-1  AGATTCGGAATCTCATGATAGGGGCTCAGCCTCTGTGCGAGTGGAGAGAAGTTTGCAGGC  236
FP5-S. enterica-3  AGATTCGGAATCTCATGATAGGGGCTCAGCCTCTGTGCGAGTGGAGAGAAGTTTGCAGGC  240
FP5-S. enterica-2  AGATTCGGAATCTCATGATAGGGGCTCAGCCTCTGTGCGAGTGGAGAGAAGTTTGCAGGC  233
                   ************************************************************

Consensus          GAGCTGAGGAGCAATTGCAGGTGATATGATGTGCTCGGCTCAAGAAGCGGGCCCGGAGAG  294
FP5-S. enterica-1  GAGCTGAGGAGCAATTGCAGGTGATATGATGTGCTCGGCTCAAGAAGCGGGCCCGGAGAG  296
FP5-S. enterica-3  GAGCTGAGGAGCAATTGCAGGTGATATGATGTGCTCGGCTCAAGAAGCGGGCCCGGAGAG  300
FP5-S. enterica-2  GAGCTGAGGAGCAATTGCAGGTGATATGATGTGCTCGGCTCAAGAAGCGGGCCCGGAGAG  293
                   ************************************************************

Consensus          GAAGAAGTCGTGCCGGGGCTAATTATTGGCAAAACGAGCTCTTGTTGTAAACATTGATCC  354
FP5-S. enterica-1  GAAGAAGTCGTGCCGGGGCTAATTATTGGCAAAACGAGCTCTTGTTGTAAACATTGATCC  356
FP5-S. enterica-3  GAAGAAGTCGTGCCGGGGCTAATTATTGGCAAAACGAGCTCTTGTTGTAAACATTGATCC  360
FP5-S. enterica-2  GAAGAAGTCGTGCCGGGGCTAATTATTGGCAAAACGAGCTCTTGTTGTAAACATTGATCC  353
                   ************************************************************

Consensus          AACTGGAATGTCACTAANNNNNNNNNNT-ATTCCATAAGGCATGATGGTTGCTCAGAGGC  413
FP5-S. enterica-1  AACTGGAATGTCACTAANNNNNNNNANT-ATTCCATAAGGCATGATGGTTGCTCAGAGGC  415
FP5-S. enterica-3  AACTGGAATGTCACTAANNNNNNNNNNNTATTCCATAAGGCATGATGGTTGCTCAGAGGC  420
FP5-S. enterica-2  AACTGGAATGTCACTAANNNNNNNNNNATATTCCATAAGGCATGATGGTTGCTCAGAGGC  413
                   ***************** *        *******************************

Consensus          AGGAGAAGAGCAACGAATACGATCCTATAAAAGATAAAACATAAATAAACAGTCTTGATT  473
FP5-S. enterica-1  NGGAGAAGAGCAACGAATACGATCCTATAAAAGATAAAACATAAATAAACAGTCTTGATT  475
FP5-S. enterica-3  AGGAGAAGAGCAACGAATACGATCCTATAAAAGATAAAACATAAATAAACAGTCTTGATT  480
FP5-S. enterica-2  AGGAGAAGAGCAACGAATACGATCCTATAAAAGATAAAACATAAATAAACAGTCTTGATT  473
                    ***********************************************************
```

TABLE 6B-continued

CLUSTAL 2.0.11 multiple sequence alignment
First Three *Salmonella enterica* MR595 sequence embedded fingerprints by primer
FP5 were aligned and used to generate a consensus sequence

```
Consensus        ATATTCTGGGTATTAAAGCCACANNNNNNNNNNNNNNTATGCTTTGTATCTTNNNNNGNCT 533
FP5-S. enterica-1   ATATTCTGGGTATTAAAGCCACANNNNNNNNGANNTATGCTTTGTATCTTNNNNNGNCT 535
FP5-S. enterica-3   ATATTCTGGGTATTAAAGCCACANNNNNNNNNNNNNTATGCTTTGTATCTTNNNNNGNCN 540
FP5-S. enterica-2   ATATTCTGGGTATTAAAGCCACAANNNNNNNNNNNNNTNTGCTTTGTATCTTTNNNNGCCT 533
                   *********************  *******   *** ************* *****  *

Consensus        TCTTCATTACCAACTGCTTCCGCGGCCACATTAAGAGAACTTGTGGTAAGATAAGAAGAT 593
FP5-S. enterica-1   TCTTCATTACCAACTGCTTCCGCGGCCACATTAAGAGAACTTGTGGTAAGATAAGAAGAT 595
FP5-S. enterica-3   TCTTCATTACCAACTGCTTCCGCGGCCACATTAAGAGAACTTGTGGTAAGATAAGAAGAT 600
FP5-S. enterica-2   TCTTCATTACCAACTGCTTCCGCGGCCACATTAAGAGAACTTGTGGTAAGATAANAANAT 593
                   ******************************************************  * **

Consensus        ATTTTATTCNNNNNNNTGACTTGCTGGATGTCGGGAAATATTCTGCATTTGATAAGAGGC 653
FP5-S. enterica-1   ATTTTATTCNNNNNNNTGACTTGCTGGATGTCGGGAAATATTCTGCATTTGATAAGAGGC 655
FP5-S. enterica-3   ATTTTATTCNNNNNNNTGACTTGCTGGATGTCGGGAAATATTCTGCATTTGATAAGAGGC 660
FP5-S. enterica-2   ATTTTATTCNNNNNNNTGACTTGCTGGATGTCGGGAAATATTCTGCATTTGATAAGAGGC 653
                   ************************************************************

Consensus        GGTTAATTGCAGATATAATTGGNNNNNNNNNNGNTCGTTGCTATGGTCACCGTGAAGCGA 713
FP5-S. enterica-1   GGTTAATTGCAGATATAATTGGNNGTNNNNNNGNNCGTTGCTATGGTCACCGTGAAGCGA 715
FP5-S. enterica-3   GGTTAATTGCAGATATAATTGGNNNNNNNNNNGNTCGTTGCTATGGTCACCGTGAAGCGA 720
FP5-S. enterica-2   GGTTAATTGCAGATATAATTNNNNNNNNNNNNGGTCGTTGCTATGGTCACCGTGAAGCGA 713
                   ********************  **  *******  *************************

Consensus        GTACNGCAGCACAAGAATGTGTGNNNNNNNNNNNNAATATTGNTTGAATATGGTAACCTG 773
FP5-S. enterica-1   GTACNNCAGCACAAGAATGTGTGNNNNNNNNNNNTAATATNGTTTGAATATGGTAACCTG 775
FP5-S. enterica-3   GTACAGCAGCACAAGAATGTGTGNNNNNNNNNNNNAATATTGNTTGAATATGGTAACCTG 780
FP5-S. enterica-2   GTNNNGCNNNNNNAGANTGNGNGGNNGNNNNNNNNNATATTGNTTGAATATGGNNNCCTG 773
                   **   *      *** ** *   ** *******  **** * ********** ** ****

Consensus        TTTTAGTCGGNTTAAAGGTAAGAAGATCTAACCNAAAACAACACTGCAGTGACTGATTGN 833
FP5-S. enterica-1   TTTTAGTCGGNTTAAAGGTAAGAAGATCTAACCAAAAACAACACTGCAGTGACNNNNNNN 835
FP5-S. enterica-3   TTTTAGTCGGTTTAAAGGTAAGAAGATCTAACCNAAAACNACACTGCAGTGACTGATTGN 840
FP5-S. enterica-2   NTTTAGTCGGNTTAAAGGTAAGAAGATCTAACCNAAAACAACACTGCAGTGACTGATTGT 833
                   ********* ******************** ***** *** *************

Consensus        AGTATNNNNNN------------------------------------------------ 844
FP5-S. enterica-1   AGTATNNNNNNTTTTACTTANNNNNAATTNTGGTGTAAACATCANCGGCGCACTTCNACC 895
FP5-S. enterica-3   AGTATNNNNNN------------------------------------------------ 851
FP5-S. enterica-2   AGNANNNNNNN------------------------------------------------ 844
                   ** * ******

Consensus        ------------------------------
FP5-S. enterica-1   NATACTCCAATGNTTTATCCATCGACATGN                              925
FP5-S. enterica-3   ------------------------------
FP5-S. enterica-2   ------------------------------
```

TABLE 7

*Staphylococcus aureus* MU3 sequence embedded fingerprint #5 was run as query sequence. Using BLASTN, low complexity filter on, with values of +2 for a match and −3 for a mismatch against the consensus sequence for all three organisms.

| Accession | Description | Max score | Total score | Query coverage | E value | Max ident | Links |
|---|---|---|---|---|---|---|---|
| | Sequences producing significant alignments: | | | | | | |
| | by primer mix FB1D1: | | | | | | |
| 25817 | *Staphalococcus aureus* MU3 | 922 | 989 | 91% | 0.0 | 92% | |
| 25816 | *Salmonella enterica* MR595 | 892 | 892 | 97% | 0.0 | 85% | |
| 25815 | *Saccharomyces cervisiae* S288C | 820 | 820 | 89% | 0.0 | 84% | |
| | by single primer FP5: | | | | | | |
| 8382 | *Staphalococcus aureus* MU3 | 1355 | 1355 | 99% | 0.0 | 98% | |
| 8381 | *Salmonella enterica* MR595 | 1128 | 1128 | 99% | 0.0 | 89% | |
| 8383 | *Saccharomyces cervisiae* S288C | 940 | 940 | 83% | 0.0 | 88% | |

TABLE 8

*Saccharomyces cerevisiae* S288C MU3 sequence embedded fingerprint #5 was run as query sequence. Using BLASTN, low complexity filter on, with values of +2 for a match and −3 for a mismatch against the consensus sequences for all three organisms

| Accession | Description | Max score | Total score | Query coverage | E value | Max ident Links |
|---|---|---|---|---|---|---|
| | Sequences producing significant alignments: | | | | | |
| | by primer mix FB1D1: | | | | | |
| 36125 | *Saccharomyces cervisiae* S288C | 594 | 963 | 82% | 8e−174 | 96% |
| 36126 | *Salmonella enterica* MR595 | 439 | 756 | 79% | 4e−127 | 93% |
| 36127 | *Staphalococcus aureus* MU3 | 459 | 736 | 75% | 4e−133 | 100% |
| | by single primer FP5: | | | | | |
| 39539 | *Saccharomyces cervisiae* S288C | 928 | 928 | 73% | 0.0 | 96% |
| 39538 | *Staphalococcus aureus* MU3 | 1088 | 1088 | 87% | 0.0 | 87% |
| 39537 | *Salmonella enterica* MR595 | 971 | 971 | 90% | 0.0 | 84% |

TABLE 9

*Salmonella enterica* MR595 sequence embedded fingerprint #5 was run as query sequence. Using BLASTN, low complexity filter on, with values of +2 for a match and −3 for a mismatch against the consensus sequence for all three organisms.

| Accession | Description | Max score | Total score | Query coverage | E value | Max ident Links |
|---|---|---|---|---|---|---|
| | Sequences producing significant alignments: | | | | | |
| | by primer mix FB1D1: | | | | | |
| 49678 | *Salmonella enterica* MR595 | 928 | 928 | 97% | 0.0 | 92% |
| 49679 | *Staphalococcus aureus* MU3 | 760 | 830 | 91% | 0.0 | 84% |
| 49677 | *Saccharomyces cervisiae* S288C | 607 | 607 | 91% | 1e−177 | 75% |
| | by single primer FP5: | | | | | |
| 20645 | *Salmonella enterica* MR595 | 1229 | 1229 | 98% | 0.0 | 96% |
| 20646 | *Staphalococcus aureus* MU3 | 1220 | 1220 | 95% | 0.0 | 92% |
| 20647 | *Saccharomyces cervisiae* S288C | 888 | 888 | 79% | 0.0 | 88% |

We claim:

1. A labeled polynucleotide comprising the nucleic acid sequence set forth in SEQ ID NO:1, SEQ ID NO:2, SEQ ID NO:3, SEQ ID NO:4, or SEQ ID NO:25.

2. A primer comprising the isolated labeled polynucleotide of claim 1.

* * * * *